(12) United States Patent
Danial et al.

(10) Patent No.: US 10,716,828 B2
(45) Date of Patent: Jul. 21, 2020

(54) METHODS OF MODULATING CELLULAR HOMEOSTATIC PATHWAYS AND CELLULAR SURVIVAL

(75) Inventors: Nika N. Danial, Boston, MA (US); Loren D. Walensky, Chestnut Hill, MA (US); Gregory Bird, Pelham, NH (US); Stanley J. Korsmeyer, Weston, MA (US); Susan R. Korsmeyer, legal representative, Weston, MA (US)

(73) Assignee: Dana-Farber Cancer Institute, Inc., Boston, MA (US)

(*) Notice: Subject to any disclaimer, the term of this patent is extended or adjusted under 35 U.S.C. 154(b) by 1104 days.

(21) Appl. No.: 12/598,479

(22) PCT Filed: May 2, 2008
(Under 37 CFR 1.47)

(86) PCT No.: PCT/US2008/062345
§ 371 (c)(1),
(2), (4) Date: Apr. 15, 2010

(87) PCT Pub. No.: WO2008/137633
PCT Pub. Date: Nov. 13, 2008

(65) Prior Publication Data
US 2010/0273704 A1    Oct. 28, 2010

Related U.S. Application Data

(60) Provisional application No. 60/915,594, filed on May 2, 2007.

(51) Int. Cl.
| | | |
|---|---|---|
| *A61K 38/02* | (2006.01) | |
| *C12N 5/0781* | (2010.01) | |
| *C07K 14/00* | (2006.01) | |
| *C07K 7/08* | (2006.01) | |
| *A61P 3/10* | (2006.01) | |
| *A61P 3/04* | (2006.01) | |
| *A61K 38/17* | (2006.01) | |

(52) U.S. Cl.
CPC ................... *A61K 38/1761* (2013.01)

(58) Field of Classification Search
None
See application file for complete search history.

(56) References Cited

U.S. PATENT DOCUMENTS

| 4,522,811 A | 6/1985 | Eppstein et al. |
|---|---|---|
| 7,192,713 B1 | 3/2007 | Verdine et al. |
| 7,202,332 B2 | 4/2007 | Arora et al. |
| 7,705,118 B2 | 4/2010 | Arora et al. |
| 7,723,469 B2 | 5/2010 | Walensky et al. |
| 7,786,072 B2 | 8/2010 | Verdine et al. |
| 2005/0250680 A1 | 11/2005 | Walensky et al. |
| 2006/0198832 A1 | 9/2006 | Satterthwait et al. |
| 2008/0262200 A1 | 10/2008 | Nash |
| 2009/0047711 A1 | 2/2009 | Nash |
| 2009/0088553 A1 | 4/2009 | Nash |
| 2009/0149630 A1 | 6/2009 | Walensky et al. |
| 2009/0176964 A1 | 7/2009 | Walensky et al. |
| 2010/0184628 A1 | 7/2010 | Nash |
| 2010/0184645 A1 | 7/2010 | Verdine et al. |
| 2010/0234563 A1 | 9/2010 | Arora et al. |
| 2011/0028753 A1 | 2/2011 | Verdine et al. |

FOREIGN PATENT DOCUMENTS

| AU | 2014202832 | 5/2016 |
|---|---|---|
| EP | 2152294 | 7/2017 |
| JP | 2006-516383 | 7/2006 |
| JP | 5883220 | 2/2016 |
| WO | WO 99/45128 | 9/1999 |
| WO | WO 99/45128 A2 | 11/1999 |
| WO | WO 99/45128 A3 | 1/2000 |
| WO | WO 00/59526 A1 | 10/2000 |
| WO | WO2004022580 A1 * | 3/2004 |
| WO | WO 2005/044839 A2 | 5/2005 |
| WO | WO 2006/103666 A2 | 10/2006 |
| WO | WO 2006/103666 A3 | 3/2007 |
| WO | WO 2008/137633 | 11/2008 |

OTHER PUBLICATIONS

Moran et al. Abstract (Pediatric Diabetes Jun. 2003;4(2):101-9).*
Goss, et al. Abstract (Transplantation Dec. 27, 2002;74(12):1761-6).*
Gurzov et al. (The Journal of Biological Chemistry vol. 285, No. 26, pp. 19910-19920, Jun. 25, 2010).*
Mehmeti et al. (Molecular and Cellular Endocrinology, vol. 332, Issues 1-2, Jan. 30, 2011, pp. 88-96).*
Bouillet et al. (Journal of Cell Science 115, 567-1574 (2002).*
Schafmeister et al. (J. Am. Chem. Soc. 2000, 122, 5891-5892).*
Hallet et al. (Nucleic Acids Research, 1997, vol. 25, No. 9 1866-1867).*
U.S. Appl. No. 13/680,905, filed Nov. 19, 2012, Verdine et al.
U.S. Appl. No. 13/097,930, filed Apr. 29, 2011, Nash.
U.S. Appl. No. 13/250,344, filed Sep. 30, 2011, Arora et al.
U.S. Appl. No. 13/252,751, filed Oct. 4, 2011, Walensky et al.
Lee, et al. A novel BH3 ligand that selectively targets Mcl-1 reveals that apoptosis can proceed without Mcl-1 degradation. J Cell Biol. Jan. 28, 2008;180(2):341-355.
Sanchez-Garcia, et al. Tumorigenic activity of the BCR-ABL oncogenes is mediated by BCL2. Proc Natl Acad Sci U S A. Jun. 6, 1995;92(12):5287-91.
U.S. Appl. No. 13/370,057, filed Feb. 9, 2012, Nash et al.
International Search Report for PCT/US2008/062345, dated Feb. 9, 2009.
Danial, et al. BAD and glucokinase reside in a mitochondrial complex that integrates glycolysis and apoptosis. Nature. Aug. 21, 2003;424(6951):952-6.

(Continued)

*Primary Examiner* — Patricia Duffy
*Assistant Examiner* — Garen Gotfredson
(74) *Attorney, Agent, or Firm* — Fish & Richardson P.C.

(57) ABSTRACT

The invention provides composition and therapeutic, methods for modulating homeostatic pathways that are useful in treatment, and prevention of diabetes, diabetes associated disorders, metabolic disorders and cancer.

14 Claims, 47 Drawing Sheets

Specification includes a Sequence Listing.

(56) References Cited

OTHER PUBLICATIONS

Accili et al, 2001, *Genetics of type 2 diabetes: insight from targeted mouse mutants*, Curr Mol Med, 1(1):9-23.
Accili, 2004, *Lilly lecture 2003: the struggle for mastery in insulin action: from triumvirate to republic*, Diabetes 53(7):1633-42.
Antinozzi et al, 2002, *Mitochondrial metabolism sets the maximal limit offuel-stimulated insulin secretion in a model pancreatic beta cell: a survey of four fuel secretagogues*, J Biol Chem, 277(14):11746-55.
Arora, et al, 1988, *Functional significance of mitochondrial bound hexokinase in tumor cell metabolism. Evidence for preferential phosphorylation of glucose by intramitochondrially generated ATP*, J Biol Chem 263(33):17422-28.
Ashcroft et al, 1999, *ATP-sensitive K+ channels and insulin secretion: their role in health and disease*, Diabetologia 42(8):903-19.
Bell et al, 2001, *Diabetes mellitus and genetically programmed defects in beta-cell function*, Nature 414(6865):788-91.
Berkowitz, et al, 1996, *Ready Access to Fluorinated Phosphonate Mimics of Secondary Phosphates. Synthesis of the (alpha,alpha-Difluoroalkyl)phosphonate Analogues of L-Phosphoserine, L-Phosphoallothreonine, and L-Phosphothreonine*, J Org Chem. 12;61(14):4666-4675.
Blackwell et al, 1998 *Highly Efficient Synthesis of Covalently Cross-Linked Peptide Helices by Ring-Closing Metathesis*, Angew Chem, Int, Ed, 37(23):3281-84.
Bracken et al, 1994 *Synthesis and Nuclear Magnetic Resonance Structure Determination of an .alpha.-Helical, Bicyclic, Lactam-Bridged Hexapeptide*, J. Am. Chem. Soc, 116 (14), pp. 6431-6432.
Brady et al, 1994, *Drug design. Reflections on a peptide*, Nature, 368(6473):692-693.
Brocklehurst et al, 2004, *Stimulation of hepatocyte glucose metabolism by novel small molecule glucokinase activators*, Diabetes 53(3):535-541.
Bruning et al, 1998, *A muscle-specific insulin receptor knockout exhibits features of the metabolic syndrome of NIDDM without altering glucose tolerance*, Mol Cell 2(5):559-69.
Brunt, 2005, *Pathology of nonalcoholic steatohepatitis*, Hepatol Res 33(2):68-71.
Bugianesi, 2005, *Insulin resistance: a metabolic pathway to chronic liver disease*, Hepatology 42(5):987-1000.
Bustamante, et al, 1977, *High aerobic glycolysis of rat hepatoma cells in culture: role of mitochondrial hexokinase*, Proc Natl Acad Sci USA 74(9):3735-3739.
Byrne et al, 1994, *Insulin secretory abnormalities in subjects with hyperglycemia due to glucokinase mutations*, J Clin Invest 93(3):1120-30.
Calle, et al, 2004, *Overweight, obesity and cancer: epidemiological evidence and proposed mechanisms*, Nat Rev Cancer 4(8):579-91.
Cheatham, et al, 1995, *Insulin action and the insulin signaling network*, Endocr Rev. Apr. 1995;16(2):117-42.
Chen et al, 1974, *Determination of the helix and beta form of proteins in aqueous solution by circular dichroism*, Biochemistry 13(16):3350-9.
Cheng, et al, 2001, *BCL-2, BCL-X(L) sequester BH3 domain-only molecules preventing BAX- and BAK-mediated mitochondrial apoptosis*, Mol Cell 8(3):705-11.
Cherrington, 1999, *Banting Lecture 1997. Control of glucose uptake and release by the liver in vivo*, Diabetes 48(5):1198-1214.
Cho et al, 2001, *Insulin resistance and a diabetes mellitus-like syndrome in mice lacking the protein kinase Akt2 (PKB beta)*,Science 292(5522):1728-31.
Christesen, 2000, *The second activating glucokinase mutation (A456V): implications for glucose homeostasis and diabetes therapy*, Diabetes 51(4):1240-6.
Clement 1996, *Assessment of insulin sensitivity in glucokinase-deficient subjects*, Diabetologia 39(1):82-90.
Cory, et al, 2002, *The Bcl2 family: regulators of the cellular life-or-death switch*, Nat Rev Cancer 2(9):647-56.
Cowey, et al, 2006, *The metabolic syndrome: A high-risk state for cancer?*, Am J Pathol 169(5):1505-22.
Cunningham et al, 1996, *Glucose-induced oscillatory insulin secretion in perifused rat pancreatic islets and clonal beta-cells (HIT)*, J Am Physiol 271(4 Pt 1):E702-10.
Danial, et al, 2004, *Cell death: critical control points*, Cell 116(2):205-19.
Datta et al, 2000, *14-3-3 proteins and survival kinases cooperate to inactivate BAD by BH3 domain phosphorylation*, Mol Cell 6(1):41-51.
Datta et al, 2002, *Survival factor-mediated BAD phosphorylation raises the mitochondrial threshold for apoptosis*, Dev Cell 3(5):631-43.
Datta et al, 1999, *Cellular survival: a play in three Akts*, Genes Dev 13(22):2905-27.
DeFronzo 1988, *Lilly lecture 1987. The triumvirate: beta-cell, muscle, liver. A collusion responsible for NIDDM*, Diabetes 37(6):667-87.
DeFronzo, 2004, *Dysfunctional fat cells, lipotoxicity and type 2 diabetes*, Int J Clin Pract Suppl 143:9-21.
DeGrado, 1988, *Design of peptides and proteins*, Adv Protein Chem, 39:51-124.
Delivani, et al, 2005, *Role for CED-9 and Egl-1 as regulators of mitochondrial fission and fusion dynamics*. Mol Cell 21(6):761-73.
Dentin, 2005, *Carbohydrate responsive element binding protein (ChREBP) and sterol regulatory element binding protein-1c (SREBP-1c): two key regulators of glucose metabolism and lipid synthesis in liver*, Biochimie, 87(1):81-6.
Dunn-Meynell, 2002, *Glucokinase is the likely mediator of glucosensing in both glucose-excited and glucose-inhibited central neurons*, Diabetes 51(7):2056-65.
Falck-Ytter, 2001, *Clinical features and natural history of nonalcoholic steatosis syndromes*, Semin Liver Dis 21(1):17-26.
Fantin, et al, 2006, *Attenuation of LDH-A expression uncovers a link between glycolysis, mitochondrial physiology, and tumor maintenance*, Cancer Cell 9(6):425-34.
Federici et al, 2001, *High glucose causes apoptosis in cultured human pancreatic islets of Langerhans: a potential role for regulation of specific Bcl family genes toward an apoptotic cell death program*, Diabetes 50(6):1290-301.
Frank, et al, 2001, *The role of dynamin-related protein 1, a mediator of mitochondrial fission, in apoptosis*, Dev Cell 1(4):515-25.
Fu et al, 2000, *14-3-3 proteins: structure, function, and regulation*, Annu Rev Pharmacol Toxicol, 40:617-47.
Gao et al, 2003, *Distinguishing features of leucine and alpha-ketoisocaproate sensing in pancreatic beta-cells*, Endocrinology, 144(5):1949-57.
Gatenby et al, 2004, *Why do cancers have high aerobic glycolysis?*, Nat Rev Cancer 4(11):891-99.
Glaser 1998, *Familial hyperinsulinism caused by an activating glucokinase mutation*, N Engl J Med 338(4):226-30.
Green et al, 2004, *The pathophysiology of mitochondrial cell death*, Science 305(5684):626-9.
Grimsby et al, 2003 *Allosteric activators of glucokinase: potential role in diabetes therapy*, Science 301(5631):370-373.
Griparic, et al, 2001, *The many shapes of mitochondrial membranes*, Traffic 2(4):235-44.
Gunter, et al, 2006, *Obesity and colorectal cancer: epidemiology, mechanisms and candidate genes*, J Nutr Biochem 17(3):145-56.
Hao, et al, 1996, *Mutation of phosphoserine 389 affects p53 function in vivo*, J Biol Chem, 271(46):29380-5.
Hatzivassiliou et al, 2005, *ATP citrate lyase inhibition can suppress tumor cell growth*, Cancer Cell 8(4):311- 21.
He et al, 1998, *A simplified system for generating recombinant adenoviruses*, Proc Natl Acad Sci USA 95(5):2509-14.
Heart et al, 2006, *Glucose-dependent increase in mitochondrial membrane potential, but not cytoplasmic calcium, correlates with insulin secretion in single islet cells*, Am J Physiol Endocrinol Metab 290(1):E143-E148.
Hetz, et al, 2006 *Proapoptotic BAX and BAK modulate the unfolded protein response by a direct interaction with IRE1alpha*, Science 312(5773):572-6.

(56) References Cited

OTHER PUBLICATIONS

Iizuka et al, 2000, *Stable overexpression of the glucose-6-phosphatase catalytic subunit attenuates glucose sensitivity of insulin secretion from a mouse pancreatic beta-cell line*, J Endocrinol 164(3):307-14.
Jameson et al, 1994, *A rationally designed CD4 analogue inhibits experimental allergic encephalomyelitis*, Nature 368(6473):744-746.
Kamer, 2005, *Proapoptotic BID is an ATM effector in the DNA-damage response*, Cell 122(4):593-603.
Kang, 2006, *Glucokinase is a critical regulator of ventromedial hypothalamic neuronal glucosensing*, Diabetes 55(2):412-20.
Karbowski, et al, 2006, *Role of Bax and Bak in mitochondrial morphogenesis*, Nature 443(7112):658-62.
Kelekar et al, 1997, *Bad is a BH3 domain-containing protein that forms an inactivating dimer with Bcl-XL*, Mol Cell Biol 18(12):7040-6.
Kirpichnikov, 2002, *Metformin: an update*, Ann Intern Med 137(1):25-33.
Klimek, et al, 1993, *Isoenzyme shift from glucokinase to hexokinase is not an early but a late event in hepatocarcinogenesis*, Carcinogenesis 14(9):1857-61.
Larsson et al, 1996, *Activation of the ATP-sensitive K+ channel by long chain acyl-CoA. A role in modulation of pancreatic beta-cell glucose sensitivity*, J Biol Chem 271(18):10623-6.
Lauro et al, 1998, *Impaired glucose tolerance in mice with a targeted impairment of insulin action in muscle and adipose tissue*, Nat Genet 20(3):294-8.
Leduc et al, 2003 *Helix-stabilized cyclic peptides as selective inhibitors of steroid receptor-coactivator interactions*, Proc, Natl, Acad, Sci, USA 100(20):11273-8.
Li, et al, 1997, *Cytochrome c and dATP-dependent formation of Apaf-1/caspase-9 complex initiates an apoptotic protease cascade*, Cell 91(4):479-89.
Li, et al, 1998, *Cleavage of BID by caspase 8 mediates the mitochondrial damage in the Fas pathway of apoptosis*, Cell 94(4):491-501.
Liang et al, 1996, *Glucose metabolism and insulin release in mouse beta HC9 cells, as model for wild-type pancreatic beta-cells*, Am J Physiol 270(5 Pt 1): E846-57.
Lindsten et al, 2000, *The combined functions of proapoptotic Bcl-2 family members bak and bax are essential for normal development of multiple tissues*, J Mol Cell 6(6):1389-99.
Lorincz, 2006, *Molecular links between obesity and breast cancer*, Endocr Relat Cancer 13(21:279-92.
Luo et al, 1998, *Bid, a Bcl2 interacting protein, mediates cytochrome c release from mitochondria in response to activation of cell surface death receptors*, Cell 94(4):481-90 1998.
Mazurek et al, 2003, *The tumor metabolome*, Anticancer Res 23(2A):1149-54.
Mazurek, et al, 1999, *Alterations in the glycolytic and glutaminolytic pathways after malignant transformation of rat liver oval cells*, J Cell Phyisol 181(1):136-46.
McDonnell, et al, 1989, *bcl-2-immunoglobulin transgenic mice demonstrate extended B cell survival and follicular lymphoproliferation*, Cell 57(1):79-88.
McDonnell, et al, 1991, *Progression from lymphoid hyperplasia to high-grade malignant lymphoma in mice transgenic for the t(14; 18)*, Nature 349(6306):254-56.
McKerrecher, et al 2005, *Discovery, synthesis and biological evaluation of novel glucokinase activators*, Bioorg Med Chem Lett 15(8):2103-2106.
Modrof et al., 2001, *Phosphorylation of Marburg virus VP30 at serines 40 and 42 is critical for its interaction with NP inclusions*, Virology 287(1):171-82.
Nakano, et al, 2001, *PUMA, a novel proapoptotic gene, is induced by p53*, Mol Cell 7(3):683-94.
Oakes, et al, 2006, *The control of endoplasmic reticulum-initiated apoptosis by the BCL-2 family of proteins*, Curr Mol Med., 6(1):99-109.

Oltvai, et al, 1993, *Bcl-2 heterodimerizes in vivo with a conserved homolog, Bax, that accelerates programmed cell death*, Cell 74(4):609-19.
O'Malley, et al, 2006, *Obesity and prostate cancer*, Can J Urol Suppl 2:11-7.
Otaka et al, 1995, Tetrahedron Letters 36:927-930.
Pende et al, 2000, *Hypoinsulinaemia, glucose intolerance and diminished beta-cell size in S6K1-deficient mice*, Nature 408(6815):994-7.
Petros et al, 2000, *Rationale for Bcl-xL/Bad peptide complex formation from structure, mutagenesis, and biophysical studies*, Protein Sci 9(12):2528-34.
Phelan et al, 1997 *A General Method for Constraining Short Peptides to an α-Helical Conformation*, J Am Chem Soc 119(3):455-460.
Plas et al, 2002, *Cell metabolism in the regulation of programmed cell death*, Trends Endocrinol Metab 13(2):75-8.
Portincasa, 2006, *Current pharmacological treatment of nonalcoholic fatty liver*, Curr Med Chem 13(24):2889-900.
Prentki et al, 2002, *Malonyl-CoA signaling, lipid partitioning, and glucolipotoxicity: role in beta-cell adaptation and failure in the etiology of diabetes*, Diabetes Suppl 3:S405-13.
Proks et al, 2002, *Sulfonylurea stimulation of insulin secretion*, Diabetes 51 Suppl 3:S368-76.
Ranger, et al, 2003, *Bad-deficient mice develop diffuse large B cell lymphoma*, Proc Natl Acad Sci USA 100(16):9324-29.
Reaven, 2004, *Insulin resistance, cardiovascular disease, and the metabolic syndrome: how well do the emperor's clothes fit?*, Diabetes Care 27(4):1011-12.
Rempel, et al, 1994, *Microheterogeneity of cytosolic and membrane-bound hexokinase II in Morris hepatoma 3924A*, Biochem J 303(Pt 1):269-74.
Robey, et al, 2006, *Mitochondrial hexokinases, novel mediators of the antiapoptotic effects of growth factors and Akt*, Oncogene 25(34):4683-96.
Rorsman, 1997, *The pancreatic beta-cell as a fuel sensor: an electrophysiologist's viewpoint*, Diabetologia 40(5):487-95.
Rutkowski et al, 2004, *A hip to the ER: coping with stress*, Trends Cell Biol 14(1):20-8.
Saltiel et al, 2001, *Insulin signalling and the regulation of glucose and lipid metabolism*, Nature 414(6865):799-806.
Samson et al, 1996, *A 35 amino acid fragment of leptin inhibits feeding in the rat.*, Endocrinology, 137(11):5182-5185.
Schultz et al, 1993, *Bioluminometric assay of ADP and ATP at high ATP/ADP ratios: assay of ADP after enzymatic removal of ATP*, Anal Biochem 215(2):302-04.
Schwartz, 2005, *Diabetes, obesity, and the brain*, Science 307(5708):375-9.
Scott, 1998, *The repression of hormone-activated PEPCK gene expression by glucose is insulin-independent but requires glucose metabolism*, J Biol Chem 273(37):24145-51.
Saghatelian, et al, 2004, *Activity-based probes for the proteomic profiling of metalloproteases*, Proc Natl Acad Sci USA 101(27):10000-5.
Semenza, 2001, *The metabolism of tumours: 70 years later.*, Novartis Found Symp 240:251-60.
Thomenius et al, 2003, *Bcl-2 on the endoplasmic reticulum: protecting the mitochondria from a distance*, J Cell Sci 116(Pt 22):4493-9.
Trus et al, 1981, *Regulation of glucose metabolism in pancreatic islets*, Diabetes 30(11):911-22.
Tuttle et al, 2001, *Regulation of pancreatic beta-cell growth and survival by the serine/threonine protein kinase Akt1/PKBalpha*, Nat Med 7(10):1133-7.
Walensky et al, 2006, *A stapled BID BH3 helix directly binds and activates BAX*, Mol Cell 24(2):199-210.
Walensky et al., 2006, *BCL-2 in the crosshairs: tipping the balance of life and death*, Cell Death Differ., 13(8):1339-50.
Walensky et al, 2004, *Activation of apoptosis in vivo by a hydrocarbon-stapled BH3 helix.*, Science 305(5689):1466-70.
Wang, et al, 1996, *BID: a novel BH3 domain-only death agonist*, Genes Dev 10(22):2859-69.

(56) References Cited

OTHER PUBLICATIONS

Wei, et al, 2000, *tBID, a membrane-targeted death ligand, oligomerizes BAK to release cytochrome c*, Genes Dev 14(16):2060-71.
Wei, et al, 2001, *Proapoptotic BAX and BAK: a requisite gateway to mitochondrial dysfunction and death*, Science 292(5517): 727-30.
Weir et al, 2001, *Beta-cell adaptation and decompensation during the progression of diabetes*, Diabetes 50 Suppl 1:S154-9.
Wiederkehr et al, 2006, *Minireview: implication of mitochondria in insulin secretion and action*, Endocrinology 147(6):2643-9.
Williams et al, 1991, *Asymmetric Synthesis of Monosubstituted and a, a-Disubstituted a-Amino Acids via Diastereoselective Glycine Enolate Alkylations*, J Am Chem Soc 113(24): 9276-9286.
Winzell et al, 2004, *The high-fat diet-fed mouse: a model for studying mechanisms and treatment of impaired glucose tolerance and type 2 diabetes*, Diabetes 53 Suppl 3:S215-9.
Yamashita et al., 2001, *A glucose-responsive transcription factor that regulates carbohydrate metabolism in the liver*, Proc Natl Acad Sci USA 98(16):9116-21.
Yang et al, 2004 *Synthesis and helical structure of lactam bridged BH3 peptides derived from pro-apoptotic Bcl-2 family proteins*, Bioorg Med Chem Lett, 14(6):1403-6.
Yang, 1999, *Hypothalamic glucose sensor: similarities to and differences from pancreatic beta-cell mechanisms*, Diabetes 48(9):1763-72.
Yang et al, 1986, *Calculation of protein conformation from circular dichroism*, Methods Enzymol 130:208-269.
Yin, et al, 1997, *Bax suppresses tumorigenesis and stimulates apoptosis in vivo*, Nature 385(6617):637-40.
Youn, 1993, *Fasting does not impair insulin-stimulated glucose uptake but alters intracellular glucose metabolism in conscious rats*, Diabetes 42(5):757-63.
Yu, et al, 2001, *PUMA induces the rapid apoptosis of colorectal cancer cells*, Mol Cell 7(3):673-82.
Zha et al, 1996, *Serine phosphorylation of death agonist BAD in response to survival factor results in binding to 14-3-3 not BCL-X(L)*, Cell 87(4):619-28.
Zha et al, 1997, *BH3 domain of BAD is required for heterodimerization with BCL-XL and pro-apoptotic activity*, J Biol Chem 272(39):24101-4.
Zhou et al, 2000, *Overexpression of Bcl-x(L) in beta-cells prevents cell death but impairs mitochondrial signal for insulin secretion*, Am J Physiol Endocrinol 278(2):E340-51.
Zhou et al, 2003 *Overexpression of repressive cAMP response element modulators in high glucose and fatty acid-treated rat islets. A common mechanism for glucose toxicity and lipotoxicity?*, J Biol Chem 278(51):51316-23.
Zinkel, et al, 2003, *Proapoptotic BID is required for myeloid homeostasis and tumor suppression*, Genes Dev 17(2):229-39.
Zinkel, et al, 2005, *A role for proapoptotic BID in the DNA-damage response*, Cell 122(4):579-91.
Zinkel, et al, 2006, *BCL2 family in DNA damage and cell cycle control*, Cell Death Differ 13(8):1351-9.
Zong, et al, 2001, *BH3-only proteins that bind pro-survival Bcl-2 family members fail to induce apoptosis in the absence of Bax and Bak*, Genes Dev 15(12):1481-86.
International Preliminary Report on Patentability in International Application No. PCT/US2008/062345, Chapter II, dated Jul. 1, 2009, 13 pages.
International Search Report and Written Opinion in International Search Report in International Application No. PCT/US2008/062345, dated Feb. 2, 2009, 15 pages.

\* cited by examiner

| COMPOUND | SEQUENCE | | | | | | | | | | | | | | | | |
|---|---|---|---|---|---|---|---|---|---|---|---|---|---|---|---|---|---|
| BAD SAHB$_A$ | N | L | W | A | A | Q | R | Y | G | R | E | L | R | * | M | S D | * F V D S F K K (SEQ ID NO: 18) |
| BID SAHB$_A$ | | | | D | I | I | R | N | I | A | R | H | L | A | * | V G D | * NL D R S I (SEQ ID NO: 19) |
| BAD SAHB$_{A(L,D→A)}$ | N | L | W | A | A | Q | R | Y | G | R | E | A | R | * | M | S A | * F V D S F K K (SEQ ID NO: 20) |
| BAD SAHB$_{A(S→PS)}$ | N | L | W | A | A | Q | R | Y | G | R | E | L | R | * | M | PS D | * F V D S F K K (SEQ ID NO: 21) |
| BAD SAHB$_{A(S→D)}$ | N | L | W | A | A | Q | R | Y | G | R | E | L | R | * | M | D D | * F V D S F K K (SEQ ID NO: 22) |

Fig. 18-1

STAPLED BAD BH3 DERIVATIVES
a. PHOSPHOMIMETIC PANEL

```
         NLWAAQRYGRELR*XSD*FVDSFKK  (SEQ ID NO: 47)
    FITC-BNLWAAQRYGRELR*XSD*FVDSFKK  (SEQ ID NO: 48)
         NLWAAQRYGRELR*XDD*FVDSFKK  (SEQ ID NO: 49)
    FITC-BNLWAAQRYGRELR*XDD*FVDSFKK  (SEQ ID NO: 50)
         NLWAAQRYGRELR*XZD*FVDSFKK  (SEQ ID NO: 51)
    FITC-BNLWAAQRYGRELR*XZD*FVDSFKK  (SEQ ID NO: 52)
         NLWAAQRYGREAR*XSA*FVDSFKK  (SEQ ID NO: 53)
    FITC-BNLWAAQRYGREAR*XSA*FVDSFKK  (SEQ ID NO: 54)
``` b. TRUNCATION PANEL

```
         NLWAAQRYGRELRRBSDEFVDSFKK  (SEQ ID NO: 23)
         NLWAAQRYGRELR^BSD^FVDSFKK  (SEQ ID NO: 55)
          LWAAQRYGRELR^BSD^FVDSFKK  (SEQ ID NO: 56)
           WAAQRYGRELR^BSD^FVDSFKK  (SEQ ID NO: 57)
            AAQRYGRELR^BSD^FVDSFKK  (SEQ ID NO: 58)
             AQRYGRELR^BSD^FVDSFKK  (SEQ ID NO: 59)
              QRYGRELR^BSD^FVDSFKK  (SEQ ID NO: 60)
                RYGRELR^BSD^FVDSFKK  (SEQ ID NO: 61)
                 YGRELR^BSD^FVDSFKK  (SEQ ID NO: 62)
         NLWAAQRYGRELR^BSD^FVDSFK   (SEQ ID NO: 63)
         NLWAAQRYGRELR^BSD^FVDSF    (SEQ ID NO: 64)
         NLWAAQRYGRELR^BSD^FVDS     (SEQ ID NO: 65)
         NLWAAQRYGRELR^BSD^FVD      (SEQ ID NO: 66)
         NLWAAQRYGRELR^BSD^FV       (SEQ ID NO: 67)
         NLWAAQRYGRELR^BSD^F        (SEQ ID NO: 68)
         NLWAAQRYGRELR^BSD^         (SEQ ID NO: 69)
          LWAAQRYGRELR^BSD^FVDSFK   (SEQ ID NO: 70)
          LWAAQRYGRELR^BSD^FVDSF    (SEQ ID NO: 71)
           WAAQRYGRELR^BSD^FVDSF    (SEQ ID NO: 72)
           WAAQRYGRELR^BSD^FVDS     (SEQ ID NO: 73)
            AAQRYGRELR^BSD^FVDS     (SEQ ID NO: 74)
            AAQRYGRELR^BSD^FVD      (SEQ ID NO: 75)
             AQRYGRELR^BSD^FVD      (SEQ ID NO: 76)
              QRYGRELR^BSD^FVD      (SEQ ID NO: 77)
```

Fig. 18-3

STAPLED BAD BH3 DERIVATIVES cont.

b. TARGET CAPTURE PANEL

FITC-BBUNLWAAQRYGRELR*XSD*FVDSFKK (SEQ ID NO: 78)
FITC-BBNLUAAQRYGRELR*XSD*FVDSFKK (SEQ ID NO: 79)
FITC-BBNLWAAQRUGRELR*XSD*FVDSFKK (SEQ ID NO: 80)
FITC-BBNLWAAQRYGRELR*XSD*UVDSFKK (SEQ ID NO: 81)
FITC-BBNLWAAQRYGRELR*XSD*FVDSUKK (SEQ ID NO: 82)
FITC-BBNLWAAQRYGRELR*XSD*FVDSFKKU (SEQ ID NO: 83)
(and U combinations thereof)

Biotin-NLWAAQRYGRELR*XSD*FVDSFKK (SEQ ID NO: 84)
Biotin-NLWAAQRYGRELR*XSD*FVDSFKK (SEQ ID NO: 84)
Biotin-NLWAAQRYGREAR^XSA^FVDSFKK (SEQ ID NO: 85)
Biotin-NLWAAQRYGREAR^XSA^FVDSFKK (SEQ ID NO: 85)

STAPLED BID BH3 DERIVATIVES

PHOSPHOMIMETIC PANEL
ESQEDIIRNIARHLA*VGD*MDRSI (SEQ ID NO: 86)
EZQEDIIRNIARHLA*VGD*MDRSI (SEQ ID NO: 87)

Key:
B=β-alanine
X=norleucine
*="S5" non-natural amino acid
^=Aminoisobutyric acid (AIB)
Z=phosphoserine
U=benzophenone

KI30928HFD

W1RCL

K18678HFD

W25766HFD

W29543HFD

| BCL-2 FAMILY MEMBERS | | AFFECTED KINASES |
|---|---|---|
| BAD BH3<br>*NLWAAQRYGRELRRMSDEFVDSFKK* | (SEQ ID NO: 88) | PKA, PKC, CAM DEP K2, AKT, CLK, ERK D-DOMAIN, PIP3 PH |
| BNIP3 BH3<br>*DIERRKEVESILKKNSDWIIDWSSR* | (SEQ ID NO: 89) | PKC, CAM DEP K2, ERK D-DOMAIN, PKA, PDK1 BINDING |
| HRK BH3<br>*SSAAQLTAARLKALGDELHQRTMWRRRARS* | (SEQ ID NO: 90) | ERK D-DOMAIN, PKC, PKC, CLK2, AKT |
| NIX BH3<br>*SSQSEEEVVEGEKEVEALKKSADWVSDWSSRPENIPPKEF* | (SEQ ID NO: 91) | AKT, CLK2, DNA PK, ATM, CK2, CLK2 KINASE, DNA PK, CK2, CK2, INTERSECTIN SH3A, PIP3 PH |
| BID BH3<br>*SQEDIIRNIARHLAQVGDSMDRSI* | (SEQ ID NO: 92) | ATM, DNA PK, CK2 |
| NOXA BH3<br>*AELEVECATQLRRFGDKLNFRQKLLNLIS* | (SEQ ID NO: 93) | DNA PK, PKC MU, PIP3-BINDING PH |
| SPIKE BH3<br>*LEAELDALGDELLADEDSSY* | (SEQ ID NO: 94) | CK2, P85 SH2, PLCG SH2 |
| BAK BH3<br>*LQPSSTMGQVGRQLAIIGDDINRRYDSE* | (SEQ ID NO: 95) | ERK D-DOMAIN, PKC MU, 14-3-3 MODE 1 |
| BAX BH3<br>*QDASTKKLSECLKRIGDELDSN* | (SEQ ID NO: 96) | GSK3, PKA |
| BOK BH3<br>*PGRLAEVCAVLLRLGDELEMIRPS* | (SEQ ID NO: 97) | INTERSECTIN SH3A, CAPC-SH3, ERK D-DOMAIN, PKA |
| BCL-2 BH3<br>*SPVPPVVHLTLRQAGDDFSRRYRRD* | (SEQ ID NO: 98) | ERK1, PLCG SH3, INTERSECTIN SH3, NCK 2ND SH3, SRC SH3, CAPC-SH3, PLCG SH3, ERK1, CDC2, ERK D-DOMAIN, PIP3 PH |
| BCL-XL BH3<br>*AVKQALREAGDEFELRYRRAFS* | (SEQ ID NO: 99) | PIP3 PH, CLK2 |
| BCL-W BH3<br>*HQAMRAAGDEFETRFRRTFSD* | (SEQ ID NO: 100) | PIP3 PH, PKA, PKC, PKA, AKT, CLK2 |
| MCL-W BH3<br>*TSRKALETLRRVGDGVQRNH* | (SEQ ID NO: 101) | PKC, PKC, PKC, AKT |

Fig. 67

SEQUENCE LISTING

<160> NUMBER OF SEQ ID NOS: 108

<210> SEQ ID NO 1
<211> LENGTH: 31
<212> TYPE: PRT
<213> ORGANISM: Artificial sequence
<220> FEATURE:
<223> OTHER INFORMATION: Chemically synthesized peptide
<220> FEATURE:
<221> NAME/KEY: MISC_FEATURE
<222> LOCATION: (1)..(10)
<223> OTHER INFORMATION: Wherein Xaa is absent or any amino acid
<220> FEATURE:
<221> NAME/KEY: MISC_FEATURE
<222> LOCATION: (17)..(19)
<223> OTHER INFORMATION: Wherein Xaa is any amino acid.

```
<220> FEATURE:
<221> NAME/KEY: MISC_FEATURE
<222> LOCATION: (21)..(21)
<223> OTHER INFORMATION: Wherein Xaa is any amino acid.
<220> FEATURE:
<221> NAME/KEY: MISC_FEATURE
<222> LOCATION: (22)..(31)
<223> OTHER INFORMATION: Wherein Xaa is absent or any amino acid.

<400> SEQUENCE: 1

Xaa Xaa Xaa Xaa Xaa Xaa Xaa Xaa Xaa Xaa Tyr Gly Arg Glu Leu Arg
1               5                   10                  15

Xaa Xaa Xaa Asp Xaa Xaa Xaa Xaa Xaa Xaa Xaa Xaa Xaa Xaa
            20                  25                  30

<210> SEQ ID NO 2
<211> LENGTH: 25
<212> TYPE: PRT
<213> ORGANISM: Artificial sequence
<220> FEATURE:
<223> OTHER INFORMATION: Chemically synthesized peptide

<400> SEQUENCE: 2

Asn Leu Trp Ala Ala Gln Arg Tyr Gly Arg Glu Leu Arg Arg Met Ser
1               5                   10                  15

Asp Glu Phe Val Asp Ser Phe Lys Lys
            20                  25

<210> SEQ ID NO 3
<211> LENGTH: 25
<212> TYPE: PRT
<213> ORGANISM: Artificial sequence
<220> FEATURE:
<223> OTHER INFORMATION: Chemically synthesized peptide

<400> SEQUENCE: 3

Asn Leu Trp Ala Ala Gln Arg Tyr Gly Arg Glu Leu Arg Arg Met Asp
1               5                   10                  15

Asp Glu Phe Val Asp Ser Phe Lys Lys
            20                  25

<210> SEQ ID NO 4
<211> LENGTH: 25
<212> TYPE: PRT
<213> ORGANISM: Artificial sequence
<220> FEATURE:
<223> OTHER INFORMATION: Chemically synthesized peptide
<220> FEATURE:
<221> NAME/KEY: MISC_FEATURE
<222> LOCATION: (2)..(2)
<223> OTHER INFORMATION: Wherein Xaa is any amino acid.
<220> FEATURE:
<221> NAME/KEY: MISC_FEATURE
<222> LOCATION: (16)..(16)
<223> OTHER INFORMATION: Wherein Xaa is any amino acid.
<220> FEATURE:
<221> NAME/KEY: MISC_FEATURE
<222> LOCATION: (20)..(20)
<223> OTHER INFORMATION: Wherein Xaa is any amino acid.
<220> FEATURE:
<221> NAME/KEY: MISC_FEATURE
<222> LOCATION: (24)..(24)
<223> OTHER INFORMATION: Wherein Xaa is any amino acid.

<400> SEQUENCE: 4

Glu Xaa Gln Glu Asp Ile Ile Arg Asn Ile Ala Arg His Leu Ala Xaa
1               5                   10                  15

Val Gly Asp Xaa Met Asp Arg Xaa Ile
```

<210> SEQ ID NO 5
<211> LENGTH: 25
<212> TYPE: PRT
<213> ORGANISM: Artificial sequence
<220> FEATURE:
<223> OTHER INFORMATION: Chemically synthesized peptide
<220> FEATURE:
<221> NAME/KEY: MISC_FEATURE
<222> LOCATION: (10)..(10)
<223> OTHER INFORMATION: Wherein Xaa is any amino acid.
<220> FEATURE:
<221> NAME/KEY: MISC_FEATURE
<222> LOCATION: (16)..(17)
<223> OTHER INFORMATION: Wherein Xaa is any amino acid.
<220> FEATURE:
<221> NAME/KEY: MISC_FEATURE
<222> LOCATION: (21)..(21)
<223> OTHER INFORMATION: Wherein Xaa is any amino acid.
<220> FEATURE:
<221> NAME/KEY: MISC_FEATURE
<222> LOCATION: (23)..(24)
<223> OTHER INFORMATION: Wherein Xaa is any amino acid.

<400> SEQUENCE: 5

Asp Ile Glu Arg Arg Lys Glu Val Glu Xaa Ile Leu Lys Lys Asn Xaa
1               5                   10                  15

Xaa Trp Ile Trp Xaa Trp Xaa Xaa Arg
            20                  25

<210> SEQ ID NO 6
<211> LENGTH: 30
<212> TYPE: PRT
<213> ORGANISM: Artificial sequence
<220> FEATURE:
<223> OTHER INFORMATION: Chemically synthesized peptide
<220> FEATURE:
<221> NAME/KEY: MISC_FEATURE
<222> LOCATION: (1)..(2)
<223> OTHER INFORMATION: Wherein Xaa is any amino acid.
<220> FEATURE:
<221> NAME/KEY: MISC_FEATURE
<222> LOCATION: (7)..(7)
<223> OTHER INFORMATION: Wherein Xaa is any amino acid.
<220> FEATURE:
<221> NAME/KEY: MISC_FEATURE
<222> LOCATION: (22)..(22)
<223> OTHER INFORMATION: Wherein Xaa is any amino acid.
<220> FEATURE:
<221> NAME/KEY: MISC_FEATURE
<222> LOCATION: (30)..(30)
<223> OTHER INFORMATION: Wherein Xaa is any amino acid.

<400> SEQUENCE: 6

Xaa Xaa Ala Ala Gln Leu Xaa Ala Ala Arg Leu Lys Ala Leu Gly Asp
1               5                   10                  15

Glu Leu His Gln Arg Xaa Met Trp Arg Arg Arg Ala Arg Xaa
            20                  25                  30

<210> SEQ ID NO 7
<211> LENGTH: 40
<212> TYPE: PRT
<213> ORGANISM: Artificial sequence
<220> FEATURE:
<223> OTHER INFORMATION: Chemically synthesized peptide
<220> FEATURE:
<221> NAME/KEY: MISC_FEATURE
<222> LOCATION: (1)..(2)
<223> OTHER INFORMATION: Wherein Xaa is any amino acid.
<220> FEATURE:
<221> NAME/KEY: MISC_FEATURE

```
<222> LOCATION: (4)..(4)
<223> OTHER INFORMATION: Wherein Xaa is any amino acid.
<220> FEATURE:
<221> NAME/KEY: MISC_FEATURE
<222> LOCATION: (26)..(26)
<223> OTHER INFORMATION: Wherein Xaa is any amino acid.
<220> FEATURE:
<221> NAME/KEY: MISC_FEATURE
<222> LOCATION: (29)..(30)
<223> OTHER INFORMATION: Wherein Xaa is any amino acid.

<400> SEQUENCE: 7

Xaa Xaa Gln Xaa Glu Glu Val Val Glu Gly Glu Lys Glu Val Glu
1               5                  10                  15

Ala Leu Lys Lys Ser Ala Asp Trp Val Xaa Asp Trp Xaa Xaa Arg Pro
            20                  25                  30

Glu Asn Ile Pro Pro Lys Glu Phe
        35                  40

<210> SEQ ID NO 8
<211> LENGTH: 24
<212> TYPE: PRT
<213> ORGANISM: Artificial sequence
<220> FEATURE:
<223> OTHER INFORMATION: Chemically synthesized peptide
<220> FEATURE:
<221> NAME/KEY: MISC_FEATURE
<222> LOCATION: (1)..(1)
<223> OTHER INFORMATION: Wherein Xaa is any amino acid.
<220> FEATURE:
<221> NAME/KEY: MISC_FEATURE
<222> LOCATION: (23)..(23)
<223> OTHER INFORMATION: Wherein Xaa is any amino acid.

<400> SEQUENCE: 8

Xaa Gln Glu Asp Ile Ile Arg Asn Ile Ala Arg His Leu Ala Gln Val
1               5                  10                  15

Gly Asp Ser Met Asp Arg Xaa Ile
            20

<210> SEQ ID NO 9
<211> LENGTH: 29
<212> TYPE: PRT
<213> ORGANISM: Artificial sequence
<220> FEATURE:
<223> OTHER INFORMATION: Chemically synthesized peptide
<220> FEATURE:
<221> NAME/KEY: MISC_FEATURE
<222> LOCATION: (9)..(9)
<223> OTHER INFORMATION: Wherein Xaa is any amino acid.
<220> FEATURE:
<221> NAME/KEY: MISC_FEATURE
<222> LOCATION: (29)..(29)
<223> OTHER INFORMATION: Wherein Xaa is any amino acid.

<400> SEQUENCE: 9

Ala Glu Leu Glu Val Glu Cys Ala Xaa Gln Leu Arg Arg Phe Gly Asp
1               5                  10                  15

Lys Leu Asn Phe Arg Gln Lys Leu Leu Asn Leu Ile Xaa
            20                  25

<210> SEQ ID NO 10
<211> LENGTH: 20
<212> TYPE: PRT
<213> ORGANISM: Artificial sequence
<220> FEATURE:
<223> OTHER INFORMATION: Chemically synthesized peptide
<220> FEATURE:
<221> NAME/KEY: MISC_FEATURE
```

```
<222> LOCATION: (18)..(19)
<223> OTHER INFORMATION: Wherein Xaa is any amino acid.

<400> SEQUENCE: 10

Leu Glu Ala Glu Leu Asp Ala Leu Gly Asp Glu Leu Leu Ala Asp Glu
1               5                   10                  15

Asp Xaa Xaa Tyr
            20

<210> SEQ ID NO 11
<211> LENGTH: 28
<212> TYPE: PRT
<213> ORGANISM: Artificial sequence
<220> FEATURE:
<223> OTHER INFORMATION: Chemically synthesized peptide
<220> FEATURE:
<221> NAME/KEY: MISC_FEATURE
<222> LOCATION: (4)..(6)
<223> OTHER INFORMATION: Wherein Xaa is any amino acid.
<220> FEATURE:
<221> NAME/KEY: MISC_FEATURE
<222> LOCATION: (25)..(25)
<223> OTHER INFORMATION: Wherein Xaa is any amino acid.
<220> FEATURE:
<221> NAME/KEY: MISC_FEATURE
<222> LOCATION: (27)..(27)
<223> OTHER INFORMATION: Wherein Xaa is any amino acid.

<400> SEQUENCE: 11

Leu Gln Pro Xaa Xaa Xaa Met Gly Gln Val Gly Arg Gln Leu Ala Ile
1               5                   10                  15

Ile Gly Asp Asp Ile Asn Arg Arg Xaa Asp Xaa Glu
            20                  25

<210> SEQ ID NO 12
<211> LENGTH: 22
<212> TYPE: PRT
<213> ORGANISM: Artificial sequence
<220> FEATURE:
<223> OTHER INFORMATION: Chemically synthesized peptide
<220> FEATURE:
<221> NAME/KEY: MISC_FEATURE
<222> LOCATION: (4)..(4)
<223> OTHER INFORMATION: Wherein Xaa is any amino acid.
<220> FEATURE:
<221> NAME/KEY: MISC_FEATURE
<222> LOCATION: (9)..(9)
<223> OTHER INFORMATION: Wherein Xaa is any amino acid.
<220> FEATURE:
<221> NAME/KEY: MISC_FEATURE
<222> LOCATION: (21)..(21)
<223> OTHER INFORMATION: Wherein Xaa is any amino acid.

<400> SEQUENCE: 12

Gln Asp Ala Xaa Thr Lys Lys Leu Xaa Glu Cys Leu Lys Arg Ile Gly
1               5                   10                  15

Asp Glu Leu Asp Xaa Asn
            20

<210> SEQ ID NO 13
<211> LENGTH: 24
<212> TYPE: PRT
<213> ORGANISM: Artificial sequence
<220> FEATURE:
<223> OTHER INFORMATION: Chemically synthesized peptide
<220> FEATURE:
<221> NAME/KEY: MISC_FEATURE
<222> LOCATION: (24)..(24)
<223> OTHER INFORMATION: Wherein Xaa is any amino acid.
```

<400> SEQUENCE: 13

Pro Gly Arg Leu Ala Glu Val Cys Ala Val Leu Leu Arg Leu Gly Asp
1               5                   10                  15

Glu Leu Glu Met Ile Arg Pro Xaa
            20

<210> SEQ ID NO 14
<211> LENGTH: 24
<212> TYPE: PRT
<213> ORGANISM: Artificial sequence
<220> FEATURE:
<223> OTHER INFORMATION: Chemically synthesized peptide
<220> FEATURE:
<221> NAME/KEY: MISC_FEATURE
<222> LOCATION: (1)..(1)
<223> OTHER INFORMATION: Wherein Xaa is any amino acid.
<220> FEATURE:
<221> NAME/KEY: MISC_FEATURE
<222> LOCATION: (10)..(10)
<223> OTHER INFORMATION: Wherein Xaa is any amino acid.
<220> FEATURE:
<221> NAME/KEY: MISC_FEATURE
<222> LOCATION: (18)..(18)
<223> OTHER INFORMATION: Wherein Xaa is any amino acid.

<400> SEQUENCE: 14

Xaa Pro Val Pro Pro Val Val His Leu Xaa Arg Gln Ala Gly Asp Asp
1               5                   10                  15

Phe Xaa Arg Arg Tyr Arg Arg Asp
            20

<210> SEQ ID NO 15
<211> LENGTH: 22
<212> TYPE: PRT
<213> ORGANISM: Artificial sequence
<220> FEATURE:
<223> OTHER INFORMATION: Chemically synthesized peptide
<220> FEATURE:
<221> NAME/KEY: MISC_FEATURE
<222> LOCATION: (17)..(17)
<223> OTHER INFORMATION: Wherein Xaa is any amino acid.
<220> FEATURE:
<221> NAME/KEY: MISC_FEATURE
<222> LOCATION: (22)..(22)
<223> OTHER INFORMATION: Wherein Xaa is any amino acid.

<400> SEQUENCE: 15

Ala Val Lys Gln Ala Leu Arg Glu Ala Gly Asp Glu Phe Glu Leu Arg
1               5                   10                  15

Xaa Arg Arg Ala Phe Xaa
            20

<210> SEQ ID NO 16
<211> LENGTH: 21
<212> TYPE: PRT
<213> ORGANISM: Artificial sequence
<220> FEATURE:
<223> OTHER INFORMATION: Chemically synthesized peptide
<220> FEATURE:
<221> NAME/KEY: MISC_FEATURE
<222> LOCATION: (18)..(18)
<223> OTHER INFORMATION: Wherein Xaa is any amino acid.
<220> FEATURE:
<221> NAME/KEY: MISC_FEATURE
<222> LOCATION: (20)..(20)
<223> OTHER INFORMATION: Wherein Xaa is any amino acid.

<400> SEQUENCE: 16

His Gln Ala Met Arg Ala Ala Gly Asp Glu Phe Glu Thr Arg Phe Arg

```
1               5                   10                  15

Arg Xaa Phe Xaa Asp
            20

<210> SEQ ID NO 17
<211> LENGTH: 20
<212> TYPE: PRT
<213> ORGANISM: Artificial sequence
<220> FEATURE:
<223> OTHER INFORMATION: Chemically synthesized peptide
<220> FEATURE:
<221> NAME/KEY: MISC_FEATURE
<222> LOCATION: (1)..(2)
<223> OTHER INFORMATION: Wherein Xaa is any amino acid.
<220> FEATURE:
<221> NAME/KEY: MISC_FEATURE
<222> LOCATION: (8)..(8)
<223> OTHER INFORMATION: Wherein Xaa is any amino acid.

<400> SEQUENCE: 17

Xaa Xaa Arg Lys Ala Leu Glu Xaa Leu Arg Arg Val Gly Asp Gly Val
1               5                   10                  15

Gln Arg Asn His
            20

<210> SEQ ID NO 18
<211> LENGTH: 25
<212> TYPE: PRT
<213> ORGANISM: Artificial sequence
<220> FEATURE:
<223> OTHER INFORMATION: Chemically synthesized peptide
<220> FEATURE:
<221> NAME/KEY: MISC_FEATURE
<222> LOCATION: (14)..(14)
<223> OTHER INFORMATION: Wherein Xaa is S-N-(9-Fluorenylmethyl
      carbamate)-2-(4'-pentenyl)alanine
<220> FEATURE:
<221> NAME/KEY: MISC_FEATURE
<222> LOCATION: (18)..(18)
<223> OTHER INFORMATION: Wherein Xaa is S-N-(9-Fluorenylmethyl
      carbamate)-2-(4'-pentenyl)alanine

<400> SEQUENCE: 18

Asn Leu Trp Ala Ala Gln Arg Tyr Gly Arg Glu Leu Arg Xaa Met Ser
1               5                   10                  15

Asp Xaa Phe Val Asp Ser Phe Lys Lys
            20                  25

<210> SEQ ID NO 19
<211> LENGTH: 21
<212> TYPE: PRT
<213> ORGANISM: Artificial sequence
<220> FEATURE:
<223> OTHER INFORMATION: Chemically synthesized peptide
<220> FEATURE:
<221> NAME/KEY: MISC_FEATURE
<222> LOCATION: (12)..(12)
<223> OTHER INFORMATION: Wherein Xaa is S-N-(9-Fluorenylmethyl
      carbamate)-2-(4'-pentenyl)alanine.
<220> FEATURE:
<221> NAME/KEY: MISC_FEATURE
<222> LOCATION: (16)..(16)
<223> OTHER INFORMATION: Wherein Xaa is S-N-(9-Fluorenylmethyl
      carbamate)-2-(4'-pentenyl)alanine.
<220> FEATURE:
<221> NAME/KEY: MISC_FEATURE
<222> LOCATION: (17)..(17)
<223> OTHER INFORMATION: Wherein Xaa is Norleucine.

<400> SEQUENCE: 19
```

```
Asp Ile Ile Arg Asn Ile Ala Arg His Leu Ala Xaa Val Gly Asp Xaa
1               5                   10                  15

Xaa Asp Arg Ser Ile
            20
```

<210> SEQ ID NO 20
<211> LENGTH: 25
<212> TYPE: PRT
<213> ORGANISM: Artificial sequence
<220> FEATURE:
<223> OTHER INFORMATION: Chemically synthesized peptide
<220> FEATURE:
<221> NAME/KEY: MISC_FEATURE
<222> LOCATION: (14)..(14)
<223> OTHER INFORMATION: Wherein Xaa is S-N-(9-Fluorenylmethyl
      carbamate)-2-(4'-pentenyl)alanine.
<220> FEATURE:
<221> NAME/KEY: MISC_FEATURE
<222> LOCATION: (18)..(18)
<223> OTHER INFORMATION: Wherein Xaa is S-N-(9-Fluorenylmethyl
      carbamate)-2-(4'-pentenyl)alanine.

<400> SEQUENCE: 20

```
Asn Leu Trp Ala Ala Gln Arg Tyr Gly Arg Glu Ala Arg Xaa Met Ser
1               5                   10                  15

Ala Xaa Phe Val Asp Ser Phe Lys Lys
            20                  25
```

<210> SEQ ID NO 21
<211> LENGTH: 25
<212> TYPE: PRT
<213> ORGANISM: Artificial sequence
<220> FEATURE:
<223> OTHER INFORMATION: Chemically synthesized peptide
<220> FEATURE:
<221> NAME/KEY: MISC_FEATURE
<222> LOCATION: (14)..(14)
<223> OTHER INFORMATION: Wherein Xaa is S-N-(9-Fluorenylmethyl
      carbamate)-2-(4'-pentenyl)alanine.
<220> FEATURE:
<221> NAME/KEY: MISC_FEATURE
<222> LOCATION: (16)..(16)
<223> OTHER INFORMATION: Phosphoserine
<220> FEATURE:
<221> NAME/KEY: MISC_FEATURE
<222> LOCATION: (18)..(18)
<223> OTHER INFORMATION: Wherein Xaa is S-N-(9-Fluorenylmethyl
      carbamate)-2-(4'-pentenyl)alanine.

<400> SEQUENCE: 21

```
Asn Leu Trp Ala Ala Gln Arg Tyr Gly Arg Glu Leu Arg Xaa Met Ser
1               5                   10                  15

Asp Xaa Phe Val Asp Ser Phe Lys Lys
            20                  25
```

<210> SEQ ID NO 22
<211> LENGTH: 25
<212> TYPE: PRT
<213> ORGANISM: Artificial sequence
<220> FEATURE:
<223> OTHER INFORMATION: Chemically synthesized peptide
<220> FEATURE:
<221> NAME/KEY: MISC_FEATURE
<222> LOCATION: (14)..(14)
<223> OTHER INFORMATION: Wherein Xaa is S-N-(9-Fluorenylmethyl
      carbamate)-2-(4'-pentenyl)alanine.
<220> FEATURE:
<221> NAME/KEY: MISC_FEATURE
<222> LOCATION: (18)..(18)
<223> OTHER INFORMATION: Wherein Xaa is S-N-(9-Fluorenylmethyl
      carbamate)-2-(4'-pentenyl)alanine.

<400> SEQUENCE: 22

Asn Leu Trp Ala Ala Gln Arg Tyr Gly Arg Glu Leu Arg Xaa Met Asp
1               5                   10                  15

Asp Xaa Phe Val Asp Ser Phe Lys Lys
            20                  25

<210> SEQ ID NO 23
<211> LENGTH: 25
<212> TYPE: PRT
<213> ORGANISM: Artificial sequence
<220> FEATURE:
<223> OTHER INFORMATION: Chemically synthesized peptide
<220> FEATURE:
<221> NAME/KEY: MISC_FEATURE
<222> LOCATION: (15)..(15)
<223> OTHER INFORMATION: Wherein Xaa is B-alanine.

<400> SEQUENCE: 23

Asn Leu Trp Ala Ala Gln Arg Tyr Gly Arg Glu Leu Arg Arg Xaa Ser
1               5                   10                  15

Asp Glu Phe Val Asp Ser Phe Lys Lys
            20                  25

<210> SEQ ID NO 24
<211> LENGTH: 25
<212> TYPE: PRT
<213> ORGANISM: Artificial sequence
<220> FEATURE:
<223> OTHER INFORMATION: Chemically synthesized pepdie
<220> FEATURE:
<221> NAME/KEY: MISC_FEATURE
<222> LOCATION: (14)..(14)
<223> OTHER INFORMATION: Wherein Xaa is norleucine.
<220> FEATURE:
<221> NAME/KEY: MISC_FEATURE
<222> LOCATION: (15)..(15)
<223> OTHER INFORMATION: Wherein Xaa is B-alanine.
<220> FEATURE:
<221> NAME/KEY: MISC_FEATURE
<222> LOCATION: (18)..(18)
<223> OTHER INFORMATION: Wherein Xaa is norleucine.

<400> SEQUENCE: 24

Asn Leu Trp Ala Ala Gln Arg Tyr Gly Arg Glu Leu Arg Xaa Xaa Ser
1               5                   10                  15

Asp Xaa Phe Val Asp Ser Phe Lys Lys
            20                  25

<210> SEQ ID NO 25
<211> LENGTH: 24
<212> TYPE: PRT
<213> ORGANISM: Artificial sequence
<220> FEATURE:
<223> OTHER INFORMATION: Chemically synthesized peptide
<220> FEATURE:
<221> NAME/KEY: MISC_FEATURE
<222> LOCATION: (13)..(13)
<223> OTHER INFORMATION: Wherein Xaa is norleucine.
<220> FEATURE:
<221> NAME/KEY: MISC_FEATURE
<222> LOCATION: (14)..(14)
<223> OTHER INFORMATION: Wherein Xaa is B-alanine.
<220> FEATURE:
<221> NAME/KEY: MISC_FEATURE
<222> LOCATION: (17)..(17)
<223> OTHER INFORMATION: Wherein Xaa is norleucine.

<400> SEQUENCE: 25

```
Leu Trp Ala Ala Gln Arg Tyr Gly Arg Glu Leu Arg Xaa Xaa Ser Asp
1               5                   10                  15

Xaa Phe Val Asp Ser Phe Lys Lys
            20
```

<210> SEQ ID NO 26
<211> LENGTH: 23
<212> TYPE: PRT
<213> ORGANISM: Artificial sequence
<220> FEATURE:
<223> OTHER INFORMATION: Chemically synthesized peptide
<220> FEATURE:
<221> NAME/KEY: MISC_FEATURE
<222> LOCATION: (12)..(12)
<223> OTHER INFORMATION: Wherein Xaa is norleucine.
<220> FEATURE:
<221> NAME/KEY: MISC_FEATURE
<222> LOCATION: (13)..(13)
<223> OTHER INFORMATION: Wherein Xaa is B-alanine.
<220> FEATURE:
<221> NAME/KEY: MISC_FEATURE
<222> LOCATION: (16)..(16)
<223> OTHER INFORMATION: Wherein Xaa is norleucine.

<400> SEQUENCE: 26

```
Trp Ala Ala Gln Arg Tyr Gly Arg Glu Leu Arg Xaa Xaa Ser Asp Xaa
1               5                   10                  15

Phe Val Asp Ser Phe Lys Lys
            20
```

<210> SEQ ID NO 27
<211> LENGTH: 22
<212> TYPE: PRT
<213> ORGANISM: Artificial sequence
<220> FEATURE:
<223> OTHER INFORMATION: Chemically synthesized peptide
<220> FEATURE:
<221> NAME/KEY: MISC_FEATURE
<222> LOCATION: (11)..(11)
<223> OTHER INFORMATION: Wherein Xaa is norleucine.
<220> FEATURE:
<221> NAME/KEY: MISC_FEATURE
<222> LOCATION: (12)..(12)
<223> OTHER INFORMATION: Wherein Xaa is B-alanine.
<220> FEATURE:
<221> NAME/KEY: MISC_FEATURE
<222> LOCATION: (15)..(15)
<223> OTHER INFORMATION: Wherein Xaa is norleucine.

<400> SEQUENCE: 27

```
Ala Ala Gln Arg Tyr Gly Arg Glu Leu Arg Xaa Xaa Ser Asp Xaa Phe
1               5                   10                  15

Val Asp Ser Phe Lys Lys
            20
```

<210> SEQ ID NO 28
<211> LENGTH: 21
<212> TYPE: PRT
<213> ORGANISM: Artificial sequence
<220> FEATURE:
<223> OTHER INFORMATION: Chemically synthesized peptide
<220> FEATURE:
<221> NAME/KEY: MISC_FEATURE
<222> LOCATION: (10)..(10)
<223> OTHER INFORMATION: Wherein Xaa is norleucine.
<220> FEATURE:
<221> NAME/KEY: MISC_FEATURE
<222> LOCATION: (11)..(11)
<223> OTHER INFORMATION: Wherein Xaa is B-alanine.
<220> FEATURE:
<221> NAME/KEY: MISC_FEATURE

```
<222> LOCATION: (14)..(14)
<223> OTHER INFORMATION: Wherein Xaa is norleucine.

<400> SEQUENCE: 28

Ala Gln Arg Tyr Gly Arg Glu Leu Arg Xaa Xaa Ser Asp Xaa Phe Val
1               5                   10                  15

Asp Ser Phe Lys Lys
            20

<210> SEQ ID NO 29
<211> LENGTH: 20
<212> TYPE: PRT
<213> ORGANISM: Artificial sequence
<220> FEATURE:
<223> OTHER INFORMATION: Chemically synthesized peptide
<220> FEATURE:
<221> NAME/KEY: MISC_FEATURE
<222> LOCATION: (9)..(9)
<223> OTHER INFORMATION: Wherein Xaa is norleucine.
<220> FEATURE:
<221> NAME/KEY: MISC_FEATURE
<222> LOCATION: (10)..(10)
<223> OTHER INFORMATION: Wherein Xaa is B-alanine.
<220> FEATURE:
<221> NAME/KEY: MISC_FEATURE
<222> LOCATION: (13)..(13)
<223> OTHER INFORMATION: Wherein Xaa is norleucine.

<400> SEQUENCE: 29

Gln Arg Tyr Gly Arg Glu Leu Arg Xaa Xaa Ser Asp Xaa Phe Val Asp
1               5                   10                  15

Ser Phe Lys Lys
            20

<210> SEQ ID NO 30
<211> LENGTH: 19
<212> TYPE: PRT
<213> ORGANISM: Artificial sequence
<220> FEATURE:
<223> OTHER INFORMATION: Chemically synthesized peptide
<220> FEATURE:
<221> NAME/KEY: MISC_FEATURE
<222> LOCATION: (8)..(8)
<223> OTHER INFORMATION: Wherein Xaa is norleucine.
<220> FEATURE:
<221> NAME/KEY: MISC_FEATURE
<222> LOCATION: (9)..(9)
<223> OTHER INFORMATION: Wherein Xaa is B-alanine.
<220> FEATURE:
<221> NAME/KEY: MISC_FEATURE
<222> LOCATION: (12)..(12)
<223> OTHER INFORMATION: Wherein Xaa is norleucine.

<400> SEQUENCE: 30

Arg Tyr Gly Arg Glu Leu Arg Xaa Xaa Ser Asp Xaa Phe Val Asp Ser
1               5                   10                  15

Phe Lys Lys

<210> SEQ ID NO 31
<211> LENGTH: 18
<212> TYPE: PRT
<213> ORGANISM: Artificial sequence
<220> FEATURE:
<223> OTHER INFORMATION: Chemically synthesized peptide
<220> FEATURE:
<221> NAME/KEY: MISC_FEATURE
<222> LOCATION: (7)..(7)
<223> OTHER INFORMATION: Wherein Xaa is norleucine.
<220> FEATURE:
<221> NAME/KEY: MISC_FEATURE
```

<222> LOCATION: (8)..(8)
<223> OTHER INFORMATION: Wherein Xaa is B-alanine.
<220> FEATURE:
<221> NAME/KEY: MISC_FEATURE
<222> LOCATION: (11)..(11)
<223> OTHER INFORMATION: Wherein Xaa is norleucine.

<400> SEQUENCE: 31

Tyr Gly Arg Glu Leu Arg Xaa Xaa Ser Asp Xaa Phe Val Asp Ser Phe
1               5                   10                  15

Lys Lys

<210> SEQ ID NO 32
<211> LENGTH: 24
<212> TYPE: PRT
<213> ORGANISM: Artificial sequence
<220> FEATURE:
<223> OTHER INFORMATION: Chemically synthesized peptide
<220> FEATURE:
<221> NAME/KEY: MISC_FEATURE
<222> LOCATION: (14)..(14)
<223> OTHER INFORMATION: Wherein Xaa is norleucine.
<220> FEATURE:
<221> NAME/KEY: MISC_FEATURE
<222> LOCATION: (15)..(15)
<223> OTHER INFORMATION: Wherein Xaa is B-alanine.
<220> FEATURE:
<221> NAME/KEY: MISC_FEATURE
<222> LOCATION: (18)..(18)
<223> OTHER INFORMATION: Wherein Xaa is norleucine.

<400> SEQUENCE: 32

Asn Leu Trp Ala Ala Gln Arg Tyr Gly Arg Glu Leu Arg Xaa Xaa Ser
1               5                   10                  15

Asp Xaa Phe Val Asp Ser Phe Lys
            20

<210> SEQ ID NO 33
<211> LENGTH: 23
<212> TYPE: PRT
<213> ORGANISM: Artificial sequence
<220> FEATURE:
<223> OTHER INFORMATION: Chemically synthesized peptide
<220> FEATURE:
<221> NAME/KEY: MISC_FEATURE
<222> LOCATION: (14)..(14)
<223> OTHER INFORMATION: Wherein Xaa is norleucine.
<220> FEATURE:
<221> NAME/KEY: MISC_FEATURE
<222> LOCATION: (15)..(15)
<223> OTHER INFORMATION: Wherein Xaa is B-alanine.
<220> FEATURE:
<221> NAME/KEY: MISC_FEATURE
<222> LOCATION: (18)..(18)
<223> OTHER INFORMATION: Wherein Xaa is norleucine.

<400> SEQUENCE: 33

Asn Leu Trp Ala Ala Gln Arg Tyr Gly Arg Glu Leu Arg Xaa Xaa Ser
1               5                   10                  15

Asp Xaa Phe Val Asp Ser Phe
            20

<210> SEQ ID NO 34
<211> LENGTH: 22
<212> TYPE: PRT
<213> ORGANISM: Artificial sequence
<220> FEATURE:
<223> OTHER INFORMATION: Chemically synthesized peptide
<220> FEATURE:
<221> NAME/KEY: MISC_FEATURE

```
<222> LOCATION: (14)..(14)
<223> OTHER INFORMATION: Wherein Xaa is norleucine.
<220> FEATURE:
<221> NAME/KEY: MISC_FEATURE
<222> LOCATION: (15)..(15)
<223> OTHER INFORMATION: Wherein Xaa is B-alanine.
<220> FEATURE:
<221> NAME/KEY: MISC_FEATURE
<222> LOCATION: (18)..(18)
<223> OTHER INFORMATION: Wherein Xaa is norleucine.

<400> SEQUENCE: 34

Asn Leu Trp Ala Ala Gln Arg Tyr Gly Arg Glu Leu Arg Xaa Xaa Ser
1               5                   10                  15

Asp Xaa Phe Val Asp Ser
            20

<210> SEQ ID NO 35
<211> LENGTH: 21
<212> TYPE: PRT
<213> ORGANISM: Artificial sequence
<220> FEATURE:
<223> OTHER INFORMATION: Chemically synthesized peptide
<220> FEATURE:
<221> NAME/KEY: MISC_FEATURE
<222> LOCATION: (14)..(14)
<223> OTHER INFORMATION: Wherein Xaa is norleucine.
<220> FEATURE:
<221> NAME/KEY: MISC_FEATURE
<222> LOCATION: (15)..(15)
<223> OTHER INFORMATION: Wherein Xaa is B-alanine.
<220> FEATURE:
<221> NAME/KEY: MISC_FEATURE
<222> LOCATION: (18)..(18)
<223> OTHER INFORMATION: Wherein Xaa is norleucine.

<400> SEQUENCE: 35

Asn Leu Trp Ala Ala Gln Arg Tyr Gly Arg Glu Leu Arg Xaa Xaa Ser
1               5                   10                  15

Asp Xaa Phe Val Asp
            20

<210> SEQ ID NO 36
<211> LENGTH: 20
<212> TYPE: PRT
<213> ORGANISM: Artificial sequence
<220> FEATURE:
<223> OTHER INFORMATION: Chemically synthesized peptide
<220> FEATURE:
<221> NAME/KEY: MISC_FEATURE
<222> LOCATION: (14)..(14)
<223> OTHER INFORMATION: Wherein Xaa is norleucine.
<220> FEATURE:
<221> NAME/KEY: MISC_FEATURE
<222> LOCATION: (15)..(15)
<223> OTHER INFORMATION: Wherein Xaa is B-alanine.
<220> FEATURE:
<221> NAME/KEY: MISC_FEATURE
<222> LOCATION: (18)..(18)
<223> OTHER INFORMATION: Wherein Xaa is norleucine.

<400> SEQUENCE: 36

Asn Leu Trp Ala Ala Gln Arg Tyr Gly Arg Glu Leu Arg Xaa Xaa Ser
1               5                   10                  15

Asp Xaa Phe Val
            20

<210> SEQ ID NO 37
<211> LENGTH: 19
<212> TYPE: PRT
```

```
<213> ORGANISM: Artificial sequence
<220> FEATURE:
<223> OTHER INFORMATION: Chemically synthsized peptide
<220> FEATURE:
<221> NAME/KEY: MISC_FEATURE
<222> LOCATION: (14)..(14)
<223> OTHER INFORMATION: Wherein Xaa is norleucine.
<220> FEATURE:
<221> NAME/KEY: MISC_FEATURE
<222> LOCATION: (15)..(15)
<223> OTHER INFORMATION: Wherein Xaa is B-alanine.
<220> FEATURE:
<221> NAME/KEY: MISC_FEATURE
<222> LOCATION: (18)..(18)
<223> OTHER INFORMATION: Wherein Xaa is norleucine.

<400> SEQUENCE: 37

Asn Leu Trp Ala Ala Gln Arg Tyr Gly Arg Glu Leu Arg Xaa Xaa Ser
1               5                   10                  15

Asp Xaa Phe

<210> SEQ ID NO 38
<211> LENGTH: 18
<212> TYPE: PRT
<213> ORGANISM: Artificial sequence
<220> FEATURE:
<223> OTHER INFORMATION: Chemically synthesized peptide
<220> FEATURE:
<221> NAME/KEY: MISC_FEATURE
<222> LOCATION: (14)..(14)
<223> OTHER INFORMATION: Wherein Xaa is norleucine.
<220> FEATURE:
<221> NAME/KEY: MISC_FEATURE
<222> LOCATION: (15)..(15)
<223> OTHER INFORMATION: Wherein Xaa is B-alanine.
<220> FEATURE:
<221> NAME/KEY: MISC_FEATURE
<222> LOCATION: (18)..(18)
<223> OTHER INFORMATION: Wherein Xaa is norleucine.

<400> SEQUENCE: 38

Asn Leu Trp Ala Ala Gln Arg Tyr Gly Arg Glu Leu Arg Xaa Xaa Ser
1               5                   10                  15

Asp Xaa

<210> SEQ ID NO 39
<211> LENGTH: 23
<212> TYPE: PRT
<213> ORGANISM: Artificial sequence
<220> FEATURE:
<223> OTHER INFORMATION: Chemically synthesized peptide
<220> FEATURE:
<221> NAME/KEY: MISC_FEATURE
<222> LOCATION: (13)..(13)
<223> OTHER INFORMATION: Wherein Xaa is norleucine.
<220> FEATURE:
<221> NAME/KEY: MISC_FEATURE
<222> LOCATION: (14)..(14)
<223> OTHER INFORMATION: Wherein Xaa is B-alanine.
<220> FEATURE:
<221> NAME/KEY: MISC_FEATURE
<222> LOCATION: (17)..(17)
<223> OTHER INFORMATION: Wherein Xaa is norleucine.

<400> SEQUENCE: 39

Leu Trp Ala Ala Gln Arg Tyr Gly Arg Glu Leu Arg Xaa Xaa Ser Asp
1               5                   10                  15

Xaa Phe Val Asp Ser Phe Lys
            20
```

```
<210> SEQ ID NO 40
<211> LENGTH: 22
<212> TYPE: PRT
<213> ORGANISM: Artificial sequence
<220> FEATURE:
<223> OTHER INFORMATION: Chemically synthesized peptide
<220> FEATURE:
<221> NAME/KEY: MISC_FEATURE
<222> LOCATION: (13)..(13)
<223> OTHER INFORMATION: Wherein Xaa is norleucine.
<220> FEATURE:
<221> NAME/KEY: MISC_FEATURE
<222> LOCATION: (14)..(14)
<223> OTHER INFORMATION: Wherein Xaa is B-alanine.
<220> FEATURE:
<221> NAME/KEY: MISC_FEATURE
<222> LOCATION: (17)..(17)
<223> OTHER INFORMATION: Wherein Xaa norleucine.
<220> FEATURE:
<221> NAME/KEY: MISC_FEATURE
<222> LOCATION: (17)..(17)
<223> OTHER INFORMATION: Wherein Xaa norleucine.

<400> SEQUENCE: 40

Leu Trp Ala Ala Gln Arg Tyr Gly Arg Glu Leu Arg Xaa Xaa Ser Asp
1               5                   10                  15

Xaa Phe Val Asp Ser Phe
            20

<210> SEQ ID NO 41
<211> LENGTH: 21
<212> TYPE: PRT
<213> ORGANISM: Artificial sequence
<220> FEATURE:
<223> OTHER INFORMATION: Chemically synthesized peptide
<220> FEATURE:
<221> NAME/KEY: MISC_FEATURE
<222> LOCATION: (12)..(12)
<223> OTHER INFORMATION: Wherein Xaa is norleucine.
<220> FEATURE:
<221> NAME/KEY: MISC_FEATURE
<222> LOCATION: (13)..(13)
<223> OTHER INFORMATION: Wherein Xaa is B-alanine.
<220> FEATURE:
<221> NAME/KEY: MISC_FEATURE
<222> LOCATION: (16)..(16)
<223> OTHER INFORMATION: Wherein Xaa is norleucine.

<400> SEQUENCE: 41

Trp Ala Ala Gln Arg Tyr Gly Arg Glu Leu Arg Xaa Xaa Ser Asp Xaa
1               5                   10                  15

Phe Val Asp Ser Phe
            20

<210> SEQ ID NO 42
<211> LENGTH: 20
<212> TYPE: PRT
<213> ORGANISM: Artificial sequence
<220> FEATURE:
<223> OTHER INFORMATION: Chemically synthesized peptide
<220> FEATURE:
<221> NAME/KEY: MISC_FEATURE
<222> LOCATION: (12)..(12)
<223> OTHER INFORMATION: Wherein Xaa is norleucine.
<220> FEATURE:
<221> NAME/KEY: MISC_FEATURE
<222> LOCATION: (13)..(13)
<223> OTHER INFORMATION: Wherein Xaa is B-alanine.
<220> FEATURE:
<221> NAME/KEY: MISC_FEATURE
<222> LOCATION: (16)..(16)
<223> OTHER INFORMATION: Wherein Xaa is norleucine.
```

<400> SEQUENCE: 42

Trp Ala Ala Gln Arg Tyr Gly Arg Glu Leu Arg Xaa Xaa Ser Asp Xaa
1               5                   10                  15

Phe Val Asp Ser
            20

<210> SEQ ID NO 43
<211> LENGTH: 19
<212> TYPE: PRT
<213> ORGANISM: Artificial sequence
<220> FEATURE:
<223> OTHER INFORMATION: Chemically synthesized peptide
<220> FEATURE:
<221> NAME/KEY: MISC_FEATURE
<222> LOCATION: (11)..(11)
<223> OTHER INFORMATION: Wherein Xaa is norleucine.
<220> FEATURE:
<221> NAME/KEY: MISC_FEATURE
<222> LOCATION: (12)..(12)
<223> OTHER INFORMATION: Wherein Xaa is B-alanine.
<220> FEATURE:
<221> NAME/KEY: MISC_FEATURE
<222> LOCATION: (15)..(15)
<223> OTHER INFORMATION: Wherein Xaa is norleucine.

<400> SEQUENCE: 43

Ala Ala Gln Arg Tyr Gly Arg Glu Leu Arg Xaa Xaa Ser Asp Xaa Phe
1               5                   10                  15

Val Asp Ser

<210> SEQ ID NO 44
<211> LENGTH: 18
<212> TYPE: PRT
<213> ORGANISM: Artificial sequence
<220> FEATURE:
<223> OTHER INFORMATION: Chemically synthesized peptide
<220> FEATURE:
<221> NAME/KEY: MISC_FEATURE
<222> LOCATION: (11)..(11)
<223> OTHER INFORMATION: Wherein Xaa is norleucine.
<220> FEATURE:
<221> NAME/KEY: MISC_FEATURE
<222> LOCATION: (12)..(12)
<223> OTHER INFORMATION: Wherein Xaa is B-alanine.
<220> FEATURE:
<221> NAME/KEY: MISC_FEATURE
<222> LOCATION: (15)..(15)
<223> OTHER INFORMATION: Wherein Xaa is norleucine.

<400> SEQUENCE: 44

Ala Ala Gln Arg Tyr Gly Arg Glu Leu Arg Xaa Xaa Ser Asp Xaa Phe
1               5                   10                  15

Val Asp

<210> SEQ ID NO 45
<211> LENGTH: 17
<212> TYPE: PRT
<213> ORGANISM: Artificial sequence
<220> FEATURE:
<223> OTHER INFORMATION: Chemically synthesized peptide
<220> FEATURE:
<221> NAME/KEY: MISC_FEATURE
<222> LOCATION: (10)..(10)
<223> OTHER INFORMATION: Wherein Xaa is norleucine.
<220> FEATURE:
<221> NAME/KEY: MISC_FEATURE
<222> LOCATION: (11)..(11)
<223> OTHER INFORMATION: Wherein Xaa is B-alanine.
<220> FEATURE:
<221> NAME/KEY: MISC_FEATURE

```
<222> LOCATION: (14)..(14)
<223> OTHER INFORMATION: Wherein Xaa is norleucine.

<400> SEQUENCE: 45

Ala Gln Arg Tyr Gly Arg Glu Leu Arg Xaa Xaa Ser Asp Xaa Phe Val
1               5                   10                  15

Asp

<210> SEQ ID NO 46
<211> LENGTH: 16
<212> TYPE: PRT
<213> ORGANISM: Artificial sequence
<220> FEATURE:
<223> OTHER INFORMATION: Chemically synthesized peptide
<220> FEATURE:
<221> NAME/KEY: MISC_FEATURE
<222> LOCATION: (9)..(9)
<223> OTHER INFORMATION: Wherein Xaa is norleucine.
<220> FEATURE:
<221> NAME/KEY: MISC_FEATURE
<222> LOCATION: (10)..(10)
<223> OTHER INFORMATION: Wherein Xaa is B-alanine.
<220> FEATURE:
<221> NAME/KEY: MISC_FEATURE
<222> LOCATION: (13)..(13)
<223> OTHER INFORMATION: Wherein Xaa is norleucine.

<400> SEQUENCE: 46

Gln Arg Tyr Gly Arg Glu Leu Arg Xaa Xaa Ser Asp Xaa Phe Val Asp
1               5                   10                  15

<210> SEQ ID NO 47
<211> LENGTH: 25
<212> TYPE: PRT
<213> ORGANISM: Artificial sequence
<220> FEATURE:
<223> OTHER INFORMATION: Chemically synthesized peptide
<220> FEATURE:
<221> NAME/KEY: MISC_FEATURE
<222> LOCATION: (14)..(14)
<223> OTHER INFORMATION: Wherein Xaa is S-N-(9-Fluorenylmethyl
      carbamate)-2-(4'-pentenyl)alanine.
<220> FEATURE:
<221> NAME/KEY: MISC_FEATURE
<222> LOCATION: (15)..(15)
<223> OTHER INFORMATION: Wherein Xaa is norleucine.
<220> FEATURE:
<221> NAME/KEY: MISC_FEATURE
<222> LOCATION: (18)..(18)
<223> OTHER INFORMATION: Wherein Xaa is S-N-(9-Fluorenylmethyl
      carbamate)-2-(4'-pentenyl)alanine.

<400> SEQUENCE: 47

Asn Leu Trp Ala Ala Gln Arg Tyr Gly Arg Glu Leu Arg Xaa Xaa Ser
1               5                   10                  15

Asp Xaa Phe Val Asp Ser Phe Lys Lys
            20                  25

<210> SEQ ID NO 48
<211> LENGTH: 26
<212> TYPE: PRT
<213> ORGANISM: Artificial sequence
<220> FEATURE:
<223> OTHER INFORMATION: Chemically synthesized peptide
<220> FEATURE:
<221> NAME/KEY: MISC_FEATURE
<222> LOCATION: (1)..(1)
<223> OTHER INFORMATION: Wherein Xaa is FITC-tagged B-alanine.
<220> FEATURE:
<221> NAME/KEY: MISC_FEATURE
<222> LOCATION: (15)..(15)
```

```
<223> OTHER INFORMATION: Wherein Xaa is S-N-(9-Fluorenylmethyl
      carbamate)-2-(4'-pentenyl)alanine.
<220> FEATURE:
<221> NAME/KEY: MISC_FEATURE
<222> LOCATION: (16)..(16)
<223> OTHER INFORMATION: Wherein Xaa is norleucine.
<220> FEATURE:
<221> NAME/KEY: MISC_FEATURE
<222> LOCATION: (19)..(19)
<223> OTHER INFORMATION: Wherein Xaa is S-N-(9-Fluorenylmethyl
      carbamate)-2-(4'-pentenyl)alanine.

<400> SEQUENCE: 48

Xaa Asn Leu Trp Ala Ala Gln Arg Tyr Gly Arg Glu Leu Arg Xaa Xaa
1               5                   10                  15

Ser Asp Xaa Phe Val Asp Ser Phe Lys Lys
            20                  25

<210> SEQ ID NO 49
<211> LENGTH: 25
<212> TYPE: PRT
<213> ORGANISM: Artificial sequence
<220> FEATURE:
<223> OTHER INFORMATION: Chemically synthesized peptide
<220> FEATURE:
<221> NAME/KEY: MISC_FEATURE
<222> LOCATION: (14)..(14)
<223> OTHER INFORMATION: Wherein Xaa is S-N-(9-Fluorenylmethyl
      carbamate)-2-(4'-pentenyl)alanine.
<220> FEATURE:
<221> NAME/KEY: MISC_FEATURE
<222> LOCATION: (15)..(15)
<223> OTHER INFORMATION: Wherein Xaa is norleucine.
<220> FEATURE:
<221> NAME/KEY: MISC_FEATURE
<222> LOCATION: (18)..(18)
<223> OTHER INFORMATION: Wherein Xaa is S-N-(9-Fluorenylmethyl
      carbamate)-2-(4'-pentenyl)alanine.

<400> SEQUENCE: 49

Asn Leu Trp Ala Ala Gln Arg Tyr Gly Arg Glu Leu Arg Xaa Xaa Asp
1               5                   10                  15

Asp Xaa Phe Val Asp Ser Phe Lys Lys
            20                  25

<210> SEQ ID NO 50
<211> LENGTH: 26
<212> TYPE: PRT
<213> ORGANISM: Artificial sequence
<220> FEATURE:
<223> OTHER INFORMATION: Chemically synthesized peptide
<220> FEATURE:
<221> NAME/KEY: MISC_FEATURE
<222> LOCATION: (1)..(1)
<223> OTHER INFORMATION: Wherein Xaa is FITC-tagged B-alanine.
<220> FEATURE:
<221> NAME/KEY: MISC_FEATURE
<222> LOCATION: (15)..(15)
<223> OTHER INFORMATION: Wherein Xaa is S-N-(9-Fluorenylmethyl
      carbamate)-2-(4'-pentenyl)alanine.
<220> FEATURE:
<221> NAME/KEY: MISC_FEATURE
<222> LOCATION: (16)..(16)
<223> OTHER INFORMATION: Wherein Xaa is norleucine.
<220> FEATURE:
<221> NAME/KEY: MISC_FEATURE
<222> LOCATION: (19)..(19)
<223> OTHER INFORMATION: Wherein Xaa is S-N-(9-Fluorenylmethyl
      carbamate)-2-(4'-pentenyl)alanine.

<400> SEQUENCE: 50

Xaa Asn Leu Trp Ala Ala Gln Arg Tyr Gly Arg Glu Leu Arg Xaa Xaa
```

```
                1               5                  10                 15
Asp Asp Xaa Phe Val Asp Ser Phe Lys Lys
                20                  25

<210> SEQ ID NO 51
<211> LENGTH: 25
<212> TYPE: PRT
<213> ORGANISM: Artificial sequence
<220> FEATURE:
<223> OTHER INFORMATION: Chemically synthesized peptide
<220> FEATURE:
<221> NAME/KEY: MISC_FEATURE
<222> LOCATION: (14)..(14)
<223> OTHER INFORMATION: Wherein Xaa is S-N-(9-Fluorenylmethyl
      carbamate)-2-(4'-pentenyl)alanine.
<220> FEATURE:
<221> NAME/KEY: MISC_FEATURE
<222> LOCATION: (15)..(15)
<223> OTHER INFORMATION: Wherein Xaa is norleucine.
<220> FEATURE:
<221> NAME/KEY: MISC_FEATURE
<222> LOCATION: (16)..(16)
<223> OTHER INFORMATION: Wherein Xaa is phosphoserine.
<220> FEATURE:
<221> NAME/KEY: MISC_FEATURE
<222> LOCATION: (18)..(18)
<223> OTHER INFORMATION: Wherein Xaa is S-N-(9-Fluorenylmethyl
      carbamate)-2-(4'-pentenyl)alanine.

<400> SEQUENCE: 51

Asn Leu Trp Ala Ala Gln Arg Tyr Gly Arg Glu Leu Arg Xaa Xaa Xaa
1               5                   10                  15
Asp Xaa Phe Val Asp Ser Phe Lys Lys
                20                  25

<210> SEQ ID NO 52
<211> LENGTH: 26
<212> TYPE: PRT
<213> ORGANISM: Artificial sequence
<220> FEATURE:
<223> OTHER INFORMATION: Chemically synthesized primer
<220> FEATURE:
<221> NAME/KEY: MISC_FEATURE
<222> LOCATION: (1)..(1)
<223> OTHER INFORMATION: Wherein Xaa is FITC-tagged B-alanine.
<220> FEATURE:
<221> NAME/KEY: MISC_FEATURE
<222> LOCATION: (15)..(15)
<223> OTHER INFORMATION: Wherein Xaa is S-N-(9-Fluorenylmethyl
      carbamate)-2-(4'-pentenyl)alanine.
<220> FEATURE:
<221> NAME/KEY: MISC_FEATURE
<222> LOCATION: (16)..(16)
<223> OTHER INFORMATION: Wherein Xaa is norleucine.
<220> FEATURE:
<221> NAME/KEY: MISC_FEATURE
<222> LOCATION: (17)..(17)
<223> OTHER INFORMATION: Wherein Xaa is phosphoserine.
<220> FEATURE:
<221> NAME/KEY: MISC_FEATURE
<222> LOCATION: (19)..(19)
<223> OTHER INFORMATION: Wherein Xaa is S-N-(9-Fluorenylmethyl
      carbamate)-2-(4'-pentenyl)alanine.

<400> SEQUENCE: 52

Xaa Asn Leu Trp Ala Ala Gln Arg Tyr Gly Arg Glu Leu Arg Xaa Xaa
1               5                   10                  15
Xaa Asp Xaa Phe Val Asp Ser Phe Lys Lys
                20                  25

<210> SEQ ID NO 53
```

```
<211> LENGTH: 25
<212> TYPE: PRT
<213> ORGANISM: Artificial sequence
<220> FEATURE:
<223> OTHER INFORMATION: Chemically synthesized peptide
<220> FEATURE:
<221> NAME/KEY: misc_feature
<222> LOCATION: (14)..(15)
<223> OTHER INFORMATION: Xaa can be any naturally occurring amino acid
<220> FEATURE:
<221> NAME/KEY: misc_feature
<222> LOCATION: (18)..(18)
<223> OTHER INFORMATION: Xaa can be any naturally occurring amino acid

<400> SEQUENCE: 53

Asn Leu Trp Ala Ala Gln Arg Tyr Gly Arg Glu Ala Arg Xaa Xaa Ser
1               5                   10                  15

Ala Xaa Phe Val Asp Ser Phe Lys Lys
            20                  25

<210> SEQ ID NO 54
<211> LENGTH: 26
<212> TYPE: PRT
<213> ORGANISM: Artificial sequence
<220> FEATURE:
<223> OTHER INFORMATION: Chemically synthesized peptide
<220> FEATURE:
<221> NAME/KEY: MISC_FEATURE
<222> LOCATION: (1)..(1)
<223> OTHER INFORMATION: Wherein Xaa is FITC-tagged B-alanine.
<220> FEATURE:
<221> NAME/KEY: MISC_FEATURE
<222> LOCATION: (15)..(15)
<223> OTHER INFORMATION: Wherein Xaa is S-N-(9-Fluorenylmethyl
      carbamate)-2-(4'-pentenyl)alanine.
<220> FEATURE:
<221> NAME/KEY: MISC_FEATURE
<222> LOCATION: (16)..(16)
<223> OTHER INFORMATION: Wherein Xaa is norleucine.
<220> FEATURE:
<221> NAME/KEY: MISC_FEATURE
<222> LOCATION: (19)..(19)
<223> OTHER INFORMATION: Wherein Xaa is S-N-(9-Fluorenylmethyl
      carbamate)-2-(4'-pentenyl)alanine.

<400> SEQUENCE: 54

Xaa Asn Leu Trp Ala Ala Gln Arg Tyr Gly Arg Glu Ala Arg Xaa Xaa
1               5                   10                  15

Ser Ala Xaa Phe Val Asp Ser Phe Lys Lys
            20                  25

<210> SEQ ID NO 55
<211> LENGTH: 25
<212> TYPE: PRT
<213> ORGANISM: Artificial sequence
<220> FEATURE:
<223> OTHER INFORMATION: Chemically synthesized peptide
<220> FEATURE:
<221> NAME/KEY: MISC_FEATURE
<222> LOCATION: (14)..(14)
<223> OTHER INFORMATION: Wherein Xaa is Aminoisobutyric acid (AIB).
<220> FEATURE:
<221> NAME/KEY: MISC_FEATURE
<222> LOCATION: (15)..(15)
<223> OTHER INFORMATION: Wherein Xaa is B-alanine.
<220> FEATURE:
<221> NAME/KEY: MISC_FEATURE
<222> LOCATION: (18)..(18)
<223> OTHER INFORMATION: Wherein Xaa is Aminoisobutyric acid (AIB).

<400> SEQUENCE: 55

Asn Leu Trp Ala Ala Gln Arg Tyr Gly Arg Glu Leu Arg Xaa Xaa Ser
```

```
1               5                   10                  15

Asp Xaa Phe Val Asp Ser Phe Lys Lys
            20                  25

<210> SEQ ID NO 56
<211> LENGTH: 24
<212> TYPE: PRT
<213> ORGANISM: Artificial sequence
<220> FEATURE:
<223> OTHER INFORMATION: Chemically synthesized peptide
<220> FEATURE:
<221> NAME/KEY: MISC_FEATURE
<222> LOCATION: (13)..(13)
<223> OTHER INFORMATION: Wherein Xaa is Aminoisobutyric acid (AIB).
<220> FEATURE:
<221> NAME/KEY: MISC_FEATURE
<222> LOCATION: (14)..(14)
<223> OTHER INFORMATION: Wherein Xaa is B-alanine.
<220> FEATURE:
<221> NAME/KEY: MISC_FEATURE
<222> LOCATION: (17)..(17)
<223> OTHER INFORMATION: Wherein Xaa is Aminoisobutyric acid (AIB).

<400> SEQUENCE: 56

Leu Trp Ala Ala Gln Arg Tyr Gly Arg Glu Leu Arg Xaa Xaa Ser Asp
1               5                   10                  15

Xaa Phe Val Asp Ser Phe Lys Lys
            20

<210> SEQ ID NO 57
<211> LENGTH: 23
<212> TYPE: PRT
<213> ORGANISM: Artificial sequence
<220> FEATURE:
<223> OTHER INFORMATION: Chemically synthesized peptide
<220> FEATURE:
<221> NAME/KEY: MISC_FEATURE
<222> LOCATION: (12)..(12)
<223> OTHER INFORMATION: Wherein Xaa is Aminoisobutyric acid (AIB).
<220> FEATURE:
<221> NAME/KEY: MISC_FEATURE
<222> LOCATION: (13)..(13)
<223> OTHER INFORMATION: Wherein Xaa is B-alanine.
<220> FEATURE:
<221> NAME/KEY: MISC_FEATURE
<222> LOCATION: (16)..(16)
<223> OTHER INFORMATION: Wherein Xaa is Aminoisobutyric acid (AIB).

<400> SEQUENCE: 57

Trp Ala Ala Gln Arg Tyr Gly Arg Glu Leu Arg Xaa Xaa Ser Asp Xaa
1               5                   10                  15

Phe Val Asp Ser Phe Lys Lys
            20

<210> SEQ ID NO 58
<211> LENGTH: 22
<212> TYPE: PRT
<213> ORGANISM: Artificial sequence
<220> FEATURE:
<223> OTHER INFORMATION: Chemically synthesized peptide
<220> FEATURE:
<221> NAME/KEY: MISC_FEATURE
<222> LOCATION: (11)..(11)
<223> OTHER INFORMATION: Wherein Xaa is Aminoisobutyric acid (AIB).
<220> FEATURE:
<221> NAME/KEY: MISC_FEATURE
<222> LOCATION: (12)..(12)
<223> OTHER INFORMATION: Wherein Xaa is B-alanine.
<220> FEATURE:
<221> NAME/KEY: MISC_FEATURE
<222> LOCATION: (15)..(15)
```

<223> OTHER INFORMATION: Wherein Xaa is Aminoisobutyric acid (AIB).

<400> SEQUENCE: 58

Ala Ala Gln Arg Tyr Gly Arg Glu Leu Arg Xaa Xaa Ser Asp Xaa Phe
1               5                   10                  15

Val Asp Ser Phe Lys Lys
            20

<210> SEQ ID NO 59
<211> LENGTH: 21
<212> TYPE: PRT
<213> ORGANISM: Artificial sequence
<220> FEATURE:
<223> OTHER INFORMATION: Chemically synthesized peptide
<220> FEATURE:
<221> NAME/KEY: MISC_FEATURE
<222> LOCATION: (10)..(10)
<223> OTHER INFORMATION: Wherein Xaa is Aminoisobutyric acid (AIB).
<220> FEATURE:
<221> NAME/KEY: MISC_FEATURE
<222> LOCATION: (11)..(11)
<223> OTHER INFORMATION: Wherein Xaa is B-alanine.
<220> FEATURE:
<221> NAME/KEY: MISC_FEATURE
<222> LOCATION: (14)..(14)
<223> OTHER INFORMATION: Wherein Xaa is Aminoisobutyric acid (AIB).

<400> SEQUENCE: 59

Ala Gln Arg Tyr Gly Arg Glu Leu Arg Xaa Xaa Ser Asp Xaa Phe Val
1               5                   10                  15

Asp Ser Phe Lys Lys
            20

<210> SEQ ID NO 60
<211> LENGTH: 20
<212> TYPE: PRT
<213> ORGANISM: Artificial sequence
<220> FEATURE:
<223> OTHER INFORMATION: Chemically synthesized peptide
<220> FEATURE:
<221> NAME/KEY: MISC_FEATURE
<222> LOCATION: (9)..(9)
<223> OTHER INFORMATION: Wherein Xaa is Aminoisobutyric acid (AIB).
<220> FEATURE:
<221> NAME/KEY: MISC_FEATURE
<222> LOCATION: (10)..(10)
<223> OTHER INFORMATION: Wherein Xaa is B-alanine.
<220> FEATURE:
<221> NAME/KEY: MISC_FEATURE
<222> LOCATION: (13)..(13)
<223> OTHER INFORMATION: Wherein Xaa is Aminoisobutyric acid (AIB).

<400> SEQUENCE: 60

Gln Arg Tyr Gly Arg Glu Leu Arg Xaa Xaa Ser Asp Xaa Phe Val Asp
1               5                   10                  15

Ser Phe Lys Lys
            20

<210> SEQ ID NO 61
<211> LENGTH: 19
<212> TYPE: PRT
<213> ORGANISM: Artificial sequence
<220> FEATURE:
<223> OTHER INFORMATION: Chemically synthesized peptide
<220> FEATURE:
<221> NAME/KEY: MISC_FEATURE
<222> LOCATION: (8)..(8)
<223> OTHER INFORMATION: Wherein Xaa is Aminoisobutyric acid (AIB).
<220> FEATURE:
<221> NAME/KEY: MISC_FEATURE
<222> LOCATION: (9)..(9)
<223> OTHER INFORMATION: Wherein Xaa is B-alanine.
<220> FEATURE:
<221> NAME/KEY: MISC_FEATURE
<222> LOCATION: (12)..(12)
<223> OTHER INFORMATION: Wherein Xaa is Aminoisobutyric acid (AIB).

<400> SEQUENCE: 61

Arg Tyr Gly Arg Glu Leu Arg Xaa Xaa Ser Asp Xaa Phe Val Asp Ser
1               5                   10                  15

Phe Lys Lys

<210> SEQ ID NO 62
<211> LENGTH: 18
<212> TYPE: PRT
<213> ORGANISM: Artificial sequence
<220> FEATURE:
<223> OTHER INFORMATION: Chemically synthesized peptide
<220> FEATURE:
<221> NAME/KEY: MISC_FEATURE
<222> LOCATION: (7)..(7)
<223> OTHER INFORMATION: Wherein Xaa is Aminoisobutyric acid (AIB).
<220> FEATURE:
<221> NAME/KEY: MISC_FEATURE
<222> LOCATION: (8)..(8)
<223> OTHER INFORMATION: Wherein Xaa is B-alanine.
<220> FEATURE:
<221> NAME/KEY: MISC_FEATURE
<222> LOCATION: (11)..(11)
<223> OTHER INFORMATION: Wherein Xaa is Aminoisobutyric acid (AIB).

<400> SEQUENCE: 62

Tyr Gly Arg Glu Leu Arg Xaa Xaa Ser Asp Xaa Phe Val Asp Ser Phe
1               5                   10                  15

Lys Lys

<210> SEQ ID NO 63
<211> LENGTH: 24
<212> TYPE: PRT
<213> ORGANISM: Artificial sequence
<220> FEATURE:
<223> OTHER INFORMATION: Chemically synthesized peptide
<220> FEATURE:
<221> NAME/KEY: MISC_FEATURE
<222> LOCATION: (14)..(14)
<223> OTHER INFORMATION: Wherein Xaa is Aminoisobutyric acid (AIB).
<220> FEATURE:
<221> NAME/KEY: MISC_FEATURE
<222> LOCATION: (15)..(15)
<223> OTHER INFORMATION: Wherein Xaa is B-alanine.
<220> FEATURE:
<221> NAME/KEY: MISC_FEATURE
<222> LOCATION: (18)..(18)
<223> OTHER INFORMATION: Wherein Xaa is Aminoisobutyric acid (AIB).

<400> SEQUENCE: 63

Asn Leu Trp Ala Ala Gln Arg Tyr Gly Arg Glu Leu Arg Xaa Xaa Ser
1               5                   10                  15

Asp Xaa Phe Val Asp Ser Phe Lys
            20

<210> SEQ ID NO 64
<211> LENGTH: 23
<212> TYPE: PRT
<213> ORGANISM: Artificial sequence
<220> FEATURE:
<223> OTHER INFORMATION: Chemically synthesized peptide
<220> FEATURE:
<221> NAME/KEY: MISC_FEATURE
<222> LOCATION: (14)..(14)

```
<223> OTHER INFORMATION: Wherein Xaa is Aminoisobutyric acid (AIB).
<220> FEATURE:
<221> NAME/KEY: MISC_FEATURE
<222> LOCATION: (15)..(15)
<223> OTHER INFORMATION: Wherein Xaa is B-alanine.
<220> FEATURE:
<221> NAME/KEY: MISC_FEATURE
<222> LOCATION: (18)..(18)
<223> OTHER INFORMATION: Wherein Xaa is Aminoisobutyric acid (AIB).

<400> SEQUENCE: 64

Asn Leu Trp Ala Ala Gln Arg Tyr Gly Arg Glu Leu Arg Xaa Xaa Ser
1               5                   10                  15

Asp Xaa Phe Val Asp Ser Phe
            20

<210> SEQ ID NO 65
<211> LENGTH: 22
<212> TYPE: PRT
<213> ORGANISM: Artificial sequence
<220> FEATURE:
<223> OTHER INFORMATION: Chemically synthesized peptide
<220> FEATURE:
<221> NAME/KEY: MISC_FEATURE
<222> LOCATION: (14)..(14)
<223> OTHER INFORMATION: Wherein Xaa is Aminoisobutyric acid (AIB).
<220> FEATURE:
<221> NAME/KEY: MISC_FEATURE
<222> LOCATION: (15)..(15)
<223> OTHER INFORMATION: Wherein Xaa is B-alanine.
<220> FEATURE:
<221> NAME/KEY: MISC_FEATURE
<222> LOCATION: (18)..(18)
<223> OTHER INFORMATION: Wherein Xaa is Aminoisobutyric acid (AIB).

<400> SEQUENCE: 65

Asn Leu Trp Ala Ala Gln Arg Tyr Gly Arg Glu Leu Arg Xaa Xaa Ser
1               5                   10                  15

Asp Xaa Phe Val Asp Ser
            20

<210> SEQ ID NO 66
<211> LENGTH: 21
<212> TYPE: PRT
<213> ORGANISM: Artificial sequence
<220> FEATURE:
<223> OTHER INFORMATION: Chemically synthesized peptide
<220> FEATURE:
<221> NAME/KEY: MISC_FEATURE
<222> LOCATION: (14)..(14)
<223> OTHER INFORMATION: Wherein Xaa is Aminoisobutyric acid (AIB).
<220> FEATURE:
<221> NAME/KEY: MISC_FEATURE
<222> LOCATION: (15)..(15)
<223> OTHER INFORMATION: Wherein Xaa is B-alanine.
<220> FEATURE:
<221> NAME/KEY: MISC_FEATURE
<222> LOCATION: (18)..(18)
<223> OTHER INFORMATION: Wherein Xaa is Aminoisobutyric acid (AIB).

<400> SEQUENCE: 66

Asn Leu Trp Ala Ala Gln Arg Tyr Gly Arg Glu Leu Arg Xaa Xaa Ser
1               5                   10                  15

Asp Xaa Phe Val Asp
            20

<210> SEQ ID NO 67
<211> LENGTH: 20
<212> TYPE: PRT
<213> ORGANISM: Artificial sequence
```

```
<220> FEATURE:
<223> OTHER INFORMATION: Chemically synthesized peptide
<220> FEATURE:
<221> NAME/KEY: MISC_FEATURE
<222> LOCATION: (14)..(14)
<223> OTHER INFORMATION: Wherein Xaa is Aminoisobutyric acid (AIB).
<220> FEATURE:
<221> NAME/KEY: MISC_FEATURE
<222> LOCATION: (15)..(15)
<223> OTHER INFORMATION: Wherein Xaa is B-alanine.
<220> FEATURE:
<221> NAME/KEY: MISC_FEATURE
<222> LOCATION: (18)..(18)
<223> OTHER INFORMATION: Wherein Xaa is Aminoisobutyric acid (AIB).

<400> SEQUENCE: 67

Asn Leu Trp Ala Ala Gln Arg Tyr Gly Arg Glu Leu Arg Xaa Xaa Ser
1               5                   10                  15

Asp Xaa Phe Val
            20

<210> SEQ ID NO 68
<211> LENGTH: 19
<212> TYPE: PRT
<213> ORGANISM: Artificial sequence
<220> FEATURE:
<223> OTHER INFORMATION: Chemically synthesized peptide
<220> FEATURE:
<221> NAME/KEY: MISC_FEATURE
<222> LOCATION: (14)..(14)
<223> OTHER INFORMATION: Wherein Xaa is Aminoisobutyric acid (AIB).
<220> FEATURE:
<221> NAME/KEY: MISC_FEATURE
<222> LOCATION: (15)..(15)
<223> OTHER INFORMATION: Wherein Xaa is B-alanine.
<220> FEATURE:
<221> NAME/KEY: MISC_FEATURE
<222> LOCATION: (18)..(18)
<223> OTHER INFORMATION: Wherein Xaa is Aminoisobutyric acid (AIB).

<400> SEQUENCE: 68

Asn Leu Trp Ala Ala Gln Arg Tyr Gly Arg Glu Leu Arg Xaa Xaa Ser
1               5                   10                  15

Asp Xaa Phe

<210> SEQ ID NO 69
<211> LENGTH: 18
<212> TYPE: PRT
<213> ORGANISM: Artificial sequence
<220> FEATURE:
<223> OTHER INFORMATION: Chemically synthesized peptide
<220> FEATURE:
<221> NAME/KEY: MISC_FEATURE
<222> LOCATION: (14)..(14)
<223> OTHER INFORMATION: Wherein Xaa is Aminoisobutyric acid (AIB).
<220> FEATURE:
<221> NAME/KEY: MISC_FEATURE
<222> LOCATION: (15)..(15)
<223> OTHER INFORMATION: Wherein Xaa is B-alanine.
<220> FEATURE:
<221> NAME/KEY: MISC_FEATURE
<222> LOCATION: (18)..(18)
<223> OTHER INFORMATION: Wherein Xaa is Aminoisobutyric acid (AIB).

<400> SEQUENCE: 69

Asn Leu Trp Ala Ala Gln Arg Tyr Gly Arg Glu Leu Arg Xaa Xaa Ser
1               5                   10                  15

Asp Xaa

<210> SEQ ID NO 70
```

```
<211> LENGTH: 23
<212> TYPE: PRT
<213> ORGANISM: Artificial sequence
<220> FEATURE:
<223> OTHER INFORMATION: Chemically synthesized peptide
<220> FEATURE:
<221> NAME/KEY: MISC_FEATURE
<222> LOCATION: (13)..(13)
<223> OTHER INFORMATION: Wherein Xaa is Aminoisobutyric acid (AIB).
<220> FEATURE:
<221> NAME/KEY: MISC_FEATURE
<222> LOCATION: (14)..(14)
<223> OTHER INFORMATION: Wherein Xaa is B-alanine.
<220> FEATURE:
<221> NAME/KEY: MISC_FEATURE
<222> LOCATION: (17)..(17)
<223> OTHER INFORMATION: Wherein Xaa is Aminoisobutyric acid (AIB).

<400> SEQUENCE: 70

Leu Trp Ala Ala Gln Arg Tyr Gly Arg Glu Leu Arg Xaa Xaa Ser Asp
1               5                   10                  15

Xaa Phe Val Asp Ser Phe Lys
            20

<210> SEQ ID NO 71
<211> LENGTH: 22
<212> TYPE: PRT
<213> ORGANISM: Artificial sequence
<220> FEATURE:
<223> OTHER INFORMATION: Chemically synthesized peptide
<220> FEATURE:
<221> NAME/KEY: MISC_FEATURE
<222> LOCATION: (13)..(13)
<223> OTHER INFORMATION: Wherein Xaa is Aminoisobutyric acid (AIB).
<220> FEATURE:
<221> NAME/KEY: MISC_FEATURE
<222> LOCATION: (14)..(14)
<223> OTHER INFORMATION: Wherein Xaa is B-alanine.
<220> FEATURE:
<221> NAME/KEY: MISC_FEATURE
<222> LOCATION: (17)..(17)
<223> OTHER INFORMATION: Wherein Xaa is Aminoisobutyric acid (AIB).

<400> SEQUENCE: 71

Leu Trp Ala Ala Gln Arg Tyr Gly Arg Glu Leu Arg Xaa Xaa Ser Asp
1               5                   10                  15

Xaa Phe Val Asp Ser Phe
            20

<210> SEQ ID NO 72
<211> LENGTH: 21
<212> TYPE: PRT
<213> ORGANISM: Artificial sequence
<220> FEATURE:
<223> OTHER INFORMATION: Chemically synthesized peptide
<220> FEATURE:
<221> NAME/KEY: MISC_FEATURE
<222> LOCATION: (12)..(12)
<223> OTHER INFORMATION: Wherein Xaa is Aminoisobutyric acid (AIB).
<220> FEATURE:
<221> NAME/KEY: MISC_FEATURE
<222> LOCATION: (13)..(13)
<223> OTHER INFORMATION: Wherein Xaa is B-alanine.
<220> FEATURE:
<221> NAME/KEY: MISC_FEATURE
<222> LOCATION: (16)..(16)
<223> OTHER INFORMATION: Wherein Xaa is Aminoisobutyric acid (AIB).

<400> SEQUENCE: 72

Trp Ala Ala Gln Arg Tyr Gly Arg Glu Leu Arg Xaa Xaa Ser Asp Xaa
1               5                   10                  15
```

```
Phe Val Asp Ser Phe
            20

<210> SEQ ID NO 73
<211> LENGTH: 20
<212> TYPE: PRT
<213> ORGANISM: Artificial sequence
<220> FEATURE:
<223> OTHER INFORMATION: Chemically synthesized peptide
<220> FEATURE:
<221> NAME/KEY: MISC_FEATURE
<222> LOCATION: (12)..(12)
<223> OTHER INFORMATION: Wherein Xaa is Aminoisobutyric acid (AIB).
<220> FEATURE:
<221> NAME/KEY: MISC_FEATURE
<222> LOCATION: (13)..(13)
<223> OTHER INFORMATION: Wherein Xaa is B-alanine.
<220> FEATURE:
<221> NAME/KEY: MISC_FEATURE
<222> LOCATION: (16)..(16)
<223> OTHER INFORMATION: Wherein Xaa is Aminoisobutyric acid (AIB).

<400> SEQUENCE: 73

Trp Ala Ala Gln Arg Tyr Gly Arg Glu Leu Arg Xaa Xaa Ser Asp Xaa
1               5                   10                  15
Phe Val Asp Ser
            20

<210> SEQ ID NO 74
<211> LENGTH: 19
<212> TYPE: PRT
<213> ORGANISM: Artificial sequence
<220> FEATURE:
<223> OTHER INFORMATION: Chemically synthesized peptide
<220> FEATURE:
<221> NAME/KEY: MISC_FEATURE
<222> LOCATION: (11)..(11)
<223> OTHER INFORMATION: Wherein Xaa is Aminoisobutyric acid (AIB).
<220> FEATURE:
<221> NAME/KEY: MISC_FEATURE
<222> LOCATION: (12)..(12)
<223> OTHER INFORMATION: Wherein Xaa is B-alanine.
<220> FEATURE:
<221> NAME/KEY: MISC_FEATURE
<222> LOCATION: (15)..(15)
<223> OTHER INFORMATION: Wherein Xaa is Aminoisobutyric acid (AIB).

<400> SEQUENCE: 74

Ala Ala Gln Arg Tyr Gly Arg Glu Leu Arg Xaa Xaa Ser Asp Xaa Phe
1               5                   10                  15
Val Asp Ser

<210> SEQ ID NO 75
<211> LENGTH: 18
<212> TYPE: PRT
<213> ORGANISM: Artificial sequence
<220> FEATURE:
<223> OTHER INFORMATION: Chemically synthesized peptide
<220> FEATURE:
<221> NAME/KEY: MISC_FEATURE
<222> LOCATION: (11)..(11)
<223> OTHER INFORMATION: Wherein Xaa is Aminoisobutyric acid (AIB).
<220> FEATURE:
<221> NAME/KEY: MISC_FEATURE
<222> LOCATION: (12)..(12)
<223> OTHER INFORMATION: Wherein Xaa is B-alanine.
<220> FEATURE:
<221> NAME/KEY: MISC_FEATURE
<222> LOCATION: (15)..(15)
<223> OTHER INFORMATION: Wherein Xaa is Aminoisobutyric acid (AIB).

<400> SEQUENCE: 75
```

```
Ala Ala Gln Arg Tyr Gly Arg Glu Leu Arg Xaa Xaa Ser Asp Xaa Phe
1               5                   10                  15

Val Asp
```

<210> SEQ ID NO 76
<211> LENGTH: 17
<212> TYPE: PRT
<213> ORGANISM: Artificial sequence
<220> FEATURE:
<223> OTHER INFORMATION: Chemically synthesized peptide
<220> FEATURE:
<221> NAME/KEY: MISC_FEATURE
<222> LOCATION: (10)..(10)
<223> OTHER INFORMATION: Wherein Xaa is Aminoisobutyric acid (AIB).
<220> FEATURE:
<221> NAME/KEY: MISC_FEATURE
<222> LOCATION: (11)..(11)
<223> OTHER INFORMATION: Wherein Xaa is B-alanine.
<220> FEATURE:
<221> NAME/KEY: MISC_FEATURE
<222> LOCATION: (14)..(14)
<223> OTHER INFORMATION: Wherein Xaa is Aminoisobutyric acid (AIB).

<400> SEQUENCE: 76

```
Ala Gln Arg Tyr Gly Arg Glu Leu Arg Xaa Xaa Ser Asp Xaa Phe Val
1               5                   10                  15

Asp
```

<210> SEQ ID NO 77
<211> LENGTH: 16
<212> TYPE: PRT
<213> ORGANISM: Artificial sequence
<220> FEATURE:
<223> OTHER INFORMATION: Chemically synthesized peptide
<220> FEATURE:
<221> NAME/KEY: MISC_FEATURE
<222> LOCATION: (9)..(9)
<223> OTHER INFORMATION: Wherein Xaa is Aminoisobutyric acid (AIB).
<220> FEATURE:
<221> NAME/KEY: MISC_FEATURE
<222> LOCATION: (10)..(10)
<223> OTHER INFORMATION: Wherein Xaa is B-alanine.
<220> FEATURE:
<221> NAME/KEY: MISC_FEATURE
<222> LOCATION: (13)..(13)
<223> OTHER INFORMATION: Wherein Xaa is Aminoisobutyric acid (AIB).

<400> SEQUENCE: 77

```
Gln Arg Tyr Gly Arg Glu Leu Arg Xaa Xaa Ser Asp Xaa Phe Val Asp
1               5                   10                  15
```

<210> SEQ ID NO 78
<211> LENGTH: 28
<212> TYPE: PRT
<213> ORGANISM: Artificial sequence
<220> FEATURE:
<223> OTHER INFORMATION: Chemically synthesized peptide
<220> FEATURE:
<221> NAME/KEY: MISC_FEATURE
<222> LOCATION: (1)..(1)
<223> OTHER INFORMATION: Wherein Xaa is FITC-tagged B-alanine.
<220> FEATURE:
<221> NAME/KEY: MISC_FEATURE
<222> LOCATION: (2)..(2)
<223> OTHER INFORMATION: Wherein Xaa is B-alanine.
<220> FEATURE:
<221> NAME/KEY: MISC_FEATURE
<222> LOCATION: (3)..(3)
<223> OTHER INFORMATION: Wherein Xaa is a benzophenone-containing amino
      acid.
<220> FEATURE:

```
<221> NAME/KEY: MISC_FEATURE
<222> LOCATION: (17)..(17)
<223> OTHER INFORMATION: Wherein Xaa is S-N-(9-Fluorenylmethyl
      carbamate)-2-(4'-pentenyl)alanine.
<220> FEATURE:
<221> NAME/KEY: MISC_FEATURE
<222> LOCATION: (18)..(18)
<223> OTHER INFORMATION: Wherein Xaa is norleucine.
<220> FEATURE:
<221> NAME/KEY: MISC_FEATURE
<222> LOCATION: (21)..(21)
<223> OTHER INFORMATION: Wherein Xaa is S-N-(9-Fluorenylmethyl
      carbamate)-2-(4'-pentenyl)alanine.

<400> SEQUENCE: 78

Xaa Xaa Xaa Asn Leu Trp Ala Ala Gln Arg Tyr Gly Arg Glu Leu Arg
1               5                   10                  15

Xaa Xaa Ser Asp Xaa Phe Val Asp Ser Phe Lys Lys
            20                  25

<210> SEQ ID NO 79
<211> LENGTH: 27
<212> TYPE: PRT
<213> ORGANISM: Artificial sequence
<220> FEATURE:
<223> OTHER INFORMATION: Chemically synthesized peptide
<220> FEATURE:
<221> NAME/KEY: MISC_FEATURE
<222> LOCATION: (1)..(1)
<223> OTHER INFORMATION: Wherein Xaa is FITC-tagged B-alanine.
<220> FEATURE:
<221> NAME/KEY: MISC_FEATURE
<222> LOCATION: (2)..(2)
<223> OTHER INFORMATION: Wherein Xaa is B-alanine.
<220> FEATURE:
<221> NAME/KEY: MISC_FEATURE
<222> LOCATION: (5)..(5)
<223> OTHER INFORMATION: Wherein Xaa is a benzophenone-containing amino
      acid.
<220> FEATURE:
<221> NAME/KEY: MISC_FEATURE
<222> LOCATION: (16)..(16)
<223> OTHER INFORMATION: Wherein Xaa is S-N-(9-Fluorenylmethyl
      carbamate)-2-(4'-pentenyl)alanine.
<220> FEATURE:
<221> NAME/KEY: MISC_FEATURE
<222> LOCATION: (17)..(17)
<223> OTHER INFORMATION: Wherein Xaa is norleucine.
<220> FEATURE:
<221> NAME/KEY: MISC_FEATURE
<222> LOCATION: (20)..(20)
<223> OTHER INFORMATION: Wherein Xaa is S-N-(9-Fluorenylmethyl
      carbamate)-2-(4'-pentenyl)alanine.

<400> SEQUENCE: 79

Xaa Xaa Asn Leu Xaa Ala Ala Gln Arg Tyr Gly Arg Glu Leu Arg Xaa
1               5                   10                  15

Xaa Ser Asp Xaa Phe Val Asp Ser Phe Lys Lys
            20                  25

<210> SEQ ID NO 80
<211> LENGTH: 27
<212> TYPE: PRT
<213> ORGANISM: Artificial sequence
<220> FEATURE:
<223> OTHER INFORMATION: Chemically synthesized peptide
<220> FEATURE:
<221> NAME/KEY: MISC_FEATURE
<222> LOCATION: (1)..(1)
<223> OTHER INFORMATION: Wherein Xaa is FITC-tagged B-alanine.
<220> FEATURE:
<221> NAME/KEY: MISC_FEATURE
<222> LOCATION: (2)..(2)
```

```
<223> OTHER INFORMATION: Wherein Xaa is B-alanine.
<220> FEATURE:
<221> NAME/KEY: MISC_FEATURE
<222> LOCATION: (10)..(10)
<223> OTHER INFORMATION: Wherein Xaa is a benzophenone-containing amino
      acid.
<220> FEATURE:
<221> NAME/KEY: MISC_FEATURE
<222> LOCATION: (16)..(16)
<223> OTHER INFORMATION: Wherein Xaa is S-N-(9-Fluorenylmethyl
      carbamate)-2-(4'-pentenyl)alanine.
<220> FEATURE:
<221> NAME/KEY: MISC_FEATURE
<222> LOCATION: (17)..(17)
<223> OTHER INFORMATION: Wherein Xaa is norleucine.
<220> FEATURE:
<221> NAME/KEY: MISC_FEATURE
<222> LOCATION: (20)..(20)
<223> OTHER INFORMATION: Wherein Xaa is S-N-(9-Fluorenylmethyl
      carbamate)-2-(4'-pentenyl)alanine.

<400> SEQUENCE: 80

Xaa Xaa Asn Leu Trp Ala Ala Gln Arg Xaa Gly Arg Glu Leu Arg Xaa
1               5                   10                  15

Xaa Ser Asp Xaa Phe Val Asp Ser Phe Lys Lys
            20                  25

<210> SEQ ID NO 81
<211> LENGTH: 27
<212> TYPE: PRT
<213> ORGANISM: Artificial sequence
<220> FEATURE:
<223> OTHER INFORMATION: Chemically synthesized peptide
<220> FEATURE:
<221> NAME/KEY: MISC_FEATURE
<222> LOCATION: (1)..(1)
<223> OTHER INFORMATION: Wherein Xaa is FITC-tagged B-alanine.
<220> FEATURE:
<221> NAME/KEY: MISC_FEATURE
<222> LOCATION: (2)..(2)
<223> OTHER INFORMATION: Wherein Xaa is B-alanine.
<220> FEATURE:
<221> NAME/KEY: MISC_FEATURE
<222> LOCATION: (16)..(16)
<223> OTHER INFORMATION: Wherein Xaa is S-N-(9-Fluorenylmethyl
      carbamate)-2-(4'-pentenyl)alanine.
<220> FEATURE:
<221> NAME/KEY: MISC_FEATURE
<222> LOCATION: (17)..(17)
<223> OTHER INFORMATION: Wherein Xaa is norleucine.
<220> FEATURE:
<221> NAME/KEY: MISC_FEATURE
<222> LOCATION: (20)..(20)
<223> OTHER INFORMATION: Wherein Xaa is S-N-(9-Fluorenylmethyl
      carbamate)-2-(4'-pentenyl)alanine.
<220> FEATURE:
<221> NAME/KEY: MISC_FEATURE
<222> LOCATION: (21)..(21)
<223> OTHER INFORMATION: Wherein Xaa is a benzophenone-containing amino
      acid.

<400> SEQUENCE: 81

Xaa Xaa Asn Leu Trp Ala Ala Gln Arg Tyr Gly Arg Glu Leu Arg Xaa
1               5                   10                  15

Xaa Ser Asp Xaa Xaa Val Asp Ser Phe Lys Lys
            20                  25

<210> SEQ ID NO 82
<211> LENGTH: 27
<212> TYPE: PRT
<213> ORGANISM: Artificial sequence
<220> FEATURE:
<223> OTHER INFORMATION: Chemically synthesized peptide
```

```
<220> FEATURE:
<221> NAME/KEY: MISC_FEATURE
<222> LOCATION: (1)..(1)
<223> OTHER INFORMATION: Wherein Xaa is FITC-tagged B-alanine.
<220> FEATURE:
<221> NAME/KEY: MISC_FEATURE
<222> LOCATION: (2)..(2)
<223> OTHER INFORMATION: Wherein Xaa is B-alanine.
<220> FEATURE:
<221> NAME/KEY: MISC_FEATURE
<222> LOCATION: (16)..(16)
<223> OTHER INFORMATION: Wherein Xaa is S-N-(9-Fluorenylmethyl
      carbamate)-2-(4'-pentenyl)alanine.
<220> FEATURE:
<221> NAME/KEY: MISC_FEATURE
<222> LOCATION: (17)..(17)
<223> OTHER INFORMATION: Wherein Xaa is norleucine.
<220> FEATURE:
<221> NAME/KEY: MISC_FEATURE
<222> LOCATION: (20)..(20)
<223> OTHER INFORMATION: Wherein Xaa is S-N-(9-Fluorenylmethyl
      carbamate)-2-(4'-pentenyl)alanine.
<220> FEATURE:
<221> NAME/KEY: MISC_FEATURE
<222> LOCATION: (25)..(25)
<223> OTHER INFORMATION: Wherein Xaa is a benzophenone-containing amino
      acid.

<400> SEQUENCE: 82

Xaa Xaa Asn Leu Trp Ala Ala Gln Arg Tyr Gly Arg Glu Leu Arg Xaa
1               5                   10                  15

Xaa Ser Asp Xaa Phe Val Asp Ser Xaa Lys Lys
            20                  25

<210> SEQ ID NO 83
<211> LENGTH: 28
<212> TYPE: PRT
<213> ORGANISM: Artificial sequence
<220> FEATURE:
<223> OTHER INFORMATION: Chemically synthesized peptide
<220> FEATURE:
<221> NAME/KEY: MISC_FEATURE
<222> LOCATION: (1)..(1)
<223> OTHER INFORMATION: Wherein Xaa is FITC-tagged B-alanine.
<220> FEATURE:
<221> NAME/KEY: MISC_FEATURE
<222> LOCATION: (2)..(2)
<223> OTHER INFORMATION: Wherein Xaa is B-alanine.
<220> FEATURE:
<221> NAME/KEY: MISC_FEATURE
<222> LOCATION: (16)..(16)
<223> OTHER INFORMATION: Wherein Xaa is S-N-(9-Fluorenylmethyl
      carbamate)-2-(4'-pentenyl)alanine.
<220> FEATURE:
<221> NAME/KEY: MISC_FEATURE
<222> LOCATION: (17)..(17)
<223> OTHER INFORMATION: Wherein Xaa is norleucine.
<220> FEATURE:
<221> NAME/KEY: MISC_FEATURE
<222> LOCATION: (20)..(20)
<223> OTHER INFORMATION: Wherein Xaa is S-N-(9-Fluorenylmethyl
      carbamate)-2-(4'-pentenyl)alanine.
<220> FEATURE:
<221> NAME/KEY: MISC_FEATURE
<222> LOCATION: (28)..(28)
<223> OTHER INFORMATION: Wherein Xaa is a benzophenone-containing amino
      acid.

<400> SEQUENCE: 83

Xaa Xaa Asn Leu Trp Ala Ala Gln Arg Tyr Gly Arg Glu Leu Arg Xaa
1               5                   10                  15

Xaa Ser Asp Xaa Phe Val Asp Ser Phe Lys Lys Xaa
            20                  25
```

```
<210> SEQ ID NO 84
<211> LENGTH: 25
<212> TYPE: PRT
<213> ORGANISM: Artificial sequence
<220> FEATURE:
<223> OTHER INFORMATION: Chemically synthesized peptide
<220> FEATURE:
<221> NAME/KEY: MISC_FEATURE
<222> LOCATION: (1)..(1)
<223> OTHER INFORMATION: Wherein Xaa is biotin-tagged asparagine.
<220> FEATURE:
<221> NAME/KEY: MISC_FEATURE
<222> LOCATION: (14)..(14)
<223> OTHER INFORMATION: Wherein Xaa is S-N-(9-Fluorenylmethyl
      carbamate)-2-(4'-pentenyl)alanine.
<220> FEATURE:
<221> NAME/KEY: MISC_FEATURE
<222> LOCATION: (15)..(15)
<223> OTHER INFORMATION: Wherein Xaa is norleucine.
<220> FEATURE:
<221> NAME/KEY: MISC_FEATURE
<222> LOCATION: (18)..(18)
<223> OTHER INFORMATION: Wherein Xaa is S-N-(9-Fluorenylmethyl
      carbamate)-2-(4'-pentenyl)alanine.

<400> SEQUENCE: 84

Xaa Leu Trp Ala Ala Gln Arg Tyr Gly Arg Glu Leu Arg Xaa Xaa Ser
1               5                   10                  15

Asp Xaa Phe Val Asp Ser Phe Lys Lys
            20                  25

<210> SEQ ID NO 85
<211> LENGTH: 25
<212> TYPE: PRT
<213> ORGANISM: Artificial sequence
<220> FEATURE:
<223> OTHER INFORMATION: Chemically synthesized peptide
<220> FEATURE:
<221> NAME/KEY: MISC_FEATURE
<222> LOCATION: (1)..(1)
<223> OTHER INFORMATION: Wherein Xaa is biotin-tagged asparagine.
<220> FEATURE:
<221> NAME/KEY: MISC_FEATURE
<222> LOCATION: (14)..(14)
<223> OTHER INFORMATION: Wherein Xaa is Aminoisobutyric acid (AIB).
<220> FEATURE:
<221> NAME/KEY: MISC_FEATURE
<222> LOCATION: (15)..(15)
<223> OTHER INFORMATION: Wherein Xaa is norleucine.
<220> FEATURE:
<221> NAME/KEY: MISC_FEATURE
<222> LOCATION: (18)..(18)
<223> OTHER INFORMATION: Wherein Xaa is Aminoisobutyric acid (AIB).

<400> SEQUENCE: 85

Xaa Leu Trp Ala Ala Gln Arg Tyr Gly Arg Glu Ala Arg Xaa Xaa Ser
1               5                   10                  15

Ala Xaa Phe Val Asp Ser Phe Lys Lys
            20                  25

<210> SEQ ID NO 86
<211> LENGTH: 25
<212> TYPE: PRT
<213> ORGANISM: Artificial sequence
<220> FEATURE:
<223> OTHER INFORMATION: Chemically synthesized peptide
<220> FEATURE:
<221> NAME/KEY: MISC_FEATURE
<222> LOCATION: (16)..(16)
<223> OTHER INFORMATION: Wherein Xaa is S-N-(9-Fluorenylmethyl
      carbamate)-2-(4'-pentenyl)alanine.
<220> FEATURE:
```

```
<221> NAME/KEY: MISC_FEATURE
<222> LOCATION: (20)..(20)
<223> OTHER INFORMATION: Wherein Xaa is S-N-(9-Fluorenylmethyl
      carbamate)-2-(4'-pentenyl)alanine.

<400> SEQUENCE: 86

Glu Ser Gln Glu Asp Ile Ile Arg Asn Ile Ala Arg His Leu Ala Xaa
1               5                   10                  15

Val Gly Asp Xaa Met Asp Arg Ser Ile
            20                  25

<210> SEQ ID NO 87
<211> LENGTH: 25
<212> TYPE: PRT
<213> ORGANISM: Artificial sequence
<220> FEATURE:
<223> OTHER INFORMATION: Chemically synthesized peptide
<220> FEATURE:
<221> NAME/KEY: MISC_FEATURE
<222> LOCATION: (2)..(2)
<223> OTHER INFORMATION: Wherein Xaa is phosphoserine.
<220> FEATURE:
<221> NAME/KEY: MISC_FEATURE
<222> LOCATION: (16)..(16)
<223> OTHER INFORMATION: Wherein Xaa is S-N-(9-Fluorenylmethyl
      carbamate)-2-(4'-pentenyl)alanine.
<220> FEATURE:
<221> NAME/KEY: MISC_FEATURE
<222> LOCATION: (20)..(20)
<223> OTHER INFORMATION: Wherein Xaa is S-N-(9-Fluorenylmethyl
      carbamate)-2-(4'-pentenyl)alanine.

<400> SEQUENCE: 87

Glu Xaa Gln Glu Asp Ile Ile Arg Asn Ile Ala Arg His Leu Ala Xaa
1               5                   10                  15

Val Gly Asp Xaa Met Asp Arg Ser Ile
            20                  25

<210> SEQ ID NO 88
<211> LENGTH: 25
<212> TYPE: PRT
<213> ORGANISM: Artificial sequence
<220> FEATURE:
<223> OTHER INFORMATION: Chemically synthesized peptide

<400> SEQUENCE: 88

Asn Leu Trp Ala Ala Gln Arg Tyr Gly Arg Glu Leu Arg Arg Met Ser
1               5                   10                  15

Asp Glu Phe Val Asp Ser Phe Lys Lys
            20                  25

<210> SEQ ID NO 89
<211> LENGTH: 25
<212> TYPE: PRT
<213> ORGANISM: Artificial sequence
<220> FEATURE:
<223> OTHER INFORMATION: Chemically synthesized peptide

<400> SEQUENCE: 89

Asp Ile Glu Arg Arg Lys Glu Val Glu Ser Ile Leu Lys Lys Asn Ser
1               5                   10                  15

Asp Trp Ile Trp Asp Trp Ser Ser Arg
            20                  25

<210> SEQ ID NO 90
<211> LENGTH: 30
<212> TYPE: PRT
```

```
<213> ORGANISM: Artificial sequence
<220> FEATURE:
<223> OTHER INFORMATION: Chemically synthesized peptide

<400> SEQUENCE: 90

Ser Ser Ala Ala Gln Leu Thr Ala Ala Arg Leu Lys Ala Leu Gly Asp
1               5                   10                  15

Glu Leu His Gln Arg Thr Met Trp Arg Arg Ala Arg Ser
            20                  25                  30

<210> SEQ ID NO 91
<211> LENGTH: 40
<212> TYPE: PRT
<213> ORGANISM: Artificial sequence
<220> FEATURE:
<223> OTHER INFORMATION: Chemically synthesized peptide

<400> SEQUENCE: 91

Ser Ser Gln Ser Glu Glu Val Val Glu Gly Glu Lys Glu Val Glu
1               5                   10                  15

Ala Leu Lys Lys Ser Ala Asp Trp Val Ser Asp Trp Ser Ser Arg Pro
            20                  25                  30

Glu Asn Ile Pro Pro Lys Glu Phe
        35                  40

<210> SEQ ID NO 92
<211> LENGTH: 24
<212> TYPE: PRT
<213> ORGANISM: Artificial sequence
<220> FEATURE:
<223> OTHER INFORMATION: Chemically synthesized peptide

<400> SEQUENCE: 92

Ser Gln Glu Asp Ile Ile Arg Asn Ile Ala Arg His Leu Ala Gln Val
1               5                   10                  15

Gly Asp Ser Met Asp Arg Ser Ile
            20

<210> SEQ ID NO 93
<211> LENGTH: 29
<212> TYPE: PRT
<213> ORGANISM: Artificial sequence
<220> FEATURE:
<223> OTHER INFORMATION: Chemically synthesized peptide

<400> SEQUENCE: 93

Ala Glu Leu Glu Val Glu Cys Ala Thr Gln Leu Arg Arg Phe Gly Asp
1               5                   10                  15

Lys Leu Asn Phe Arg Gln Lys Leu Leu Asn Leu Ile Ser
            20                  25

<210> SEQ ID NO 94
<211> LENGTH: 20
<212> TYPE: PRT
<213> ORGANISM: Artificial sequence
<220> FEATURE:
<223> OTHER INFORMATION: Chemically synthesized peptide

<400> SEQUENCE: 94

Leu Glu Ala Glu Leu Asp Ala Leu Gly Asp Glu Leu Leu Ala Asp Glu
1               5                   10                  15

Asp Ser Ser Tyr
            20
```

<210> SEQ ID NO 95
<211> LENGTH: 28
<212> TYPE: PRT
<213> ORGANISM: Artificial sequence
<220> FEATURE:
<223> OTHER INFORMATION: Chemically synthesized peptide

<400> SEQUENCE: 95

Leu Gln Pro Ser Ser Thr Met Gly Gln Val Gly Arg Gln Leu Ala Ile
1               5                   10                  15

Ile Gly Asp Asp Ile Asn Arg Arg Tyr Asp Ser Glu
            20                  25

<210> SEQ ID NO 96
<211> LENGTH: 22
<212> TYPE: PRT
<213> ORGANISM: Artificial sequence
<220> FEATURE:
<223> OTHER INFORMATION: Chemically synthesized peptide

<400> SEQUENCE: 96

Gln Asp Ala Ser Thr Lys Lys Leu Ser Glu Cys Leu Lys Arg Ile Gly
1               5                   10                  15

Asp Glu Leu Ser Asp Asn
            20

<210> SEQ ID NO 97
<211> LENGTH: 24
<212> TYPE: PRT
<213> ORGANISM: Artificial sequence
<220> FEATURE:
<223> OTHER INFORMATION: Chemically synthesized peptide

<400> SEQUENCE: 97

Pro Gly Arg Leu Ala Glu Val Cys Ala Val Leu Leu Arg Leu Gly Asp
1               5                   10                  15

Glu Leu Glu Met Ile Arg Pro Ser
            20

<210> SEQ ID NO 98
<211> LENGTH: 25
<212> TYPE: PRT
<213> ORGANISM: Artificial sequence
<220> FEATURE:
<223> OTHER INFORMATION: Chemically synthesized peptide

<400> SEQUENCE: 98

Ser Pro Val Pro Pro Val Val His Leu Thr Leu Arg Gln Ala Gly Asp
1               5                   10                  15

Asp Phe Ser Arg Arg Tyr Arg Arg Asp
            20                  25

<210> SEQ ID NO 99
<211> LENGTH: 22
<212> TYPE: PRT
<213> ORGANISM: Artificial sequence
<220> FEATURE:
<223> OTHER INFORMATION: Chemically synthesized peptide

<400> SEQUENCE: 99

Ala Val Lys Gln Ala Leu Arg Glu Ala Gly Asp Glu Phe Glu Leu Arg
1               5                   10                  15

Tyr Arg Arg Ala Phe Ser
            20

```
<210> SEQ ID NO 100
<211> LENGTH: 21
<212> TYPE: PRT
<213> ORGANISM: Artificial sequence
<220> FEATURE:
<223> OTHER INFORMATION: Chemically synthesized peptide

<400> SEQUENCE: 100

His Gln Ala Met Arg Ala Ala Gly Asp Glu Phe Glu Thr Arg Phe Arg
1               5                   10                  15

Arg Thr Phe Ser Asp
            20

<210> SEQ ID NO 101
<211> LENGTH: 20
<212> TYPE: PRT
<213> ORGANISM: Artificial sequence
<220> FEATURE:
<223> OTHER INFORMATION: Chemically synthesized peptide

<400> SEQUENCE: 101

Thr Ser Arg Lys Ala Leu Glu Thr Leu Arg Arg Val Gly Asp Gly Val
1               5                   10                  15

Gln Arg Asn His
            20

<210> SEQ ID NO 102
<211> LENGTH: 4
<212> TYPE: PRT
<213> ORGANISM: Artificial sequence
<220> FEATURE:
<223> OTHER INFORMATION: Chemically synthesized peptide

<400> SEQUENCE: 102

Ala Ala Gln Arg
1

<210> SEQ ID NO 103
<211> LENGTH: 5
<212> TYPE: PRT
<213> ORGANISM: Artificial sequence
<220> FEATURE:
<223> OTHER INFORMATION: Chemically synthesized peptide

<400> SEQUENCE: 103

Trp Ala Ala Gln Arg
1               5

<210> SEQ ID NO 104
<211> LENGTH: 6
<212> TYPE: PRT
<213> ORGANISM: Artificial sequence
<220> FEATURE:
<223> OTHER INFORMATION: Chemically synthesized peptide

<400> SEQUENCE: 104

Leu Trp Ala Ala Gln Arg
1               5

<210> SEQ ID NO 105
<211> LENGTH: 7
<212> TYPE: PRT
<213> ORGANISM: Artificial sequence
<220> FEATURE:
<223> OTHER INFORMATION: Chemically synthesized peptide
```

```
<400> SEQUENCE: 105

Asn Leu Trp Ala Ala Gln Arg
1               5

<210> SEQ ID NO 106
<211> LENGTH: 4
<212> TYPE: PRT
<213> ORGANISM: Artificial sequence
<220> FEATURE:
<223> OTHER INFORMATION: Chemically synthesized peptide

<400> SEQUENCE: 106

Val Asp Ser Phe
1

<210> SEQ ID NO 107
<211> LENGTH: 5
<212> TYPE: PRT
<213> ORGANISM: Artificial sequence
<220> FEATURE:
<223> OTHER INFORMATION: Chemically synthesized peptide

<400> SEQUENCE: 107

Val Asp Ser Phe Lys
1               5

<210> SEQ ID NO 108
<211> LENGTH: 6
<212> TYPE: PRT
<213> ORGANISM: Artificial sequence
<220> FEATURE:
<223> OTHER INFORMATION: Chemically synthesized peptide

<400> SEQUENCE: 108

Val Asp Ser Phe Lys Lys
1               5
```

METHODS OF MODULATING CELLULAR HOMEOSTATIC PATHWAYS AND CELLULAR SURVIVAL

RELATED APPLICATIONS

This application is a national stage application, filed under 35 U.S.C. § 371, of International Application No. PCT/US2008/062345, filed May 2, 2008, which claims the benefit of U.S. Ser. No. 60/915,594, filed May 2, 2007, the contents of which are incorporated by reference in their entireties.

STATEMENT AS TO FEDERALLY SPONSORED RESEARCH

This invention was made with government support under grant numbers R37 CA050239, K01 CA106596, and HL074049 awarded by The National Institutes of Health. The government has certain rights in the invention.

FIELD OF THE INVENTION

This invention relates to methods modulating β-islet cell function and survival and provides methods for treating diabetes and inhibiting pancreatic islet cell death. Moreover, the invention describes methods to control the discrete activities of individual BH3-only proteins through phosphomimetic-based modification of bioactive BH3 peptidic compounds.

BACKGROUND OF THE INVENTION

Diabetes is an impaired metabolic response to our body's own insulin so that active muscle cells cannot take up glucose as easily as they should. When diabetes, or reduced insulin sensitivity, exists, the body attempts to overcome this resistance by secreting more insulin from the pancreas. In that physiologic circumstance, the blood insulin levels are chronically higher which inhibits fat cells from releasing their energy stores to allow for weight loss. Diabetes is associated with obesity, hypertension, abnormal triglycerides and glucose intolerance. BCL-2 family proteins, such as BAD, are well known to play critical roles in organism homeostasis by regulating programmed cell death or apoptosis. In recent years, novel non-apoptotic functions have been identified for select BCL-2 family members and these newly identified roles are vital to maintaining organism homeostasis. Deregulation of the apoptotic functions of BCL-2 family members can lead to excessive cell loss or excessive cell survival, giving rise to diseases such as neurodegeneration and cancer, respectively. Deregulation of the non-apoptotic functions of BCL-2 family members, such as BAD, can produce a diabetogenic phenotype that is unrelated to BAD's role in cell death physiology. The ability of select BCL-2 family proteins to toggle between distinct functions is a critical aspect of their physiologic activity. The molecular mechanisms by which they achieve dual roles can be mediated by their bioactive BH3 domain and, specifically, its phosphorylation state. Therefore, the ability to generate selective compounds that mimic phosphorylated BH3 domains has significant therapeutic potential in treating human disease.

BCL-2 Family Proteins: Critical Intra-Cellular Checkpoints of Apoptosis

Programmed cell death is a genetically conserved pathway essential for proper embryonic development and the maintenance of tissue homeostasis (Cory, S. and Adams, J. M. 2002. *Nat Rev Cancer* 2, 647-56). Aberrant regulation of this pathway participates in the genesis of multiple human diseases, including cancer, autoimmunity, neurodegenerative disorders, and diabetes. The mammalian apoptotic pathway provides evidence for the participation of organelles, especially mitochondria (Green, D. R. and Kroemer, G. 2004. *Science* 305, 626-9). Besides providing most of the cellular ATP, mitochondria participate in apoptosis by releasing cytochrome c and other apoptogenic factors. Once released, cytochrome c is assembled together with APAF-1 and caspase-9 to form the "apoptosome", which in turn activates downstream caspases, leading ultimately to cellular demise (Li, P. et al., 1997. *Cell* 91:479-89). Mitochondria are also responsible for cellular respiration and coordinate multiple metabolic pathways, yet the interrelationship of these functions with apoptosis has remained uncertain.

The BCL-2 family of proteins constitutes a critical control point in apoptosis residing immediately upstream to irreversible cellular damage, where the members control the release of apoptogenic factors from mitochondria (Danial, N. N. and Korsmeyer, S. J. 2004. *Cell* 116:205-19). Several Bcl-2 proteins reside at sub-cellular membranes, including the mitochondrial outer membrane, ER and nuclear membranes. The family consists of both death agonists and antagonists, which share sequence homology within one or more segments known as BCL-2 homology (BH) domains (FIG. 1). All anti-apoptotic members, such as BCL-2 and BCL-$X_L$, and a subset of pro-apoptotic family members, such as BAX and BAK, are "multi-domain" proteins sharing sequence homology within 3-4 BH domains. The "BH3-only" subset of pro-apoptotic molecules, including BAD, BID, BIM, NOXA and PUMA show sequence homology only within a single α helical segment, the BH3 domain, which is also known as the critical death domain (Wang, K. et al., 1996. *Genes Dev* 10:2859-69). BAX and BAK constitute a requisite gateway to the mitochondrial pathway of apoptosis in that cells doubly deficient for these proteins are resistant to all apoptotic stimuli that signal through the intrinsic pathway (Lindsten, T. et al., 2000. *Mol Cell* 6, 1389-99; Wei, M. C. et al., 2001. *Science* 292, 727-30). All BH3-only molecules operate upstream of BAX and BAK connecting proximal death and survival signals to the core apoptotic pathway (FIG. 2) (Cheng, E. H. et al., 2001. *Mol Cell* 8, 705-11; Zong, W. X. et al., 2001. *Genes Dev* 15, 1481-86). Upon receipt of death signals, BAX and BAK undergo allosteric activation at the mitochondria, resulting in permeabilization of the outer membrane and release of cytochrome c Wei, M. C. et al., 2000. *Genes Dev* 14, 2060-71) (FIG. 2).

The balance between anti- and pro-apoptotic sub-classes of BCL-2 molecules sets a "rheostat" that determines death susceptibility (Oltvai, Z. et al., 1993. *Cell* 74, 609-19). BH3-only pro-apoptotic molecules like BAD, BID, BIM actively adjust this "rheostat" and their function is dynamically regulated by distinct mechanisms, including transcriptional control and post-translational modifications. For example, cytosolic BID is activated upon cleavage by caspase-8, leading to mitochondrial translocation, BAX/BAK activation, and cytochrome c release (Li, H. et al., 1998. *Cell* 94, 491-501; Luo, X. et al., 1998. *Cell* 94, 481-90 1998). NOXA and PUMA are transcriptional targets of p53 with select roles in apoptosis induced by genotoxic stress (Nakano, K. et al., 2001. *Mol Cell* 7, 683-94; #328; Yu, J. et al., 2001. *Mol Cell* 7, 673-82). Additionally, BAD's pro-apoptotic activity is inhibited by phosphorylation in response to extra-cellular growth or survival factors (Zha, J. et al., 1996. *Cell* 87, 619-281996).

While in vitro studies show that overexpression of BH3-only molecules leads to apoptosis in a variety of cell lines, loss of function mouse models indicate that individual BH3-only proteins serve as cell death initiators responding to selected signals in restricted cell types. The cell type and signal-specific in vivo function of BH3-only molecules suggest that either the functional redundancy of these molecules is tissue type specific, or that BH3-only molecules may have distinct roles in other pathways. Indeed, recent discoveries have unraveled physiologic roles for BCL-2 family proteins beyond apoptosis. The following are but four examples of the integration of apoptosis with cellular homeostatic pathways.

(i) The BCL-2 Family Proteins and Cellular Metabolism:

We previously conducted a proteomic analysis of liver mitochondria, which revealed that the BCL-2 family protein BAD resides in a glucokinase (GK)-containing complex that regulates glucose driven whole cell respiration (Danial N. N. et al., 2003. *Nature* 424, 952-6) (FIG. 4). The Bad-null genetic model showed that BAD is needed for complex assembly and the non-phosphorylatable Bad 3SA knockin mouse model provided evidence that phosphorylated BAD is required for full mitochondria-tethered GK activity. Consistent with a role for BAD in supporting GK activity, both the Bad-deficient and the Bad 3SA animals display abnormal glucose homeostasis marked by fasting hyperglycemia and glucose intolerance. Because Bad-null and Bad 3SA represent loss and gain of function models for the pro-apoptotic activity of BAD, respectively, the common metabolic abnormalities in these animals suggested that the role of BAD in glucose metabolism may be distinct from its capacity to sensitize cells to apoptosis. Indeed the experiments presented in this application show specific roles for BAD in both pancreas and liver, each with significant physiologic consequences.

(ii) The BCL-2 Family Protein BID and Cellular Response to DNA Damage:

In response to DNA damage, cells either arrest from proliferation to allow sufficient time to repair their DNA or undergo apoptosis. The pro-apoptotic protein BID functions in both apoptosis and in DNA damage checkpoints within cells (Zinkel, S. et al., 2006. *Cell Death Differ* 13, 1351-9). Loss of BID results in genomic instability and myeloid malignancies (Zinkel, S. et al., 2003. *Genes Dev* 17, 229-39). BID is a substrate for DNA damage kinase ATM in the nucleus and modulates the intra-S phase checkpoint within cells with damaged DNA (Zinkel, S. et al., 2005. *Cell* 122, 579-91; Kamer, I. 2005. *Cell* 122, 593-603). Importantly, while the BH3 domain of BID is required for its apoptotic function at mitochondria, it is dispensable for its cell cycle checkpoint function in the nucleus (Zinkel, S. et al., 2005. *Cell* 122, 579-91) (FIG. 68).

(iii) The Cross Talk Between Protein Quality Control and Apoptosis:

Proper folding of proteins is essential for the functional integrity of the cells. Consequently, the cells have devised sophisticated mechanisms to ensure proper "protein homeostasis" (Rutkowski, D. T. and Kaufman, R. J. 2004. *Trends Cell Biol* 14, 20-8). Accumulation of misfolded proteins at the endoplasmic reticulum (ER), also known as ER stress, activates a cellular adaptive response referred to as UPR (Unfolded Protein Response). ER stress is implicated in the pathophysiology of multiple neurodegenerative diseases, including Huntington's Disease and Alzheimer's (Oakes, S. A. et al., 2006. *Curr Mol Med* 6, 99-109). The BCL-2 family proteins BAX and BAK were recently shown to be required for the proper execution of the signaling pathways involved in UPR by physically associating with several components of this pathway (Hetz, C. et al., 2006. *Science* 312:572-6). It has been proposed that BAX/BAK serve to link UPR at the ER with the core apoptotic machinery at the mitochondria and thus orchestrate the cellular response to misfolded proteins through either proper execution of an adaptive response or cell death.

(iv) BCL-2 Family Proteins and Regulation of Mitochondrial Morphology During Life and Death:

Mitochondrial shape and reticular structure is dynamically regulated by fusion and fission processes (Griparic, L. and Van der Bliek, A. M. 2001. *Traffic* 2, 235-44). This ensures exchange of material between different mitochondria and elimination of those organelles unfit for function. The dynamic changes in mitochondrial morphology directly impact the metabolic fitness of the cell. During apoptosis, mitochondria undergo fragmentation prior o caspase activation (Frank, S. et al., 2001. *Dev Cell* 1, 515-25). Several BCL-2 family proteins are implicated in these processes. Anti-apoptotic molecules BCL-2/BCL-$X_L$ have pro-fusion activity that seems to be preserved throughout evolution. This coincides with their capacity to bind mitofusion-2 (Mfn-2), a protein known to govern mitochondrial fusion (Delivani, P. et al., 2005. *Mol Cell* 21, 761-73). The pro-apoptotic BAX regulate the activity of Mfn-2 directly (Karbowski, M. et al., 2006. Nature 443, 658-62). It is noteworthy that the role of BCL-2 family members in mitochondrial dynamics is also essential in healthy cells that have not received a death stimulus. It has been suggested that the BH3 domain of BAX is required for regulation of mitochondrial dynamics (Karbowski, M. et al., 2006. Nature 443, 658-62). Thus the same domain in BAX has the capacity to regulate two distinct functions; apoptosis and mitochondrial shape.

Glucose Homeostasis, Diabetes and the Metabolic Syndrome

Type 2 diabetes mellitus (T2DM) is a multigenetic disease that includes multiple metabolic abnormalities that commonly manifest in a failed glucose tolerance. The basic physiological tenets of T2DM include abnormalities in insulin production and function (Saltiel, A. R. and Kahn, C. R. 2001. *Nature* 414, 799-806). This involves changes in the function of pancreas, muscle, fat and liver. Pancreatic β-cells and hepatocytes are the main glucose sensors within the body (Accili, D. 2004. *Diabetes* 53, 1633-42). In response to blood glucose fluctuation, β-cells secrete insulin in a dose responsive manner. Insulin in turn stimulates glucose uptake by peripheral tissues such as muscle and fat and prompts proper storage of glucose as glycogen in the liver. Pancreatic islets are also prone to adapt their mass in order to meet the insulin secretory demands in the body (Bell G. I. and Polonsky K. S., 2001. *Nature* 414, 788-91; Weir G. C. et al., 2001. *Diabetes* 50 Suppl 1, S154-9; DeFronzo R. A., 1988. *Diabetes* 37, 667-87; Accili D. et al., 2001. *Curr Mol Med* 1, 9-23). The lack of proper glucose sensing and/or mass adaptation by islets contribute to T2DM. Hepatocytes sense fluctuations in blood glucose and adjust their function to either produce glucose during fasting, which helps keep adequate glucose supply to the brain, or to store glucose as glycogen when blood glucose levels exceed their normal range (Cherrington, A. D. 1999. *Diabetes* 48, 1198-1214). In addition to the regulation of carbohydrate metabolism, insulin also impacts fat metabolism by suppressing lipolysis in fat cells (DeFronzo, R. A. 2004. Int J Clin Pract Suppl 143, 9-21). Insulin resistance is a state in which muscle, fat and liver are insensitive to the action of insulin. Metabolic syndrome is defined as a cluster of metabolic deficiencies that include insulin resistance, dyslipidemia (including abnormal levels of plasma triglycerides), obesity and diabetes (Reaven, G. M. 2004. *Diabetes Care* 27, 1011-12).

Glucose Metabolism and Cancer

Individual cells depend on the availability of growth/survival factors that characteristically regulate both cellular metabolism and cell survival (Plas, D. R. and Thompson, C. B. 2002. *Trends Endocrinol Metab* 13, 75-8). Cellular metabolism is a term used to describe a group of chemical reactions that take place in a living cell or organism where nutrients like glucose are broken down to yield energy for vital processes. Insulin, insulin-like-growth factor (IGF-1) and multiple cytokines transduce signals via PI3K through the serine/threonine kinase AKT and related kinases to regulate glucose transport and metabolism (Cheatham, B. and Kahn, C. R. 1995. *Endocr Rev* 16, 117-42). Signaling downstream of AKT impacts glucose metabolism by regulating the levels of glucose transporters (Glut 1 and Glut 4) (FIG. 3). Consequently, mice lacking AKT2 exhibit low levels of Glut4 and develop marked insulin resistance (Cho, H. et al., 2001. *Science* 292, 1728-31). A second mechanism whereby AKT regulates glucose metabolism is by stimulating recruitment of hexokinase (HK) to mitochondria (Robey, R. B. and Hay, N. 2006. *Oncogene* 25, 4683-96). Hexokinase is the enzyme that catalyzes the first step in glucose metabolism (glycolysis) converting glucose to glucose-6 phosphate. The molecular mechanism underlying mitochondrial localization of HK is not fully known. As mitochondria-associated hexokinase has immediate access to mitochondrial ATP and escapes product inhibition by glucose 6 phosphate (G6P), this may explain how activated AKT augments glucose-6 phosphorylating activity (Bustamante, E. and Pdersern, P. L. 1977. *Proc Natl Acad Sci USA* 74, 3735-39; Arora, K. K. and Pedersen, P. L. 1988. *J Biol Chem* 263, 17422-28). Activated AKT further promotes survival by stimulating expression of several anti-apoptotic proteins, such as BCL-$X_L$ and MCL-1 as well as phosphorylating several key cellular players, including Forkhead transcription factors, BAD and NFκB (Datta, S. R. et al., 1999. *Genes Dev* 13, 2905).

Resistance to apoptosis and increased cellular metabolism are common characteristics of tumors. BCL-2 was originally discovered due to its chromosomal translocation in follicular lymphoma. In addition, mouse models of BCL-2 family proteins clearly indicate that defects in apoptosis can be a primary oncogenic event (McDonnel, T. J. et al., 1989. *Cell* 57, 79-88; McDonnel, T. J. et al., *Nature* 349, 254-56). The chromosomal translocation in the Bcl-2 gene found in follicular lymphoma in humans juxtaposes the Bcl-2 coding sequence next to immunoglobulin (Ig) gene sequences. Importantly, recapitulating this chromosomal translocation using Bcl-2-Ig transgenic mice was sufficient to cause diffuse large-cell lymphoma over time. Likewise, several findings suggest that the pro-apoptotic BCL-2 family members may function as tumor suppressors in that their loss of function contributes to malignancy. Increased incidence of choroid plexus tumors in Bax-null mice expressing a truncated SV40 T antigen and of chronic myelomonocytic leukemia (CMML) in Bid-deficient mice reflect their importance in neuronal cell survival and myeloid homeostasis, respectively (Zinkel, S. et al., 2003. *Genes Dev* 17, 229-39; Yin, C. et al., 1997. Nature 385, 637-40). Bad-null mice progress to diffuse large B cell lymphoma (DLBCL) of germinal center origins (Ranger, A. M. et al., 2003. *Proc Natl Acad Sci USA* 100, 9324-29). This may reflect a potential role for BAD in regulating the cellular homeostasis of mature B cells as they migrate to germinal centers.

The relevance of cellular metabolism to malignancy was originally recognized by Warburg, who noted that tumors often display high glycolytic rates. Glycolysis accounts for ~60% of ATP within tumor cells and provides metabolic intermediates for synthesis of macromolecules including nucleic acids needed for DNA synthesis and their rapid proliferation. Indeed several well characterized oncogenes in human cancers, including Ras, Myc, Akt are known to target the glycolytic pathway (Semenza, G. L. 2001. *Novartis Found Symp* 240, 251-60). Warburg's hypothesis further suggested that high glycolytic rates might be due to impaired mitochondrial respiration; however, this finding has proven somewhat variable in tumors. Recent studies have shown that even in the presence of fully functional oxidative phosphorylation (OXPHOS) capacity by mitochondria, tumor cells preferentially support their bioenergetic demands through glycolysis (Fantin, V. R. et al., 2006. *Cancer Cell* 9, 425-34). This switch is required for tumor maintenance as interference with glycolysis is associated with a compensatory increase in OXPHOS concomitant with a decline in proliferative capacity of tumor cells. Possible rationale for this "glycolytic switch" in tumors may be that in addition to providing ATP at a faster rate, glycolytic products (mainly pyruvate) are used as intermediates for synthesis of fatty acids (FIG. 3). This ensures that tumor cells have sufficient supply of fatty acids for new membrane synthesis to keep up with the high rate of cellular proliferation. Furthermore, reliance on glycolysis rather than OXPHOS ensures that tumors can grow in the absence of oxygen (hypoxia) prior to vascularization (Gatenby. R. A. and Gillies, R. J. 2004. *Nat Rev Cancer* 4, 891-99). In several human tumors, multiple key enzymes involved in glucose metabolism exhibit increased activity when compared to normal tissues. These include hexokinase (HK), phosphofructokinase (PFK), pyruvate kinase (PK) and lactate dehydrogenase (LDH). Mechanisms underlying increased activity have been best studied in the case of HK enzymes and include increased expression (secondary to gene amplification and/or promoter activation), increased binding to mitochondria and/or a switch in gene expression from high (hexokinase IV) to low km (hexokinase I-III) isoforms (Rempel, A, et al., 1994. *Biochem J* 303, 269-74; Klimek, F. et al., 1993. *Carcinogenesis* 14, 1857-61; Mazurek, S. et al., 1999. *J cell Phyisol* 181, 136-46). These observations underscore the importance of targeting glycolysis or the use of glycolytic intermediate in specific pathways in tumors as a promising therapeutic strategy.

Recent evidence also suggests that obesity and metabolic syndrome are associated with high risk of cancer, including colorectal cancer (Gunter, M. J. and Leizmann, M. F. 2006. *J Nutr Biochem* 17, 145-56), breast cancer (Lorincz, A. M. 2006. *Endocr Relat Cancer* 13, 279-92) and prostate cancer (O'Malley, R. L. and Taneja, S. S. 2006. *Can J Urol Suppl* 2, 11-7). Although, the molecular links between these metabolic abnormalities and cancer is not fully understood, several studies suggest that elevated levels of plasma insulin, as seen in insulin resistant state, activates cellular proliferation in epithelial cells. Furthermore, insulin can increase the levels of Insulin-like Growth Factor 1 (IGF-1), a growth hormone with significant proliferative and anti apoptotic activity (Cowey, S, and Hardy, R. W. 2006. *Amer J Pathol* 169, 1505-22). Insulin and IGF-1 also regulate the sex steroids, which in turn modulate the activity of estrogen and androgens and consequently development of cancers dependent on sex hormones, including breast and prostate cancers (Calle, E. E. and Kaaks, R. 2004. *Nat Rev Cancer* 4, 579-91). Furthermore, hormones produced by fat cells, adipokines, have proliferative, angiogenic and pro-inflammatory effects. Adipokines influence cancer cells either directly through these effects or indirectly by causing insulin resistance (and thus hyperinsulinemia) (Cowey, S, and Hardy, R. W. 2006. *Amer J Pathol* 169, 1505-22).

SUMMARY OF THE INVENTION

The ability of select BCL-2 family proteins to toggle between distinct functions is a critical aspect of their physiologic activity. The present invention is based on the discovery that the pro-apoptotic BCL-2 family member BAD regulates the efficiency of mitochondria to use glucose as a fuel through mechanisms that can be targeted and mimicked distinctively from its capacity to activate the apoptotic machinery at the mitochondria. In both liver and pancreas, two major tissues involves in regulation of blood sugar, BAD modulates the activity of a key glucose sensor in mammalians, glucokinase (Hexokinase IV). The molecular mechanisms by which BAD achieves dual roles is mediated by its bioactive BH3 domain. Specifically, the phosphorylation status of a key residue, which can be mimicked and manipulated genetically and chemically, is found to instruct BAD to assume either a metabolic or an apoptotic function. Phosphorylated BAD or its mimietics regulate glucokinase activity, glucose-driven mitochondrial respiration and insulin secretion in β-cells of the pancreas and simultaneously endow them with an advantageous adaptive response in an insulin resistant state (FIG. 4). This is one of many examples provided herein as to the significance and benefits of genetic and chemical manipulation of cellular homeostatic pathways and cell survival through BCL-2 family regulators known to carry dual roles in apoptosis and other cellular physiologic pathways. Importantly, this regulation can be manipulated by a peptidic compound containing a phosphomimetic moiety and has significant potential in treating human disease.

The present invention provides for both prophylactic and therapeutic methods of treating a subject at risk of (or susceptible to) a disorder or having a disorder associated with aberrant (e.g., insufficient or excessive) glucose metabolism or extrinsic or intrinsic apoptotic pathway abnormalities.

Diabetes (e.g., Type I or Type II) is treated or the onset is delayed by administering to a subject in need thereof a composition containing a BAD BH3 domain peptide or mimetic thereof. The subject is for example, hyperglycemic, obese or insulin resistant.

β-cell survival is increased by contacting a β-cell with a composition contacting a BAD BH3 domain peptide or mimetic thereof. In various aspects the cell is contacted prior to or after transplantation into a subject.

Insulin secretion is induced or glucokinase activity is increased by exposing, e.g., contacting a tissue (e.g., pancreas tissue) or cell (e.g., β-cells) with a BAD BH3 peptide or mimetic.

Tumor growth is modulated or a tumor cell is sensitized to a therapeutic agent, e.g., chemotherapeutic agent or radiation by contacting tumor cell with a BH3 domain peptide or mimetic thereof.

The cell cycle or a homeostatic pathway is modulated by contacting a cell with a BH3 domain peptide or mimetic thereof. The cell is a liver cell or a neuronal cell.

The BH3 domain peptide, BAD BH3 domain peptide or mimetic thereof is phosphorylated. Preferably, the alpha helical structure BH3 domain peptide or BAD BH3 domain peptide is stabilized. For example the peptides are stabilized by hydrocarbon stapling or chemical cross-linking The BAD BH3 domain peptide comprises the amino acid sequence of SEQ ID NO: 1-3 and 5-17 or fragments thereof.

Also included in the invention is a peptide having the amino acid sequence of SEQ ID NO 1, 2 or 3, wherein $X_3$ is phosphorylated or SEQ ID NO 4-17, wherein $X_1$ is phosphorylated.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In the case of conflict, the present specification, including definitions, will control. In addition, the materials, methods, and examples are illustrative only and are not intended to be limiting.

Other features and advantages of the invention will be apparent from the following detailed description and claims.

BRIEF DESCRIPTION OF THE DRAWINGS

FIG. 67 lists the phosphorylation sites within the BH3 sequences of multiple BCL-2 family proteins defined through bioinformatics and subsequently tested. Derivatization of these sites in BH3 mimetic compounds will allow manipulation of BCL-2 family proteins that toggle between apoptosis and other homeostatic function.

DETAILED DESCRIPTION OF THE INVENTION

Figure 1:
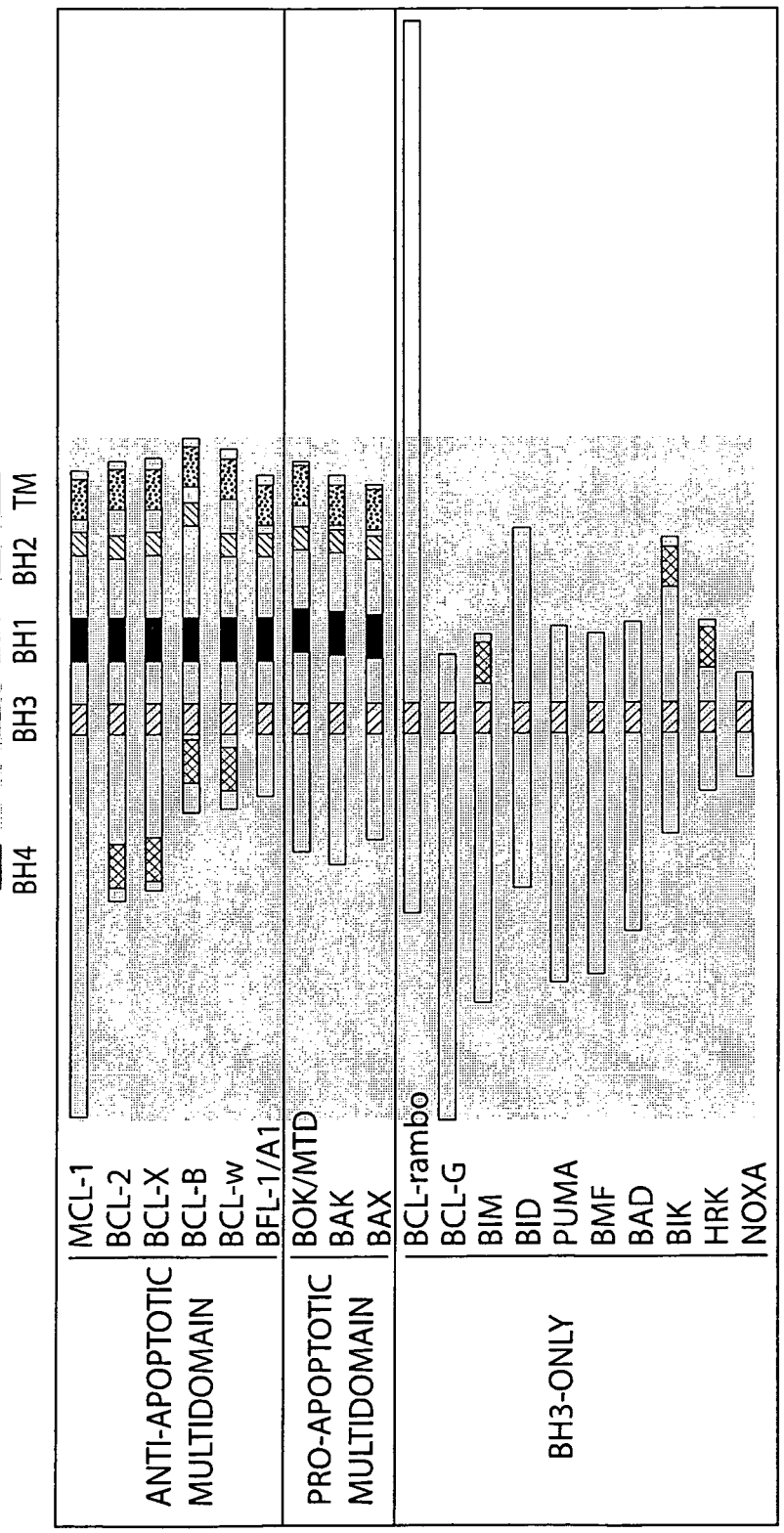
FIG. 1 is a diagram showing the BCL-2 family members having one or more conserved BCL-2 homology (BH) domains.

The present invention is based in part on the discovery that the pro-apoptotic BCL-2 family member BAD resides in a glucokinase-containing complex that regulates glucose-driven respiration. More specifically, the invention is based on the discovery of a physiologic role for BAD in glucose-stimulated mitochondrial respiration, glucose sensing and glucose-stimulated insulin secretion by pancreatic β-cells through modulation of β-cell glucokinase. BAD's novel function is specifically dependent upon phosphorylation of its BH3 sequence, previously defined as an essential death domain. Chemically stabilized versions of a phosphorylated BAD BH3 domain peptide were used to restore glucokinase activity glucose-driven mitochondrial respiration and insulin secretion in BAD-deficient islets was corrected. Thus, the BH3 domain of BAD modulates two separate functions: apoptosis and metabolism. Importantly, phosphorylation of a defined serine residue within the BH3 sequence constitutes a molecular switch that instructs BAD to assume a metabolic role. Signaling by growth and survival factors impacts both cellular metabolism and the core apoptotic machinery. Multiple recent studies have assigned novel roles to BCL-2 family proteins in normal homeostatic pathways, such as glucose metabolism, ER $Ca^{2+}$ homeostasis, and the DNA damage response. Whether these novel roles represent separate functions for these proteins that are otherwise known as regulators of cell death is under active investigation. The pro-apoptotic protein BAD belongs to a subset of BCL-2 family members that share a conserved amphipathic α-helical BH3 motif. The pro-apoptotic activity of BAD is regulated by phosphorylation mediated by kinases localized to the mitochondrial membrane. To elucidate BAD's role at the mitochondrion, proteomic analysis of liver mitochondria was conducted which revealed that BAD resides in a glucokinase (GK)-containing complex that regulates glucose-driven respiration. The Bad-null genetic model showed that BAD is needed for complex assembly and the non-phosphorylatable Bad 3SA knockin mice provided evidence that phosphorylated BAD is needed for full activation of mitochondrial-tethered GK (Danial N. N. et al., 2003. Nature 424, 952-6). Consistent with a role for BAD in modulating GK activity, both the Bad-deficient and the Bad 3SA animals displayed abnormal glucose homeostasis. Because Bad-null and Bad 3SA represent loss and gain of function models for the pro-apoptotic activity of this molecule, respectively, the common metabolic abnormalities in these animals suggested that the role of BAD in glucose metabolism may be distinct from its capacity to sensitize cells to apoptosis. GK is mainly expressed in hepatocytes and pancreatic β-cells and constitutes a key component of the mammalian glucose sensing machinery. In the liver, GK controls glycogen synthesis and glucose output, whereas in the pancreas it regulates insulin secretion by β-cells. Thus, the glucose homeostasis defect observed in Bad mouse models may derive from deficiencies in either or both tissues. Genetic approaches and novel chemical tools elucidated an essential role for BAD in regulating glucose-stimulated insulin secretion (GSIS) by β-cells.

Accordingly, the invention provides methods of treating, alleviating a symptom of or delaying the onset of diabetes and obesity by administering to a subject a derivatized BAD BH3 domain peptide or mimetic thereof. Furthermore, the invention provides methods of improving the survival and function of islet transplants in subjects suffering from loss of β-cell mass.

BH3 Peptides and Mimetics

A BH3 peptide contains the amphipathic α-helical BH3 domain from the Bcl-2 family protein. A BH3 peptide includes a BH3 domain from BID, NOXA, BAD, BNIP3, HRK, NIX, SPIKE, BAK, BAX, BOK, BCL-2, BCL-XL, BCL-W, MCL-1, PUMA, BIK, BIM and other BH3-domain containing homologues. No particular length is implied by the term "peptide". The term "peptide" is meant s two or more naturally or synthetic amino acids linked by a covalent bond (e.g., an amide bond).

A BH3 domain peptide is less than 195 amino acids in length, e.g., less than or equal to 150, 100, 75, 50, 35, 25, 15 or 10 amino acid in length. Preferably, the BH3 domain peptide is less than 25 amino acids. The term "peptide" further includes two or more naturally or synthetic amino acids linked by a covalent bond (e.g., an amide bond). The term "amino acid" refers to a molecule containing both an amino group and a carboxyl group. Suitable amino acids include, without limitation, both the D- and L-isomers of the 20 common naturally occurring amino acids found in peptides (e.g., A, R, N, C, D, Q, E, G, H, I, L, K, M, F, P, S, T, W, Y, V (as known by the one letter abbreviations)) as well as the naturally occurring and unnaturally occurring amino acids prepared by organic synthesis or other metabolic routes.

The BH3 peptides are phosphorylated at one or more Serine, Threoine or Tyrosine residues. Alternatively, the BH3 peptides are phosphopeptide mimetic. By phosphopeptide mimetic is meant that phosphopeptide mimetic closely approximates the functionality of natural phosphorylated residue. For example, the phoshorylatable amino acids are replaced with amino acids that mimic the negative charge of the phosphorus atom, such as glutamic acid or aspartic acid. Preferably, the phosphopeptide mimetic is chemically stable (e.g. resistant to dephosphorylation by phosphatases, For example, the phosphopeptide mimetics contains a non-hydrolyzable linkage between the carbon backbone and the phosphorous atom. This is achieved, with a synthetic molecule that comprises the amino acid atomic structure with a non-hydrolyzable linkage to a phosphate moiety, in lieu of the naturally occurring oxygen bridge. For example, a $CF_2$ group links the amino acid to the phosphate. Mimetics of several amino acids which are phosphorylated in nature can be generated by this approach. Mimetics of phosphoserine, phosphothreonine, and phosphotyrosine are generated by placing a $CF_2$ linkage from the appropriate carbon to the phosphate moiety. Optionally, the mimetic molecule L-2-amino-4-(diethylphosphono)-4,-4-difluorobutanoic acid substitutes for phosphoserine (Otaka et al., Tetrahedron Letters 36: 927-930 (1995)), L-2-amino-4-phosphono-4,-4-difluoro-3-methylbutanoic acid substitutes for phospho-threonine, and L-2-amino-4-phosphono (difluoromethyl) phenylalanine substitutes for phosphotyrosine. Other methods of making a non-hydrolyzable linkage or otherwise stable phosphomimetics are known to those skilled in the art Phosphomimetics of serine, threonine, and tyrosine employ species that mimic the electronic properties of the phosphate group as well as prevent hydrolysis of the phosphate group by endogenous cellular phosphatases, thus maintaining the biological properties and activity of the phosphopeptide. There are two approaches which possess the above properties currently in mainstream usage by the biomedical research community.

Aspartic acid and glutamic acid both approximate the side chain and net negative charge of phosphoserine, phosphothreonine, and phosphotyrosine, and have found utility for their ease of incorporation and simplicity. (Hao, Lowy et al. 1996; Fu, Subramanian et al. 2000; Modrof, Moritz et al. 2001) More exact mimics of non-hydrolyzable phosphoserine/phosphothreonine/phosphotyrosine mimetics include phosphonomethylene alanine (Pma), (Shapiro, Buechler et al. 1993) phosphonodifluoromethylene alanine (Pfa), (Berkowitz, Eggen et al. 1996) phosphonomethylene phenylalanine (Pmp), (Burke, Russ et al. 1991), phosphonodifluoromethylene phenylalanine (F2Pmp), (Burke, Smyth et al. 1994) with both substituting the labile oxygen of the phosphate group with a non-labile carbon. These more precise phosphomimetics are more useful because they maintain more of the native hydrogen bonding potential than would be possible with aspartic acid and glutamic acid phosphomimetics.

A BAD BH3 domain peptide includes an α-helical BH3 domain from BAD. An exemplary BAD BH3 domain peptide includes the sequence:

```
[Xaa]_n YGR ELRX_1X_2X_3DX_1 [Xbb]_n    (SEQ ID NO: 1)
``` wherein; X1 and X2 is any natural or non-natural amino, X3 is G, D, E, S, T, Y, or phosphomimetics thereof. For example, X2 is norleucine.

Xaa and Xbb is independently an amino acid and N is an integer from 0-10.

Other examples of BAD-like BH3 at least 5, 6, 7, 8, 9, 10, 11, 12, 13, 14, 15 or more amino acids of:

```
1          11          21
NLWAAQRYGR ELRRMSDEFV DSFKK;    (SEQ ID NO: 2)

1          11          21
NLWAAQRYGR ELRRMDDEFV DSFKK     (SEQ ID NO: 3)
```

Figures 2, 18:
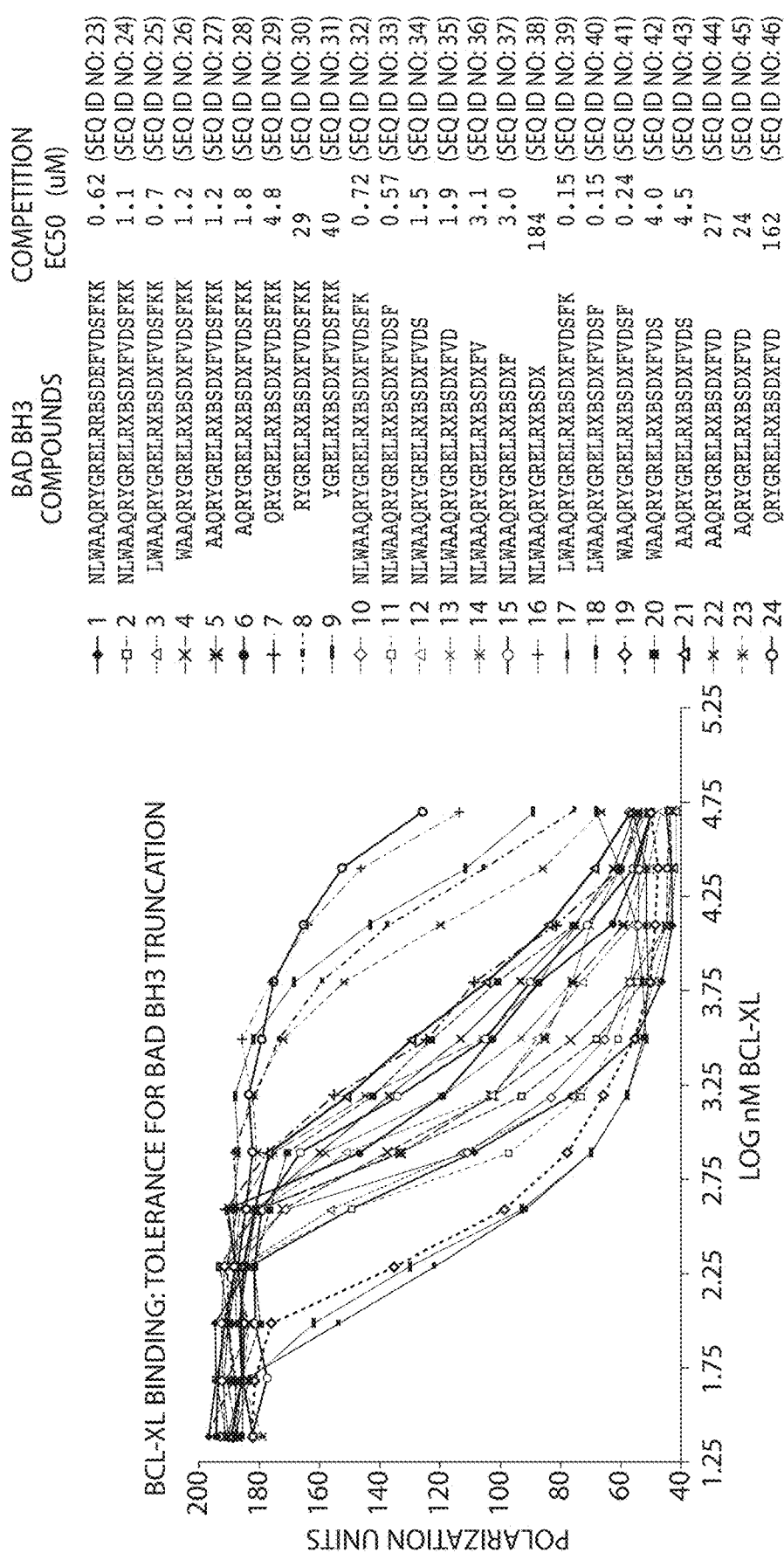
FIG. 18 is a chart listing the SAHB compounds used in (c). Conserved L151 and D156 residues within the BAD and BID BH3 domains are highlighted in yellow and S155 is marked in grey. Residues altered in different SAHB compounds are marked in green. $N_L$ in BID SAHB$_A$: Norleucine, *: The S5 non-natural amino acid (see FIG. 33). The truncation library of BAD BH3 compounds and their capacity of binding to BCL-X$_L$ is shown. The complete list of BAD SAHB derivatives generated to date, including the phosphomimetic compounds and compounds for target capture and SAHB-based immunoprecipitation or crosslinking is provided.

NLWAAQRYGR ELRRMDDEFV DSFKK (SEQ ID NO:3) or SEQ ID NO:18-87 as shown in FIG. 18.

In preferred embodiments $X_1$ is either S5 or aminobutyric acid and $X_2$ preferably is norleucine. When $X_{1s}$ are S5, the S5 amino acids can be reacted to form an all hydrocarbon crosslink. Preferably, the $X_3$ amino acid is modified such that is contains a net negative charge mimicking a phosphate moiety or modified such that the net negative charge is masked so it enter the cell. For example the $X_3$ amino acid is phosphorylated, sulphonated, oxygenated, nitrated or fluorinated or a functional equivalent thereof. Optionally the $X_3$ amino acid has undergone esterification or sterification.

In various embodiments $[Xaa]_n$ is R, QR, AQR, AAQR (SEQ ID NO: 102), WAAQR (SEQ ID NO: 103), LWAAQR (SEQ ID NO: 104) or NLWAAQR (SEQ ID NO: 105) and $[Xbb]_n$ V, VD, VDS, VDSF (SEQ ID NO: 106), VDSFK (SEQ ID NO: 107), or VDSFKK (SEQ ID NO: 108).

A BID BH3 domain peptide includes an α-helical BH3 domain from BID. An exemplary BID BH3 domain peptide includes the sequence:
EX_1QEDIIRNIARHLAX_2VGDX_3MDR X_4I (SEQ ID NO:4)
wherein; $X_1$ and/or $X_4$ is G, D, E, S, T, Y or phosphomimetics thereof and $X_2$ or $X_3$ is any natural or non-natural amino acid. In preferred embodiments $X_2$ and $X_3$ are both S5. When $X_2$ and $X_3$ are both S5, the S5 amino acid can be reacted to form an all-hydrocarbon crosslink. Preferably, the $X_1$ amino acid is modified such that is contains a net negative charge mimicking a phosphate moiety or modified such that the net negative charge is masked so it can enter the cell. For example the $X_1$ and/or the $X_4$ amino acid is phosphorylated, sulphonated, oxygenated, nitrated or fluorinated. For example, $X_1$ is D, E, S, T, Y or phosphomimetics thereof. In some embodiments X2 is Q and or X3 is S, T or Y. Optionally when X3 is S, T, or Y the amino acid is phosphorylated, sulphonated, oxygenated, nitrated or fluorinated.

Also included in the invention are BH3 peptides derived from other BH3 domain containing peptides; these peptides and phosphomimetics thereof are useful in modulating enzymatic activities (e.g. kinases and phosphatases) and protein-protein interactions (e.g., MCL-1/BAK interactions and therefore are involved in the manipulation of many cellular homeostatic pathways. (See, FIG. 67) Exemplary BH3 peptides included SEQ ID NO:5-17 shown below.

```
BNIP3 BH3
                                            (SEQ ID NO: 5)
DIERRKEVEX₁ILKKNX₁X₁WIWX₁WX₁X₁R

HRK BH3
                                            (SEQ ID NO: 6)
X₁X₁AAQLX₁AARLKALGDELHQRX₁MWRRRARX₁

NIX BH3
                                            (SEQ ID NO: 7)
X₁X₁QX₁EEEVVEGEKEVEALKKSADWVX₁DWX₁X₁RPENIPPKEF

BID BH3
                                            (SEQ ID NO: 8)
X₁QEDIIRNIARHLAQVGDSMDRX₁I

NOXABH3
                                            (SEQ ID NO: 9)
AELEVECAX₁QLRRFGDKLNFRQKLLNLIX₁

SPIKE BH3
                                            (SEQ ID NO: 10)
LEAELDALGDELLADEDX₁X₁Y

BAK BH3
                                            (SEQ ID NO: 11)
LQPX₁X₁X₁MGQVGRQLAIIGDDINRRX₁DX₁E

BAX BH3
                                            (SEQ ID NO: 12)
QDAX₁TKKLX₁ECLKRIGDELDX₁N

BOK BH3
                                            (SEQ ID NO: 13)
PGRLAEVCAVLLRLGDELEMIRPX₁

BCL-2 BH3
                                            (SEQ ID NO: 14)
X₁PVPPVVHLX₁RQAGDDFX₁RRYRRD

BCL-XLBH3
                                            (SEQ ID NO: 15)
AVKQALREAGDEFELRX₁RRAF X₁

BCL-WBH3
                                            (SEQ ID NO: 16)
HQAMRAAGDEFETRFRRX₁FX₁D

MCL-1 BH3
                                            (SEQ ID NO: 17)
X₁X₁RKALEX₁LRRVGDGVQRNH
```

Wherein $X_1$ is any natural or non-natural amino acid. Preferably $X_1$ is, E, D S, T or Y or a phosphomimetic thereof.

In these and other embodiments, non-natural amino acids (e.g. S5) in the BH3 peptides are located either upstream or downstream of $X_1$ to allow for hydrocarbon stapling. The non-natural amino acids are 2, 3, 4, 5, 6, 7, 8, 9 or 10 amino acid residues apart from each other. For example, the two non-natural amino acids are one or two helical turns (i.e., about 3.4 or about 7 amino acids) apart from each other. Accordingly, amino acids positioned at i and i+3; i and i+4; or i and i+7 are ideal candidates for chemical modification and crosslinking. Thus, for example, where a peptide has the sequence $Xaa_1$, $Xaa_2$, $Xaa_3$, $Xaa_4$, $Xaa_5$, $Xaa_6$, $Xaa_7$, $Xaa_8$, $Xaa_9$ . . . , crosslinks between $Xaa_1$ and $Xaa_4$, or between $Xaa_1$ and $Xaa_5$, or between $Xaa_1$ and $Xaa_8$ are useful as are crosslinks between $Xaa_2$ and $Xaa_5$, or between $Xaa_2$ and $Xaa_6$, or between $Xaa_2$ and $Xaa_9$, etc.

The BH3 peptides can be polymers of L-amino acids, D-amino acids, or a combination of both. For example, in various embodiments, the peptides are D retro-inverso peptides. The term "retro-inverso isomer" refers to an isomer of a linear peptide in which the direction of the sequence is reversed and the chirality of each amino acid residue is inverted. See, e.g., Jameson et al., *Nature,* 368, 744-746 (1994); Brady et al., Nature, 368, 692-693 (1994). The net result of combining D-enantiomers and reverse synthesis is that the positions of carbonyl and amino groups in each amide bond are exchanged, while the position of the side-chain groups at each alpha carbon is preserved. Unless specifically stated otherwise, it is presumed that any given L-amino acid sequence of the invention may be made into a D retro-inverso peptide by synthesizing a reverse of the sequence for the corresponding native L-amino acid sequence.

Optionally, the BH3 peptides include chemically-modified amino acids, including amino acid analogs (such as penicillamine, 3-mercapto-D-valine), naturally-occurring non-proteogenic amino acids (such as for example, norleucine, β-alanine, ornithine, taurine hydroxyproline or hydroxylysine), and chemically-synthesized compounds that have properties known in the art to be characteristic of an amino acid. The term "proteogenic" indicates that the amino acid can be incorporated into a protein in a cell through well-known metabolic pathways. Additionally the BH3 peptides include non-natural amino acids such as the R and S enantiomers of the 5-carbon olefinic amino acid and the S enantiomer of the 8-carbon olefinic amino acid.

Also included in the invention are peptides that biologically or functional equivalent to the peptides described herein. The term "biologically equivalent" or functional equivalent" is intended to mean that the compositions of the present invention are capable of demonstrating some or all of the same glucose stimulated insulin secretion modulatory effects or homeostatic pathway regulation, although not necessarily to the same degree as the BH3 domain polypeptide deduced from sequences identified from cDNA libraries of human, rat or mouse origin or produced from recombinant expression symptoms.

BH3 peptides can also include derivatives of BH3 peptides which are intended to include hybrid and modified forms of BH3 peptides including fusion proteins and BH3 peptide fragments and hybrid and modified forms in which certain amino acids have been deleted or replaced and modifications such as where one or more amino acids have been changed to a modified amino acid or unusual amino acid and modifications such as glycosylation so long as the hybrid or modified form retains the biological activity of BH3 peptides. The terms induced and stimulated are used interchangeably throughout the specification. Biological activity of the BH3 peptides includes simulation of physiologic BAD activity and restoration of glucose-stimulated insulin homeostasis and other consequences of BAD deficiency. Biological activity also included binding to its natural ligand.

Preferred variants are those that have conservative amino acid substitutions made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). In addition, non-natural amino acids may be incorporated. Thus, a predicted nonessential amino acid residue in a BH3 domain polypeptide is replaced with another amino acid residue from the same side chain family. Alternatively, in another embodiment, mutations can be introduced randomly along all or part of a BH3 coding sequence (thus including mutation at non-essential and essential sites), such as by saturation mutagenesis, and the resultant mutants can be screened to identify mutants that retain activity. Also included within the meaning of substantially homologous is any BH3 peptide which may be isolated by virtue of cross-reactivity with antibodies to the BH3 peptide described herein or whose encoding nucleotide sequences including genomic DNA, mRNA or cDNA may be isolated through hybridization with the complementary sequence of genomic or subgenomic nucleotide sequences or cDNA of the BH3 peptides herein or fragments thereof.

Derivatives, variants and analogs may be full length or other than full length, if the derivative or analog contains a modified nucleic acid or amino acid. Derivatives or analogs of the BH3 peptides include, e.g., molecules including regions that are substantially homologous to the peptides, in various embodiments, by at least about 30%, 50%, 70%, 80%, or 95%, 98%, or even 99%, identity over an amino acid sequence of identical size or when compared to an aligned sequence in which the alignment is done by a computer homology program known in the art. For example sequence identity can be measured using sequence analysis software (Sequence Analysis Software Package of the Genetics Computer Group, University of Wisconsin Biotechnology Center, 1710 University Avenue, Madison, Wis. 53705), with the default parameters therein.

In various embodiments, the BH3 peptide maintains its secondary structure, e.g. α-helical structure. Methods of helix stabilization are known in the art.

Preferably, the BH3 peptide is a stable peptide. By "stable" it is meant that the peptide possess stability sufficient to allow the manufacture and which maintains the integrity of the compound for a sufficient period of time to be useful for the purposes detailed herein. For example the peptides are covalently stabilized using polar and or labile crosslinks (Phelan et al. 1997 J. Am. Chem. Soc. 119:455; Leuc et al. 2003 Proc. Nat'l. Acad. Sci. USA 100:11273; Bracken et al., 1994 J. Am. Chem. Soc. 116:6432; Yan et al. 2004 Bioorg. Med. Chem. 14:1403). Alternatively, the peptides are stabilized using the metathesis-based approach, which employed .alpha., .alpha.-disubstituted non-natural amino acids containing alkyl tethers (Schafmeister et al., 2000 J. Am. Chem. Soc. 122:5891; Blackwell et al. 1994 Angew Chem. Int. Ed. 37:3281). Preferably the peptides are stabilized using hydrocarbon stapling. Stapled peptides are chemically braced or "stapled" peptides so that their shape, and therefore their activity, is restored and/or maintained. Stably cross-linking a polypeptide having at least two modified amino acids (a process termed "hydrocarbon stapling") can help to conformationally bestow the native secondary structure of that polypeptide. For example, cross-linking a polypeptide predisposed to have an alpha-helical secondary structure can constrain the polypeptide to its native alpha-helical conformation. The constrained secondary structure can increase resistance of the polypeptide to proteolytic cleavage and also increase hydrophobicity. Stapled BH3 peptides are produced for example, as described in WO05044839A2, herein incorporate by reference in its entirety. Alternatively, the BH3 peptides are cyclic peptides. Cyclic peptides are prepared by methods known in the art. For example, macrocyclization is often accomplished by forming an amide bond between the peptide N- and C-termini, between a side chain and the N- or C-terminus [e.g., with $K_3Fe(CN)_6$ at pH 8.5] (Samson et al., *Endocrinology,* 137: 5182-5185 (1996)), or between two amino acid side chains. See, e.g., DeGrado, *Adv Protein Chem,* 39: 51-124 (1988).

Alternatively, the BH3 domain is a non-natural ligand, e.g., a mimetic. Exemplary BH3 mimetic includes Gossypol, ABT263 and ABT 737. Other BH3 mimetic include those described in Cell Death and Differentiation (2006) 13: 1339-1350, the contents of which are hereby incorporated by reference in its entirety. A BH3 domain mimetic is an agent that is capable of binding Bcl-2 family members and inducing one or more BH3 activities. Mimetics include for example, polypeptides, such as antibodies, cell ghosts, or small molecules. Small molecules include, but are not limited to, peptides, peptidomimetics (e.g., peptoids), amino acids, amino acid analogs, peptidenucleic acids, peptide-nucleic acid conjugates, polynucleotides, polynucleotide analogs, nucleotides, nucleotide analogs, organic and inorganic compounds (including heterorganic and organometallic compounds) having a molecular weight less than about 5,000 grams per mole organic or inorganic compounds having a molecular weight less than about 2,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds.

BH3 peptides or mimetic thereof are operatively (e.g., covalently) linked to a non-BH3 peptide to form a chimeric species. A non-BH3 peptide refers to a polypeptide having an amino acid sequence corresponding to a protein that is not substantially homologous to the BH3 peptide. The non-BH3 peptide allows the addition of a functionality to the BH3 peptide. For example the non-BH3 peptide is a translocation sequence, a GST protein or a portion of an immunoglobulin molecule, e.g. the Fc region, or a nucleic acid derivative.

The BH3 peptides described herein may likewise be conjugated to detectable groups such as biotin, radiolabels (e.g., 35 S, 125 I, 131 I, 111 In), enzyme labels (e.g., horseradish peroxidase, alkaline phosphatase), and fluorescent labels (e.g., fluorescein) in accordance with known techniques.

BH3 peptides are easily prepared using modern cloning techniques, or may be synthesized by solid state methods or by site-directed mutagenesis. A domain BH3 peptide may include dominant negative forms of a polypeptide. In one embodiment, native BH3 peptides can be isolated from cells or tissue sources by an appropriate purification scheme using standard protein purification techniques. In another embodiment, BH3 domain polypeptides are produced by recombinant DNA techniques.

Alternative to recombinant expression, BH3 peptides are synthesized chemically using standard peptide synthesis techniques. Synthetic chemistry transformations and protecting group methodologies (protection and deprotection) useful in synthesizing the compounds described herein are known in the art and include, for example, those such as described in R. Larock, Comprehensive Organic Transformations, VCH Publishers (1989); T. W. Greene and P. G. M. Wuts, Protective Groups in Organic Synthesis, 2d. Ed., John Wiley and Sons (1991); L. Fieser and M. Fieser, Fieser and Fieser's Reagents for Organic Synthesis, John Wiley and Sons (1994); and L. Paquette, ed., Encyclopedia of Reagents for Organic Synthesis, John Wiley and Sons (1995), and subsequent editions thereof. The peptides of this invention can be made by chemical synthesis methods, which are well known to the ordinarily skilled artisan. See, for example, Fields et al., Chapter 3 in Synthetic Peptides: A User's Guide, ed. Grant, W. H. Freeman & Co., New York, N.Y., 1992, p. 77. Hence, peptides can be synthesized using the automated Merrifield techniques of solid phase synthesis with the α-$NH_2$ protected by either t-Boc or F-moc chemistry using side chain protected amino acids on, for example, an Applied Biosystems Peptide Synthesizer Model 430A or 431.

One manner of making of the peptides described herein is using solid phase peptide synthesis (SPPS). The C-terminal amino acid is attached to a cross-linked polystyrene resin via an acid labile bond with a linker molecule. This resin is insoluble in the solvents used for synthesis, making it relatively simple and fast to wash away excess reagents and by-products. The N-terminus is protected with the Fmoc group, which is stable in acid, but removable by base. Any side chain functional groups are protected with base stable, acid labile groups. Longer peptides could be made by conjoining individual synthetic peptides using native chemical ligation. Alternatively, the longer synthetic peptides can be synthesized by well known recombinant DNA techniques. Such techniques are provided in well-known standard manuals with detailed protocols. To construct a gene encoding a peptide of this invention, the amino acid sequence is reverse translated to obtain a nucleic acid sequence encoding the amino acid sequence, preferably with codons that are optimum for the organism in which the gene is to be expressed. Next, a synthetic gene is made, typically by synthesizing oligonucleotides which encode the peptide and any regulatory elements, if necessary. The synthetic gene is inserted in a suitable cloning vector and transfected into a host cell. The peptide is then expressed under suitable conditions appropriate for the selected expression system and host. The peptide is purified and characterized by standard methods.

The peptides can be made in a high-throughput, combinatorial fashion, e.g., using a high-throughput polychannel combinatorial synthesizer available from Advanced Chemtech.

An "isolated" or "purified" protein or biologically active portion thereof is substantially free of cellular material or other contaminating proteins from the cell or tissue source from which the BH3 peptide is derived, or substantially free from chemical precursors or other chemicals when chemically synthesized. The language "substantially free of cellular material" includes preparations of BH3 peptides in which the protein is separated from cellular components of the cells from which it is isolated or recombinantly produced. In one embodiment, the language "substantially free of cellular material" includes preparations of BH3 peptides having less than about 30% (by dry weight) of non-BH3 peptide a (also referred to herein as a "contaminating protein"), more preferably less than about 20% of non-BH3 peptide and/or non-transduction domain peptides, still more preferably less than about 10% of non-BH3 peptide, and most preferably less than about 5% non-BH3 peptide and/or non-transduction domain peptides. When the BH3 peptide or biologically active portion thereof is recombinantly produced, it is also preferably substantially free of culture medium, i.e., culture medium represents less than about 20%, more preferably less than about 10%, and most preferably less than about 5% of the volume of the protein preparation.

The language "substantially free of chemical precursors or other chemicals" includes preparations of BH3 peptides in which the protein is separated from chemical precursors or other chemicals that are involved in the synthesis of the protein. In one embodiment, the language "substantially free of chemical precursors or other chemicals" includes preparations of BH3 peptides having less than about 30% (by dry weight) of chemical precursors or non-BH3 peptide and/or non-transduction domain peptides chemicals, more preferably less than about 20% chemical precursors or non-BH3 peptide and/or non-transduction domain peptides chemicals, still more preferably less than about 10% chemical precursors or non-BH3 peptide chemicals, and most preferably less than about 5% chemical precursors or non-BH3 peptide and/or non-transduction domain peptides chemicals.

Therapeutic Methods

The present invention provides for both prophylactic and therapeutic methods of treating a subject at risk of (or susceptible to) a disorder or having a disorder associated with aberrant (e.g., insufficient or excessive) glucose metabolism or extrinsic or intrinsic apoptotic pathway abnormalities. As used herein, the term "treatment" is defined as the application or administration of a therapeutic agent to a patient, or application or administration of a therapeutic agent to an isolated tissue or cell line from a patient, who has a disease, a symptom of disease or a predisposition toward a disease, with the purpose to cure, heal, alleviate, relieve, alter, remedy, ameliorate, improve or affect the disease, the symptoms of disease or the predisposition toward disease.

Insulin secretion is induced by exposing, e.g., contacting a tissue (e.g., pancreas tissue) or cell (e.g., β-cells) with a BAD BH3 peptide or mimetic. By inducing is meant an increase in insulin production compared to a tissue or cell that has not been in contact with BAD BH3 peptide or mimetic. Tissues or cells are directly contacted with BAD BH3 peptide or mimetic. Alternatively, the BAD BH3 peptide or mimetic is administered systemically. BAD BH3 peptide or mimetics are administered in an amount sufficient to increase (e.g., activate) glucokinase activity, increase intracellular Ca2+ concentration or lower blood glucose levels. Insulin secretion is measured by known in the art, such as for example an insulin specific ELISA assay. Alternatively, insulin secretion is evaluated by measuring blood glucose levels. A return to baseline (e.g. normal) glucose levels also indicates an increase in insulin secretion.

β-cell survival is increased by exposing, a β-islet cell with a BAD BH3 peptide or mimetic. By an increase in survival is meant a decrease of cell death compared to a cell that has not been in contact with BAD BH3 peptide or mimetic. Cell death is measure by methods known in the art such as trypan blue exclusion. Cells are directly contacted with BAD BH3 peptide or mimetic. Alternatively, the BAD BH3 peptide or mimetic is administered systemically. The cell is contacted with the BAD BH3 peptide or mimetic before, during or after cell transplantation in a subject.

The methods are useful to treat, alleviate the symptoms of, or delay the onset of diabetes or insulin resistance. Diabetes includes Type I diabetes or Type II diabetes. Type I diabetes or insulin dependent diabetes is caused by the gradual destruction of the beta cells in the pancreas, resulting in the inability of the pancreas to produce insulin. Type II diabetes or non-insulin dependent diabetes is due to a combination of defective insulin secretion and defective responsiveness to insulin (often termed reduced insulin sensitivity). Mature onset diabetes in youth (MODY) is a genetic form of type II diabetes.

Insulin resistance (e.g., pre-diabetes) is the condition in which normal amounts of insulin are inadequate to produce a normal insulin response from fat, muscle and liver cells. Insulin resistance in fat cells results in hydrolysis of stored triglycerides, which elevates free fatty acids in the blood plasma. Insulin resistance in muscle reduces glucose uptake whereas insulin resistance in liver reduces glucose storage, with both effects serving to elevate blood glucose. High plasma levels of insulin and glucose due to insulin resistance often lead to the metabolic syndrome and type 2 diabetes.

The subject is suffering from or at risk of developing diabetes, cardiovascular disease, hypertension, obesity, diabetic retinopathy or diabetic neuropathies. Subjects suffering from or at risk of developing diabetes, diabetic retinopathy, diabetic neuropathies cardiovascular disease, hypertension or obesity are identified by methods known in the art. For example diabetes is diagnosed by for example by measuring fasting blood glucose levels or insulin or by glucose tolerance test. Normal adult glucose levels are 60-126 mg/dl. Normal insulin levels are 7 mU/mL±3 mU. Hypertension is diagnosed by a blood pressure consistently at or above 140/90. Cardiovascular disease is diagnosed by measuring cholesterol levels. For example, LDL cholesterol above 137 or total cholesterol above 200 is indicative of cardiovascular disease. Obesity is diagnosed for example, by body mass index. Body mass index (BMI) is measured (kg/m$^2$ (or lb/in$^2$×704.5)). Alternatively, waist circumference (estimates fat distribution), waist-to-hip ratio (estimates fat distribution), skinfold thickness (if measured at several sites, estimates fat distribution), or bioimpedance (based on principle that lean mass conducts current better than fat mass (i.e., fat mass impedes current), estimates % fat) is measured. The parameters for normal, overweight, or obese individuals is as follows: Underweight: BMI <18.5; Normal: BMI 18.5 to 24.9; Overweight: BMI=25 to 29.9. Overweight individuals are characterized as having a waist circumference of >94 cm for men or >80 cm for women and waist to hip ratios of ≥0.95 in men and ≥0.80 in women. Obese individuals are characterized as having a BMI of 30 to 34.9, being greater than 20% above "normal" weight for height, having a body fat percentage >30% for women and 25% for men, and having a waist circumference >102 cm (40 inches) for men or 88 cm (35 inches) for women. Individuals with severe or morbid obesity are characterized as having a BMI of ≥35.

The methods described herein lead to a reduction in the severity or the alleviation of one or more symptoms of diabetes, insulin resistance, a disorder associated with diabetes or a disorder associated with aberrant glucose metabolism. Symptoms of diabetes include for example elevated fasting blood glucose levels, blood pressure at or above 140/90 mm/Hg; abnormal blood fat levels, such as high-density lipoproteins (HDL) less than or equal to 35 mg/dL, or triglycerides greater than or equal to 250 mg/dL (mg/dL=milligrams of glucose per deciliter of blood). Efficacy of treatment is determined in association with any known method for diagnosing or treating diabetes, insulin resistance or a disorder associated with diabetes. Alleviation of one or more symptoms of the diabetes, insulin resistance or a disorder associated with diabetes indicates that the compound confers a clinical benefit. Disorders associated with diabetes include for example, renal failure, blindness, neuropathy, and coronary artery disease. Diabetes, insulin resistance or a disorder associated with diabetes are diagnosed and or monitored, typically by a physician using standard methodologies For example, diabetes is diagnosed by a fasting plasma glucose test or an oral glucose test. Fasting glucose levels below 99 mg/dL are normal. Fasting glucose level is 100 to 125 mg/dL, indicate pre-diabetes. Glucose level of 126 mg/dL or above, are indicative of diabetes A BAD BH3 peptide or mimetic are administered with an anti-diabetic compound. Examples of anti-diabetic compounds include, but are not limited to, insulin, sulfonylurea drugs, meglitinides, biguanides, alpha-glucosidase inhibitors, thiazolidinediones or GK activator compounds (GKA). Exemplary GKA compounds include Roche compound RO-28-1675, Lilly compound LY2121260 and astraZeneca compounds GKA1 and 2 (See, Grimsby et al. Science (2003) 301:370-373. McKerrecher, et al Bioorganic an Med Chem Letters (2005) 2103-2106; and Brocklehurst et al. Diabetes (2004) 53: 535-541, each of which are incorporated by reference in their entireties).

Tumor growth or cellular proliferation is modulated, increased or decreased by contacting a tumor cell with a with a BH3 peptide or mimetic. For example by inhibiting glucose utilization in a tumor cell, cell growth is decreased. Alternatively, by increasing glucose utilization in a tumor cell growth is increased. Both increasing and decreasing tumor growth has therapeutic benefit. Decreasing tumor growth slows the progression of the tumor, whereas increasing tumor growth may make the tumor more sensitive to therapeutic agents such as chemotherapy or radiation. Alternatively, modulating tumor growth may be achieved by toggling BH3 function between homeostatic and pro-apoptotic pathways, and thereby reactivating cell death in cancer.

Cellular homeostatic pathways are modulated by contacting a cell with a BH3 peptide or mimetic thereof. For example, the cell's progression through the cell cycle may be modulated by administration of a BID NH3 peptide, a mimetic or phosphomometic thereof.

The cell is any cell, such as a liver cell or a brain cell.

The subject can be e.g., any mammal, e.g., a human, a primate, mouse, rat, dog, cat, cow, horse, pig.

Therapeutic Administration

The compounds, e.g., BH3 peptides or mimetics (also referred to herein as "active compounds") of the invention, and derivatives, fragments, analogs and homologs thereof, can be incorporated into pharmaceutical compositions suitable for administration. Such compositions typically comprise the peptide or mimetic, and a pharmaceutically acceptable carrier. As used herein, "pharmaceutically acceptable carrier" is intended to include any and all solvents, dispersion media, coatings, antibacterial and antifungal agents, isotonic and absorption delaying agents, and the like, compatible with pharmaceutical administration. Suitable carriers are described in the most recent edition of Remington's Pharmaceutical Sciences, a standard reference text in the field, which is incorporated herein by reference. Preferred examples of such carriers or diluents include, but are not limited to, water, saline, finger's solutions, dextrose solution, and 5% human serum albumin. Liposomes and non-aqueous vehicles such as fixed oils may also be used. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., a BH3 peptide or mimetic) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811, incorporated fully herein by reference.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved.

The pharmaceutical compositions can be included in a container, pack, or dispenser together with instructions for administration.

Screening Assays

The invention provides methods (also referred to herein as "screening assays") for identifying agents which modulate the activity of glucokinase or modulate the cell cycle.

A labeled, e.g. fluorescently labeled BH3 peptide or fragment thereof (e.g. BID, BAD, BAK, BAX, etc) in the presence of its target protein (e.g. glucokinase) can be exposed to varying concentrations of a candidate compound (e.g., 1 nM, 10 nM, 100 nM, 1 µM, 10 µM, 100 µM, 1 mM, and 10 mM) to identify molecular inhibitors of this interaction. Optionally the BH3 peptide is phosphorylated. The effect of each concentration of candidate compound is then analyzed to determine the effect of the candidate compound on glucokinase activity, the cell cycle, or the in vitro BH3-target protein binding activity. The candidate compound can modulate glucose kinase activity or the cell cycle in a competitive or non-competitive manner. Direct binding assays can also be performed between BCL-2 family proteins and fluorescently labeled candidate compounds to determine the $K_d$ for the binding interaction. Candidate compounds could also be screened for biological activity in vitro, for example, by measuring their dose-responsive efficacy in triggering cytochrome c release from purified mitochondria, mitochondrial membrane potential or glucokinase activity as assessed by glucose-6-phosphaet dehydrogenase mediated production of NADH.

The assays described herein can be performed with individual candidate compounds or can be performed with a plurality of candidate compounds. Where the assays are performed with a plurality of candidate compounds, the assays can be performed using mixtures of candidate compounds or can be run in parallel reactions with each reaction having a single candidate compound. The test compounds or agents can be obtained using any of the numerous approaches in combinatorial library methods known in the art.

In one embodiment, an assay is a biochemical assay, whereby hydrocarbon-stapled polypeptides can be linked to affinity resin in order to purify or identify new or known interactive partners in homeostatic pathways, such as the glucokinase pathway or cell cycle. In another embodiment the hydrocarbon-stapled protein contains a photoactivatable moiety that enables a covalent crosslink to form with a new or known interactive partner in homeostatic pathways, such as the glucokinase pathway or cell cycle.

The invention will be further described in the following examples, which do not limit the scope of the invention described in the claims.

Example 1. The Role of BAD in β Cell Function

Figure 5:
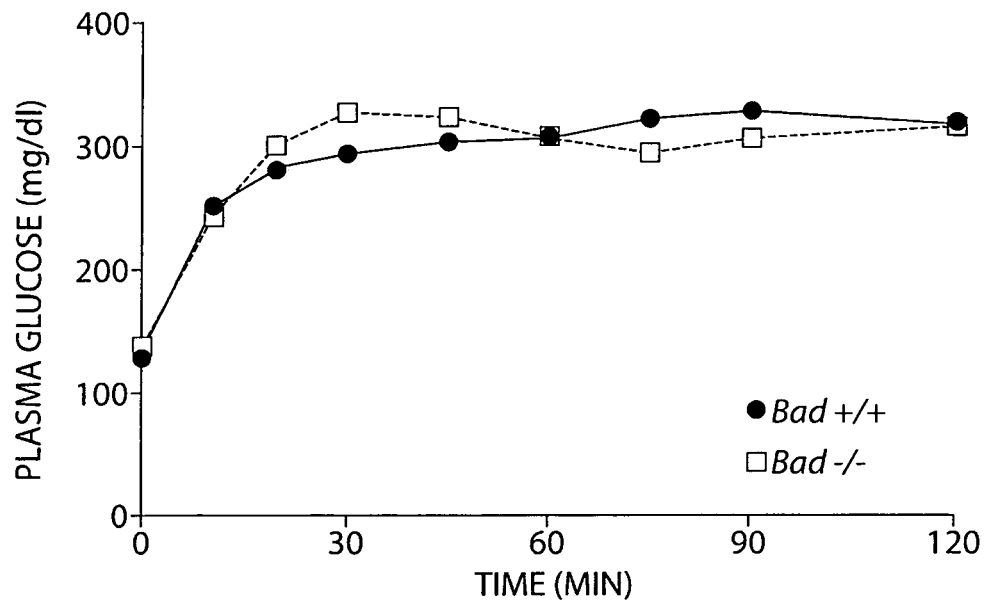
FIG. 5 is a line graph showing plasma glucose levels during a hyperglycemic clamp analysis. Glucose levels were raised and maintained at 300 mg/dl throughout the analysis of Bad +/+ (n=10) and Bad -/- (n=12) mice.
Figure 6:
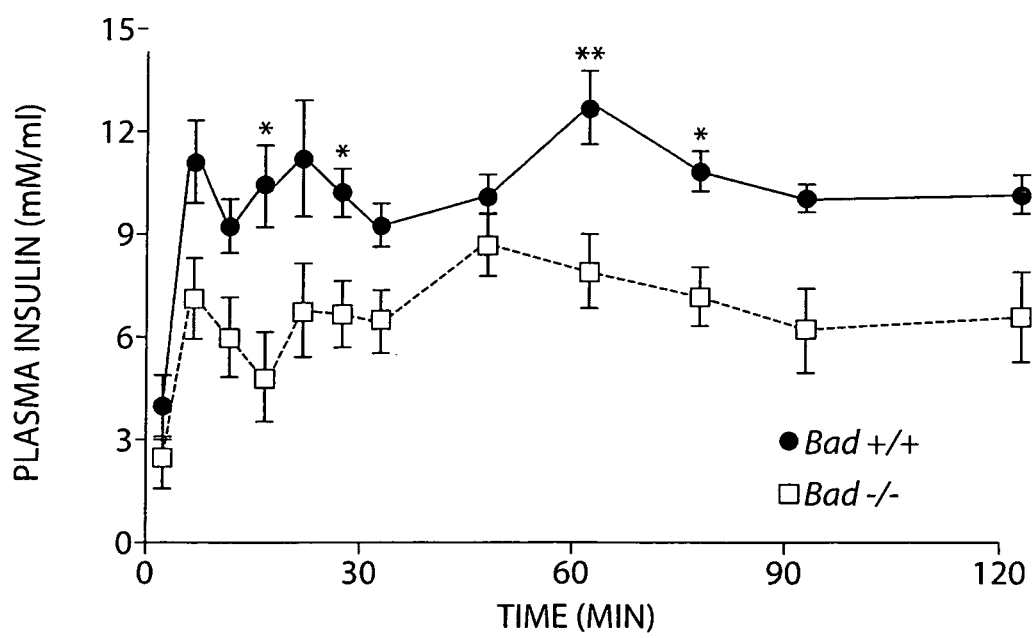
FIG. 6 is a line graph showing plasma insulin levels in Bad +/+ (n=10) and Bad -/- (n=12) mice. Asterisks: $p<0.05$; double asterisks, $p<0.01$, unpaired two tailed t-test.
Figure 7:
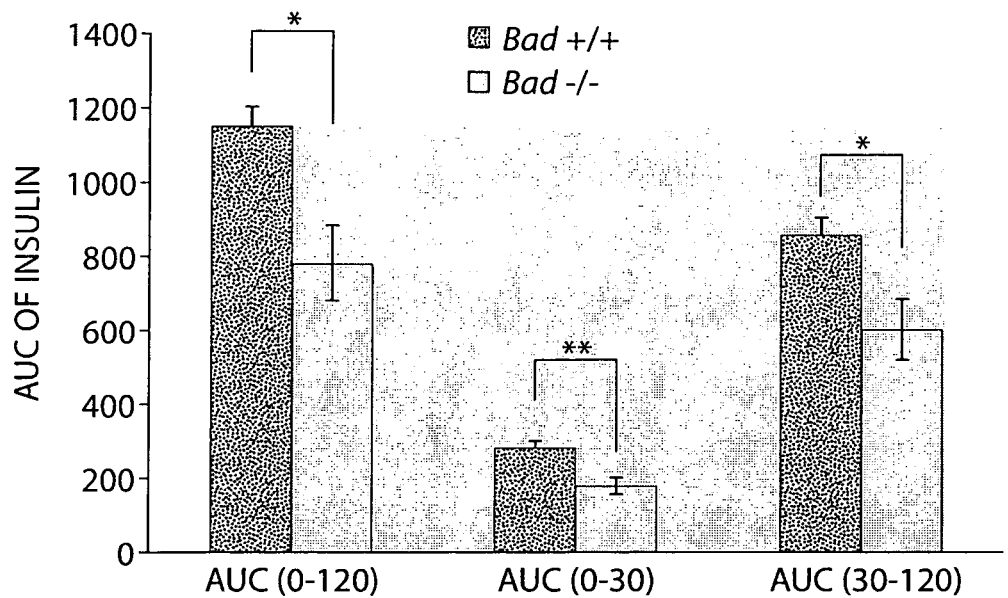
FIG. 7 is a bar graph, which quantitates the area under the curve (AUC) for insulin secretion throughout the experiment (0-120 min), or during acute (0-30 min) and late (30-120 min) phases of secretion. Asterisks: $p<0.05$; double asterisks, $p<0.01$, unpaired two tailed t-test.

To examine the role of BAD in β-cells, insulin secretion was assessed in a cohort of Bad +/+ and Bad −/− mice using hyperglycemic clamp analysis. A 2-hour clamp was conducted with a primed and variable infusion of 20% glucose to raise and maintain plasma glucose concentrations at 300 mg/dl in Bad +/+ (n=10) and Bad −/− (n=12) mice. (FIG. 5). Analysis of plasma insulin levels at multiple time points during the clamp period indicated significant impairment of insulin secretion in Bad-deficient mice (FIG. 6). The area under the curve (AUC) for insulin response throughout the experiment (0-120 min) showed a 32% reduction in Bad −/− mice (p<0.05, FIG. 7). The acute (0-30 min) and late (30-120 min) phases of secretion were marked by 37% (p<0.01) and 30% (p<0.05) reduction, respectively (FIG. 7).

Figure 8:
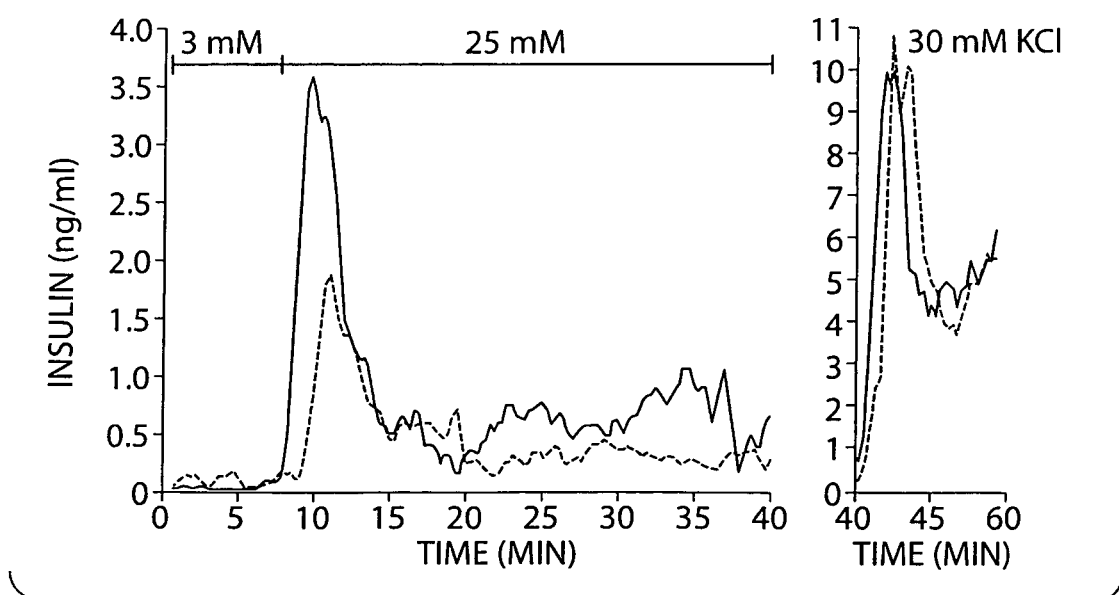
FIG. 8 is a line graph depicting insulin secretion from perifused islets purified from Bad +/+ and Bad -/- mice. Following a 25 min pre-perifusion period with 3 mM glucose, 120 islets from each genotype were perifused with 3 mM and 25 mM glucose as indicated. After 40 min, the perifusion solution was switched to 30 mM KCl to depolarize the plasma membrane and release the total pool of insulin granules. DNA content per islet was 12.4 ng and 14.6 ng for Bad +/+ and Bad −/− mice, respectively. AUC for the first phase of release (min 8-15) was 12.50 vs. 5.98, and for the second phase (min 15-40) 15.05 vs. 8.44, Bad +/+ and Bad −/− respectively. Representative of 3 independent experiments is shown.

To determine whether this insulin secretion defect likewise manifests in vitro, islets purified from Bad −/− mice were subjected to perifusion assays (Cunningham B. A. et al., 1996. *Am J Physiol* 271, E702-10) (FIG. 8). Following a 25 min pre-perifusion period with 3 mM glucose, 120 islets from each genotype were perifused with 3 mM and 25 mM glucose as indicated. After 40 min, the perifusion solution was switched to 30 mM KCl to depolarize the plasma membrane and release the total pool of insulin granules. DNA content per islet was 12.4 ng and 14.6 ng for Bad +/+ and Bad −/− mice, respectively. AUC for the first phase of release (min 8-15) was 12.50 vs. 5.98, and for the second phase (min 15-40) 15.05 vs. 8.44, Bad +/+ and Bad −/− respectively. Bad −/− islets perifused with 25 mM glucose secreted significantly lower levels of insulin during both the first and second phases of the secretory response. However, the total pool of insulin released by KCl was unaltered (FIG. 8). While the magnitude of insulin release was lower, the oscillatory pattern of secretion in Bad −/− islets was comparable to control islets (data not shown). These results indicate that Bad deficiency compromises the capacity of β-cells to secrete insulin in response to glucose, which may have contributed, at least in part, to the abnormal glucose tolerance previously reported in Bad −/− mice (Danial N. N. et al., 2003. *Nature* 424, 952-6).

Figure 9:
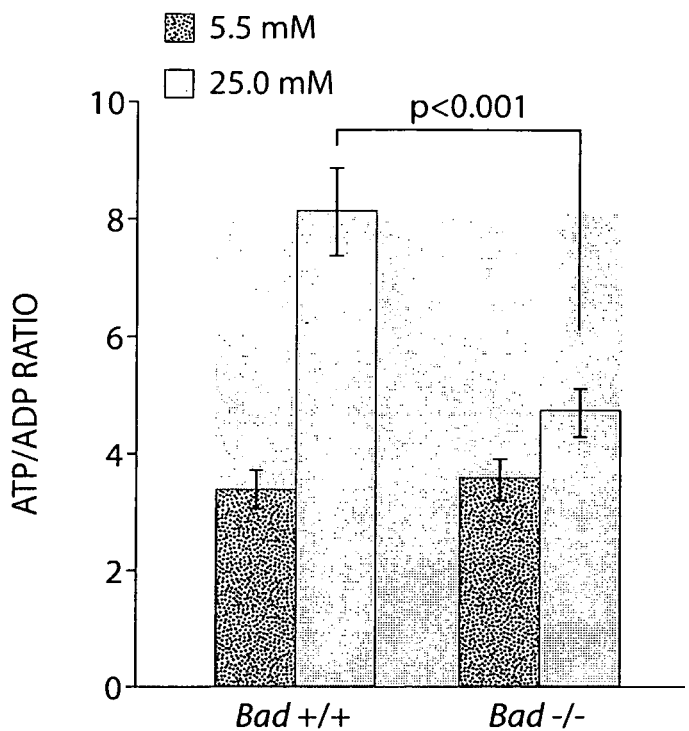
FIG. 9 is a bar graph demonstrating ATP/ADP ratio in Bad +/+ and Bad −/− islets upon increase in glucose from 5.5 mM to 25 mM.

Example 2. The Role of Components of the Insulin Secretion Pathway in the Insulin Secretory Defect in Bad −/− β-Cells The glucose-induced insulin secretion pathway in β-cells consists of both mitochondrial proximal and distal events (Wiederkehr A. and Wollheim C. B., 2006. *Endocrinology* 147, 2643-9). Mitochondria generate the metabolic coupling factors required for the induction of insulin release by glucose and other nutrients. The increase in intracellular ATP/ADP ratio is an important metabolic coupling factor in this process leading to closure of ATP-sensitive K ($K_{ATP}$) channels at the plasma membrane, followed by membrane depolarization and opening of the voltage-sensitive $Ca^{2+}$ channels (Ashcroft F. M. and Gribble F. M., 1999. *Diabetologia* 42, 903-19; Rorsman P, 1997. *Diabetologia* 40, 487-95). The increase in intracellular $Ca^{2+}$ concentration $[Ca^{2+}]_i$ in turn stimulates insulin release. Consistent with their secretory defect in response to glucose, Bad −/− islets failed to show a robust increase in ATP/ADP ratio (FIG. 9) suggesting a lack of sufficient metabolic coupling.

Figure 10:
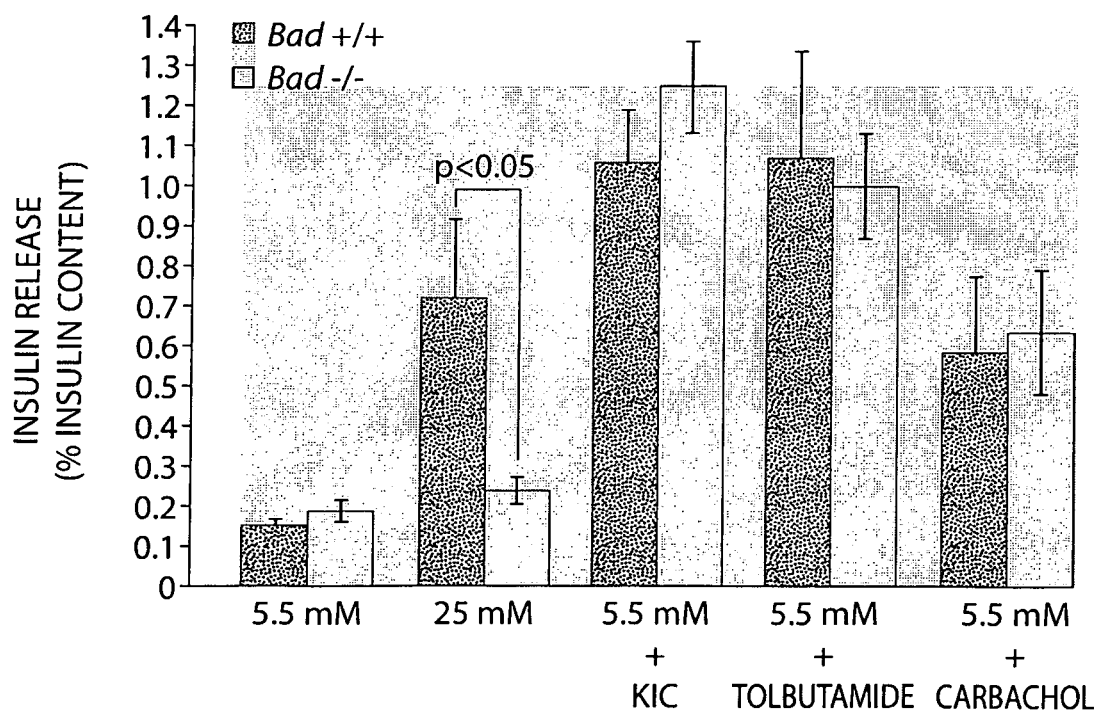
FIG. 10 is a bar graph showing insulin release in Bad +/+ and Bad −/− islets in response to secretagogues. Bad +/+ and Bad −/− islets were cultured in media containing the indicated amount of glucose in the presence or absence of 10 mM 2-ketoisocaproic acid (KIC), 0.25 mM tolbutamide or 0.25 mM carbachol. Insulin secretion was measured using the static incubation method. n=8-11 per group. Insulin content per islet was 115.1±4.64 and 118.49±4.09 ng, Bad +/+ and Bad −/−, respectively. Asterisk, $p<0.05$, Bad +/+ vs. Bad −/−, unpaired two tailed t-test. n=8-11 per group. $p<0.05$, Bad +/+ vs. Bad −/−, unpaired two tailed t-test.

To examine whether the mitochondrial distal and proximal steps involved in insulin release are intact in Bad −/− islets, several well-characterized secretagogues were tested. KIC (α-ketoisocaproic acid) is a nutrient secretagogue that fuels the mitochondrial TCA cycle independent of glucose phosphorylation by GK (Gao Z, et al., 2003. *Endocrinology* 144, 1949-57). Bad +/+ and Bad −/− islets were cultured in media containing the indicated amount of glucose in the presence or absence of 10 mM 2-ketoisocaproic acid (KIC), 0.25 mM tolbutamide or 0.25 mM carbachol. Insulin secretion was measured using the static incubation method. Insulin content per islet was 115.1±4.64 and 118.49±4.09 ng, Bad +/+ and Bad −/−, respectively. KIC-induced insulin secretion by Bad-deficient islets was robust and comparable to that seen in controls (FIG. 10). The mitochondrial distal steps, including those culminating in $[Ca^{2+}]_i$ augmentation and activation of the secretory machinery were tested using the sulfonylurea tolbutamide and the muscarinic receptor agonist carbachol. Tolbutamide binds and closes the $K_{ATP}$ channel independent of changes in ATP/ADP ratio (Proks P. et al., 2002. *Diabetes* 51 Suppl 3, S368-76), allowing examination of signaling downstream of this channel. Carbachol was used to assess whether the IP3-mediated release of intracellular $Ca^{2+}$ stores occurred properly. The response of Bad −/− islets to both tolbutamide and carbachol was comparable to wild type islets (FIG. 10). This pharmacologic analysis of insulin secretion suggests that the Bad −/− islets are not globally impaired in their secretory response.

Figure 11:
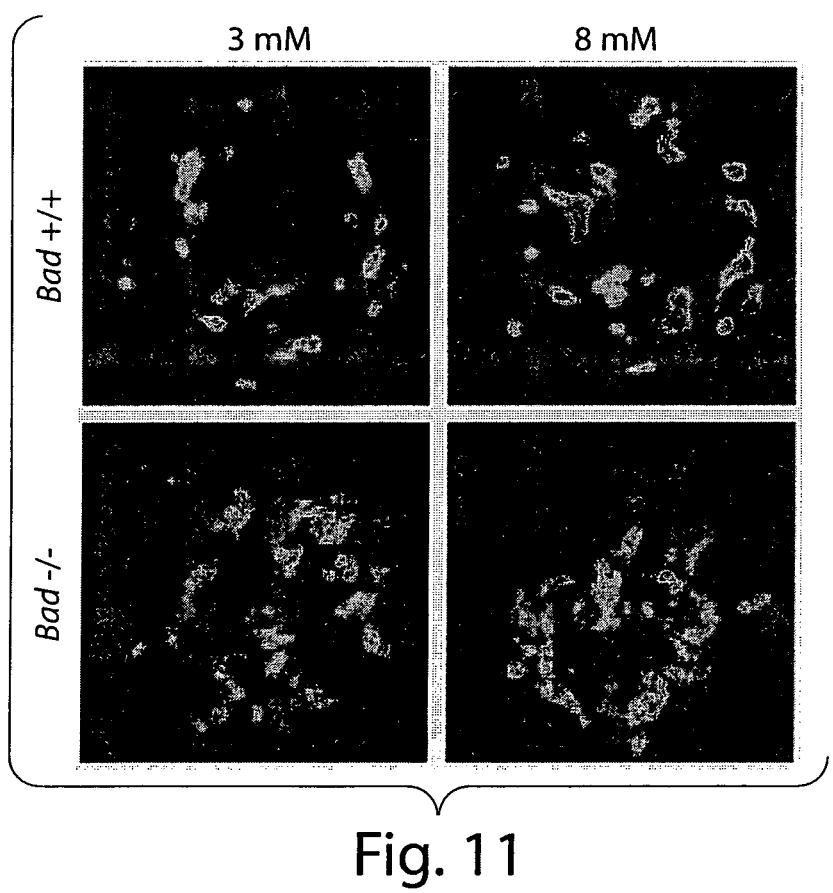
FIG. 11 is an illustration demonstrating changes in TMRE fluorescence intensity from individual Bad +/+ and Bad −/− β cells upon increase of glucose concentration from 3 to 8 mM. Images are color-coded for fluorescence intensity; blue (low) and red (high).
Figure 12:
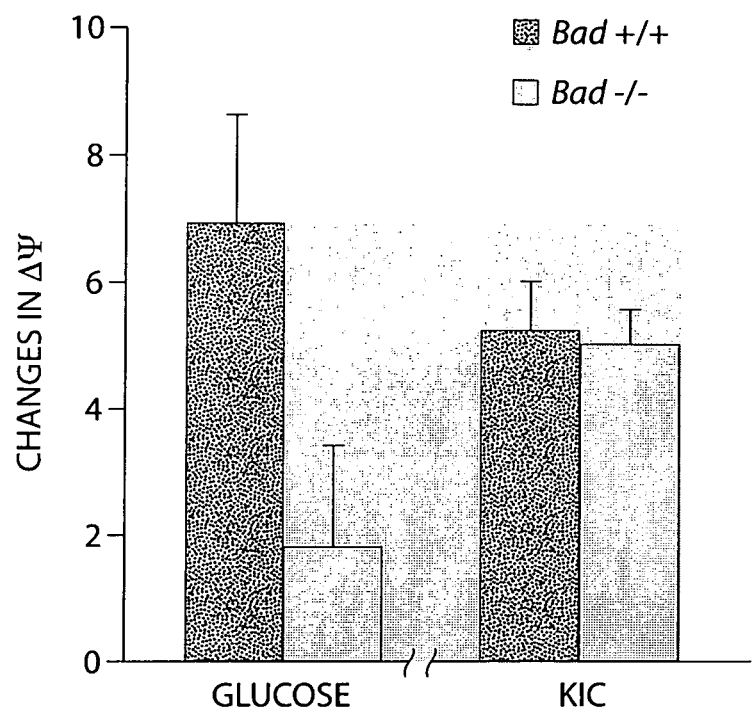
FIG. 12 is a bar graph showing changes in $\Delta\Psi$ from individual Bad +/+ and Bad −/− β cells following the addition of 10 mM KIC in the presence of 3 mM glucose.

The efficiency of glucose and other fuel secretagogues to stimulate insulin secretion tightly correlates with their capacity to hyperpolarize the mitochondrial membrane potential ($\Delta\psi_m$) (Antinozzi P. A. et al., 2002. *J Biol. Chem.* 277, 11746-55). In β-cells, the characteristic features of glucose-driven respiration correlate with that of glucose phosphorylation by GK (Liang Y, et al., 1996. *Am J Physiol* 270, E846-57). Glucose-induced mitochondrial membrane hyper-polarization was assessed in Bad +/+ and Bad −/− β-cells. To calculate $\Delta\psi$, changes in tetramethyl rhodamine ethyl ester (TMRE) fluorescence intensity were analyzed on multiple individual cells upon increase in glucose from 3 mM to 8 mM or following the addition of 10 mM KIC in the presence of 3 mM glucose (Heart E. et al., 2006. *Am J Physiol Endocrinol Metab* 290, E143-E148). Dispersed islets were co-loaded with mitotracker and the potentiometric dye TMRE. Alterations in $\Delta\psi_m$ were recorded from individual Bad +/+ and Bad −/− β-cells (FIG. 11). An increase in TMRE fluorescence intensity reflects hyper-polarization of the mitochondrial membrane potential and is used as an index for respiration. Glucose-induced changes in $\Delta\psi_m$ were significantly reduced in Bad −/− β-cells (FIG. 12, 1.84±1.58 in Bad −/− vs. 6.88±1.71 in Bad +/+, n=10), while KIC induced comparable changes in $\Delta\psi_m$ in both genotypes (FIG. 12). These data indicate that the insulin secretion defect in Bad −/− β-cells involves a glucose-selective, mitochondrial proximal component.

Example 3. The Effects of BAD on GK Activity and Glucose Sensing by β-Cells

Figure 31:
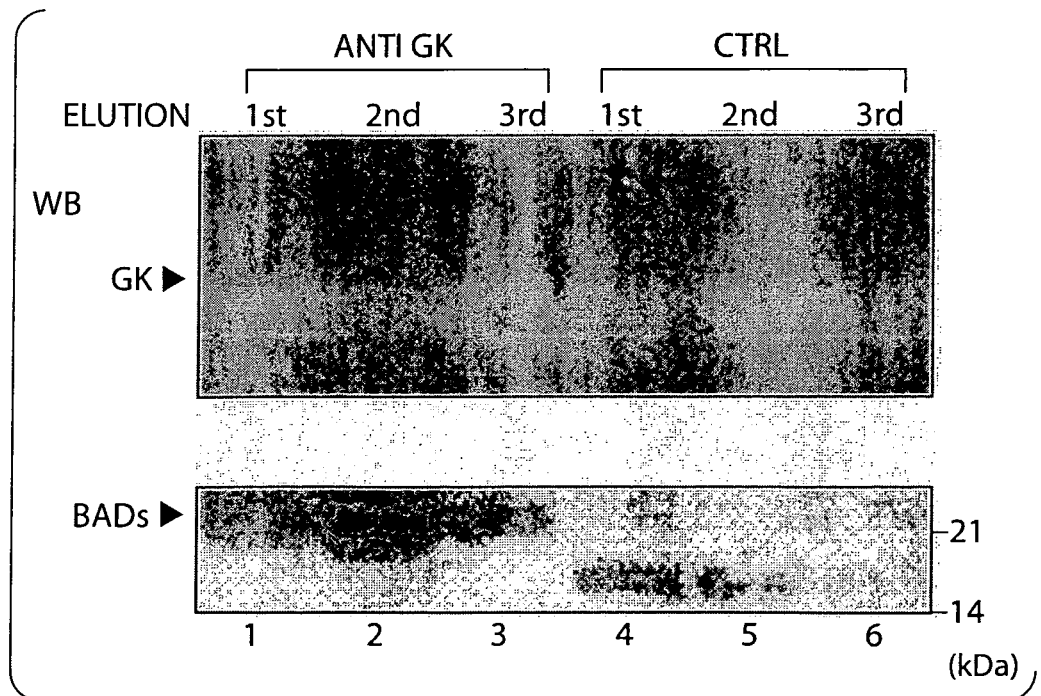
FIG. 31 is a photograph of a Western blot showing the results of incubating anti-glucokinase antibody (lanes 1-3) or control rabbit IgG (lanes 4-6) with CHAPS-solubilized mitochondria-enriched heavy membrane (HM) fraction prepared from MIN6 β cells.
Figure 32:
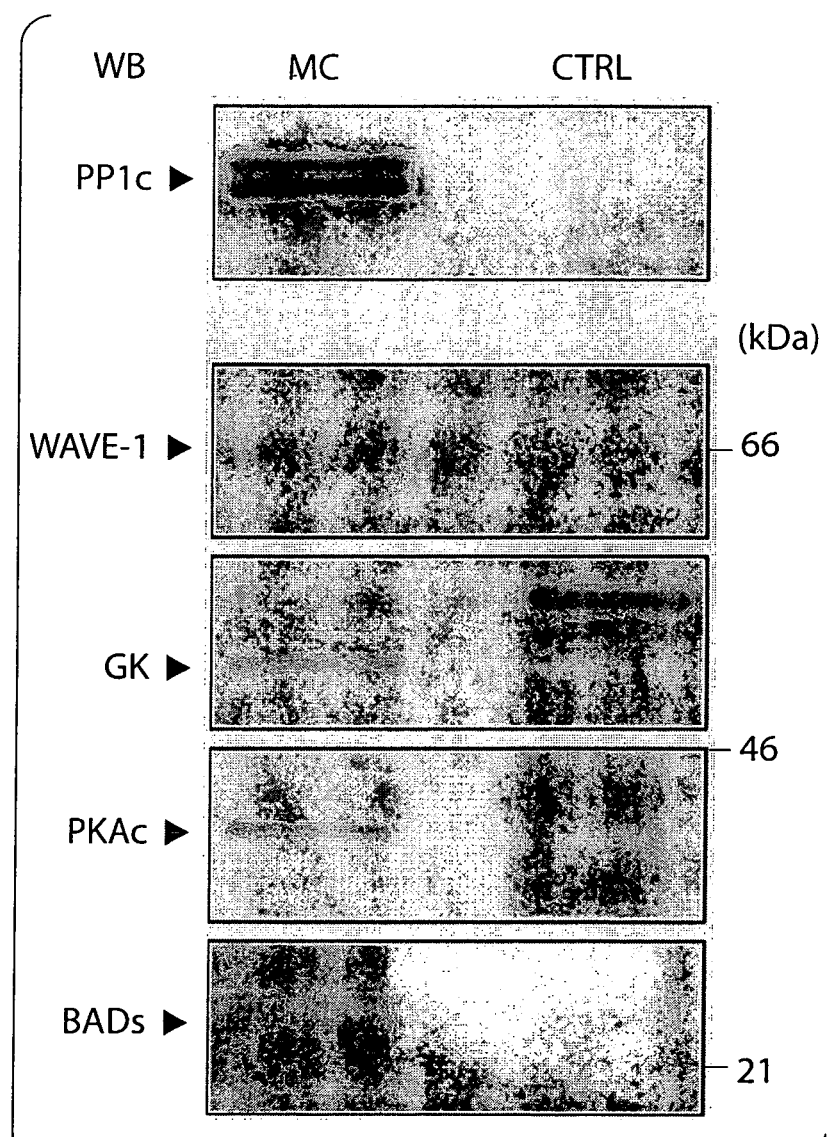
FIG. 32 is a photograph of a Western blot showing the results of incubating CHAPS-solubilized mitochondria-enriched heavy membrane (HM) fraction isolated from MIN6 β cells with microcystin (MC)-coupled agarose beads. Bound proteins were resolved by SDS-PAGE and immunoblotted with the indicated antibodies. Uncoupled beads serve as control (ctrl).

The glucose-selective aspect of the defect in Bad −/− β-cells prompted close examination of GK in these cells. It has been previously reported by the inventors that BAD associates with the hepatic isoform of GK at mitochondria, and that Bad-null hepatocytes exhibit blunted mitochondria-tethered GK activity and glucose-driven respiration (Danial N. N. et al., 2003. *Nature* 424, 952-6). Because the hepatic and β-cell isoforms of GK are regulated differently, evaluating the potential regulatory effect of BAD on the β-cell isoform of the enzyme was warranted. To determine the ability of glucokinase to associate with BAD in β-cells, anti GK antibody (lanes 1-3) or control rabbit IgG (lanes 4-6) were covalently linked to AminoLink Plus Coupling gel (Pierce) as per manufacturer's instructions and incubated with CHAPS-solubilized mitochondria-enriched heavy membrane (HM) fraction prepared from MIN6 β-cells (FIG. 31). Bound material was sequentially eluted, resolved on SDS-PAGE and immunoblotted (WB) with anti glucokinase or anti BAD antibodies. Similarly, FIG. 32 shows the results of microcystin affinity purification of PP1-interacting proteins in mitochondria isolated from MIN6 β cells. Mitochondria-enriched HM fraction was solubilized in 15 mM CHAPS and incubated with microcystin (MC)-coupled agarose beads (Danial N. N. et al., 2003. *Nature* 424, 952-6). Bound proteins were resolved by SDS-PAGE and immunoblotted (WB) with the indicated antibodies. The β-cell isoform of GK associates with BAD at the mitochondria in a complex similar to that found in hepatocytes (Danial N. N. et al., 2003. *Nature* 424, 952-6).

Figure 13:
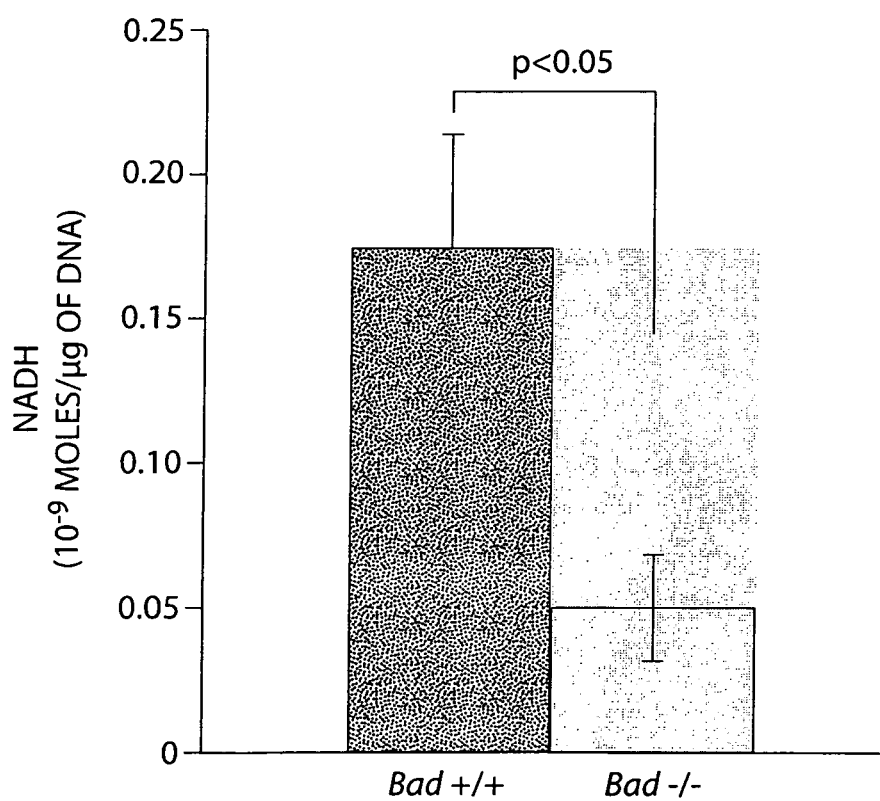
FIG. 13 is a bar graph demonstrating NADH fluorescence as an indication of glucokinase activity in homogenates of primary islets isolated from Bad +/+ and Bad −/− mice.
Figure 14:
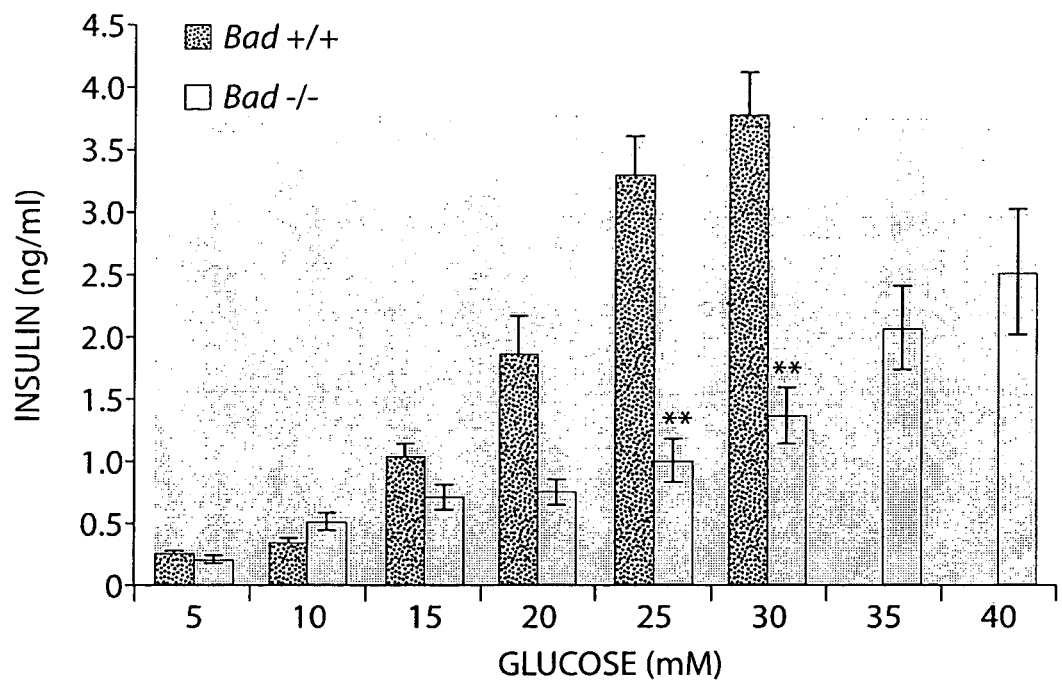
FIG. 14 is a bar chart showing insulin secretion in Bad +/+ and Bad −/− islets perifused with increasing doses of glucose. Double asterisks, $p<0.01$, unpaired two tailed t-test, Bad +/+ vs. Bad −/− islets for the indicated glucose concentration.

FIG. 13 shows glucokinase activity in homogenates of primary islets isolated from Bad +/+ and Bad −/− mice. Glucokinase activity was measured as the difference between glucose phosphorylating activity at 100 mM and 0.5 mM glucose. Glucose phosphorylating activity was measured as the increase in NADH fluorescence in a glucose-6-phosphate dehydrogenase-driven reaction (Trus M. D. et al., 1981. *Diabetes* 30, 911-22). GK assays on homogenates prepared from primary Bad −/− islets showed reduced enzyme activity compared to control islets (FIG. 13). A characteristic signature of β-cell dysfunction associated with blunted GK activity is loss of glucose-sensing, evident from a rightward shift in the glucose dose-response of insulin secretion (Byrne M. M. et al., 1994. *J Clin Invest* 93, 1120-30). To further delineate the significance of blunted GK activity in the secretory defect of Bad-null β-cells, pancreatic islets were perifused with increasing concentrations of glucose (FIG. 14). 120 islets from each genotype were perifused as in FIG. 8 and fractions corresponding to the first peak of insulin release were collected for insulin measurements prior to switching to the next glucose dose. Bad-null islets required more glucose to release the same magnitude of insulin secreted by control islets. For example, the amount of insulin released by Bad −/− islets at 25 and 35 mM glucose was comparable to that released by Bad +/+ islets at 15 and 20 mM glucose, respectively (FIG. 14). Control islets showed the greatest fold induction in insulin release from 10 to 15 mM, followed by smaller but significant increases with additional increments of glucose up to 25 mM glucose. The increase in insulin release at these same glucose concentrations was significantly blunted in Bad −/− islets (FIG. 14). These results are consistent with abnormalities in GK and glucose sensing in Bad-null islets.

Example 4. The Role of BAD BH3 Domain in Insulin Secretion

As a stringent test to determine whether the secretory defect in Bad −/− islets is directly related to BAD's function in β-cells or secondary to other changes in Bad −/− mice, BAD expression was restored in purified Bad −/− islets using adenoviruses. Insulin release was assayed as in FIG. 10. Prior to genetic correction, Bad −/− islets failed to exhibit a stepwise increase in insulin release with incremental increases in glucose concentrations (FIG. 15, Bad −/− vs. Bad +/+ infected with control GFP virus). Re-introduction of BAD in these islets was sufficient to correct the defect and conferred a robust dose responsive secretory behavior with increasing concentration of glucose (p<0.001, FIG. 15, Bad −/−:GFP-BAD, release at 12.5 mM vs. 5.5 mM and p<0.01 at 25 mM vs. 12.5 mM glucose). Insulin content per islet was 122.75±12.34 and 127.13±5.09 ng, Bad +/+ and Bad −/−, respectively. These data are consistent with the conclusion that BAD loss in the β-cell confers an insulin secretory defect.

BAD mutants allowed for a further dissection of the molecular requirements for BAD's novel function. As the best established biochemical property of BAD is high affinity binding to anti-apoptotic partners, whether BAD's effect on insulin secretion was mediated by its binding to BCL-2/$X_L$ warranted detailed examination. The BH3 domain of BAD is an amphipathic α-helix that binds the hydrophobic pocket of BCL-2/$X_L$ thereby neutralizing their anti-apoptotic activity (Zha J. et al., 1997. *J Biol Chem* 272, 24101-4; Kelekar A. et al., 1997. *Mol Cell Biol* 17, 7040-6; Petros A. M. et al., 2000. *Protein Sci* 9, 2528-34). Leucine 151 (mouse $BAD_L$ enumeration) of the BH3 domain is important BCL-2/$X_L$ binding, consequently the L→A mutation abrogates the pro-apoptotic activity of BAD (Zha J. et al., 1997. *J Biol Chem* 272, 24101-4). Unlike wild-type BAD, genetic correction with an L→A mutant BAD was not capable of correcting the GSIS defect in Bad −/− islets (FIG. 15, p>0.05 at all glucose concentrations, Bad −/−:GFP vs. Bad −/−: GFP-BAD L→A), thus confirming the specificity of the observed wild-type BAD effect.

Figure 16:
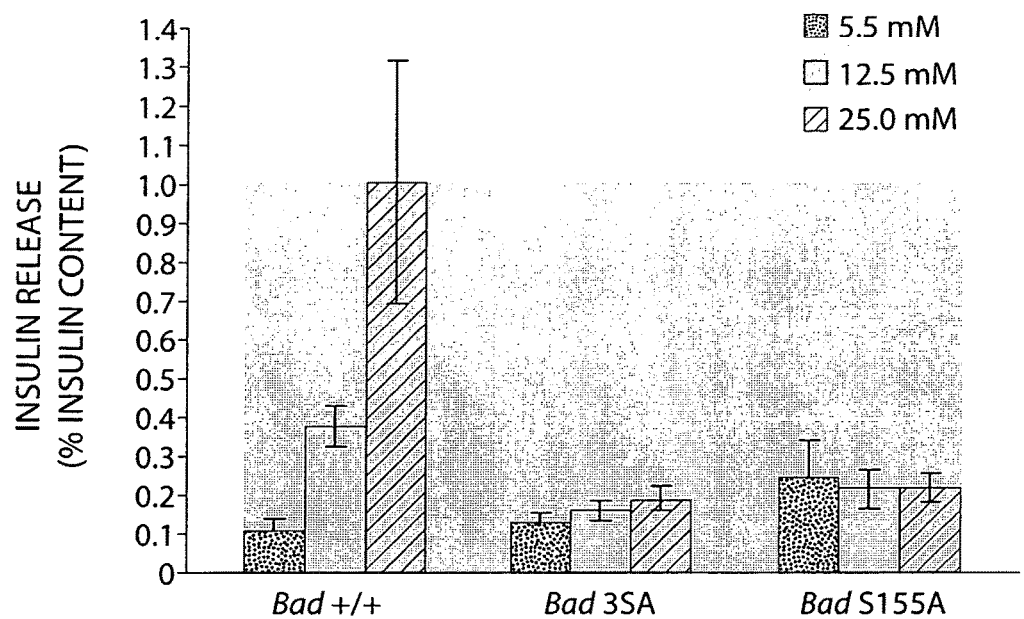
FIG. 16 is a bar graph showing GSIS in Bad +/+ mice or animals expressing the non-phosphorylatable mutants of BAD (Bad 3SA and Bad S155A). n per group: Bad +/+ (n=10), Bad 3SA (n=8), Bad S155A (n=12).

Example 5. BAD Phosphorylation: a Molecular Determinant of BAD Apoptotic Versus Metabolic Functions The requirement of an intact BAD BH3 domain in GSIS raised the possibility that this activity could be mediated by BCL-2/$X_L$ binding. To further explore this mechanism, a BAD mutant in which the 3 serine phosphorylation sites (S112, S136 and S155) were converted to alanine (BAD 3SA) was employed (Datta S. R. et al., 2002. *Dev Cell* 3, 631-43). As the interaction between BAD and BCL-2/$X_L$ is inhibited by phosphorylation (Zha J. et al., 1996. *Cell* 87, 619-28), BAD 3SA constitutes a non-repressible mutant that lowers the threshold for apoptosis (Datta S. R. et al., 2002. *Dev Cell* 3, 631-43). Because adenoviruses carrying this mutant were toxic to islets in genetic reconstitution assays, islets isolated from the non-phosphorylatable Bad 3SA knockin mice were studied. Of note, Bad 3SA mice show blunted GK activity in islets (data not shown) and in liver (Danial N. N. et al., 2003. *Nature* 424, 952-6). Like Bad −/− islets, Bad 3SA islets displayed impaired GSIS (FIG. 16). Insulin secretion was assessed using the static incubation method as above. Insulin content per islet was 118.74±3.86, 96.46±3.42 and 106.5±6.24 ng, Bad +/+, Bad 3SA and Bad S155A, respectively. Whereas the 3SA and L→A mutations share similar defects in insulin secretion, they display opposite capacities to engage BCL-$X_L$. These findings suggest that the ability of BAD to regulate insulin secretion and its ability to counteract pro-survival partners do not co-segregate, highlighting a novel function for the BAD BH3 domain apart from its role in regulating apoptosis.

Example 6. The Role of BAD Mimetic Compounds in Insulin Release

To determine whether the BAD BH3 domain itself is sufficient to correct the GSIS defect observed in Bad-null islets, pancreatic islets were treated with a panel of "stapled" peptides corresponding to this region. BH3 sequences were modified by a chemical method known as hydrocarbon stapling, recently used to generate stabilized alpha-helices of BCL-2 domains (SAHBs) that recapitulate BH3 bioactivity (FIG. 17-18 and FIG. 33) (Walensky L. D. et al., 2004. *Science* 305, 1466-70).

Figure 15:
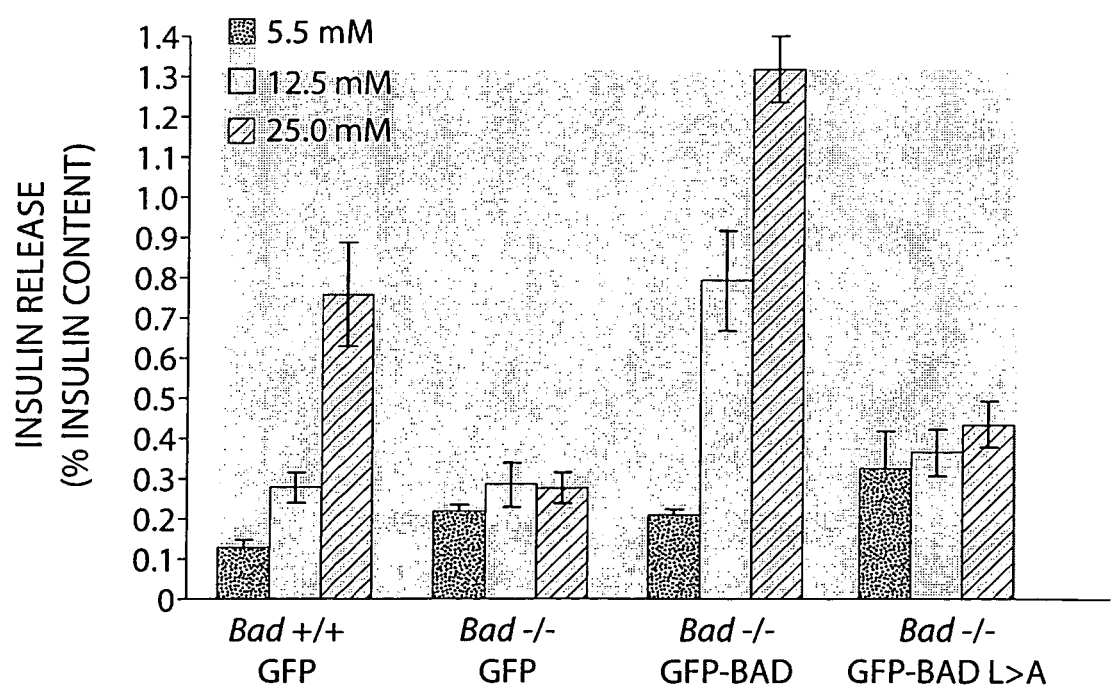
FIG. 15 is a bar chart demonstrating glucose stimulated insulin secretion (GSIS) in Bad +/+ and Bad −/− islets infected with adenoviruses expressing GFP alone, GFP-BAD or GFP-BAD L→A. n=10-15 per group. Representative of three independent experiments with two independent preparations of viral stocks is shown.
Figure 19:
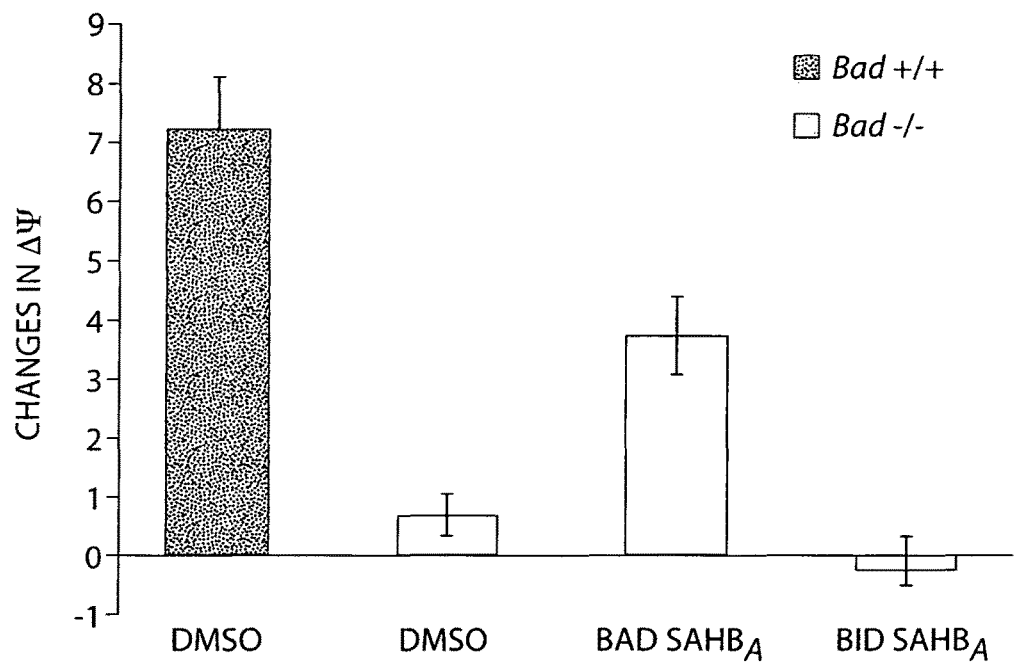
FIG. 19 is a bar graph showing the effect of SAHB compounds on glucose-induced changes in mitochondrial membrane potential ($\Delta\Psi$).
Figure 33:
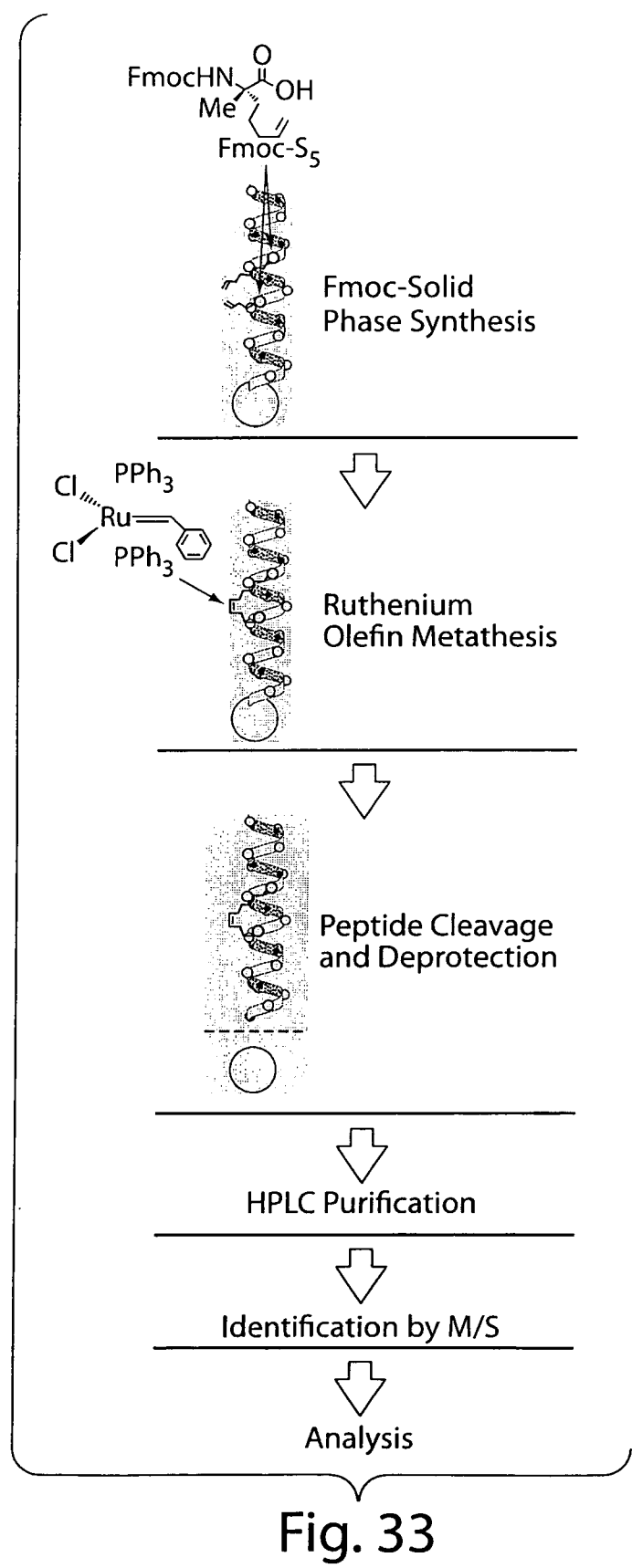
FIG. 33 is a schematic of the hydrocarbon-stapling synthetic strategy. Asymmetric synthesis of S-N-(9-Fluorenylmethyl carbamate)-2-(4'-pentenyl)alanine ("S5") was performed as previously described. SAHB compounds were generated by replacing two amino acids of the BH3 sequence with non-natural amino acids at discrete locations that flank 3 natural amino acids (i, i+4 positions). Peptide synthesis, olefin metathesis, FITC-derivatization, reverse-phase HPLC purification, and microanalysis were performed as previously reported for BID SAHB. The native methionine of BID BH3 was replaced with norleucine ($N_L$) in BID SAHB due to the incompatibility of sulfur with the ruthenium-catalyzed metathesis reaction.
Figure 34:
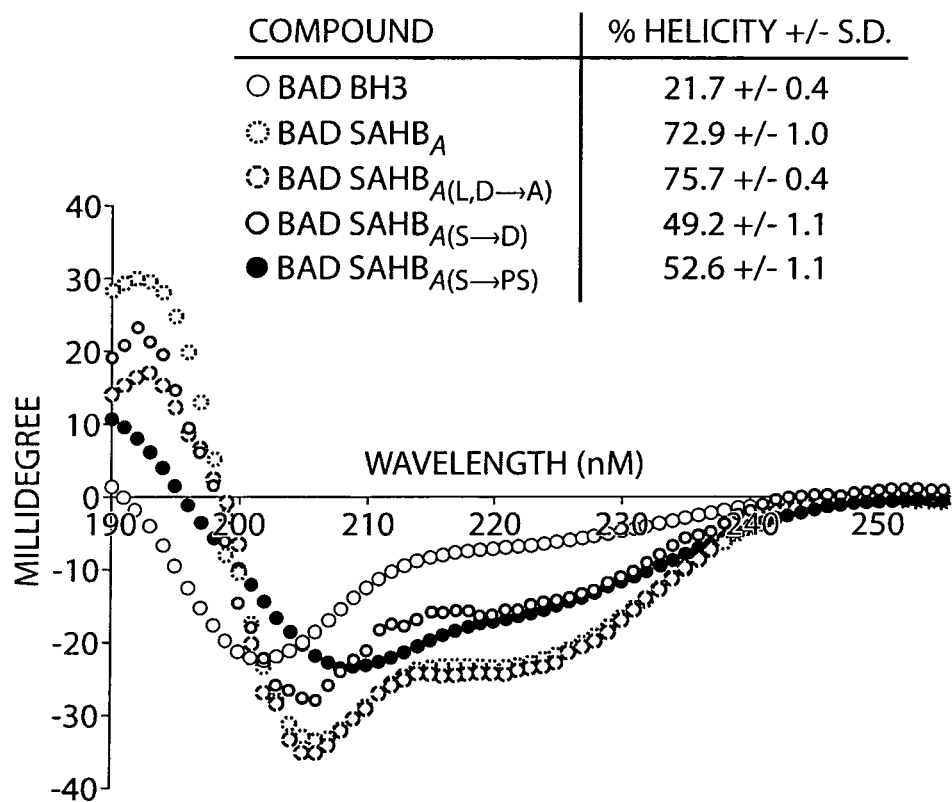
FIG. 34 is a dot plot showing that circular dichroism spectra demonstrate enhanced α-helicity of SAHBs compared to their corresponding unmodified peptides.

FIG. 33 shows a schematic of the hydrocarbon-stapling synthetic strategy. Asymmetric synthesis of S-N-(9-Fluorenylmethyl carbamate)-2-(4'-pentenyl)alanine ("S5") was performed as previously described (Schafmeister C. et al., 2000. *J Am Chem Soc* 122, 5891-5892; Williams R. M. and Im M. N., 1991. *J Am Chem Soc* 113, 9276-9286). SAHB compounds were generated by replacing two amino acids of the BH3 sequence with non-natural amino acids at discrete locations that flank 3 natural amino acids (i, i+4 positions). Peptide synthesis, olefin metathesis, FITC-derivatization, reverse-phase HPLC purification, and microanalysis were performed as previously reported for BID SAHB (Walensky L. D. et al., 2004. *Science* 305, 1466-70). The native methionine of BID BH3 was replaced with norleucine ($N_L$) in BID SAHB due to the incompatibility of sulfur with the ruthenium-catalyzed metathesis reaction. Characterization of the stapled compounds revealed comparable helicity (FIG. 34) and cell permeability (data not shown). A truncation library was also evaluated to assess the tolerance for shortening the BAD BH3 bioactive peptide as assessed by retention of high affinity BCL-XL binding activity (see truncation figure sequences and binding isotherm in FIG. 18). Strikingly, BAD SAHB$_A$ restored the secretion defect in Bad −/− islets at 3 µM, a concentration that is not toxic to islets (p<0.001, FIG. 17, secretion at 12.5 vs. 5.5 mM and p<0.05 secretion at 25 vs. 12.5 mM glucose in Bad −/− treated with BAD SAHB$_A$). Although, the effect of BAD SAHB$_A$ on restoring insulin release did not reach the magnitude of that observed with replacing the full length protein used in genetic reconstitution, statistically significant correction was observed. In contrast to BAD SAHB$_A$, a distinct SAHB, modeled after BID BH3 did not correct the secretory defect in Bad −/− islets (p>0.05, FIG. 17, Bad −/−, DMSO vs. Bad −/− treated with BID SAHB$_A$), thus demonstrating the sequence specificity of the observed BAD SAHB effect. Mutating the conserved L151 and D156 residues of BAD SAHB (BAD SAHB$_{A(L,D→A)}$) abrogated its effect on insulin release (FIG. 17, p>0.05, Bad −/− DMSO vs. Bad −/− treated with BAD SAHB$_{A(L,D→A)}$). These results are consistent with genetic reconstitution studies using the L→A mutant (FIG. 15). Importantly, the efficiency of BAD SAHB$_A$ in restoring GSIS accompanied its effect on mitochondrial membrane potential (FIG. 19). Dispersed islets were treated with 1 µM of compounds for 4 hours and changes in Δψ measured as in FIG. 12. At 1 µM concentration, BAD but not BID SAHB conferred significant hyper polarization of the mitochondrial membrane potential (Δψ$_m$) upon glucose treatment, while the effect of BID SAHB on Δψ$_m$ was statistically indistinguishable from DMSO-treated β-cells.

These findings indicate that the BAD BH3 domain is sufficient to restore the insulin secretion defect in Bad −/− β-cells and further predict that administration of BAD SAHB compounds will improve glucose tolerance in Bad −/− mice. In fact, pilot experiments indicated that 60 minutes following an intra-peritoneal glucose challenge, blood glucose levels in Bad −/− mice injected with BAD SAHBA were 66% of that in vehicle-injected Bad −/− mice.

Example 7. The Role of BAD Phosphomimetic Compounds in Insulin Release

Figure 36:
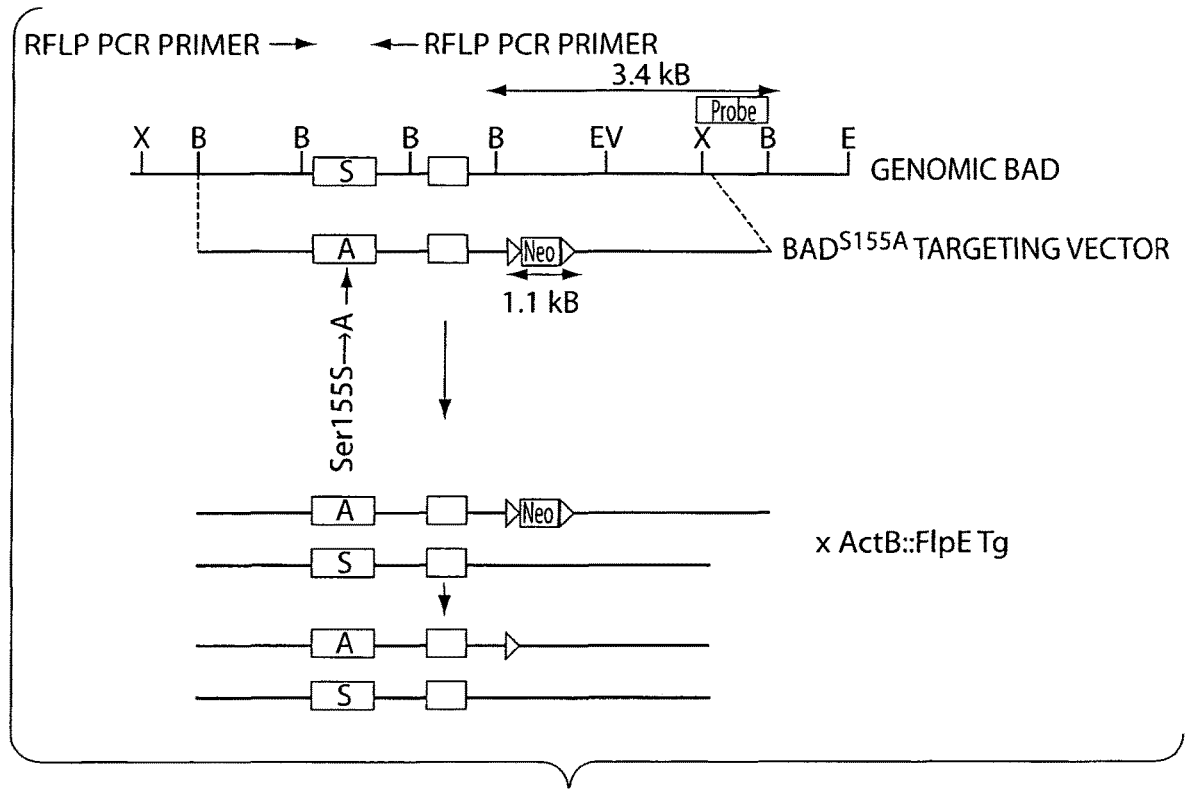
FIG. 36 is a schematic showing the knockin targeting strategy. Map of the BAD locus marks the restriction sites X, Xba1; B, BamH1; EV, EcoRV; S, SmaI; E, EcoR1 and boxes denote exons. The serine 155 to alanine mutation was linked to RFLP (EcoR1), and a PGK-NEO cassette with flanked FRT sites (blue triangles) was inserted downstream of the 3' UTR. The NEO cassette was excised after generation of the Bad S155A$^{(neo)/+}$ by crossing to FlpE transgenic mice.
Figure 37:
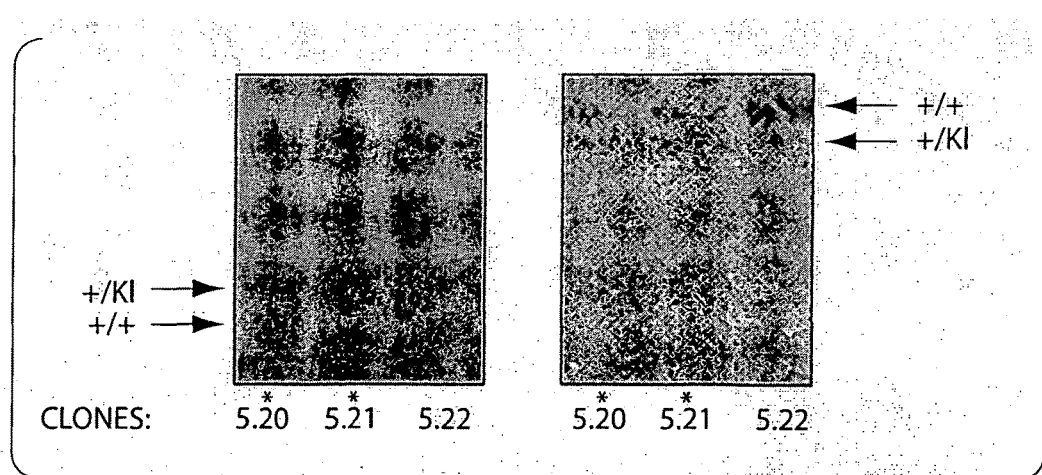
FIG. 37 is a photograph of a Southern blot verifying appropriate targeting. The probes indicated in FIG. 36 were used to show insertion of the FRT-Neo-FRT cassette (left panel) and the integration of the EcoRI RFLP into BAD (right panel). Clones marked with (*) were positive for both insert and RFLP.
Figure 38:
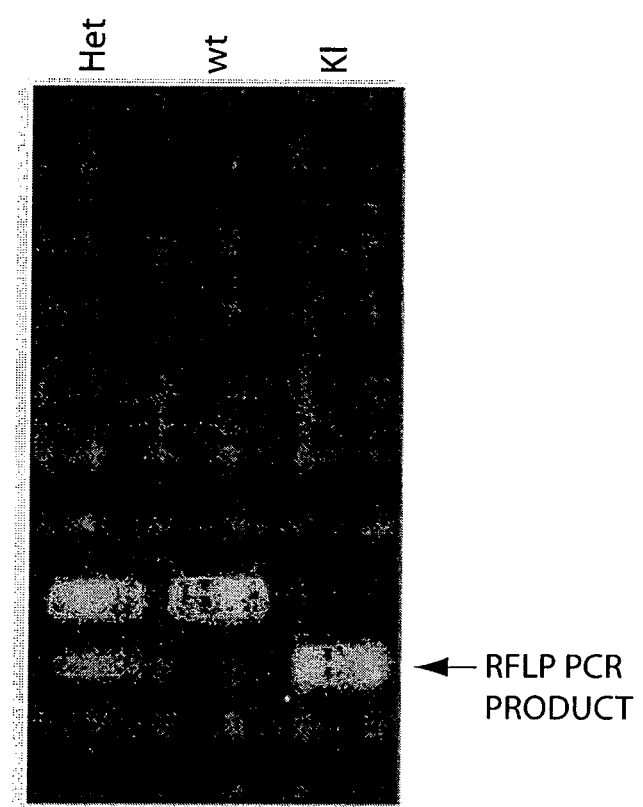
FIG. 38 is a photograph showing the PCR fragment for the RFLP mutation marker for S155A after digestion with EcoR1 used to genotype the S155A progenies of Bad S155A$^{(neo)/+}$ crossed to FlpE mice.
Figure 39:
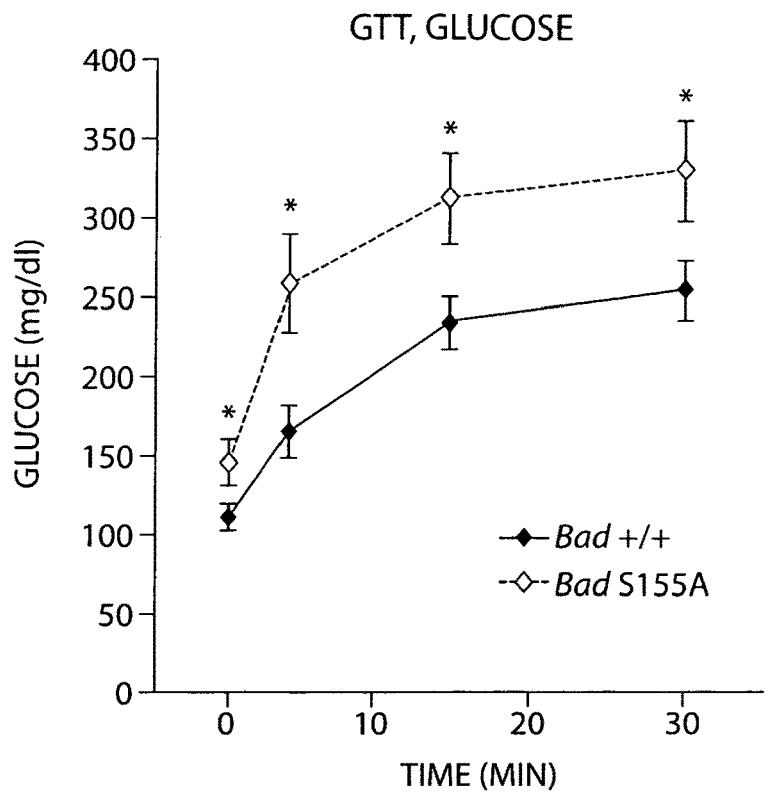
FIG. 39 is a line graph demonstrating blood glucose levels following an intraperitoneal glucose tolerance test (ipGTT), in which, following an overnight fast mice were injected with 1 g/kg of glucose, i.p. (time 0). Blood glucose and insulin levels were measured before and 5, 15, and 30 min into the ipGTT. n per group: WT=10 and Bad S155A=10. Asterisks: p<0.05.
Figure 40:
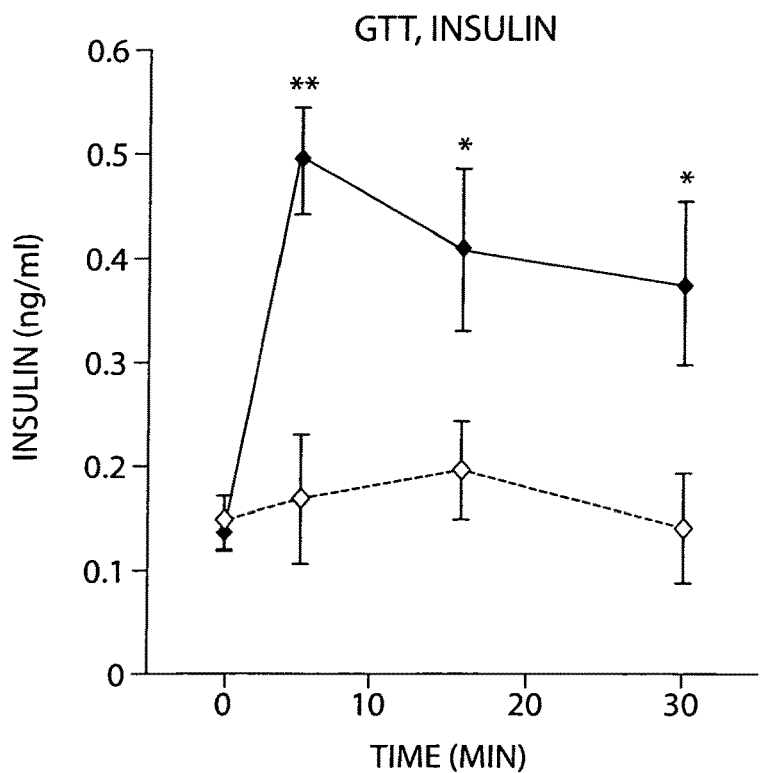
FIG. 40 is a line graph depicting blood insulin levels following an intraperitoneal glucose tolerance test as in FIG. 39. Asterisks: p<0.05; double asterisks in (e), p<0.01, unpaired two tailed t-test, Bad +/+ vs. Bad S155A.

The specificity of the BAD BH3 domain compared to BID BH3 sequence in regulating insulin release raises the possibility that residues other than L151 and D156, which are conserved across the BH3 domains of all BCL-2 family members, may also be required. Interestingly, serine 155 is a distinguishing feature of the BAD BH3 sequence. Structural modeling revealed that Ser 155 of BAD points toward the hydrophobic cleft of BCL-$X_L$, which upon phosphorylation by PKA creates significant steric hindrance for the BAD/BCL-$X_L$ association (Datta S. R. et al., 2000. *Mol Cell* 6, 41-51). To test the role of S155 in insulin secretion, a knockin genetic model was generated in which only this serine residue was replaced with alanine (FIGS. 36-38). The Bad S155A β-cells show abnormalities in insulin secretion both in vitro, when purified islets were examined (FIG. 16), and in vivo, when insulin levels were assessed in intra-peritoneal glucose tolerance test (ip-GTT) (FIGS. 39-40).

Figure 17:
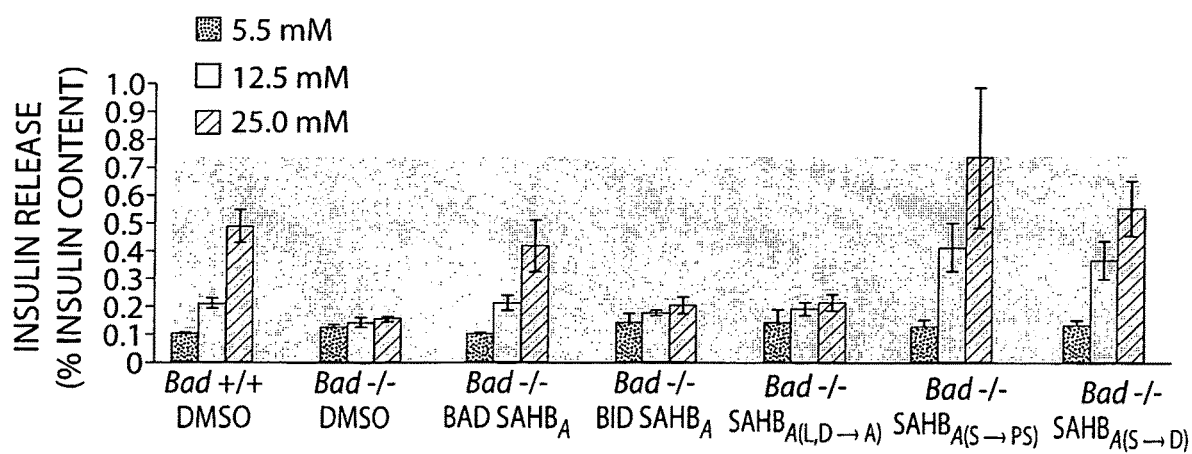
FIG. 17 is a bar chart demonstrating GSIS in Bad +/+ and Bad −/− islets treated with 3 μM of the indicated stabilized alpha-helices of BCL-2 domains (SAHBs) listed in FIG. 18 or vehicle control (DMSO). n=8 per group.
Figure 35:
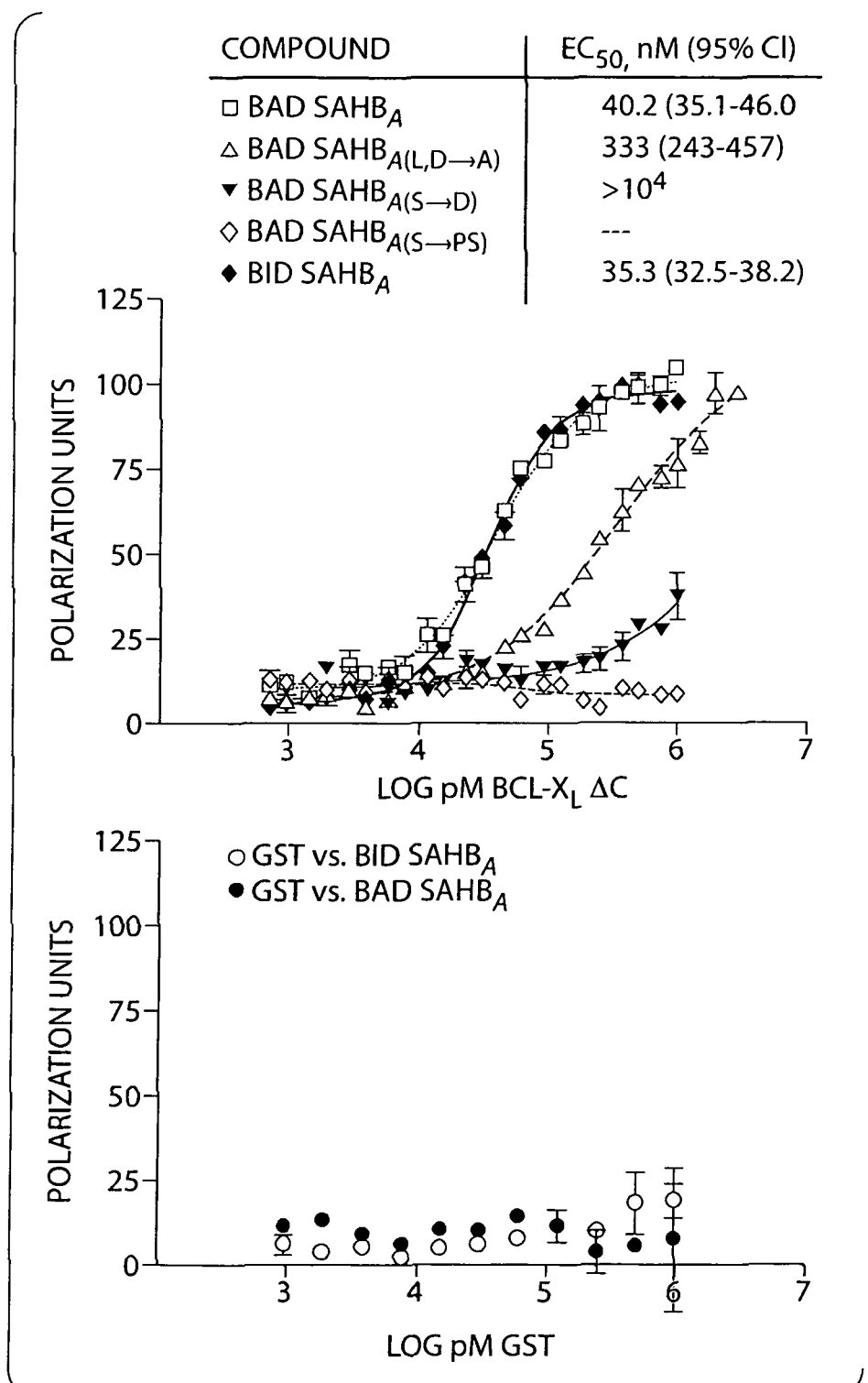
FIG. 35 is a line graph and dot plot illustrating the binding affinities of SAHB compounds to purified BCL-X$_L$ ΔC or control GST protein.

These findings suggest that phosphorylation within the BAD BH3 domain may dictate BAD's regulatory effect on insulin release. To test this hypothesis, phosphomimetic BAD SAHB compounds were generated (SAHB$_{A(S→PS)}$ and SAHB$_{A(S→D)}$, FIGS. 17-18 and FIG. 34). SAHB$_{A(S→PS)}$ contains a phosphorylated serine residue at position 155 of the BAD BH3 sequence, whereas SAHB$_{A(S→D)}$ contains and aspartic acid replacement previously shown to simulate a constitutively phosphorylated residue by mimicking the negative charge of a phosphate group (Datta S. R. et al., 2000. *Mol Cell* 6, 41-51). Both compounds corrected the GSIS defect in Bad −/− islets (FIG. 17). Importantly, these phosphomimetic compounds restored insulin secretion despite their inability to bind BCL-$X_L$ (FIG. 35). Fluorescence polarization binding assays were performed using FITC-labeled peptides (50 nM) and BCL-$X_L$ ΔC at the indicated concentrations (FIG. 35). $EC_{50}$ values for binding were determined by nonlinear regression analysis of dose-response curves using Prism 4.0 software (Graphpad). These observations are consistent with data from the Bad 3SA and S155A knockin mice, providing a pharmacologic confirmation that the effect of BAD BH3 domain on insulin release does not co-segregate with BCL-$X_L$ binding.

Example 8. BAD Mimetic Compounds: Novel GK Activators

Figure 20:
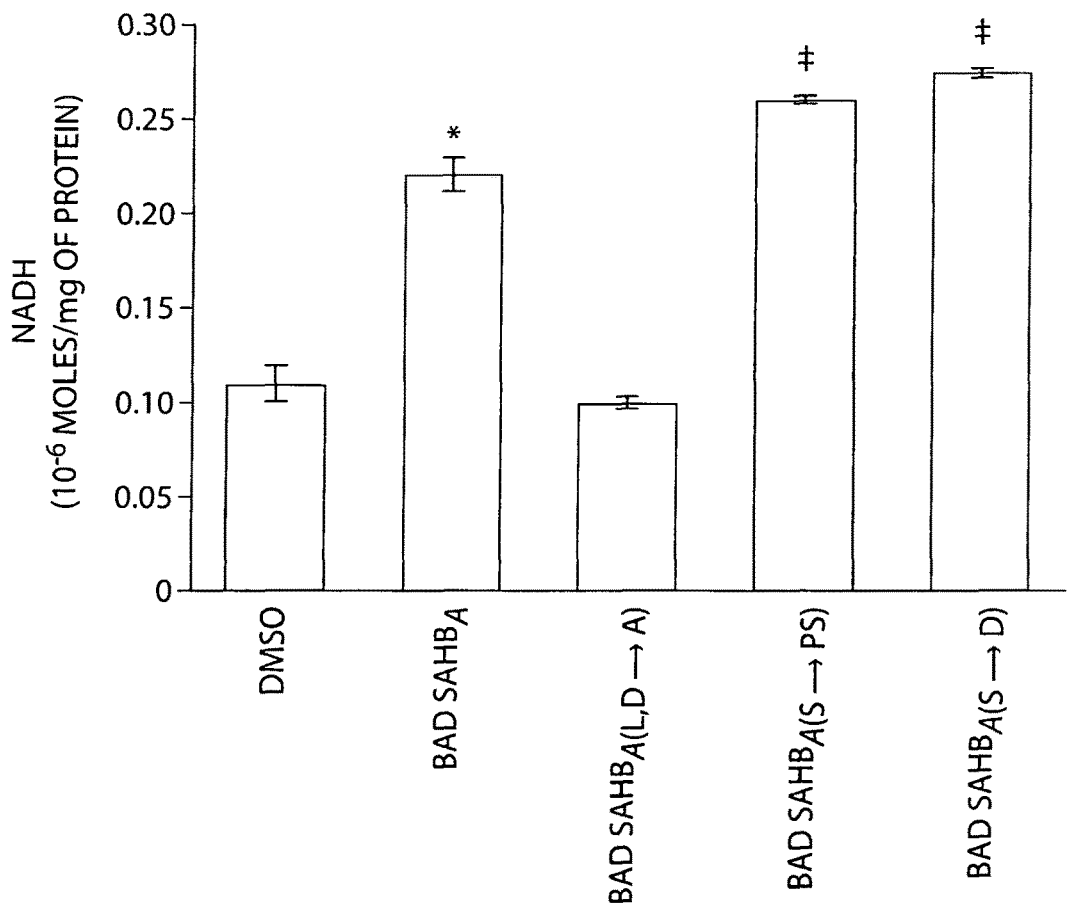
FIG. 20 is a bar chart demonstrating NADH fluorescence as an indication of glucokinase activity in homogenates prepared from MIN6 β-cells treated for 4 hours with 3 μM of the indicated compounds. Asterisk: $p<0.05$ BAD SAHB$_A$ versus DMSO, double dagger: $p<0.01$ BAD SAHB$_{A(S \to PS)}$ or BAD SAHB$_{A(S \to D)}$ versus BAD SAHB$_A$.

To interrogate the mechanism by which BAD SAHB compounds restore GSIS, their effect on GK activation was examined. BAD $SAHB_A$ and its phosphomimetic analogs stimulate endogenous GK activity in the MIN6 β-cell line, whereas BAD $SAHB_{A(L,D \rightarrow A)}$ does not (FIG. 20). Collectively, the data presented in FIG. 19-20 suggest that the ability of BAD BH3 domain to activate insulin release parallels its effects on GK activation and glucose-induced hyper polarization of the mitochondrial membrane potential.

Figure 70:
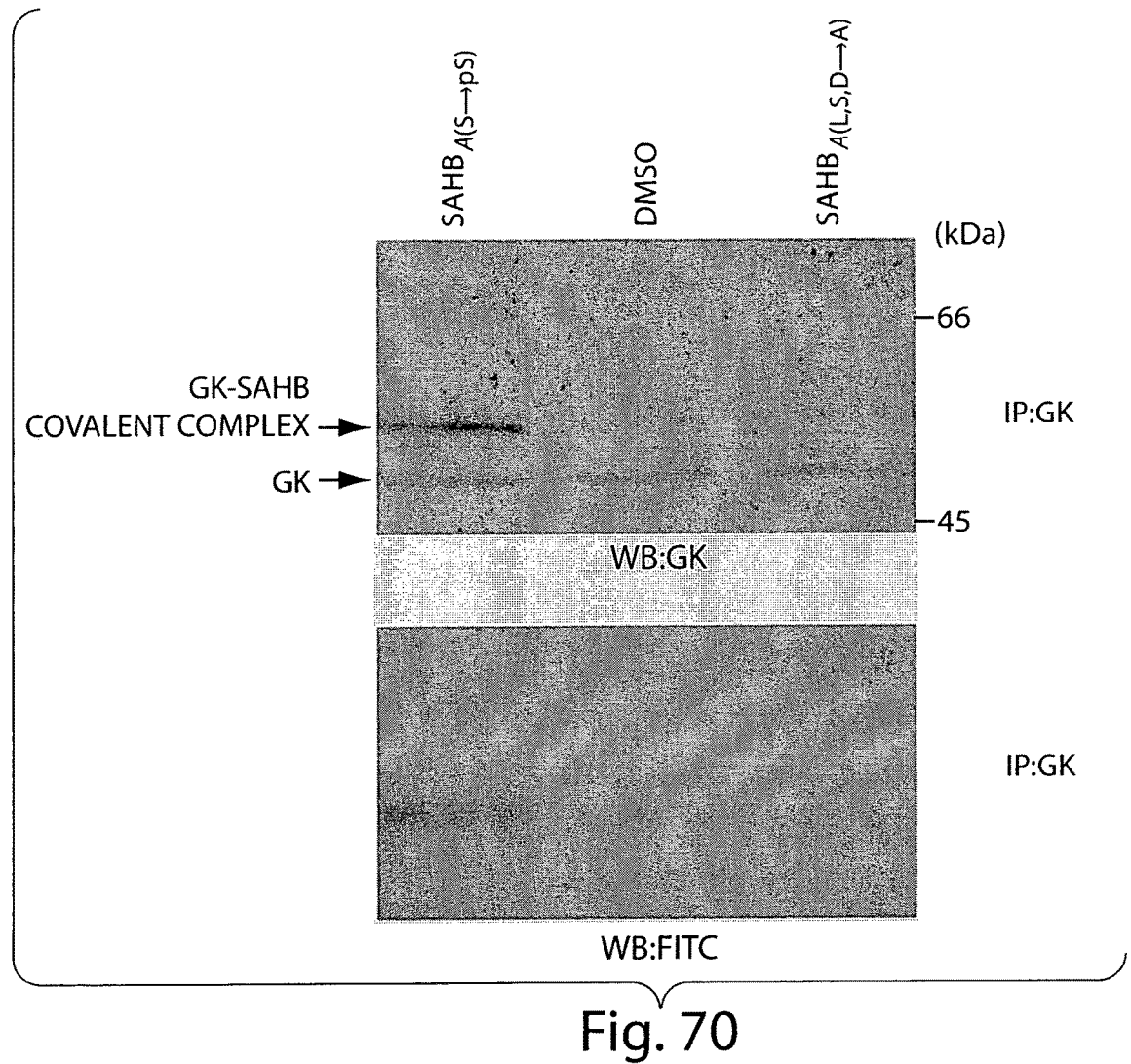
FIG. 70 is a photograph of an immunoblot showing glucokinase as a direct BAD BH3 target. 20 μM of the BAD SAHB compounds containing photoactivatable benzophenone moiety were preincubated with extracts prepared from INS-1 cells for 30 min at 23° C. followed by exposure to 350 nm light for 2 h at 4° C. The covalent binding of SAHBs to GK was detected by GK immunoprecipitation (IP). Bound material was eluted, gel-fractionated, and blotted (WB) using anti-GK or anti-FITC antibodies.
Figure 71:
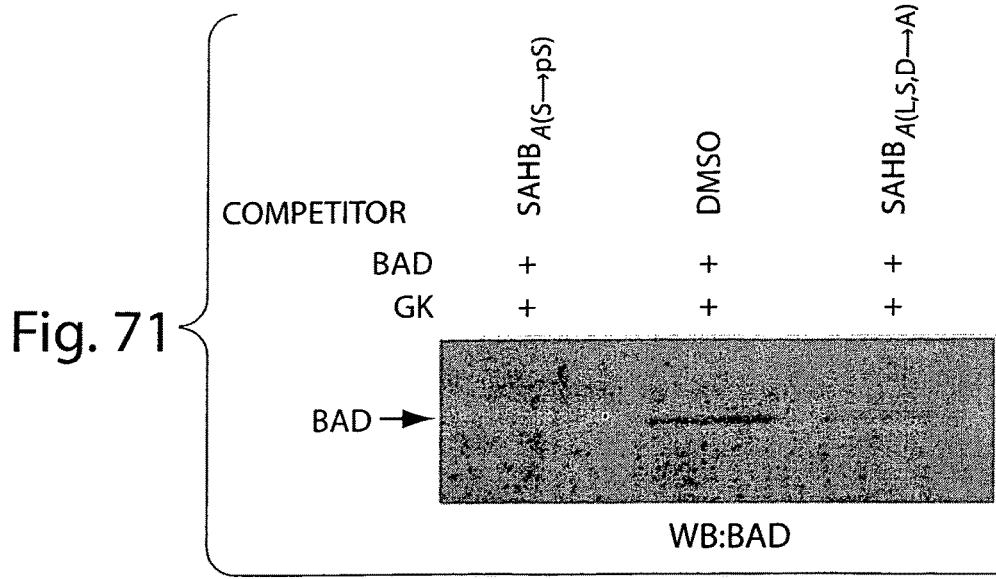
FIG. 71 is a photograph of an immunoblot showing competition of BAD SAHB compounds with full length recombinant BAD for binding to recombinant glucokinase. BAD and GK were co-translated using in vitro transcription-translation (IVTT) in a rabbit reticulocyte lysate system. GK and BAD were co-immunoprecipitated in the presence of 30 μM SAHB compounds or DMSO in RIPA buffer using the GK affinity columns described FIG. 31. Immune complexes were resolved on SDS-PAGE and probed (WB) with anti-BAD antibody.

Importantly, the effects of BAD SAHB compounds on GK activation and GSIS parallel their capacity to directly bind GK (FIG. 70-71).

Example 9. The Role of BAD in β-Cell Survival

β-cell dysfunction and failure to compensate for the secretory demands of hyperglycemia contribute significantly to the patho-physiology of type 2 diabetes. Destruction of β-cell mass ensues when apoptosis exceeds the rate of β-cell replication. Our studies have identified a role for the BH3 domain of BAD and the phosphorylation state of the molecule in insulin release. Because the same molecular features are known to regulate the apoptotic function of BAD, we investigated whether this BH3-only protein impacts β-cell survival.

Figure 41:
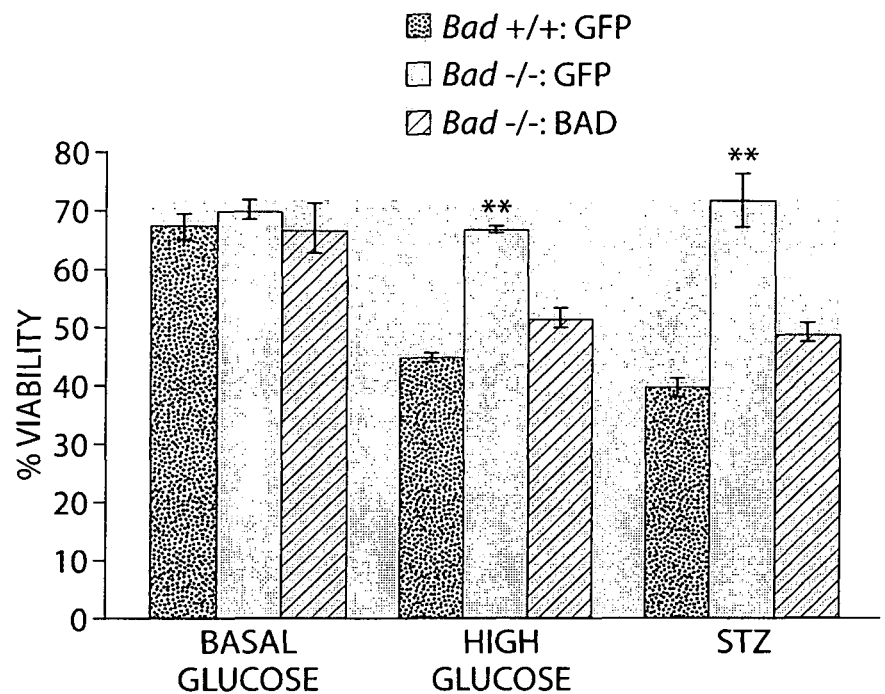
FIG. 41 is a bar graph demonstrating the effect of chronic exposure to high glucose or STZ in Bad −/− islets. Bad +/+ Bad +/+ were infected with adenoviruses expressing GFP alone or GFP and BAD, respectively. GFP-expressing islets in each group were then hand picked and cultured for 48 hrs in medium containing 5.5 mM (normal glucose), 16.7 mM (high glucose) or 5.5 mM and 1.2 mM STZ. Islets were dispersed by mild trypsinization and viability was assessed by trypan blue exclusion.
Figure 42:
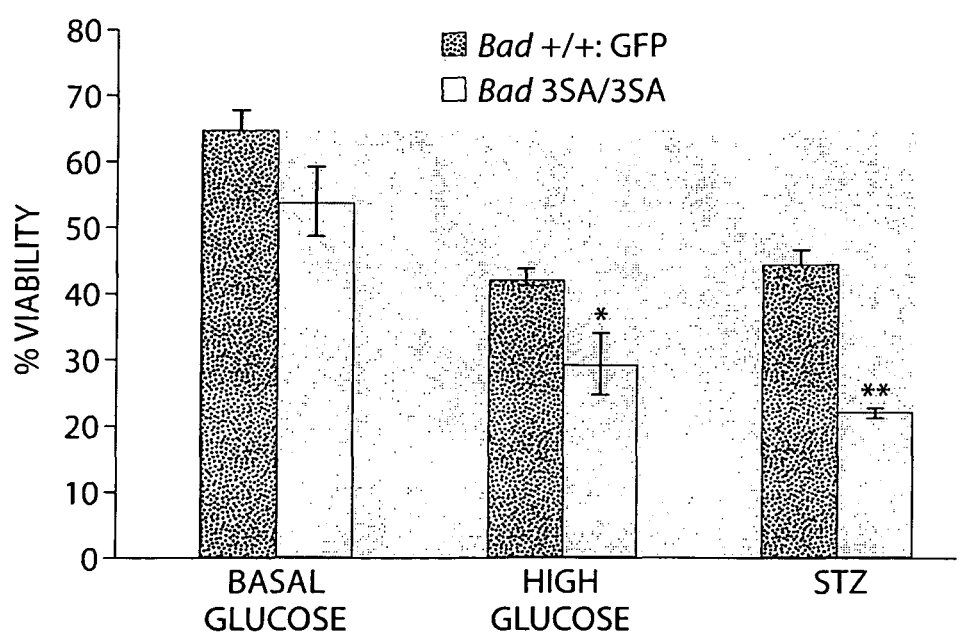
FIG. 42 is a bar graph demonstrating the effect of chronic exposure to high glucose or STZ. Bad +/+ and Bad 3SA islets were exposed to chronic high glucose or STZ and viability as assessed above. The results of at least three independent experiments read in triplicates are shown. Asterisk compares Bad −/− vs. Bad +/+, or Bad 3SA vs. Bad +/+.

While short-term exposure of β-cells to glucose stimulates insulin secretion, chronic incubation under high glucose concentrations activates the apoptotic pathway. Of note, under these "glucotoxic" conditions, the expression of several pro-apoptotic genes including Bad are up-regulated (Federici M. et al., 2001. *Diabetes* 50, 1290-301). Bad-deficient islets were significantly protected under these conditions (p<0.01, FIG. 41, % viability in high glucose, Bad +/+ vs. Bad −/−). Genetic correction using Bad adenoviruses restored sensitivity to apoptosis (FIG. 41). Furthermore, interfering with BAD phosphorylation lowered the threshold for apoptosis as apparent from enhanced sensitivity of Bad 3SA islets to glucotoxicity-induced apoptosis (FIG. 42). Collectively, these data provide genetic evidence that BAD plays a role in glucotoxicity-induced death.

Figure 43:
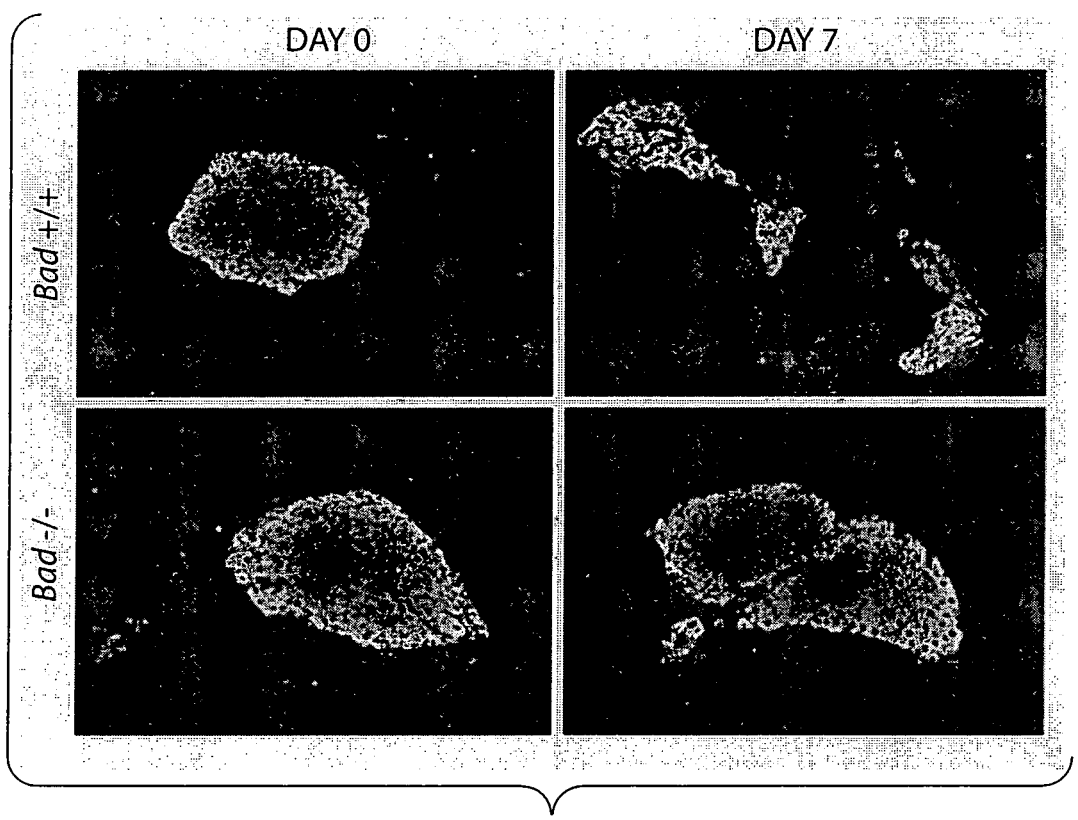
FIG. 43 is a photograph showing fluorescence microscopy of pancreatic sections prepared from Bad −/− and Bad +/+ mice on day 0 or day 7 after STZ treatment doubly stained with antibodies to insulin (red) and glucagon (green).
Figure 44:
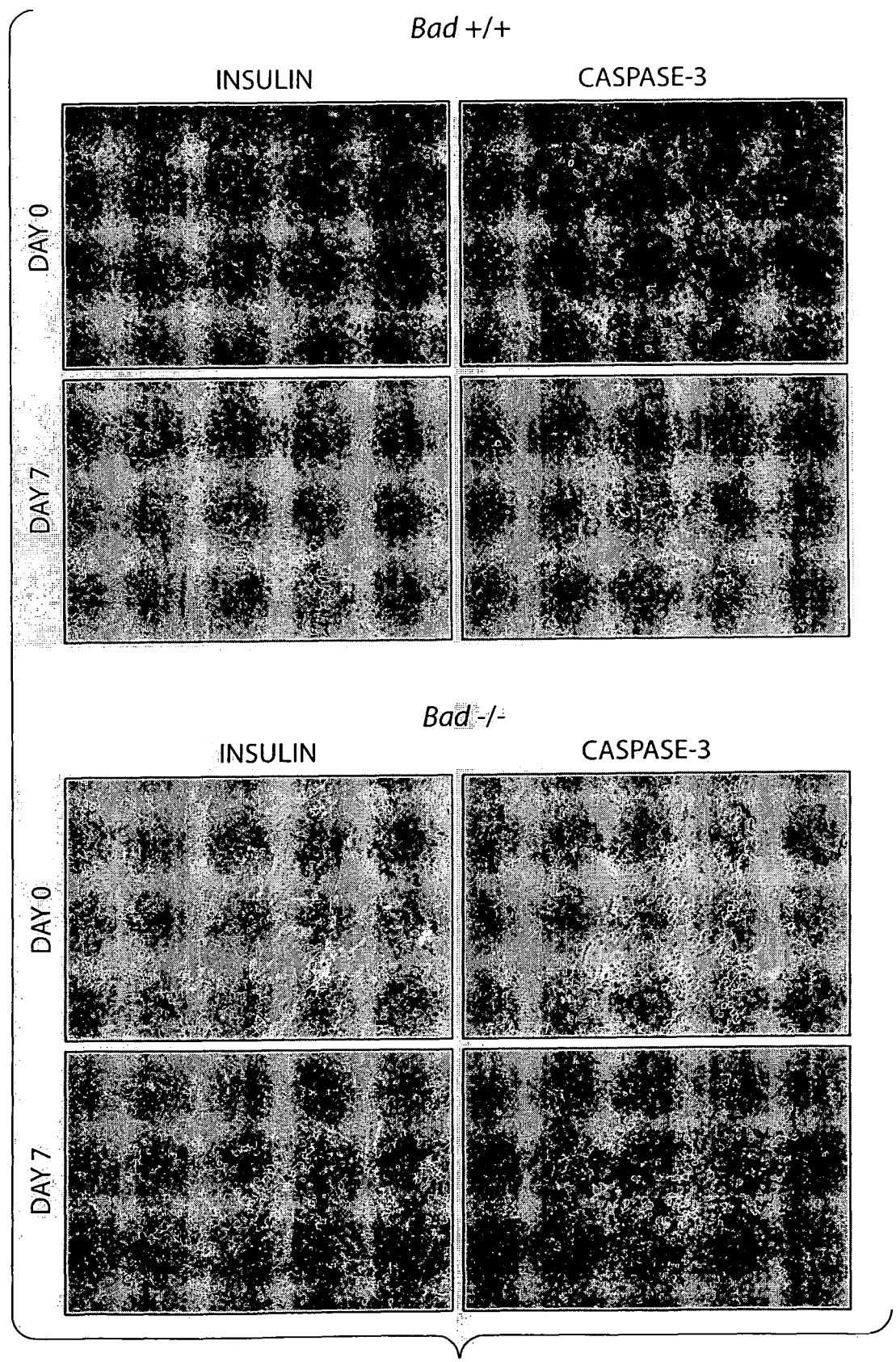
FIG. 44 is a photograph showing immuno-histochemistry of pancreatic sections from the experiment in FIG. 43 upon staining with antibodies to insulin or active caspase-3 followed by counterstaining with hematoxylin and eosin.
Figure 45:
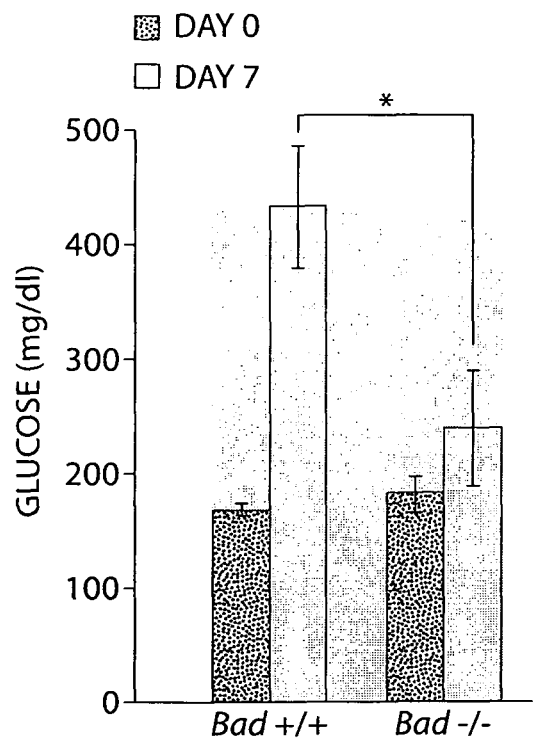
FIG. 45 is a bar chart demonstrating serum insulin levels on day 0 and day 7 in the same cohort of Bad +/+ (n=7) and Bad −/− (n=8) mice used in (FIG. 43-44). Asterisk, p<0.05; double asterisks, p<0.01, unpaired two tailed t-test.
Figure 46:
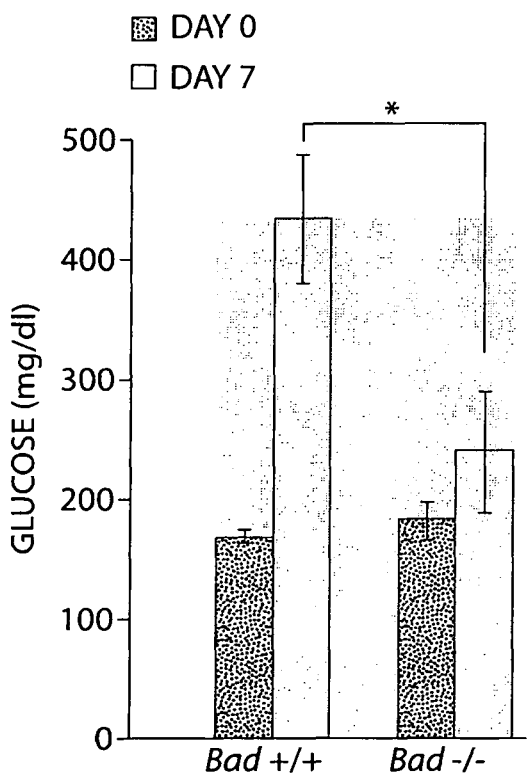
FIG. 46 is a bar graph showing glucose levels on day 0 and day 7 in the same cohort of Bad +/+ (n=7) and Bad −/− (n=8) mice used in (FIG. 43-44). Asterisk, p<0.05.

The β-cell toxin, streptozotocin (STZ), specifically depletes β-cells and is commonly used in animal models of experimentally-induced diabetes. BAD-deficient islets were resistant to STZ-induced death while those isolated from the BAD 3SA animals showed enhanced sensitivity to STZ (FIG. 41-42). The requirement for BAD in STZ-induced β-cell destruction was tested by examining a cohort of Bad −/− and Bad +/+ mice after single intra-peritoneal injection of this compound. The resistance of Bad-deficient mice to STZ was evident when islets were examined in pancreatic sections (FIG. 43). STZ caused the collapse of islet architecture in Bad +/+ mice marked by significant reduction of insulin signal concomitant with glucagon staining inside the islets (FIG. 43). In marked contrast, Bad-null pancreatic sections demonstrated near complete preservation of islets (FIG. 43). These results are consistent with differences in caspase-3 activity in Bad +/+ versus Bad −/− β-cells on day 7 (FIG. 44). Resistance of Bad −/− β cells to apoptosis was also evident in the levels of insulin and glucose detected after STZ treatment. On day 0, blood insulin levels were nearly 1.5 fold higher in Bad −/− mice compared to Bad +/+ controls (p<0.01, FIG. 45). By day 7, as islets underwent apoptosis, insulin level in Bad +/+ animals plummeted by 86%, while Bad-deficient mice sustained a 44% decrease in the hormone. The absolute value of serum insulin on day 7 was ~6 fold higher in Bad −/− versus Bad +/+ mice (FIG. 45, p<0.01). Furthermore, BAD-deficient mice are protected against the hyperglycemic effect of STZ (FIG. 46, day 7 glucose at 434.29±53.34 mg/dl in Bad +/+ versus 239.83±50.86 mg/dl in Bad −/−, p<0.05). Thus, Bad deficiency affords protection against STZ-induced β cell-destruction and the resultant diabetic phenotype.

Example 10. BAD: A Determinant of High Fat Diet-Induced Diabetes

β-cells normally undergo compensatory changes to meet the secretory demand under insulin resistant state. These adaptive mechanisms include changes in the β-cell signaling pathways and gene expression programs resulting in β-cell hyperplasia and hypertrophy. Consequently, a lack of proper adaptation results in diabetes (Bell G. I. and Polonsky K. S., 2001. *Nature* 414, 788-91; Weir G. C. et al., 2001. *Diabetes* 50 Suppl 1, S154-9; DeFronzo R. A., 1988. *Diabetes* 37, 667-87; Accili D. et al., 2001. *Curr Mol Med* 1, 9-23). Furthermore, chronic exposure to high glucose and lipids can eventually lead to impairment of insulin secretion (glucolipotoxicity) and β-cell apoptosis (Prentki M. et al., 2002. *Diabetes* 51 Suppl 3, S405-13).

The studies described above have identified a role for BAD BH3 domain and its phosphorylated derivative in regulating insulin release. Interestingly, the same peptidic motif is known to regulate the apoptotic function of BAD and evidence suggests that BAD is an important sentinel in β-cell survival under chronic high glucose exposure or streptozotocin treatment (FIG. 41-46) and in neonatal β-cell death (Hettiarachchi K. D. et al., 2006. submitted).

Figure 21:
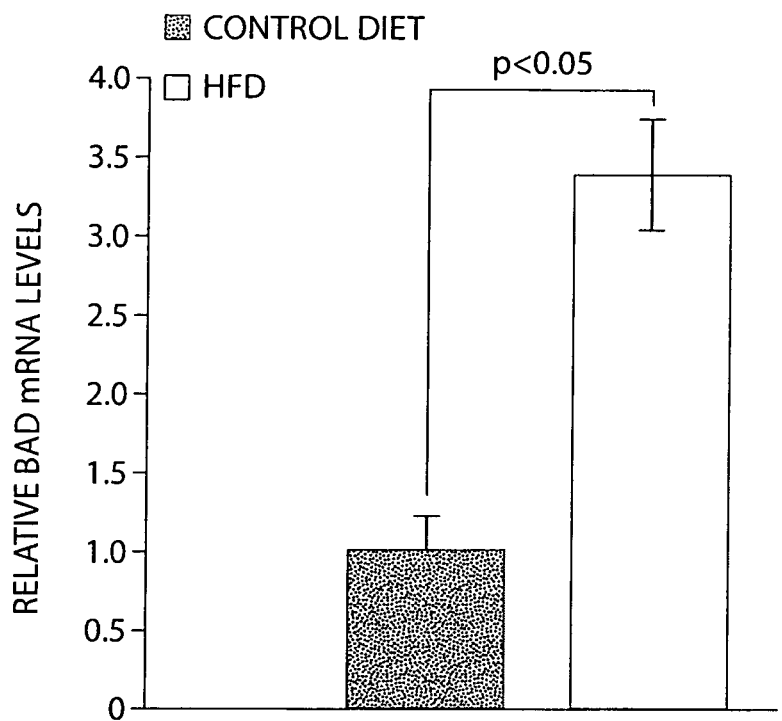
FIG. 21 is a bar graph depicting islet BAD mRNA levels in wild type mice on a high fat diet (HFD) for 16 weeks or control diet.
Figure 23:
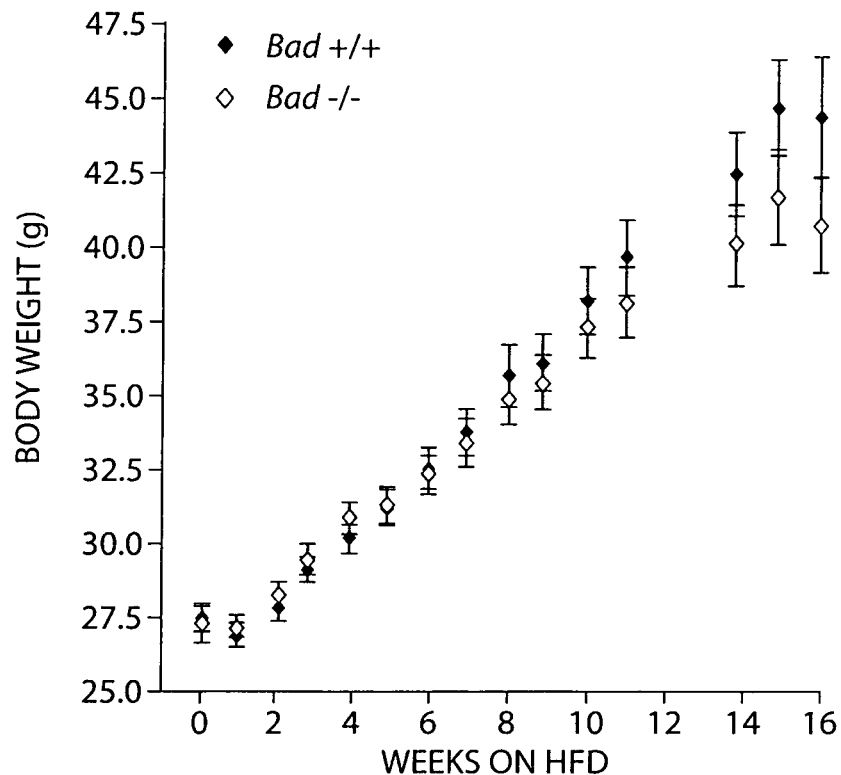
FIG. 23 is a dot plot depicting weekly body weights of a cohort of Bad +/+ and Bad −/− (n=20) placed on HFD for 16 weeks.
Figure 24:
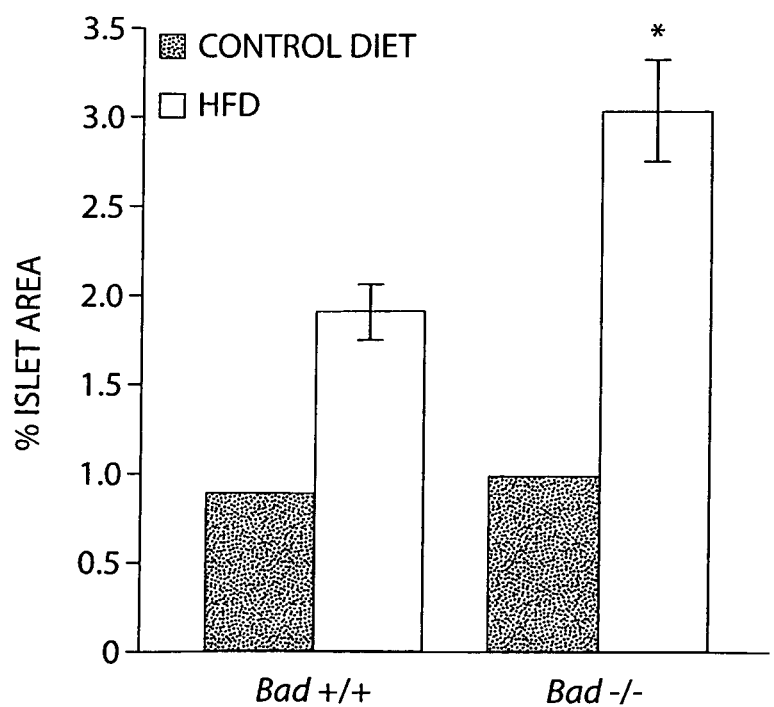
FIG. 24 is a bar graph illustrating percent islet area in pancreatic sections prepared from the cohorts on control or HFD. Asterisk: $p<0.05$, Bad −/− vs. Bad +/+ on HFD.
Figure 25:
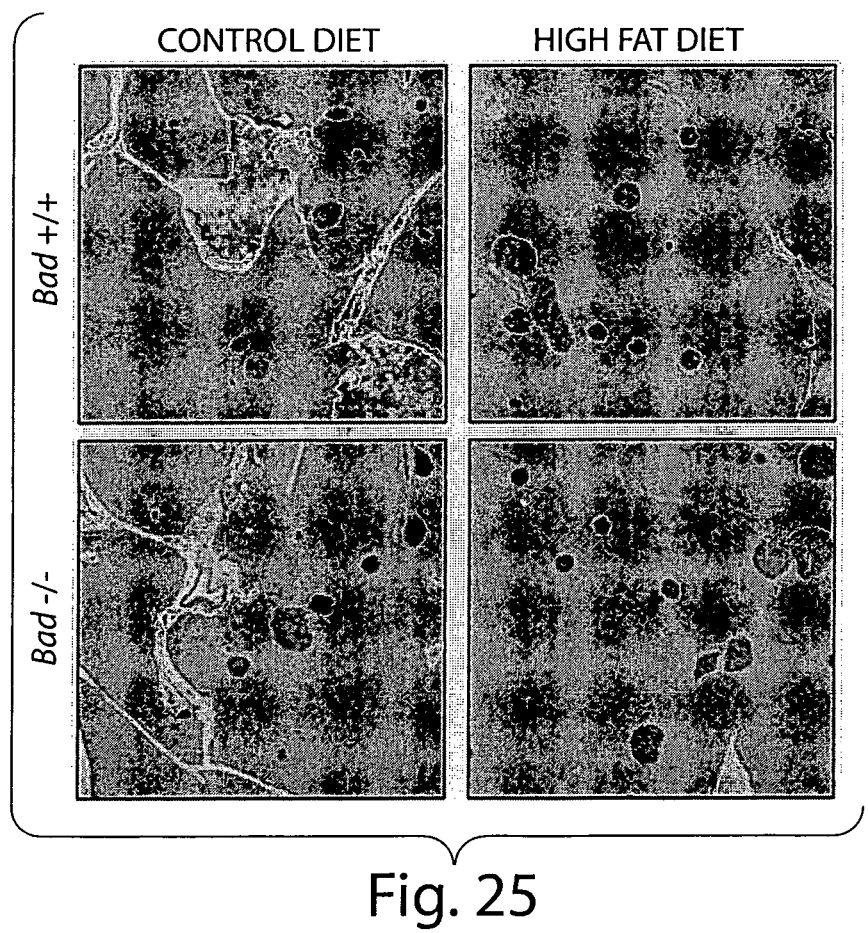
FIG. 25 is an illustration demonstrating immuno-histochemical analysis of representative pancreatic sections prepared from the above cohorts developed with anti insulin antibody.

To examine how the metabolic and apoptotic functions of BAD in β-cells may be relevant to the pathophysiology of diabetes, its role in β-cell adaptation associated with a high fat diet (HFD)-associated model of insulin resistance was interrogated. Relative BAD mRNA levels increase significantly in islets isolated from wild type mice subjected to HFD (FIG. 21). To examine the significance of this observation, a cohort of Bad +/+ and Bad −/− mice was subjected to HFD for 16 weeks. A parallel cohort was kept on control diet. On control diet, the body weight and fed glucose levels in Bad +/+ and Bad −/− mice were comparable throughout the study (data not shown). On HF diet, however, Bad −/− mice were resistant to the development of hyperglycemia (FIG. 22) despite gaining weight at a similar rate as control animals (FIG. 23). This resistance was associated with an increase in percent islet area, which was significantly higher in Bad −/− mice compared to controls (FIG. 24-25).

Figure 26:
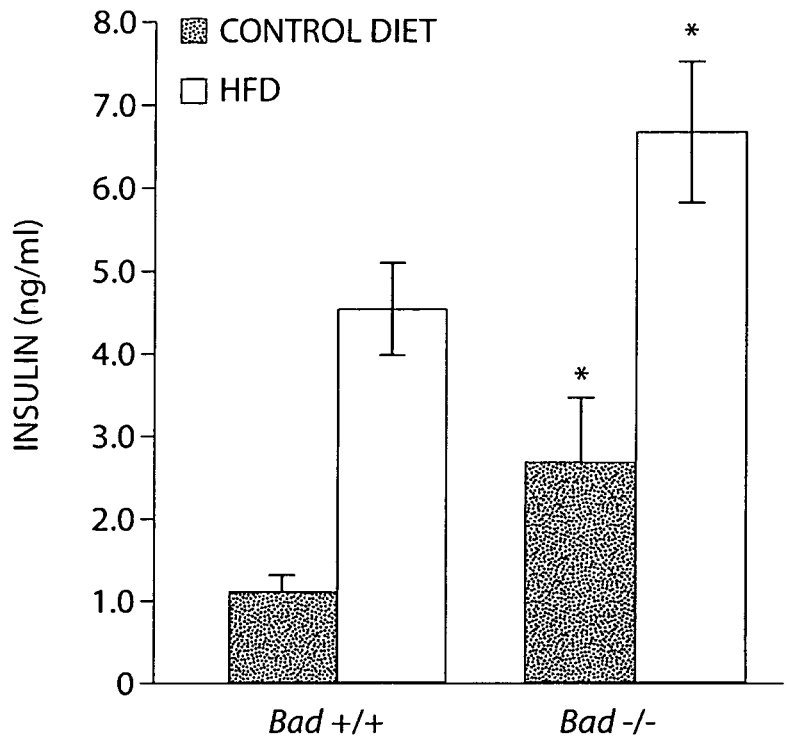
FIG. 26 is a bar chart indicating fed blood insulin levels of Bad +/+ and Bad −/− on control or HFD for 8 weeks.
Figure 47:
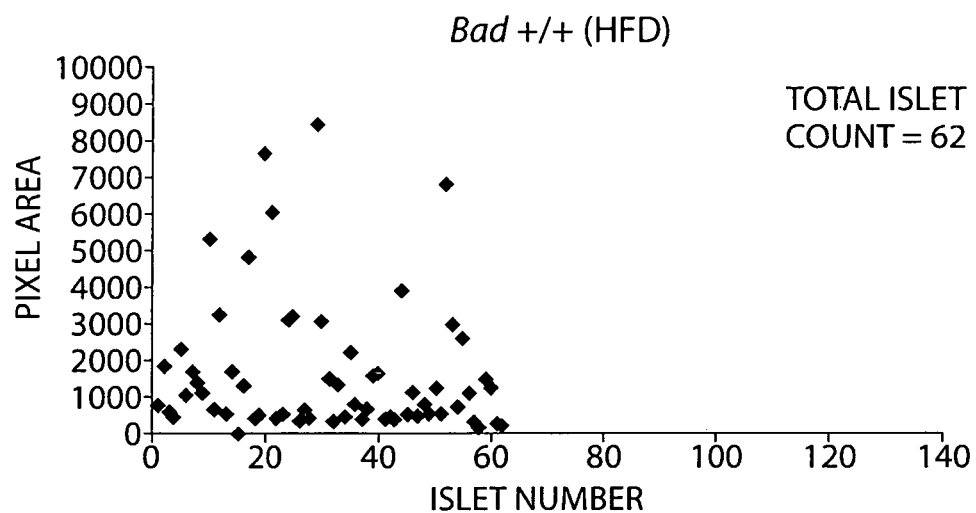
FIG. 47 histogram showing the number of islets and their size distribution in representative pancreatic sections prepared from Bad +/+ mice after 16 weeks on HFD. Histogram showing the number of islets and their size distribution in representative pancreatic sections prepared from Bad +/+ mice after 16 weeks on HFD. Each diamond represents an islet that was immuno-stained with anti insulin antibody. The vertical axis demonstrates the pixel area assigned to islets traced by the MetaMorph software program. The horizontal axis denotes islets. For each representative pair of genotypes shown (Bad +/+ vs. Bad −/− and Bad +/+ vs. Bad 3SA) the total section area was comparable. Bad −/− sections contain significantly more islets for the same total tissue area, while Bad 3SA mice have significantly fewer islets. Multiple sections from at least 3 animals per group were analyzed in a similar fashion
Figure 48:
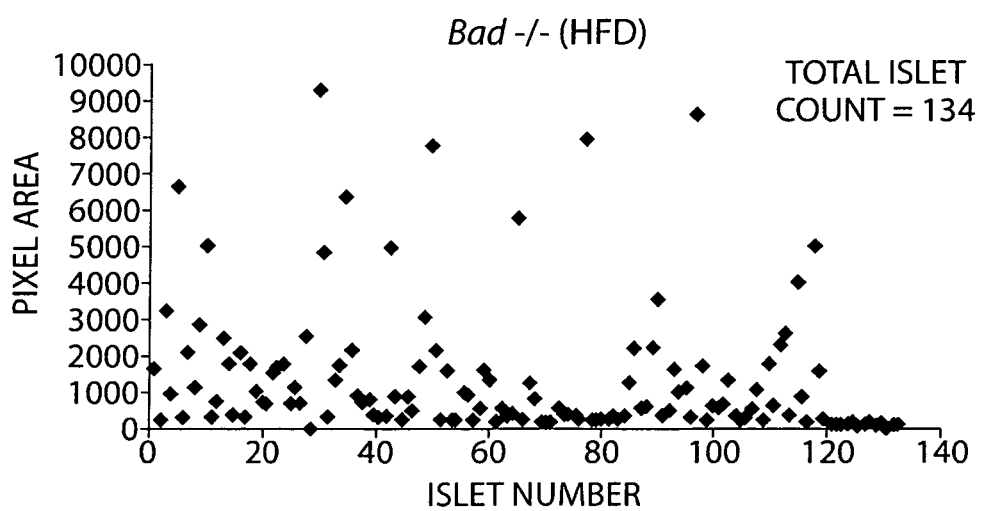
FIG. 48 is a histogram demonstrating the number of islets and their size distribution in representative pancreatic sections prepared from Bad −/− mice after 16 weeks on HFD.

Whether the increase in total β-cell area under HFD is dependent on BAD and its phosphorylation status was determined next. In FIGS. 47-50, each diamond represents an islet that was immuno-stained with anti insulin antibody. The vertical axis demonstrates the pixel area assigned to islets traced by the MetaMorph software program. The horizontal axis denotes islets. For each representative pair of genotypes shown (Bad +/+ vs. Bad −/− and Bad +/+) the total section area was comparable. Bad −/− sections contain significantly more islets for the same total tissue area. Multiple sections from at least 3 animals per group were analyzed in a similar fashion. Analysis of Bad −/− pancreatic sections revealed that the increase derived from a higher number of islets compared to Bad +/+ HFD sections (FIG. 47-48). Parallel to these observations, blood insulin levels were higher in Bad −/− mice compared to Bad +/+ controls (p<0.05, FIG. 26). Thus the Bad −/− β-cells appear to have an advantageous adaptive response irrespective of their defect in GSIS.

Figure 27:
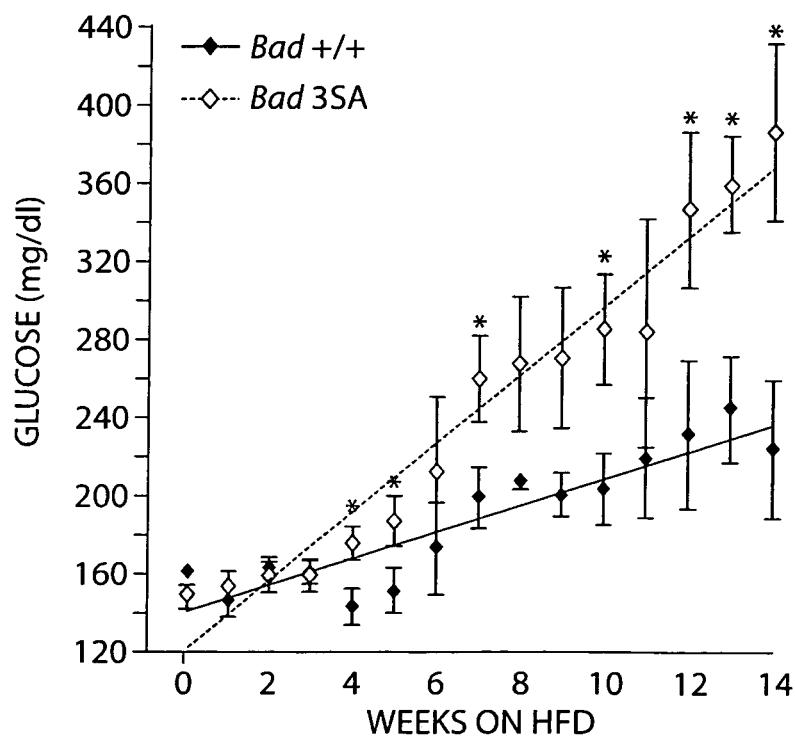
FIG. 27 is a line graph depicting weekly blood glucose levels of a cohort of Bad +/+ and Bad 3SA (n=8) placed on HFD for 16 weeks.
Figure 28:
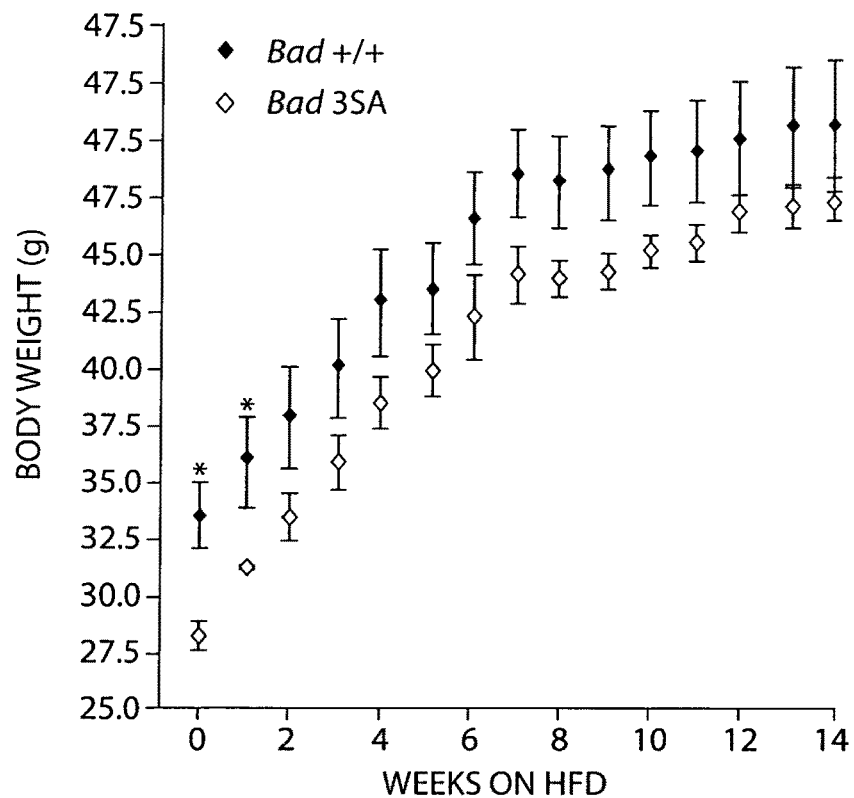
FIG. 28 is a dot plot showing the body weights of a cohort of Bad +/+ and Bad 3SA (n=8) placed on HFD for 16 weeks.
Figure 29:
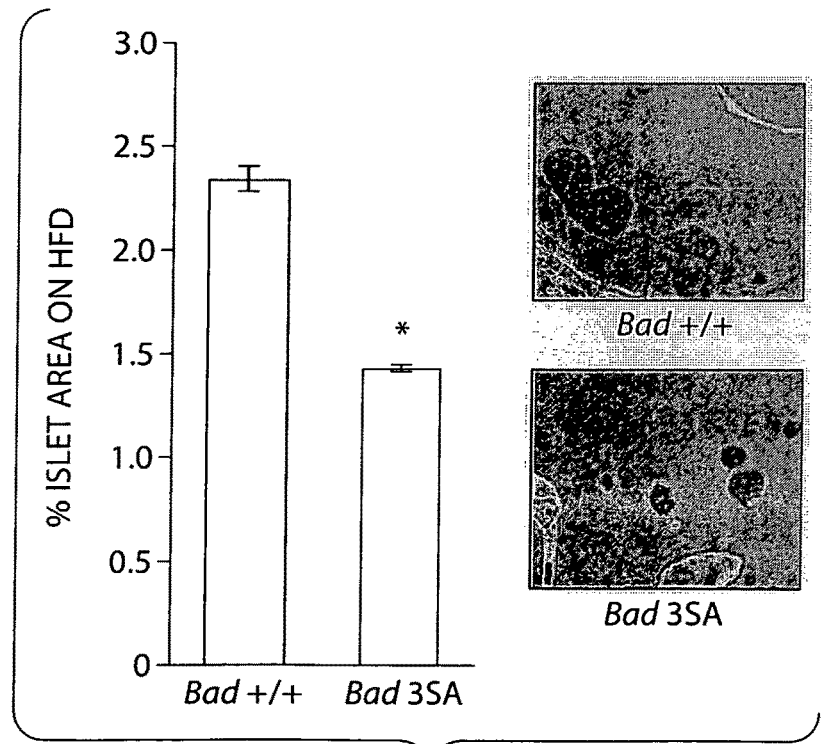
FIG. 29 is a bar graph and photograph showing percent islet area in pancreatic sections prepared from cohorts shown in (27-28) above.
Figure 30:
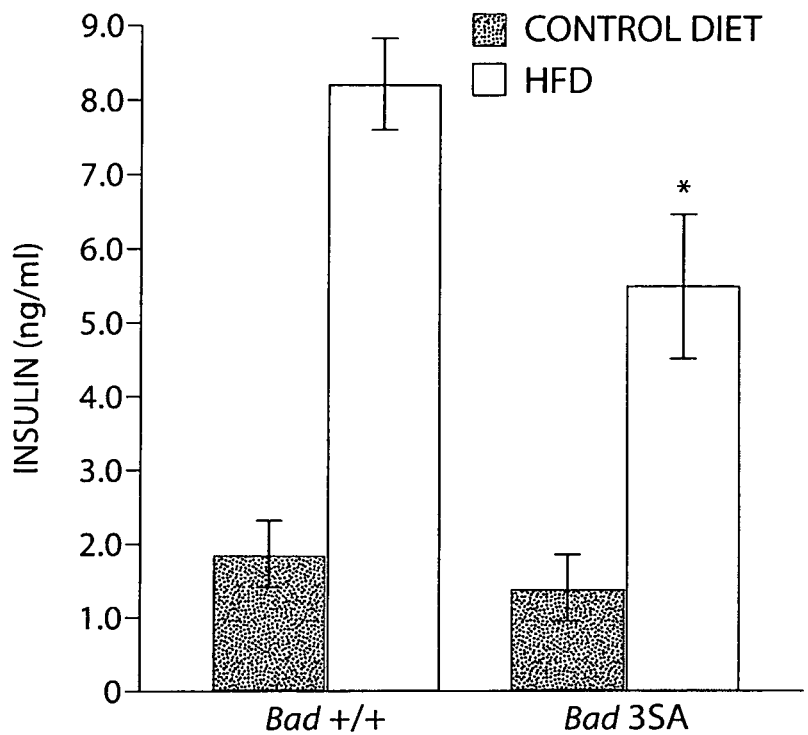
FIG. 30 is a bar chart demonstrating fed blood insulin levels of Bad +/+ and Bad3SA on control or HFD for 8 weeks. Asterisk: $p<0.05$, Bad 3SA vs. Bad +/+ on HFD.
Figure 49:
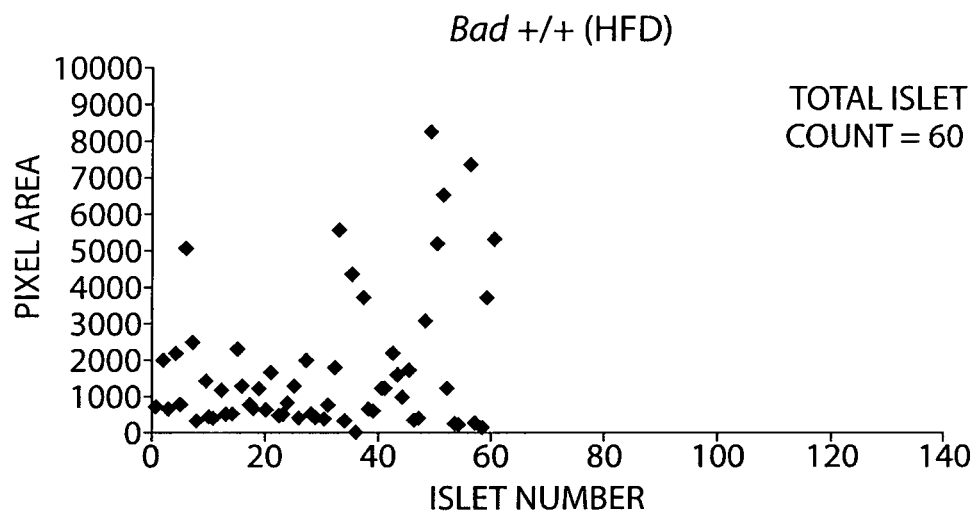
FIG. 49 is a histogram showing the number of islets and their size distribution in representative pancreatic sections prepared from Bad +/+ mice after 16 weeks on HFD.
Figure 50:
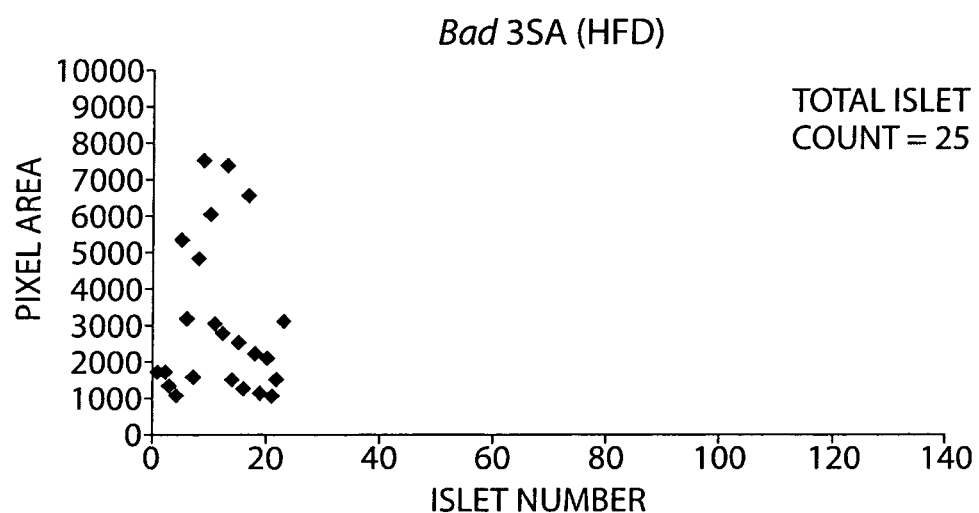
FIG. 50 is a histogram indicating the number of islets and their size distribution in representative pancreatic sections prepared from Bad 3SA mice after 16 weeks on HFD.

BAD is a target of survival signaling pathways including AKT and S6P70 networks that are known to impact β-cell survival (Tuttle R. L. et al. 2001. *Nat Med* 7, 1133-7; Pende M. et al., 2000. *Nature* 408, 994-7). Both AKT and S6P70 can phosphorylate and inactivate BAD's pro-apoptotic function. To assess whether the effect of BAD in β-cell adaptation in the HFD model co-segregates with its apoptotic function, a parallel cohort of Bad 3SA mice and their corresponding littermate controls were examined as described above. Unlike Bad −/− mice, Bad 3SA animals were more sensitive to the HFD challenge, showing on average higher blood glucose levels (FIG. 27). The body weights of Bad 3SA mice were initially lower than control cohorts (p<0.05, weeks 0 and 1, FIG. 28) but did not show any significant differences during the subsequent weeks of study. The percent islet area in pancreatic sections was significantly lower in Bad 3SA mice compared to littermate controls, suggesting that β-cell mass adaptation may have been inefficient (FIG. 29). Bad 3SA sections contain significantly fewer islets (FIG. 49-50). These data were consistent with measurements of blood insulin levels, which were significantly lower in Bad 3SA mice on HFD (FIG. 30). Collectively, the findings suggest that the accompanying β-cell compensation and sensitivity to HFD is influenced by BAD phosphorylation status. Furthermore, the opposite response of Bad −/− and Bad 3SA to a HFD challenge in spite of the common metabolic abnormalities in these genetic models suggest that the role of BAD in determining the sensitivity to HFD parallels its apoptotic function rather than its effect on GK, further highlighting BAD's dual role, each having important physiologic consequences.

Exploiting the role of BCL-2 proteins in therapeutic manipulation of islet function requires a careful assessment of the impact of distinct family members on both metabolism as well as β-cell survival. This is especially relevant considering the emerging roles of BCL-2 family proteins at the mitochondria (Green D. R. and Kroemer G., 2004. *Science* 305, 626-9) and the ER (Thomenius M. J. and Distelhorst C. W., 2003. *J Cell Sci* 116, 4493-9). The role of BAD in glucose-stimulated insulin release by β-cells is consistent with its capacity to impact GK and regulate glucose-driven respiration. The BAD BH3 domain, which is required for the pro-apoptotic function of the molecule, is also required for insulin secretion. Indeed, SAHB compounds derived from the BAD BH3 domain proved ideal molecular probes of BAD-regulation of insulin secretion. Using BAD mutants and peptides that are either defective in binding to BCL-$X_L$ (SAHB$_{A(L,D \to A,A)}$, BAD SAHB$_{A(S \to PS)}$ and BAD SAHB$_{A(S \to D)}$) or those whose binding cannot be repressed (BAD 3SA and 155A), it was demonstrated that BAD BH3 has distinct functionalities in regulating insulin secretion and binding BCL-$X_L$. These findings are consistent with the observation that loss of BAD does not entirely phenocopy BCL-$X_L$ over-expression. In a β-cell-specific BCL-$X_L$ transgenic model, enhanced islet survival was accompanied by perturbations in mitochondrial function, $Ca^{2+}$ handling and insulin secretion (Zhou Y. P. et al., 2000. *Am J Physiol Endocrinol Metab* 278, E340-51). Bcl-$X_L$ transgenic islets displayed significant secretory defects in response to $Ca^{2+}$-mobilizing secretagogues (KCl and tolbutamide) and mitochondrial fuels, such as KIC (Zhou Y. P. et al., 2000. *Am J Physiol Endocrinol Metab* 278, E340-51). On the other hand, Bad −/− islets have a robust response to all of these same secretagogues. Thus, while the enhanced survival of β-cells is common in both genetic models, the nature of the islet secretory defect is not. This in turn may be due to the effects of BCL-$X_L$ on cellular bioenergetics that are not dependent on its interaction with BAD.

Figure 4:
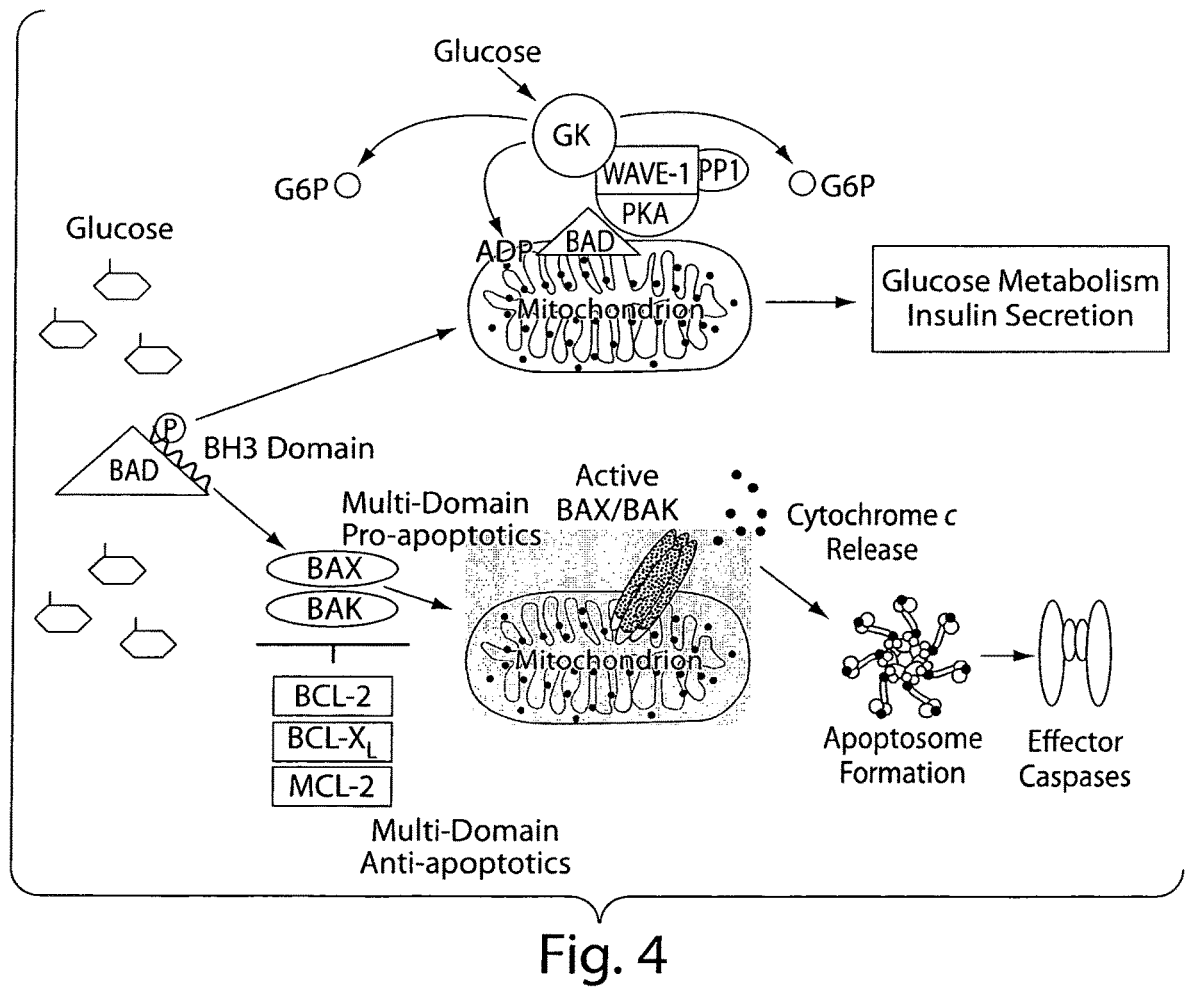
FIG. 4 is a schematic showing that the BH3 domain of BAD may serve to integrate cellular metabolic cues to engage distinct sets of molecular partners that determine the fate of a β cell with regard to insulin secretion versus apoptosis. Phosphorylation of serine 155 in the BAD BH3 domain instructs the protein to assume a metabolic role though its effect on GK, glucose-driven respiration and insulin secretion.

BAD sets a precedent for the possibility that BH3-only molecules function as integral components of distinct signaling pathways, regulating physiologic processes beyond controlling apoptosis. By acquiring a BH3 domain, these proteins may have evolved to integrate apoptosis with other homeostatic pathways. Due to its ability to regulate glucose-driven mitochondrial respiration, BAD is uniquely positioned to register glucose metabolism and any cellular bioenergetic consequences that follow glucose utilization. The BAD BH3 domain has the capacity to selectively engage in discrete protein interactions that regulate glucose metabolism/insulin secretion (FIG. 4). This dual capacity is determined by the phosphorylation state of the BH3 domain. While BCL-$X_L$ is the BH3 target through which BAD engages the apoptotic machinery, the nature of the BH3 target that allows it to activated GK awaits further investigation. Future studies will evaluate whether BAD SAHB operates by displacing a negative regulator within the complex or making an activator available to GK, and will determine how these events are orchestrated by the phosphorylation status of BAD BH3. Characterizing the specific features of BAD BH3 targets that operate under distinct conditions and the precise metabolic signals involved in their selection will provide major insights into the mechanism underlying the BAD-dependent binary decision between metabolism and apoptosis. These findings also suggest that the two functions of BAD may be targeted separately for therapeutic purposes. Because BAD phosphorylation has opposite effects on BCL-$X_L$ binding and GSIS, a phosphorylated BAD BH3 mimetic that facilitates GSIS but is unable to bind BCL-$X_L$ to promote apoptosis, may serve as a prototype therapeutic in diabetes and islet transplantation.

Example 11. Peripheral Insulin Resistance

Type 2 diabetes stems from deficiencies in both insulin action and pancreatic β-cell function. Three tissues, namely skeletal muscle, adipocytes and liver constitute the sites of insulin resistance with critical roles in glucose uptake, lipolysis and hepatic glucose production, respectively. However, the primary site of insulin resistance has been subject to active investigation (Accili D. 2003. *Diabetes* 53, 1633-42). Genetic evidence suggests that the failure of liver to properly regulate glucose metabolism in response to insulin constitutes the primary site of insulin resistance in type 2 diabetes (Lauro D. et al., 1998. *Nat Genet.* 20:294-8; Bruning J. C. et al., 1998. *Mol Cell* 2:559-69). Inability to balance hepatic glucose production versus glucose uptake and storage has dramatic effect on blood glucose levels. Consequently, significant efforts in therapeutic control of diabetes have focused on suppression of Hepatic Glucose Production (HGP). For example, the prominent feature of the antidiabetic drug metformin commonly used for the treatment of type 2 diabetes is its effect on HGP (Kirpichnikov D., 2002. *Ann Intern Med* 137:25-33).

The balance between hepatic glucose production and glucose disposal/storage is largely dependent on the opposing function of two important enzymes respectively, namely glucokinase, which controls glucose phosphorylation and glucose-6-phosphatase, which converts glucose-6-phosphate back to glucose. Furthermore, by utilizing glucose, glucokinase directly affects the transcription of gluconeogenic genes in the liver involved in HGP, whose expression requires the presence of glucose (Vaulont D., 2001. *Proc Natl Acad Sci USA* 98:9116-21; Scott D. K., 1998. *J Biol Chem* 273:24145-51). This effect of GK on gene expression is consistent with its role as a glucose sensor in liver. Consequently, small molecule activators of GK have efficacy in suppressing HGP in various murine models of diabetes (Grimsby J. et al., 2003. *Science* 301:370-3)

Figure 51:
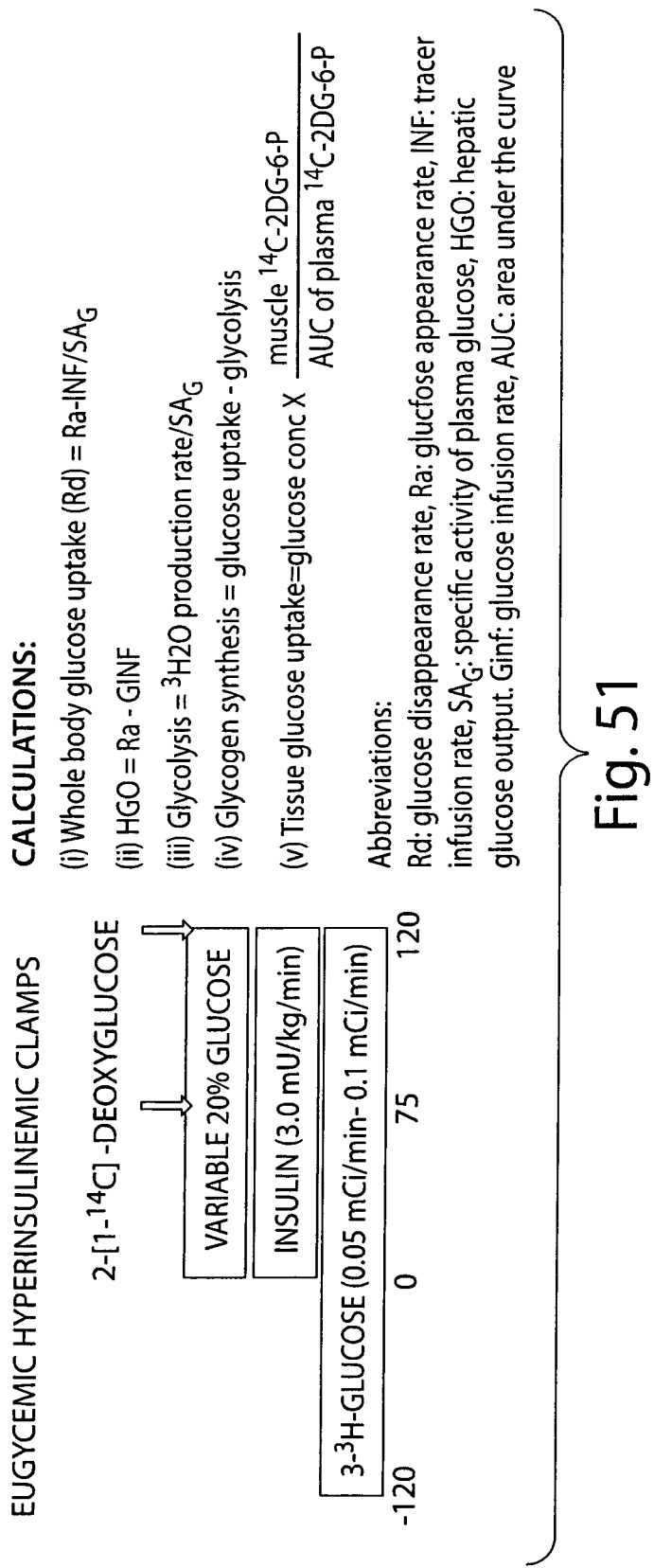
FIG. 51 briefly describes the euglycemic-hyperinsulinemic clamp method and the formula used to calculate various metabolic parameters.
Figure 52:
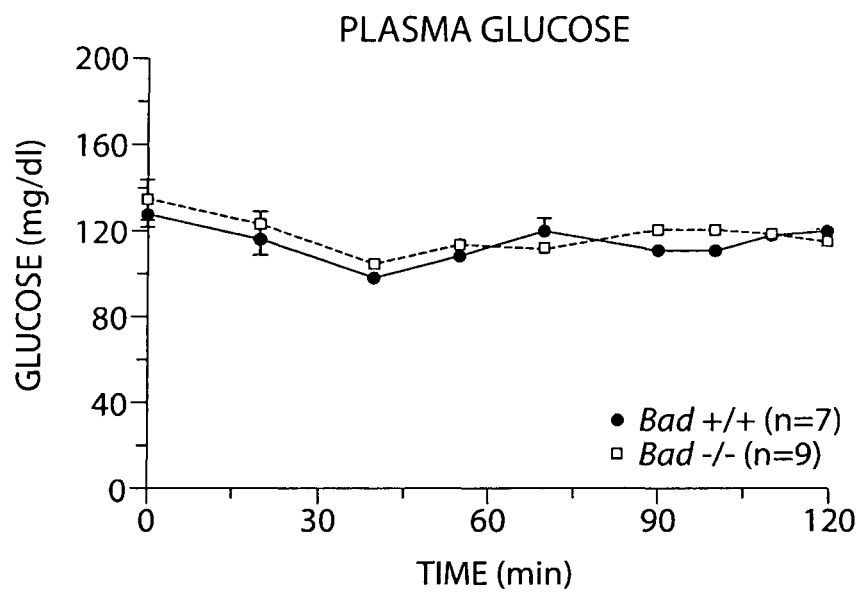
FIG. 52 is a line graph documenting that euglycemia was reached and maintained in Bad +/+ (n=7) and Bad −/− (n=9) mice throughout the clamp period.
Figure 53:
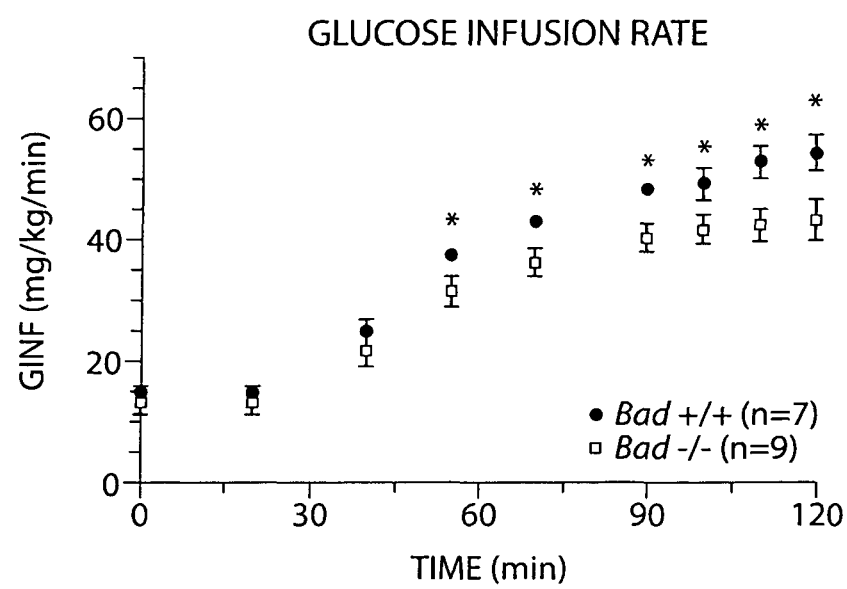
FIG. 53 is a line graph showing the glucose infusion rate (GINF) in Bad +/+ (n=7) and Bad −/− (n=9) mice subjected to euglycemic-hyperinsulinemic clamp analysis.
Figure 54:
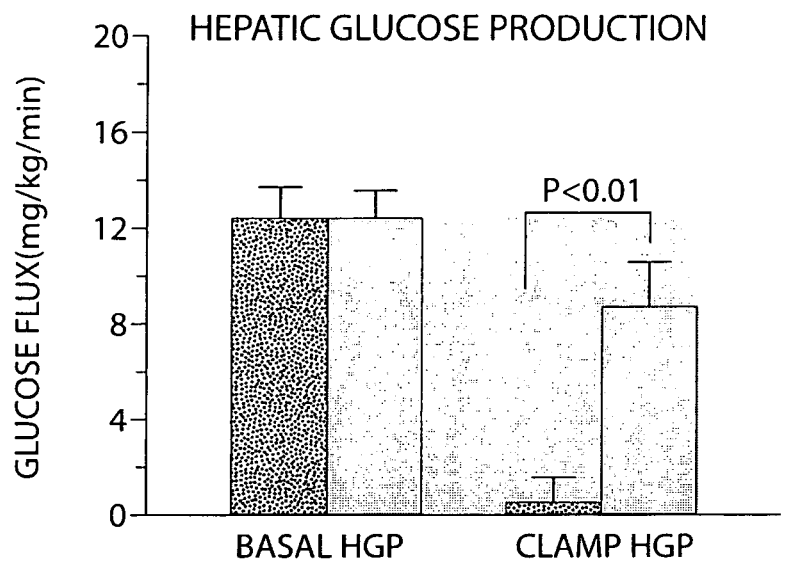
FIG. 54 is a bar chart demonstrating the hepatic glucose production calculated using the formula in FIG. 51 (HGO).
Figure 55:
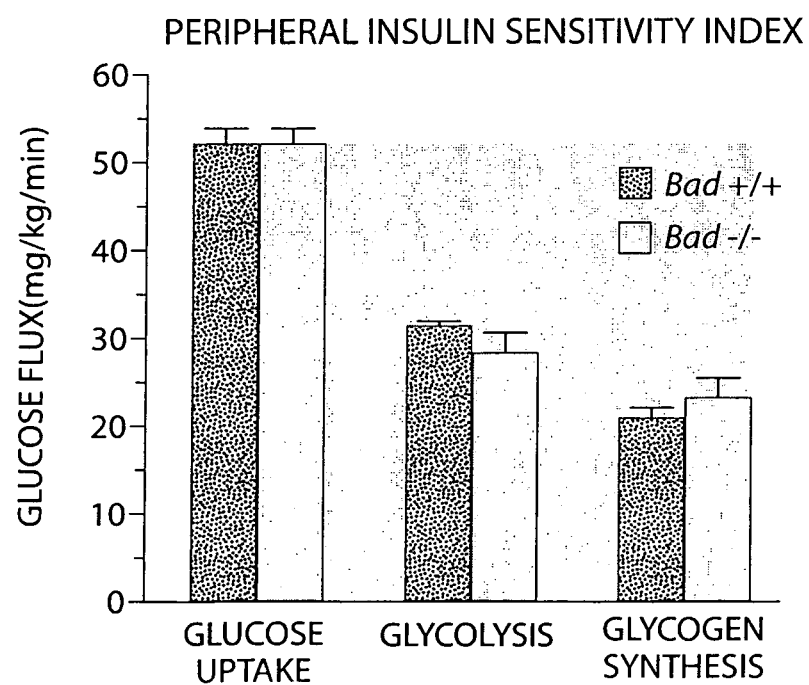
FIG. 55 is a bar chart showing the peripheral insulin sensitivity index, which includes glucose uptake, glycolysis and glycogen synthesis all measured using the formula provided in FIG. 51.
Figure 56:
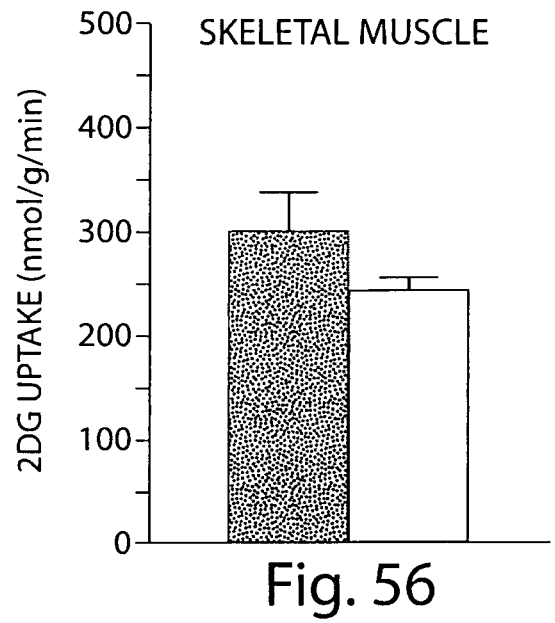
FIG. 56 is a bar chart documenting glucose uptake in skeletal muscle obtained from Bad +/+ and Bad −/− animals subjected to the euglycemic-hyperinsulinemic clamp analysis.
Figure 57:
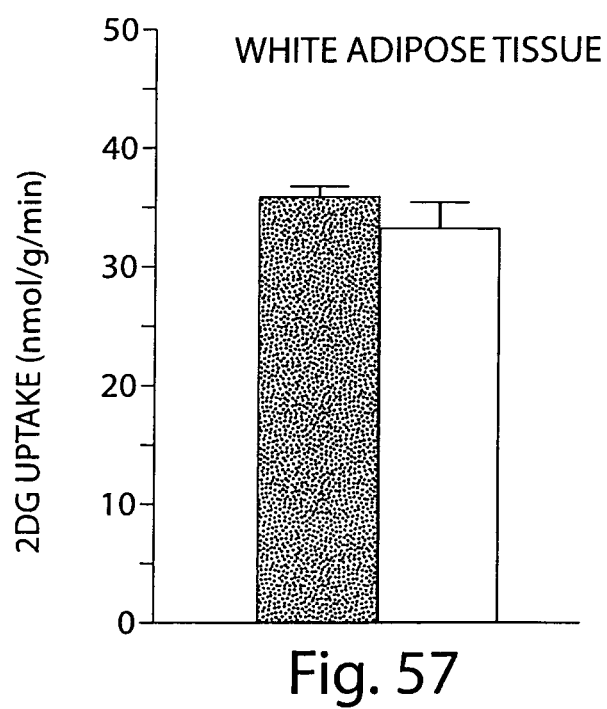
FIG. 57 is a bar chart showing glucose uptake in white adipose tissues isolated from Bad +/+ and Bad −/− animals subjected to the euglycemic-hyperinsulinemic clamp analysis.

To delineate the role of BAD in peripheral insulin resistance, the sensitivity of liver, muscle and fat to insulin was assessed in BAD-deficient mice using the euglycemic hyperinsulinemic clamp analysis (FIG. 51-52). Glucose infusion rates required under these conditions are determined by the insulin response in muscle, liver and adipose tissues. We find a small (but statistically significant) decrease in the glucose infusion rate (~17%) in Bad –/– versus Bad +/+ animals (FIG. 53). This difference can be entirely attributed to the lack of suppression of hepatic glucose production (FIG. 54). We found no difference in glycogen synthesis as indicated by glucose flux studies (FIG. 55) or in glucose uptake in muscle and WAT (FIGS. 56 and 57). These data indicate that BAD plays an important role in mediating the action of insulin in liver that is consistent with its effect on GK activity. Activating GK through BAD mimetic compounds (FIG. 18) may, therefore, prove effective in suppressing hepatic glucose production and normalizing blood glucose levels.

Figure 58:
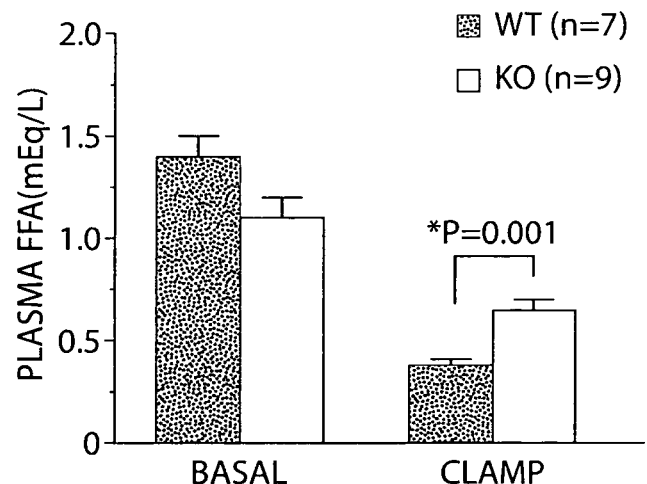
FIG. 58 is a bar chart showing the effect of insulin on plasma free fatty acid (FFA) in Bad +/+ and Bad −/− animals subjected to the euglycemic-hyperinsulinemic clamp analysis.
Figure 59:
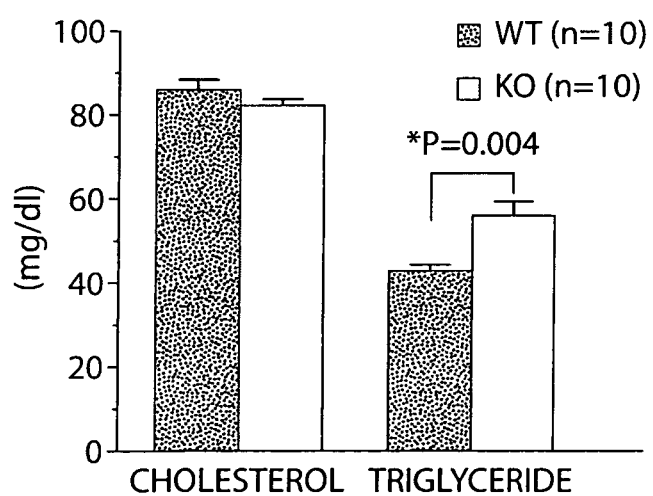
FIG. 59 is a bar chart showing the effect of insulin on plasma lipids in Bad +/+ and Bad −/− animals subjected to the euglycemic-hyperinsulinemic clamp analysis.
Figure 60:
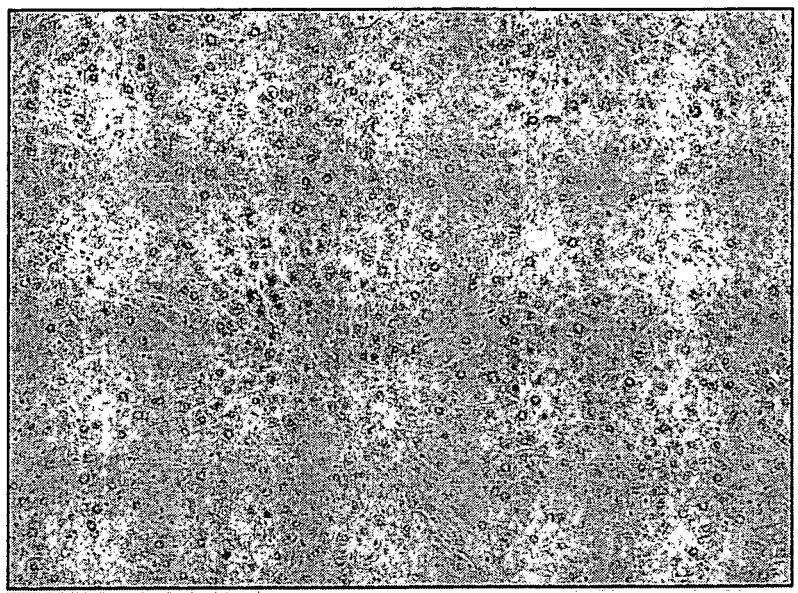
FIG. 60 is a photograph showing immunohistochemical analysis of tissue section prepared from livers excised from Bad −/− mice fed on control diet for 16 weeks.
Figure 61:
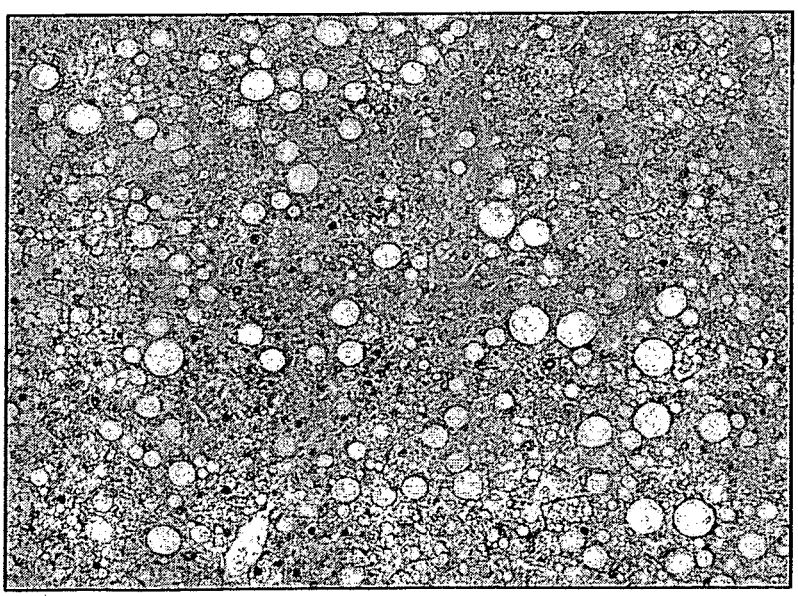
FIG. 61 is a photograph showing immunohistochemical analysis of tissue section prepared from livers excised from Bad 3SA mice fed on high fat diet for 16 weeks.
Figure 62:
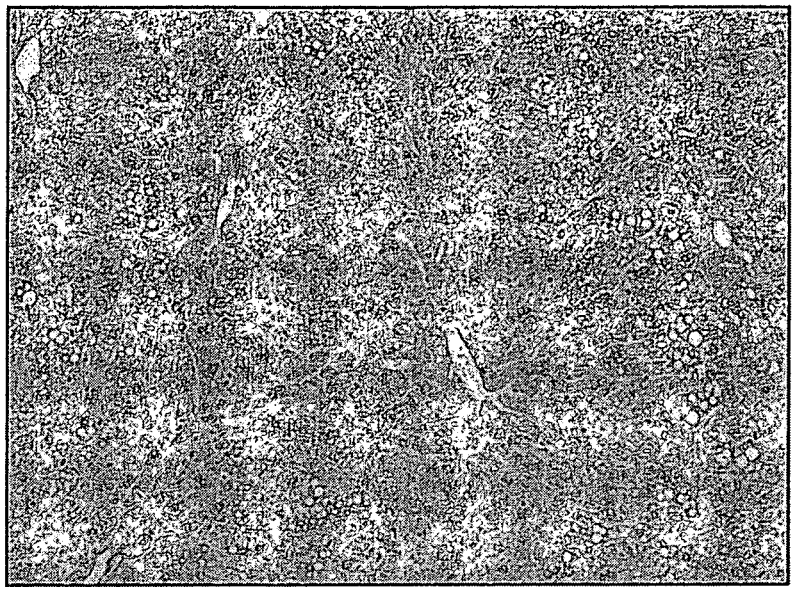
FIG. 62 is a photograph showing immunohistochemical analysis of tissue section prepared from livers excised from Bad +/+ mice fed on control diet for 16 weeks.
Figure 63:
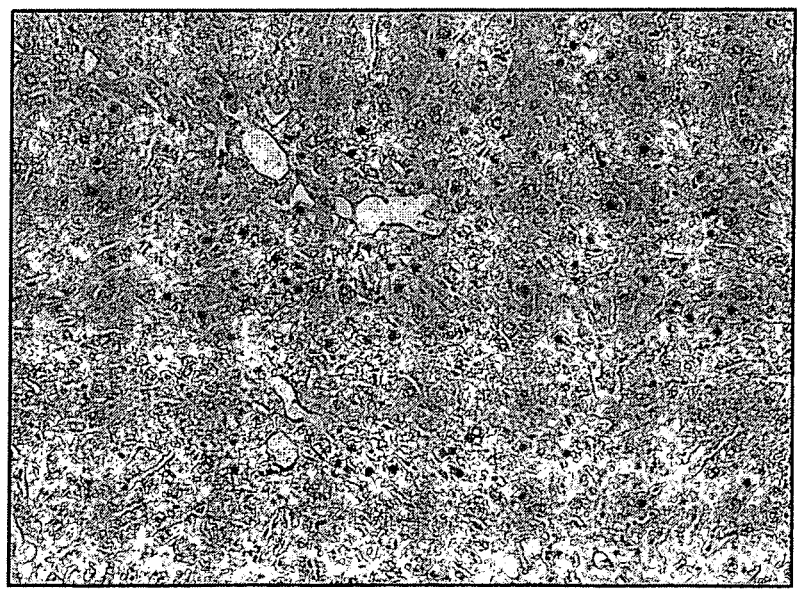
FIG. 63 is a photograph showing immunohistochemical analysis of tissue section prepared from livers excised from Bad −/− mice fed on high fat diet for 16 weeks.

Furthermore, insulin-mediated suppression of plasma fatty acids was decreased (FIG. 58) and higher levels of lipids were detected in Bad –/– mice during the insulin clamp (FIG. 59). These data indicate abnormal lipid profiles in BAD-deficient mice and suggest a role for BAD in mediating the effect of insulin in adipose tissues.

Example 12. Glucokinase-Linked Hypoglycemia

While inactivating mutations in glucokinase, as those isolated from MODY 2 (Maturity-Onset Diabetes of the Young type 2) patients, are associated with metabolic disorders marked by loss of glucose sensing and loss of insulin effect on suppression of hepatic glucose production, activating mutations in glucokinase are associated with congenital hyperinsulinism (Byrne M. M. et al., 1994. *J Clin Invest* 93, 1120-30; Clement K., 1996. *Diabetologica* 39:82-90), a subtype of clinical disorder of hyperinsulinemic hypoglycemia of infancy (Glaser B., 1998. *N Engl J Med* 338:226-30; Christesen H. B. T., 2000. *Diabetes* 51:1240-6).

Preventing BAD phosphorylation diminishes glucokinase activity (Danial N. N. et al., 2003. *Nature* 424, 952-6). Derivatives of BAD SAHB compounds mimicking the serine 155 to alanine mutation (FIG. 18), which renders this amino acid residue unphosphorylatable, may prove important therapeutic tools in inhibiting glucokinase in this disease setting. This modification in combination with mutation of L151 and D156 in BAD BH3 domain, which blocks its ability to activate apoptosis and insulin secretion can serve as the basis for BAD mimetic compounds that may prevent GK activation without inducing apoptosis in target cells in this disease setting.

Example 13. Glucose Sensing in the Brain

Glucosensing neurons are specialized neurons mainly found in the hypothalamus and the medulla (Yang X., 1999. *Diabetes* 48:1763-72; Dunn-Maynell A. A., 2002. *Diabetes* 51:2056-65), which, unlike other neurons, use glucose as a signaling molecule to regulate their activity. Glucosensing neurons function in a very analogous way to pancreatic β-cells with GK serving as the gatekeeper of glucose-induced neuronal activity. Furthermore, similar to β-cell pathway for stimulus-coupled secretion, ATP production is the main metabolic factor that couples glucose metabolism to neuronal activity by inactivating the $K_{ATP}$ channels and prompting the subsequent influx of $Ca^{2+}$ followed by propagation of action potential (Levin B., 2006. *Physiol Behav* in press). This neuronal activity in turn regulates an integrated neuronal pathway that controls energy uptake, expenditure and storage.

As GK activity in glucosensing neurons is essential for their physiological function (Kang L., 2006. *Diabetes* 55:412-20), activators of GK, including BAD SAHB compounds (FIG. 18), are predicted to affect the neuroendocrine regulation of energy homeostasis, which in turn has been shown to have important implication for metabolic disorders associated with diabetes and obesity (Schwartz M. W., 2005. *Science* 307:375).

Example 15. Chronic Liver Disease

The liver plays a central role in controlling whole body glucose/lipid utilization. Through glycogen synthesis and gluconeogenesis, the liver determines glucose production and storage in the body (Dentin, R., 2005. *Biochimie* 87:81). On the other hand, through β-oxidation (the mitochondrial pathway in charge of breaking down fat for energy production) and fatty acid synthesis, the liver affects lipid metabolism. Abnormalities in glucose and lipid metabolism in liver are integral to insulin resistant (IR) state and are thought to contribute to chronic liver disease, including nonalcoholic fatty liver disease (NAFLD) and its more severe from nonalcoholic steatohepatitis (NASH) (Bugianesi, E., 2005. *Hepatology* 42:987).

NAFLD is the hepatic presentation of the metabolic syndrome, a group of metabolic disorders that include IR, obesity, type II diabetes, hypertension, hyperlipidemia (Falck-Ytter, Y. 2001. *Semin Liver Dis* 21; 17). In the more severe form of the disease, NASH, loss of the proper architecture of liver due to cell injury (liver cirrhosis) is observed (Brunt, E. M. 2005. *Hepathol Res* 33:68). Fatty liver, also known as steatosis or steatohepatitis, is a histological hallmark of NAFLD/NASH, marked by high levels of triglyceride accumulation in hepatocytes. Current treatment strategies for NAFLD/NASH include agents that lower lipids or those that sensitize hepatocytes to the action of insulin.

Figure 22:
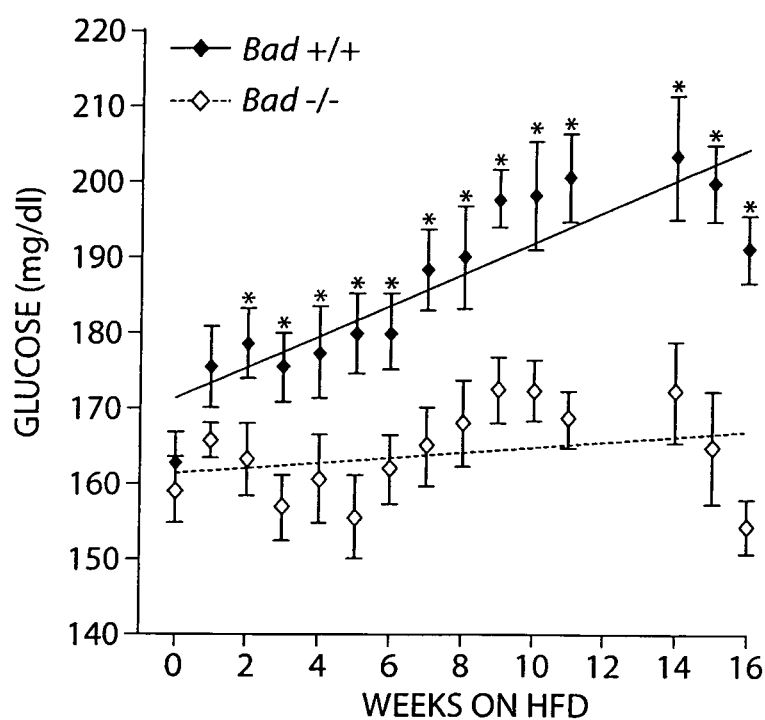
FIG. 22 is a line graph demonstrating weekly blood glucose levels of a cohort of Bad +/+ and Bad −/− (n=20) placed on HFD for 16 weeks.
Figure 64:
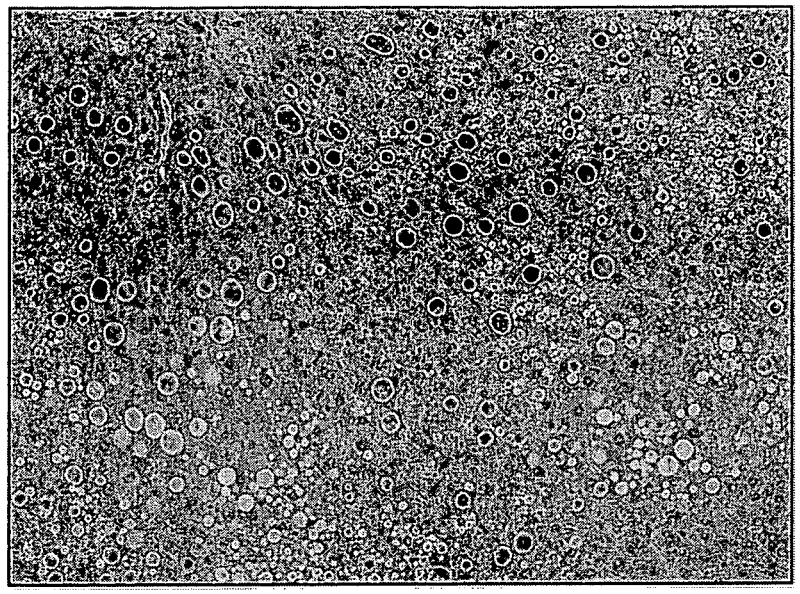
FIG. 64 is a photograph showing immunohistochemical analysis of tissue section prepared from livers excised from Bad +/+ mice fed on high fat diet for 16 weeks.
Figure 65:
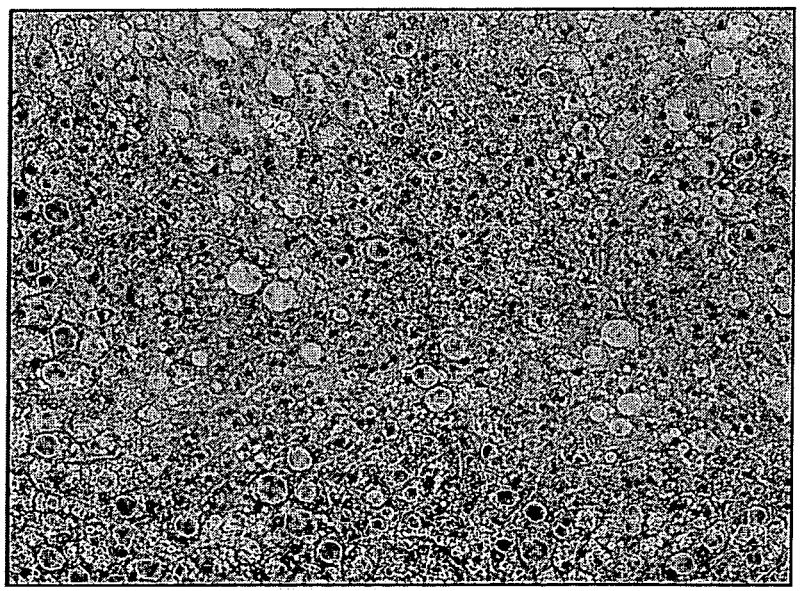
FIG. 65 is a photograph showing Immunohistochemical analysis of tissue section prepared from livers excised from Bad +/+ mice fed on high fat diet for 16 weeks.
Figure 66:
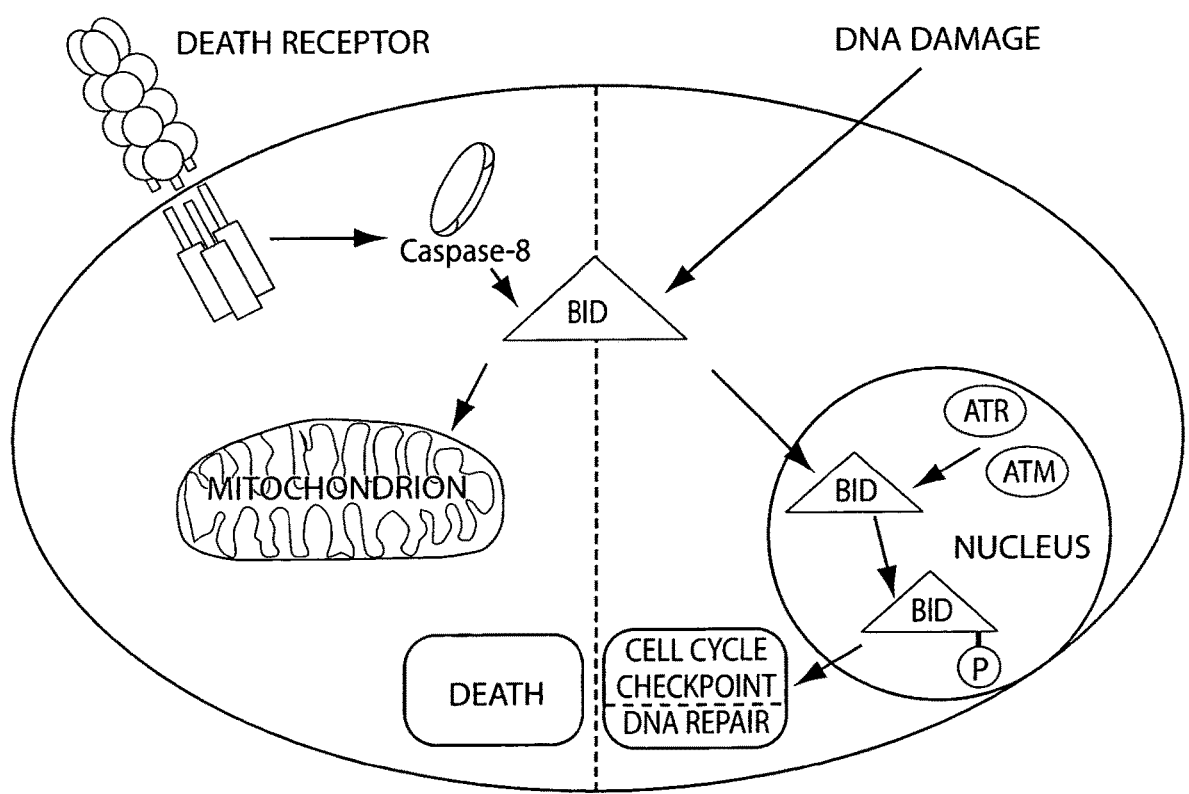
FIG. 66 depicts a model for the dual function of BID in apoptosis and DNA damage checkpoint. Both roles are regulated through post-translational modification of BID on distinct residue. Downstream of death receptor signaling, BID is cleaved by Caspase-8. Cleaved BID is then modified by addition of lipid moieties (myristoyl groups) and translocates to mitochondria to activate apoptosis. On the other hand, downstream of DNA damage, BID translocates to the nucleus where it is modified by phosphorylation by cell cycle checkpoint kinases ATM/ATR on specific residues close to its BH3 domain. This modification allows BID to function in cell cycle arrest (intra-S phase checkpoint), which ultimately prevents cells to repair their damage DNA prior to proliferation.

These findings provide evidence that ablation of Bad in mice is associated with resistance to hyperglycemia induced in a HFD model of IR and type II diabetes (FIG. 22). The differential response of Bad +/+ and Bad -/- mice to this treatment is also evident in the striking difference in the emergence of fatty livers (FIG. 60-63). BAD-null animals do not develop fatty livers. Importantly, this resistance is associated with the phosphorylation status of BAD (FIGS. 64-65). Mice expressing a mutant form of BAD that can never be phosphorylated (Bad 3SA) are more sensitive to hyperglycemia induced by HFD (FIG. 27) and are more prone to develop fatty livers compared to their wild type littermate controls (FIG. 64-65).

Given these findings, preventing the apoptotic function of BAD may prove to be an effective therapeutic strategy in NAFLD/NASH by preventing liver injury and function. Importantly, this strategy may be considered in combination of current pharmacologic treatment for NASH (Portincasa, P. 2006. *Curr Med Chem* 13:2889).

Example 16. The Glycolytic Switch in Tumors

Figure 3:
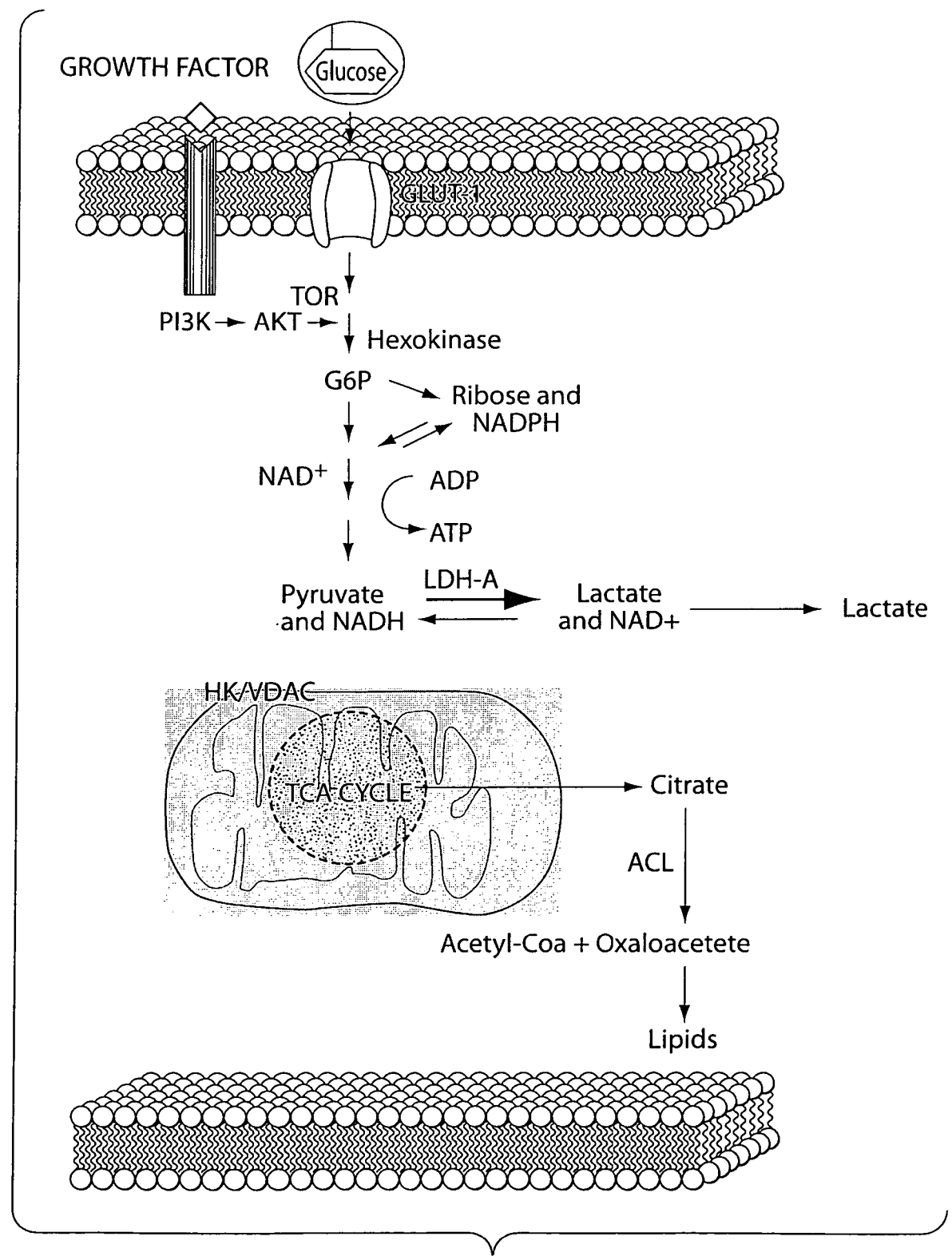
FIG. 3 highlights the distinct metabolism of cancer cells, which undergo a glycolytic switch and activate glycolysis in a constitutive manner. See test for details.

Tumors are known to be highly glycolytic (Gatenby. R. A. and Gillies, R. J. 2004. *Nat Rev Cancer* 4, 891-99). This has been attributed to either defective oxidative phosphorylation (OXPHOS) though mitochondria or "re-wiring" of the metabolic pathways in tumors to utilize glycolysis and its intermediates as the main source of ATP, reducing equivalent and macromolecular synthesis to support their high bioenergetic demands. (Mazurek S, and Eigenbrodt E. 2003. *Anticancer Res* 23, 1149-54). Examples of such metabolic shifts or "re-wiring" include a truncated TCA (Tricarboxylic acid) cycle whereby the TCA intermediate citrate, which is generated through the utilization of pyruvate by mitochondria provides cytosolic Acetyl-CoA for fatty acid synthesis (FIG. 3) (Hatzivassiliou G. et al. 2005. *Cancer Cell* 8, 311-21). Another example of tumor cell metabolic shift is the utilization of pyruvate to generate lactate through a reaction catalyzed by lactate dehydrogenase (FIG. 3) (Fantin, V. R. et al., 2006. *Cancer Cell* 9, 425-34).

Through its capacity to regulate the efficiency by which mitochondria utilize glucose as a carbon source for respiration, BAD may determine the availability of pyruvate to be used in the above metabolic pathways. Bad-deficient mice progress to diffuse large B cell lymphoma (DLBCL) (Ranger, A. M. et al., 2003. *Proc Natl Acad Sci USA* 100, 9324-29), tumors known to be highly glycolytic. This may be indicative of both loss of proper apoptotic control as well as enhancement of the metabolic switch from OXPHOS to glycolysis in Bad-deficient DLBCL.

Example 17. General Methods

Animal Models.

The Bad -/- and Bad 3SA knockin genetic models have been previously described (Datta S. R. et al., 2002. *Dev Cell* 3, 631-43; Ranger A. M et al., 2003. *Proc Natl Acad Sci USA* 100, 9324-9). The Bad S155A knockin model was generated as described in FIG. 7.

Hyperglycemic Clamp Studies.

Hyperglycemic clamps studies were performed on 10 week old male mice following the standardized procedures established at the Yale University Mouse Metabolic Phenotyping Center. At least 5 days before the clamp analysis, mice were anesthetized and an indwelling catheter inserted into the right internal jugular vein for intravenous infusion of glucose. Mice were fasted overnight and the clamp analysis was conducted on animals in awake and minimally-stressed state. A 3-way connector was attached to the jugular vein catheter for intravenous infusion and blood samples obtained. A 2-hour hyperglycemic clamp was conducted with a primed and variable infusion of 20% glucose to raise and maintain plasma glucose concentrations at ~300 mg/dl. Blood samples (20 µl) were collected at 10-20 min intervals for the immediate measurement of plasma glucose concentrations using the Beckman Glucose Analyzer II (Beckman, Fullerton, Calif.). Plasma insulin was measured by radioimmunoassay using the kit supplied by Linco Research (St. Charles, Mo.).

Hyperinsulinemic-Euglycemic Clamp Studies.

Four days before the hyperinsulinemic-euglycemic studies, mice had body composition assessed by $^1$H magnetic resonance spectroscopy (Bruker BioSpin, Billerica, Mass.). Jugular venous catheters were implanted and the mice allowed to recover for 4 days. After an overnight fast, [3-$^3$H]glucose (HPLC purified; Perkin Elmer, Boston, Mass.) was infused at a rate of 0.05 µCi/min for 2 h to assess the basal glucose turnover. Following the basal period, the hyperinsulinemic-euglycemic clamp was conducted for 120 min with a primed/continuous infusion of human insulin (300-pmol/kg prime, 15-pmol·kg$^{-1}$·min$^{-1}$ infusion) (Novo Nordisk, Princeton, N.J.) and a variable infusion of 20% dextrose to maintain euglycemia (~100-120 mg/dl). Plasma samples were obtained from the tail at 20, 40, 55, 70, 75, 80, 95, and 120 min [3-$^3$H]glucose was infused at a rate of 0.1 µCi/min throughout the clamps and 2-deoxy-D-[1-$^{14}$C]glucose (DOG; Perkin Elmer) was injected as bolus at the 75th min of the clamp to estimate the rate of insulin-stimulated tissue glucose uptake as previously described (Youn J. H., 1993. *Diabetes* 42:757-63). At the end of clamp, mice were anesthetized with pentobarbital sodium injection (150 mg/kg), and all tissues were taken within 4 min, frozen immediately using liquid N$_2$-cooled aluminum tongs, and stored at −80° C. for later analysis.

Islet Preparation.

Mouse pancreata were perfused with collagenase and islets were isolated as previously described (Larsson O. et al., 1996. *J Biol Chem* 271, 10623-6). Islets were routinely cultured for 1-2 days prior to insulin secretion (perifusion or static incubation) assays.

Islet Perifusion Assays.

Figure 2:
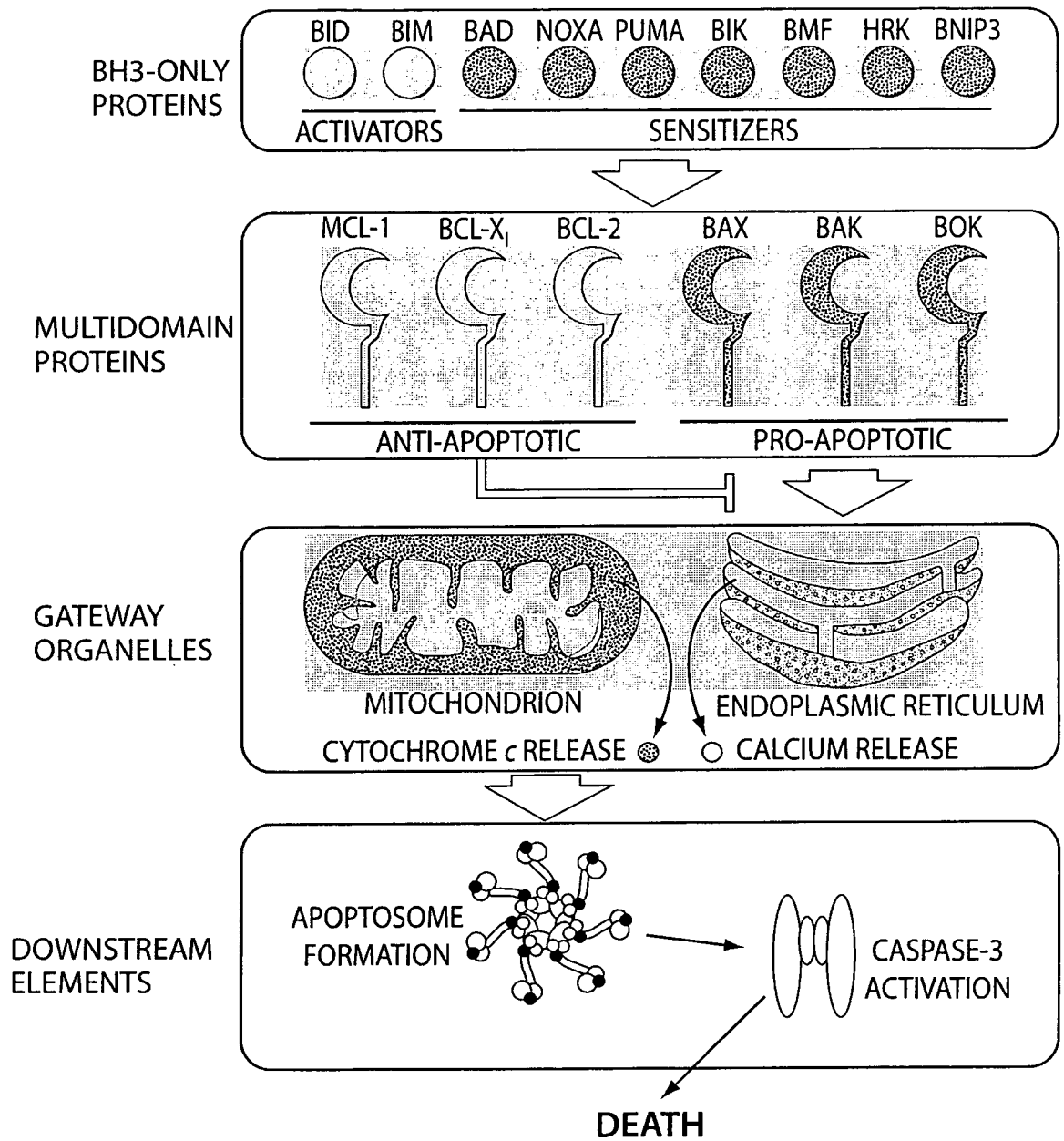
FIG. 2 is a schematic representation of the intrinsic apoptotic pathway in which organelles including mitochondria and the endoplasmic reticulum (ER) play major roles. BH3-only molecules serve as upstream sentinels that selectively respond to specific death signals and ultimately regulate BAX and BAK activation directly or indirectly. This process is in turn inhibited by anti-apoptotic BCL-2 family members. BAX and BAK serve as gateways to apoptosis regulating both cytochrome c release from mitochondria and $Ca^{2+}$ release from the ER.

Perifusion assays were carried out as described in (Cunningham B. A. et al., 1996. *Am J Physiol* 271, E702-10). Briefly, 120 islets were sandwiched in a column between two layers of Cytodex-3 micro-carrier beads (Pharmacia) and perifused with Krebs buffer (119 mM NaCl, 4.6 mM KCl, 1 mM MgSO$_4$, 0.15 mM Na$_2$HPO$_4$, 0.4 mM KH$_2$PO$_4$, 25 mM NaHCO$_3$, 2 mM CaCl$_2$, 20 mM HEPES, pH 7.4, 0.05% bovine serum albumin) containing the indicated concentration of glucose or KCl. The perifusion solution was pumped using a high precision multi-channel pump (IP Istamec model #78023-02, Cole-Parmer Instruments Co.) at a flow rate of 0.3 ml/min to ensure islets were not exposed to excessive pressure during the course of perifusion. Prior to fraction collection, islets were pre-perifused with 3 mM glucose for 25 min. Eluted fractions were collected every 15 sec using a BioRad fraction collector (Model #2128). The entire system was maintained in a chamber at 37° C. The glucose concentration in perifusion solution was changed at indicated times (FIG. 1*d*). For glucose dose response assessment of insulin secretion (FIG. 2*f*), fractions corresponding to the first peak of insulin release were collected for insulin measurements prior to increasing the glucose concentration to the next increment. Insulin was measured by radioimmunoassay.

ATP/ADP Ratio Measurements.

Batches of 50 size matched islets were washed and pre-incubated in Krebs buffer containing 3 mM glucose for 30 min. The buffer was then switched to Krebs solution containing 5.5 mM or 25 mM glucose followed by 1 hour incubation at 37° C. in Krebs buffer. ATP and ADP contents were measured as described in (Schultz V. et al., 1993. *Anal Biochem* 215, 302-04) using a bioluminescence-based approach.

Sahb Synthesis.

To generate BID and BAD SAHB derivatives, Fmoc-based peptide synthesis, olefin metathesis, FITC-derivatization, reverse-phase HPLC purification, and microanalyses were performed as previously reported (Walensky L. D. et al., 2004. *Science* 305, 1466-70; Walensky L. D. et al., 2006. *Mol Cell* in press). An initial panel of BID and BAD SAHB phosphoryl derivatives were synthesized as described (FIG. 18).

Target Identification by SAHB-Based Immunoprecipitation or Crosslinking.

Figure 68:
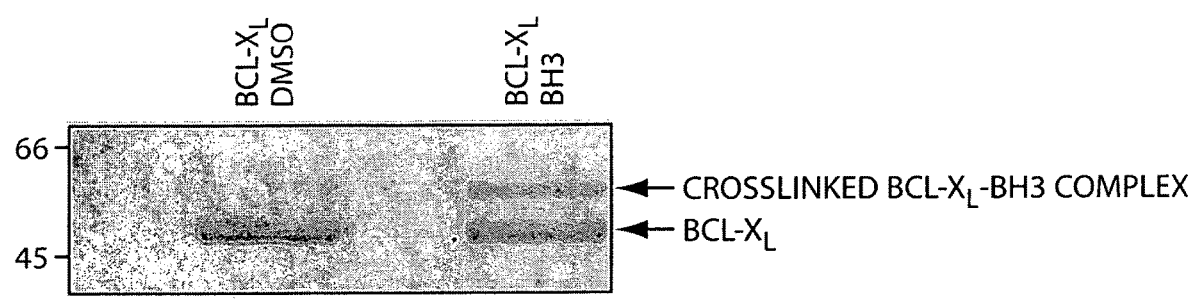
FIG. 68 is a photographs of a protein gel stained with coomassie showing the crosslinking methodology for target capture assays using the BAD BH3 sequence. Target capture assays using crosslinking methodology and photoactivatable BAD BH3 sequence. 20 μM of the FITC derivative of a BAD BH3 peptide containing 4-benzyolphenylalanine (see target capture panel in FIG. 18) was incubated with 5 μM of purified GST tagged BCL-$X_L$ in the path of 350 nm light from TLC transluminator for 135 min. BCL-$X_L$ treated with vehicle control (DMSO) served as control. Proteins were loaded onto an SDS-PAGE gel and stained with coomassie. Photoactivation results in covalent crosslinking of BCL-$X_L$ and the BH3 peptide resulting in a mobility shift of the BCL-$X_L$ protein as indicated.
Figure 69:
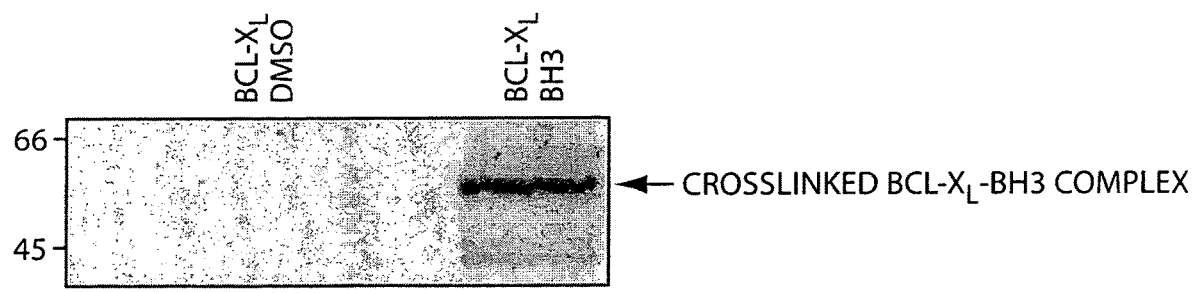
FIG. 69 is a photographs of a protein gel subjected to a fluorescent gel scan showing the crosslinking methodology for target capture assays using the BAD BH3 sequence. The protein complex containing BCL-$X_L$ crosslinked to the FITC BAD BH3 peptide is detected.

SAHBs synthesized with a "handle" for immunoprecipitation (eg. FITC, biotin) are employed to identify the intracellular target(s) of BH3-based binding and biological activities as previously described (Walensky L. W. et al., 2006. *Mol Cell* 24, 199-210). An alternative in situ crosslinking methodology has also been employed in which the SAHB compounds are derivatized to directly crosslink to intracellular targets upon photostimulation or other triggers (Seghatelian, A. et al., 2004. *Proc Natl Acad Sci USA* 101, 10000-5). (FIG. 68-69).

Static Incubation (Batch Release) Method for Insulin Release in Isolated Primary β-Islets.

Islets were washed 3 times and picked at 5 islets per tube in Krebs buffer containing 3 mM glucose. The tubes were incubated for 30 min at 37° C. Islets were then pelleted and the buffer replaced with Krebs solution containing the indicated concentration of glucose or secretagogues. After 1 hour incubation at 37° C., the islets were pelleted and supernatant collected for insulin measurement. The pellet was solubilized to assess intracellular insulin content. Insulin was measured by ELISA using mouse insulin as a standard (Insulin ELISA Kit, cat. #INSKR020, Crystal Chem. Inc., Chicago, Ill.). For genetic reconstitution assays, batches of 150 freshly isolated islets were incubated in RPMI medium containing 11 mM glucose, 10% serum in the presence of adenoviruses at $10^8$ plaque forming units for 90 min at 37° C. (Zhou Y. P. et al., 2003. *J Biol Chem* 278, 51316-23). At this pfu, infections did not cause significant islet apoptosis. The medium was then replaced with fresh RPMI and islets were cultured for 24-48 hrs prior to insulin release assays. GFP-expressing islets in each group were hand picked for batch release assays as described above. For treatment with the SAHB compounds, 150 freshly isolated islets were incubated overnight in RPMI medium containing 11 mM glucose, 10% serum and 3 µM of the indicated compounds or DMSO vehicle control. Islets were washed and insulin release assays were performed in Krebs buffer as above.

Measurement of Mitochondrial Membrane Potential.

Islets were dispersed, plated on coverslips and incubated overnight at 37° C. On the day of experiment, β-cells were pre-incubated in 3 mM glucose for 3 hours. Prior to imaging, cells were loaded with 7 nM tetramethyl rhodamine ethyl ester (TMRE) and 100 nM MitoTracker Green (MTG) (Invitrogen, Carlsbad, Calif.) for 45 min and 30 min, respectively. MTG was removed from the media and cells were imaged using an inverted Leica TCS SP2 confocal microscope (Wetzlar, Germany). Four stacked images were taken from multiple individual cells before and after raising the extracellular glucose concentration from 3 mM to 8 mM or before addition of 10 mM KIC. TMRE fluorescence intensity was analyzed as described previously (Heart E. et al., 2006. *Am J Physiol Endocrinol Metab* 290, E143-E148). In studies assessing the effects of SAHB compounds on $\Delta\psi$, dispersed β-cells were incubated with DMSO vehicle control or with 1 µM of the indicated SAHB compound for 4 hours prior to imaging. Four stacked images were taken from multiple individual cells before and after raising the extracellular glucose concentration from 3 mM to 8 mM.

Glucokinase Assays in Primary Islets and MIN6 β-Cell Line.

The procedure described by Trus et al. (Trus M. D. et al., 1981. *Diabetes* 30, 911-22) was followed. The assays were adapted to 96 well format using a SpectraMax M5 (Molecular Devices, Sunnyvale, Calif.) plate reader. Briefly, ~900-1000 mouse islets (FIG. 2*e*) or 5-6×$10^6$ MIN6 β-cells (FIG. 3*f*) were homogenized in buffer containing 30 mM Tris-HCl pH 8.2, 4 mM EDTA, 150 mM KCl, 4 mM $MgCl_2$, 2.5 mM DTT, 1 mM 5'AMP, 3 mM Potassium Phosphate pH 7.4, 1 mM $K_2SO_4$, 15 mM β-mercaptoethanol and 0.2% BSA using a Teflon pestle and a rotary homogenizer. A small aliquot of homogenates was saved for DNA or protein content measurement. Glucose phosphorylating activity was detected in a glucose-6-phosphate dehydrogenase (G6PDH)-driven NADH production reaction. Glucokinase activity was calculated as the difference in NADH produced at glucose concentrations of 100 mM (glucokinase activity) and 0.5 mM (hexokinase activity) in a reaction buffer that in addition to glucose contained 50 mM HEPES HCl pH 7.7, 100 mM KCl, 7.4 mM $MgCl_2$, 15 mM β-mercaptoethanol, 0.5 mM $NAD^+$, 0.05% BSA, 2.5 µg/ml (0.7 U/ml) G6PDH (sigma) and 5 mM ATP. The reactions were incubated for 90 min at 31° C. in a total volume of 100 µl (Trus M. D. et al., 1981. *Diabetes* 30, 911-22). The values routinely obtained in these assays are within range of those previously reported for GK in primary islets (Trus M. D. et al., 1981. *Diabetes* 30, 911-22) and in MIN6 β-cell line (Iizuka K. et al., 2000. *J Endocrinol* 164, 307-14). For studies presented in FIG. 3*f*, MIN6 cells were treated with 3 µM of the SAHB compounds for 4 hours prior to preparation of homogenates.

Preparation of Adenoviral Stock.

Recombinant adenoviruses expressing GFP alone or GFP and wild type or mutant $BAD_s$ were generated using the pAdEasy system as described in (He T. C. et al., 1998. *Proc Natl Acad Sci USA* 95, 2509-14). Virus amplification, purification, titration and verification were performed at the Vector Core of the Harvard Gene Therapy Initiative, Harvard Medical School, Boston, Mass.

Real-Time PCR Assays.

Total RNA was prepared from islets using the Rneasy Plus Mini Kit (Qiagen). At least three separate animals were used for RNA preparations and the RNA samples were prepared in duplicate or triplicate and control cDNA synthesis reactions containing no reverse transcriptase enzyme were performed for each sample. The PCR reactions were run in triplicates. 1 µg of total RNA was used in 20 µl cDNA synthesis reactions using standard techniques. The cDNA was diluted 20 fold and 2 µl used in a 25 µl PCR reaction using primers for BAD. Another set of control reactions contained primers for ribosomal protein (RPL4), which served as an internal control for the quality of RNA. Reaction mixture contained 300 nM of each primer and 1×SYBR Green PCR Master Mix (Applied Biosystems). The PCR products were detected with the ABI Prism 7700

Sequence Detector (Applied Biosystems) and the threshold values ($C_T$) were determined as a measure of the cycle number at which a statistically significant increase in fluorescence intensity is first detected. The abundance of the amplified gene was calculated using $C_T$ values and normalized to the average values of RPL4 to obtain relative abundance. The relative abundance was then normalized to that of control group (Bad +/+ samples) and the ratios plotted. The sequence of primers is available upon request.

High Fat Diet Studies and Blood Chemistries.

Male Bad −/− and Bad 3SA mice and their corresponding littermate controls were placed on a diet composed of high fat (58% fat energy, D12331, Research Diets, Inc. New Brunswick, N.J.) 16 weeks (Winzell M. S, and Ahren B., 2004. *Diabetes* 53 Suppl 3, S215-9). A parallel cohort was kept on normal diet. Body weights and fed blood glucose levels were monitored weekly. Blood glucose levels were measured using a glucometer (One Touch, Lifescan, Milpitas, Calif.). Serum insulin concentrations were assessed using mouse insulin as a standard (Insulin ELISA Kit, cat. #INSKR020, Crystal Chem. Inc., Chicago, Ill.).

Immuno-Staining and Islet Area Measurements.

Pancreata were fixed in 10% formalin, and embedded in paraffin. Serial 5-µm pancreatic sections were stained as described below. Immuno-histochemistry was performed using a guinea pig anti human insulin serum #4011-01 (Linco Research Inc., St. Charles, Mo.), followed by incubation with peroxidase conjugated AffiPure secondary antibodies (Jackson Immuno Research). The sections were developed using 3,3-diaminobenzidine tetrahydrochloride and then counterstained with hematoxylin and eosin. For islet area measurements, sections were stained with the above anti insulin antibody followed by biotinylated secondary antibody and labeled with Texas Red conjugated streptavidin (Molecular Probes). For each section, an average of 14 low magnification fields were examined under the microscope and captured on digital images, which were then analyzed using the MetaMorph software. Briefly, islets from each section were traced and thresholded using the MetaMorph software and insulin positive area was calculated. The sum of insulin positive area (total islet area) was divided by the total tissue area on each slide and the number expressed as percentage islet area. Multiple sections from at least three mice per group were analyzed.

Generation of S155A Bad Knockin Mice.

The knockin strategy was similar to that used in generating the 3SA alleles (Datta S. R. et al., 2002. *Dev Cell* 3, 631-43). Briefly, the Serine to Alanine mutation of S155 in the BAD BH3 domain with silent RFLP encoding and EcoR1 site was introduced into BAD exon 3 by QuickChange using pBR322BAD as template. A 900 by SexA1/RsrII fragment containing this mutation was swapped into a new pBR322BAD construct. An FRT-PGK-NEO-FRT cassette was cloned into an NsiI site 1.4 kB distal to the BAD 3′UTR, and a diphtheria toxin-negative selection cassette was introduced into genomic BAD/pBR322 junction at the 5′ end of the BAD locus. This vector was electroporated into 129 J1 ES cells and injected into C57B6 blastocysts. Homologous recombinants were identified by standard procedures. The SexA1/RsrII fragment was reisolated from mice positive for the RFLP marker and sequenced to verify the mice carried the correct mutation.

Fluorescence Polarization Binding Assay.

A glutathione S-transferase fusion protein of BCL-$X_L$ (residues 1-212) lacking the C-terminal transmembrane domain (GST-BCL-$X_L$ ΔC) was expressed in *E. coli* BL21 using pGEX2T (Pharmacia Biotech), and purified by affinity chromatography using glutathione-agarose beads (Sigma) and fast protein liquid chromatography (FPLC). Protein concentration was determined using the Bradford Assay. Fluorescinated SAHBs (50 nM) were incubated with GST-BCL-$X_L$ ΔC (0.25-1000 nM) in binding buffer (140 mM NaCl, 50 mM Tris-HCl [pH 7.4]) at room temperature. Binding activity was measured by fluorescence polarization using a POLARstar OPTIMA microplate reader (BMG labtech). $EC_{50}$ values were determined by nonlinear regression analysis using Prism software (Graphpad).

Circular dichroism. SAHB peptides were dissolved in water at neutral pH to concentrations of 25-50 µM. CD spectra were obtained on a Jasco J-710 spectropolarimeter at 20° C. using the following standard measurement parameters: wavelength, 190-260 nm; step resolution, 0.5 nm; speed, 20 nm/sec; accumulations, 10; response, 1 sec; bandwidth, 1 nm; path length, 0.1 cm. The α-helical content of each peptide was calculated from the mean residue molar ellipticity value at 222 nm ([θ]222) (Chen Y. H. et al., 1974. *Biochemistry* 13, 3350-9; Yang J. T. et al., 1986. *Methods Enzymol* 130, 208-269).

Other Embodiments

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of treating diabetes, the method comprising administering to a human subject in need thereof a peptide, wherein the peptide is less than 100 amino acids in length and comprises the amino acid sequence of any one of the following:
   a) NLWAAQRYGRELRX$_1$MSDX$_2$FVDSFKK (SEQ ID NO: 18);
   b) NLWAAQRYGRELRX$_1$XSDX$_2$FVDSFKK (SEQ ID NO: 47);
   c) NLWAAQRYGRELRX$_1$MZDX$_2$FVDSFKK (SEQ ID NO: 21);
   d) NLWAAQRYGRELRX$_1$XZDX$_2$FVDSFKK (SEQ ID NO: 51);
   e) NLWAAQRYGRELRX$_1$MDDX$_2$FVDSFKK (SEQ ID NO: 22);
   f) NLWAAQRYGRELRX$_1$XDDX$_2$FVDSFKK (SEQ ID NO: 49);
   g) NLWAAQRYGRELRX$_1$BSDX$_2$FVDSF (SEQ ID NO: 64);
   h) LWAAQRYGRELRX$_1$BSDX$_2$FVDSFK (SEQ ID NO: 70);
   i) LWAAQRYGRELRX$_1$BSDX$_2$FVDSF (SEQ ID NO: 71); or
   j) WAAQRYGRELRX$_1$BSDX$_2$FVDSF (SEQ ID NO: 72);
wherein X$_1$ and X$_2$ are independently any non-natural amino acid;

wherein Z is phosphoserine;
wherein X is norleucine; and
wherein B is β-alanine.

2. The method of claim 1, wherein said X$_1$ and X$_2$ are either S-N-(9-Fluorenylmethyl carbamate)-2-(4'-pentenyl) alanine (S5) or aminobutyric acid.

3. The method of claim 1, wherein X$_1$ and X$_2$ of said peptide are S-N-(9-Fluorenylmethyl carbamate)-2-(4'-pentenyl) alanine (S5), said peptide includes an intermolecular cross-link between X$_1$ and X$_2$, and said peptide, if it includes a serine between X$_1$ and X$_2$, is phosphorylated on the serine.

4. The method of claim 1, wherein said peptide consists of the amino acid sequence of any one of the following:
   a) NLWAAQRYGRELRX$_1$MSDX$_2$FVDSFKK (SEQ ID NO: 18);
   b) NLWAAQRYGRELRX$_1$XSDX$_2$FVDSFKK (SEQ ID NO: 47);
   c) NLWAAQRYGRELRX$_1$MZDX$_2$FVDSFKK (SEQ ID NO: 21);
   d) NLWAAQRYGRELRX$_1$XZDX$_2$FVDSFKK (SEQ ID NO: 51);
   e) NLWAAQRYGRELRX$_1$MDDX$_2$FVDSFKK (SEQ ID NO: 22);
   f) NLWAAQRYGRELRX$_1$XDDX$_2$FVDSFKK (SEQ ID NO: 49);
   g) NLWAAQRYGRELRX$_1$BSDX$_2$FVDSF (SEQ ID NO: 64);

h) LWAAQRYGRELRX$_1$BSDX$_2$FVDSFK (SEQ ID NO: 70);
i) LWAAQRYGRELRX$_1$BSDX$_2$FVDSF (SEQ ID NO: 71); or
j) WAAQRYGRELRX$_1$BSDX$_2$FVDSF (SEQ ID NO: 72);

wherein X$_1$ and X$_2$ are independently any non-natural amino acid;
wherein Z is phosphoserine;
wherein X is norleucine; and
wherein B is β-alanine.

5. The method of claim 1, wherein X$_1$ and X$_2$ of said peptide are S-N-(9-Fluorenylmethyl carbamate)-2-(4'-pentenyl) alanine (S5), and said peptide includes an intermolecular cross-link between X$_1$ and X$_2$.

6. The method of claim 4, wherein X$_1$ and X$_2$ of said peptide are S-N-(9-Fluorenylmethyl carbamate)-2-(4'-pentenyl) alanine (S5), and said peptide includes an intermolecular cross-link between X$_1$ and X$_2$.

7. The method of claim 1, wherein the peptide comprises the amino acid sequence of any one of the following:
   a) NLWAAQRYGRELRX$_1$MSDX$_2$FVDSFKK (SEQ ID NO: 18);
   b) NLWAAQRYGRELRX$_1$XSDX$_2$FVDSFKK (SEQ ID NO: 47);
   c) NLWAAQRYGRELRX$_1$MZDX$_2$FVDSFKK (SEQ ID NO: 21);
   d) NLWAAQRYGRELRX$_1$XZDX$_2$FVDSFKK (SEQ ID NO: 51);
   e) NLWAAQRYGRELRX$_1$MDDX$_2$FVDSFKK (SEQ ID NO: 22);
   f) NLWAAQRYGRELRX$_1$XDDX$_2$FVDSFKK (SEQ ID NO: 49);

wherein X$_1$ and X$_2$ are independently any non-natural amino acid;
wherein Z is phosphoserine; and
wherein X is norleucine.

8. The method of claim 1, wherein the peptide comprises the amino acid sequence of NLWAAQRYGRELRX$_1$XDDX$_2$FVDSFKK (SEQ ID NO: 49), wherein X$_1$ and X$_2$ are independently any non-natural amino acid; and wherein X is norleucine.

9. The method of claim 4, wherein the peptide consists of the amino acid sequence of any one of the following:
   a) NLWAAQRYGRELRX$_1$MSDX$_2$FVDSFKK (SEQ ID NO: 18);
   b) NLWAAQRYGRELRX$_1$XSDX$_2$FVDSFKK (SEQ ID NO: 47);
   c) NLWAAQRYGRELRX$_1$MZDX$_2$FVDSFKK (SEQ ID NO: 21);
   d) NLWAAQRYGRELRX$_1$XZDX$_2$FVDSFKK (SEQ ID NO: 51);
   e) NLWAAQRYGRELRX$_1$MDDX$_2$FVDSFKK (SEQ ID NO: 22);
   f) NLWAAQRYGRELRX$_1$XDDX$_2$FVDSFKK (SEQ ID NO: 49);

wherein X$_1$ and X$_2$ are independently any non-natural amino acid;
wherein Z is phosphoserine; and
wherein X is norleucine.

10. The method of claim 4, wherein the peptide consists of the amino acid sequence of NLWAAQRYGRELRX$_1$XDDX$_2$FVDSFKK (SEQ ID NO: 49), wherein X$_1$ and X$_2$ are independently any non-natural amino acid; and wherein X is norleucine.

11. The method of claim 7, wherein X$_1$ and X$_2$ of said peptide are S-N-(9-Fluorenylmethyl carbamate)-2-(4'-pentenyl) alanine (S5), and said peptide includes an intermolecular cross-link between X$_1$ and X$_2$.

12. The method of claim 8, wherein X$_1$ and X$_2$ of said peptide are S-N-(9-Fluorenylmethyl carbamate)-2-(4'-pentenyl) alanine (S5), and said peptide includes an intermolecular cross-link between X$_1$ and X$_2$.

13. The method of claim 9, wherein X$_1$ and X$_2$ of said peptide are S-N-(9-Fluorenylmethyl carbamate)-2-(4'-pentenyl) alanine (S5), and said peptide includes an intermolecular cross-link between X$_1$ and X$_2$.

14. The method of claim 10, wherein X$_1$ and X$_2$ of said peptide are S-N-(9-Fluorenylmethyl carbamate)-2-(4'-pentenyl) alanine (S5), and said peptide includes an intermolecular cross-link between X$_1$ and X$_2$.

* * * * *